US009121110B2

(12) United States Patent
Gouliaev et al.

(10) Patent No.: US 9,121,110 B2
(45) Date of Patent: Sep. 1, 2015

(54) QUASIRANDOM STRUCTURE AND FUNCTION GUIDED SYNTHESIS METHODS

(75) Inventors: Alex Haahr Gouliaev, Vekso Sjaelland (DK); Anette Holtmann, Ballerup (DK); Henrik Pedersen, Bagsvaerd (DK); Thomas Franch, Snekkersten (DK)

(73) Assignee: Nuevolution A/S, Copenhagen (DK)

(*) Notice: Subject to any disclaimer, the term of this patent is extended or adjusted under 35 U.S.C. 154(b) by 1645 days.

(21) Appl. No.: 10/539,288

(22) PCT Filed: Dec. 19, 2003

(86) PCT No.: PCT/DK03/00921
§ 371 (c)(1),
(2), (4) Date: Jan. 28, 2008

(87) PCT Pub. No.: WO2004/056994
PCT Pub. Date: Jul. 8, 2004

(65) Prior Publication Data
US 2008/0193983 A1    Aug. 14, 2008

Related U.S. Application Data

(60) Provisional application No. 60/434,386, filed on Dec. 19, 2002, provisional application No. 60/507,111, filed on Oct. 1, 2003.

(51) Int. Cl.
*C40B 50/00* (2006.01)
*C40B 20/04* (2006.01)
(Continued)

(52) U.S. Cl.
CPC ............ *C40B 30/04* (2013.01); *C12N 15/1068* (2013.01); *C40B 20/04* (2013.01); *C40B 40/06* (2013.01); *C40B 50/08* (2013.01); *C40B 50/04* (2013.01); *Y10T 436/145555* (2015.01)

(58) Field of Classification Search
None
See application file for complete search history.

(56) References Cited

U.S. PATENT DOCUMENTS 4,822,731 A    4/1989   Watson et al.
(Continued)

FOREIGN PATENT DOCUMENTS

DE    19646372    6/1997
(Continued)

OTHER PUBLICATIONS

Thermo Scientific (retrieved on Nov. 5, 2013 from the following webpage: <http://www.piercenet.com/method/avidin-biotin-interaction>).*
(Continued)

*Primary Examiner* — Robert T Crow
*Assistant Examiner* — Joseph G Dauner
(74) *Attorney, Agent, or Firm* — Merchant & Gould P.C.

(57) ABSTRACT

The present invention is directed to the synthesis of molecules guided by connector polynucleotides (CPNs) capable of hybridizing to complementary connector polynucleotides (CCPNs) harboring at least one functional entity comprising at least one reactive group. At least one of the CCPNs is capable of hybridizing to at least two CPNs. Each CPN will "call" for one or more CCPNs capable of hybridization to the CPN. Following the formation of a supramolecular hybridization complex comprising a plurality of CPNs and a plurality of CCPNs, the reaction of reactive groups results in the formation of a molecule comprising covalently linked functional entities. The formation of the molecule involves the transfer of functional entities from one or more "donor CCPNs" to at least one "acceptor CCPN" with which the transferred functional entities were not associated prior to the transfer.

133 Claims, 51 Drawing Sheets

Example Library

(51) Int. Cl.

| | |
|---|---|
| *C40B 30/00* | (2006.01) |
| *C40B 50/10* | (2006.01) |
| *C12Q 1/68* | (2006.01) |
| *C07H 21/02* | (2006.01) |
| *C40B 30/04* | (2006.01) |
| *C12N 15/10* | (2006.01) |
| *C40B 40/06* | (2006.01) |
| *C40B 50/08* | (2006.01) |
| *C40B 50/04* | (2006.01) |

(56) References Cited

U.S. PATENT DOCUMENTS

| | | | |
|---|---|---|---|
| 5,047,519 A | | 9/1991 | Hobbs, Jr. et al. |
| 5,324,829 A | * | 6/1994 | Bahl et al. .................... 536/23.1 |
| 5,432,272 A | | 7/1995 | Benner |
| 5,437,977 A | * | 8/1995 | Segev .......................... 435/6.12 |
| 5,449,613 A | | 9/1995 | Dordick et al. |
| 5,451,503 A | | 9/1995 | Hogan et al. |
| 5,473,060 A | | 12/1995 | Gryaznov et al. |
| 5,474,796 A | | 12/1995 | Brennan |
| 5,476,930 A | | 12/1995 | Letsinger et al. |
| 5,503,805 A | | 4/1996 | Sugarman et al. |
| 5,571,677 A | | 11/1996 | Gryaznov |
| 5,571,903 A | | 11/1996 | Gryaznov et al. |
| 5,573,905 A | | 11/1996 | Lerner et al. |
| 5,604,097 A | | 2/1997 | Brenner |
| 5,635,400 A | | 6/1997 | Brenner |
| 5,639,603 A | | 6/1997 | Dower et al. |
| 5,643,722 A | | 7/1997 | Rothschild et al. |
| 5,654,413 A | | 8/1997 | Brenner |
| 5,656,739 A | * | 8/1997 | Cubicciotti ................... 536/23.1 |
| 5,663,046 A | | 9/1997 | Baldwin et al. |
| 5,665,975 A | | 9/1997 | Kedar et al. |
| 5,681,943 A | | 10/1997 | Letsinger et al. |
| 5,684,169 A | | 11/1997 | Hamada et al. |
| 5,686,243 A | | 11/1997 | Royer et al. |
| 5,708,153 A | | 1/1998 | Dower et al. |
| 5,723,320 A | | 3/1998 | Dehlinger |
| 5,723,598 A | | 3/1998 | Lerner et al. |
| 5,739,386 A | | 4/1998 | Holmes |
| 5,741,643 A | | 4/1998 | Gryaznov et al. |
| 5,763,175 A | | 6/1998 | Brenner |
| 5,763,263 A | | 6/1998 | Dehlinger |
| 5,770,358 A | * | 6/1998 | Dower et al. ..................... 506/18 |
| 5,770,455 A | | 6/1998 | Cargill et al. |
| 5,780,613 A | | 7/1998 | Letsinger et al. |
| 5,789,162 A | | 8/1998 | Dower et al. |
| 5,789,172 A | | 8/1998 | Still et al. |
| 5,795,976 A | | 8/1998 | Oefner et al. |
| 5,804,563 A | | 9/1998 | Still et al. |
| 5,817,795 A | | 10/1998 | Gryaznov et al. |
| 5,824,471 A | | 10/1998 | Mashal et al. |
| 5,830,658 A | | 11/1998 | Gryaznov et al. |
| 5,840,485 A | | 11/1998 | Lebl et al. |
| 5,843,650 A | | 12/1998 | Segev |
| 5,843,701 A | | 12/1998 | Gold et al. |
| 5,846,719 A | | 12/1998 | Brenner et al. |
| 5,880,972 A | | 3/1999 | Horlbeck |
| 5,942,609 A | | 8/1999 | Hunkapiller et al. |
| 5,948,648 A | | 9/1999 | Khan et al. |
| 6,001,579 A | | 12/1999 | Still et al. |
| 6,056,926 A | | 5/2000 | Sugarman et al. |
| 6,060,596 A | | 5/2000 | Lerner et al. |
| 6,090,912 A | | 7/2000 | Lebl et al. |
| 6,096,500 A | * | 8/2000 | Oprandy et al. ............... 435/6.18 |
| 6,096,875 A | | 8/2000 | Khan et al. |
| 6,132,970 A | | 10/2000 | Stemmer |
| 6,140,489 A | | 10/2000 | Brenner |
| 6,140,493 A | | 10/2000 | Dower et al. |
| 6,143,497 A | | 11/2000 | Dower et al. |
| 6,143,503 A | | 11/2000 | Baskerville et al. |
| 6,150,516 A | | 11/2000 | Brenner et al. |
| 6,165,717 A | | 12/2000 | Dower et al. |
| 6,165,778 A | | 12/2000 | Kedar et al. |
| 6,172,214 B1 | | 1/2001 | Brenner |
| 6,194,550 B1 | | 2/2001 | Gold et al. |
| 6,197,555 B1 | | 3/2001 | Khan et al. |
| 6,207,446 B1 | | 3/2001 | Szostak et al. |
| 6,210,900 B1 | | 4/2001 | Yamashita et al. |
| 6,232,066 B1 | | 5/2001 | Felder et al. |
| 6,235,475 B1 | | 5/2001 | Brenner et al. |
| 6,235,889 B1 | | 5/2001 | Ulanovsky |
| 6,248,568 B1 | | 6/2001 | Khan et al. |
| 6,274,385 B1 | | 8/2001 | Hochlowski et al. |
| 6,287,765 B1 | | 9/2001 | Cubicciotti et al. |
| 6,297,053 B1 | | 10/2001 | Stemmer |
| 6,306,587 B1 | | 10/2001 | Royer et al. |
| 6,352,828 B1 | | 3/2002 | Brenner |
| 6,416,949 B1 | | 7/2002 | Dower et al. |
| 6,429,300 B1 | | 8/2002 | Kurz et al. |
| 6,479,264 B1 | | 11/2002 | Louwrier |
| 6,503,759 B1 | | 1/2003 | Still et al. |
| 6,514,736 B1 | | 2/2003 | Erlich et al. |
| 6,537,776 B1 | | 3/2003 | Short |
| 6,593,088 B1 | | 7/2003 | Saito et al. |
| 6,613,508 B1 | | 9/2003 | Ness et al. |
| 6,620,584 B1 | | 9/2003 | Chee et al. |
| 6,620,587 B1 | | 9/2003 | Taussig et al. |
| 6,780,981 B1 | | 8/2004 | Southern et al. |
| 6,936,477 B2 | | 8/2005 | Still et al. |
| 7,070,928 B2 | | 7/2006 | Liu et al. |
| 7,223,545 B2 | | 5/2007 | Liu et al. |
| 7,413,854 B2 | * | 8/2008 | Pedersen et al. .................. 435/6 |
| 7,442,160 B2 | | 10/2008 | Liu et al. |
| 7,479,472 B1 | | 1/2009 | Harbury et al. |
| 7,491,494 B2 | | 2/2009 | Liu et al. |
| 7,557,068 B2 | | 7/2009 | Liu et al. |
| 7,704,925 B2 | | 4/2010 | Gouliaev et al. |
| 7,727,713 B2 | * | 6/2010 | Pedersen et al. .................. 435/6 |
| 7,771,935 B2 | | 8/2010 | Liu et al. |
| 7,915,201 B2 | | 3/2011 | Franch et al. |
| 7,998,904 B2 | | 8/2011 | Liu et al. |
| 8,206,901 B2 | | 6/2012 | Freskgard et al. |
| 2002/0048760 A1 | | 4/2002 | Drmanac et al. |
| 2002/0055125 A1 | | 5/2002 | Charych et al. |
| 2002/0072887 A1 | | 6/2002 | Szalma et al. |
| 2002/0081714 A1 | | 6/2002 | Jain et al. |
| 2002/0115068 A1 | | 8/2002 | Tomlinson et al. |
| 2002/0127598 A1 | | 9/2002 | Zhou et al. |
| 2002/0142335 A1 | | 10/2002 | Strittmatter |
| 2003/0004122 A1 | | 1/2003 | Beigelman et al. |
| 2003/0050453 A1 | | 3/2003 | Sorge |
| 2003/0113738 A1 | * | 6/2003 | Liu et al. ............................ 435/6 |
| 2003/0182068 A1 | | 9/2003 | Battersby et al. |
| 2003/0186233 A1 | | 10/2003 | Chesnut et al. |
| 2004/0049008 A1 | | 3/2004 | Pedersen et al. |
| 2004/0110213 A1 | * | 6/2004 | Namsaraev ........................ 435/6 |
| 2004/0161741 A1 | | 8/2004 | Rabani et al. |
| 2004/0185484 A1 | | 9/2004 | Costa et al. |
| 2004/0191812 A1 | | 9/2004 | Davydova et al. |
| 2004/0197845 A1 | | 10/2004 | Hassibi et al. |
| 2004/0209282 A1 | | 10/2004 | Ault-Riche et al. |
| 2005/0025766 A1 | | 2/2005 | Liu et al. |
| 2005/0042669 A1 | | 2/2005 | Liu et al. |
| 2005/0130173 A1 | | 6/2005 | Leamon et al. |
| 2005/0142583 A1 | | 6/2005 | Liu |
| 2005/0158765 A1 | | 7/2005 | Morgan et al. |
| 2005/0170376 A1 | | 8/2005 | Liu |
| 2006/0099592 A1 | | 5/2006 | Freskgard et al. |
| 2006/0121470 A1 | | 6/2006 | Pedersen |
| 2006/0234231 A1 | | 10/2006 | Freskgard et al. |
| 2006/0246450 A1 | | 11/2006 | Franch et al. |
| 2006/0269920 A1 | | 11/2006 | Freskgard et al. |
| 2006/0292603 A1 | | 12/2006 | Gouliaev et al. |
| 2007/0026397 A1 | | 2/2007 | Freskgard et al. |
| 2007/0042401 A1 | | 2/2007 | Morgan et al. |
| 2007/0224607 A1 | | 9/2007 | Morgan et al. |
| 2008/0193983 A1 | | 8/2008 | Gouliaev et al. |
| 2008/0305957 A1 | | 12/2008 | Thisted et al. |
| 2009/0035824 A1 | | 2/2009 | Liu et al. |
| 2009/0143232 A1 | | 6/2009 | Pedersen et al. |
| 2009/0149347 A1 | | 6/2009 | Liu et al. |
| 2009/0239211 A1 | | 9/2009 | Freskgard et al. |

(56) References Cited

U.S. PATENT DOCUMENTS

| | | |
|---|---|---|
| 2009/0264300 A1 | 10/2009 | Franch et al. |
| 2010/0016177 A1 | 1/2010 | Pedersen et al. |
| 2011/0230419 A1 | 9/2011 | Lundorf et al. |
| 2012/0028812 A1 | 2/2012 | Freskgard et al. |

FOREIGN PATENT DOCUMENTS

| | | |
|---|---|---|
| DE | 196 42 751 | 4/1998 |
| EP | 0324616 | 7/1989 |
| EP | 0542770 | 5/1993 |
| EP | 0604552 | 7/1994 |
| EP | 0643778 | 3/1995 |
| EP | 0695305 | 2/1996 |
| EP | 0766826 | 4/1997 |
| EP | 0773227 | 5/1997 |
| EP | 0776330 | 6/1997 |
| EP | 0778280 | 6/1997 |
| EP | 0879219 | 11/1998 |
| EP | 0962527 | 12/1999 |
| EP | 1324045 | 7/2003 |
| EP | 1402024 | 3/2004 |
| EP | 1483585 | 12/2004 |
| EP | 1514938 | 3/2005 |
| EP | 1533385 | 5/2005 |
| EP | 1828381 | 9/2007 |
| EP | 1832567 | 9/2007 |
| EP | 2 305 808 | 4/2011 |
| JP | 2003-505331 | 11/1993 |
| JP | 05292967 | 11/1993 |
| JP | 7-505530 | 1/1996 |
| JP | 08000268 | 1/1996 |
| WO | WO/9005785 | 5/1990 |
| WO | WO/9105058 | 4/1991 |
| WO | WO 91/19818 | 12/1991 |
| WO | WO 92/00091 | 1/1992 |
| WO | WO 92/02536 | 2/1992 |
| WO | WO 92/22875 | 12/1992 |
| WO | WO/9303172 | 2/1993 |
| WO | WO 93/06121 | 4/1993 |
| WO | WO 93/20242 | 10/1993 |
| WO | WO 94/08051 | 4/1994 |
| WO | WO 94/13623 | 6/1994 |
| WO | WO 94/24143 | 10/1994 |
| WO | WO 95/04160 | 2/1995 |
| WO | WO 95/06293 | 3/1995 |
| WO | WO 9512608 | 5/1995 |
| WO | WO 96/03418 | 2/1996 |
| WO | WO/9609316 | 3/1996 |
| WO | WO 96/11878 | 4/1996 |
| WO | WO/9612014 | 4/1996 |
| WO | WO 96/24061 | 8/1996 |
| WO | WO 96/24847 | 8/1996 |
| WO | WO/9635699 | 11/1996 |
| WO | WO 96/40201 | 12/1996 |
| WO | WO 96/41011 | 12/1996 |
| WO | WO97/04131 | 2/1997 |
| WO | WO 97/11958 | 4/1997 |
| WO | WO 97/19039 | 5/1997 |
| WO | WO 97/27317 | 7/1997 |
| WO | WO 97/35198 | 9/1997 |
| WO | WO 98/01562 | 1/1998 |
| WO | WO/9831700 | 7/1998 |
| WO | WO 98/47613 | 10/1998 |
| WO | WO 98/58256 | 12/1998 |
| WO | WO/9856904 | 12/1998 |
| WO | WO 99/42605 | 8/1999 |
| WO | WO 99/51546 | 10/1999 |
| WO | WO/9951773 | 10/1999 |
| WO | WO 99/64378 | 12/1999 |
| WO | WO 00/20639 | 4/2000 |
| WO | WO 00/23456 | 4/2000 |
| WO | WO 00/23458 | 4/2000 |
| WO | WO/0021909 | 4/2000 |
| WO | WO/0023458 | 4/2000 |
| WO | WO 00/24882 | 5/2000 |
| WO | WO/0032823 | 6/2000 |
| WO | WO/0040695 | 7/2000 |
| WO | WO/0047775 | 8/2000 |
| WO | WO/0061775 | 10/2000 |
| WO | WO/0100876 | 1/2001 |
| WO | 01/07690 | 2/2001 |
| WO | WO 01/07657 | 2/2001 |
| WO | WO 01/53539 | 7/2001 |
| WO | WO 01/56955 | 8/2001 |
| WO | WO 01/90414 | 11/2001 |
| WO | WO 02/03067 | 1/2002 |
| WO | WO 02/10186 | 2/2002 |
| WO | WO 02/34948 | 5/2002 |
| WO | WO 02/40664 | 5/2002 |
| WO | WO 02/074978 | 9/2002 |
| WO | WO/02074929 | 9/2002 |
| WO | WO02074929 A2 * | 9/2002 |
| WO | WO 02/083951 | 10/2002 |
| WO | WO 02/099078 | 12/2002 |
| WO | WO 02/103008 | 12/2002 |
| WO | WO/02102820 | 12/2002 |
| WO | WO/02103008 | 12/2002 |
| WO | WO 03/025567 | 3/2003 |
| WO | WO 03/062417 | 7/2003 |
| WO | WO 03/076943 | 9/2003 |
| WO | WO/03078050 | 9/2003 |
| WO | WO/03078445 | 9/2003 |
| WO | WO/03078446 | 9/2003 |
| WO | WO/03078625 | 9/2003 |
| WO | WO/03078626 | 9/2003 |
| WO | WO/03078627 | 9/2003 |
| WO | WO/03082901 | 10/2003 |
| WO | WO 03/106679 | 12/2003 |
| WO | WO/2004001042 | 12/2003 |
| WO | WO 2004/007529 | 1/2004 |
| WO | WO/2004009814 | 1/2004 |
| WO | WO/2004013070 | 2/2004 |
| WO | WO/2004016767 | 2/2004 |
| WO | WO/2004024929 | 3/2004 |
| WO | WO 2004/039962 | 5/2004 |
| WO | WO 2004/042019 | 5/2004 |
| WO | WO/2004039825 | 5/2004 |
| WO | WO 2004/056994 | 7/2004 |
| WO | WO/2004074429 | 9/2004 |
| WO | WO/2004074501 | 9/2004 |
| WO | WO/2004083427 | 9/2004 |
| WO | WO/2004099441 | 11/2004 |
| WO | WO/2004110964 | 12/2004 |
| WO | WO 2005/008240 | 1/2005 |
| WO | WO/2005003778 | 1/2005 |
| WO | WO/2005026387 | 3/2005 |
| WO | WO/2005058479 | 6/2005 |
| WO | WO/2005078122 | 8/2005 |
| WO | WO 2005/090566 | 9/2005 |
| WO | WO 2005/116213 | 12/2005 |
| WO | WO 2006/048025 | 5/2006 |
| WO | WO 2006/053571 | 5/2006 |
| WO | WO 2006/069063 | 6/2006 |
| WO | WO 2006/079061 | 7/2006 |
| WO | WO 2006/128138 | 11/2006 |
| WO | WO 2006/130669 | 12/2006 |
| WO | WO 2006/133312 | 12/2006 |
| WO | WO 2006/135654 | 12/2006 |
| WO | WO 2006/135786 | 12/2006 |
| WO | WO 2006/138560 | 12/2006 |
| WO | WO 2006/138666 | 12/2006 |
| WO | WO 2007/008276 | 1/2007 |
| WO | WO 2007/011722 | 1/2007 |
| WO | WO 2007/016488 | 2/2007 |
| WO | WO 2007/053358 | 5/2007 |
| WO | WO 2007/062664 | 6/2007 |
| WO | WO 2007/124758 | 11/2007 |
| WO | WO 2008/014238 | 1/2008 |
| WO | WO 2008/036273 | 3/2008 |
| WO | WO 2008/054600 | 5/2008 |
| WO | WO 2009/018003 | 2/2009 |

(56) References Cited

FOREIGN PATENT DOCUMENTS

| WO | WO 2009/077173 | 6/2009 |
|---|---|---|
| WO | WO 2009/152824 | 12/2009 |
| WO | WO 2011/127933 | 10/2011 |

OTHER PUBLICATIONS

Nemoto, N. et al. "In vitro virus: bonding of mRNA bearing puromycin at the 3'-terminal end to the C-terminal end of its encoded protein on the ribosome in vitro". FEBS Lett. Sep. 8, 1997;414(2):405-8.

Roberts, RW et al. "RNA-peptide fusions for the in vitro selection of peptides and proteins". Proc Natl Acad Sci U S A. Nov. 11, 1997;94(23):12297-302.

Kurz, M et al. "An efficient synthetic strategy for the preparation of nucleic acid-encoded peptide and protein libraries for in vitro evolution protocols" Fourth International Electronic Conference on Synthetic Organic Chemistry (ECSOC-4), www.mdpi.org/ecsoc-4.htm, Sep. 1-30, 2000.

Kurz, M et al. Psoralen photo-crosslinked mRNA-puromycin conjugates: a novel template for the rapid and facile preparation of mRNA-protein fusions. Nucleic Acids Res. Sep. 15, 2000;28(18):E83.

Keiler et al. "Role of a peptide tagging system in degradation of proteins synthesized from damaged messenger RNA". Science. Feb. 16, 1996;271(5251):990-3.

Benner, SA. "Expanding the genetic lexicon: incorporating non-standard amino acids into proteins by ribosome-based synthesis". Trends Biotechnol. May 1994;12(5):158-63.

Mendel, D. "Site-directed mutagenesis with an expanded genetic code". Annu. Rev. Biophys. Biomol. Struc. 1995. 24:463-93.

Liu DR et al. "Engineering a tRNA and aminoacyl-tRNA synthetase for the site-specific incorporation of unnatural amino acids into proteins in vivo". Proc Natl Acad Sci U S A. Sep. 16, 1997;94(19):10092-7.

Liu Dr et al. "Progress toward the evolution of an organism with an expanded genetic code". Proc Natl Acad Sci USA. Apr. 27, 1999;96(9):4780-5.

Liu, R et al. "Optimized synthesis of RNA-protein fusions for in vitro protein selection". Methods Enzymol. 2000;318:268-93.

Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.

Ellman J.A., et al. "Biosynthetic method for introducing Unnatural Amino acids site specifically into proteins". Methods Enzymol. 202, 301-336 (1992).

José Sales et al. "Biosynthetic Polydeoxynucleotides as Direct Templates for Polypeptide Synthesis". J. of Biological Chemistry, vol. 243, No. 6, 1968, p. 1012-1015.

Walder JA, Walder RY, Heller MJ, Freier SM, Letsinger RL, Klotz IM. "Complementary carrier peptide synthesis: general strategy and implications for prebiotic origin of peptide synthesis". Proc Natl Acad Sci U S A. Jan. 1979;76(1):51-5.

Bruick et al. "Template-directed ligation of peptides to oligonucleotides" Chemistry and Biology, vol. 3, No. 1, Jan. 1996, p. 49-56.

Tamura K, Schimmel P. "Oligonucleotide-directed peptide synthesis in a ribosome- and ribozyme-free system". Proc Natl Acad Sci U S A. Feb. 13, 2001;98(4):1393-7.

Lewis RJ, Hanawalt PC. "Ligation of oligonucleotides by pyrimidine dimers—a missing 'link' in the origin of life?", Nature, 22;298(5872):393-6.

Liu J, Taylor JS. "Template-directed photoligation of oligodeoxyribonucleotides via 4-thiothymidine". Nucleic Acids Res. Jul. 1, 1998;26(13):3300-4.

Fujimoto et al. "Template-directed photoreversible ligation of deoxyoligonucleotides via 5-Vinyldeoxyuridine" J. Am. Soc. 2000, 122, 5646-5647.

Kenzo Fujimoto, Shigeo Matsuda, Naoki Ogawa, Masayuki Hayashi & Isao Saito "Template-directed reversible photocircularization of DNA via 5-vinyldeoxycytidine". Tetrahedron Letters 2000, 41:33:6451-6454.

Kenzo Fujimoto, Naoki Ogawa, Masayuki Hayashi, Shigeo Matsuda & Isao Saito, "Template directed photochemical synthesis of branched oligodeoxynucleotides via 5-carboxyvinyldeoxyuridine". Tetrahedron Letters 2000, 41:49:9437-40.

Gryaznov et al. "Chemical Ligation of oligonucleotides in the presence and absence of a template". J. Amer. Chem. Soc. 1993, 115, 3808-9.

Gryaznov SM, Letsinger RL. "Template controlled coupling and recombination of oligonucleotide blocks containing thiophosphoryl groups". Nucleic Acids Res. Mar. 25, 1993;21(6):1403-8.

Gryaznov SM, Schultz R, Chaturvedi SK, Letsinger RL. "Enhancement of selectivity in recognition of nucleic acids via chemical autoligation". Nucleic Acids Res. Jun. 25, 1994;22(12):2366-9.

Herrlein MK, Letsinger RL. "Selective chemical autoligation on a double-stranded D NA template". Nucleic Acids Res. Nov. 25, 1994;22(23):5076-8.

Letsinger, RL; Wu, T; Elghanian, R "Chemical and photochemical ligation of oligonucleotide blocks". Nucleosides and nucleotides, 16(5&6), 643-652 (1997).

Visscher J, Schwartz AW "Template-directed synthesis of acyclic oligonucleotide analogues". J Mol Evol. Dec. 1988-Feb. 1989;28(1-2):3-6.

Visscher J, Bakker CG, van der Woerd R, Schwartz AW "Template-directed oligomerization catalyzed by a polynucleotide analog". Science. Apr. 21, 1989;244(4902):329-31.

Visscher J, van der Woerd R, Bakker CG, Schwartz AW. "Oligomerization of deoxynucleoside-bisphosphate dimers: template and linkage specificity". Orig Life Evol Biosph. 1989;19(1):3-6.

Zhan, ZJ and Lynn, DG "Chemical Amplification through template-directed synthesis". J. Am. Chem. Soc. 1997, 119, 12420-1.

Bruick RK, Koppitz M, Joyce GF, Orgel LE. "A simple procedure for constructing 5'-amino-terminated oligodeoxynucleotides in aqueous solution Nucleic Acids Res". Mar. 15, 1997;25(6):1309-10.

Albagli, D; Atta, RVA; Cheng, P; Huan, B and Wood, ML. "Chemical amplification (CHAMP) by a continuous, self-replicating oligonucleotide-based system" J. Am. Chem. Soc. 1999, 121, 6954-6955. Pub. on the web Jul. 14, 1999.

Xu, Y and Kool, E "Rapid and Selective selenium-mediated autoligation of DNA strands" J. Am. Chem. Soc. 2000, 122, 9040-1 Pub. on web Aug. 31, 2000.

Xu Y, Karalkar NB, Kool ET. "Nonenzymatic autoligation in direct three-color detection of RNA and DNA point mutations". Nat Biotechnol. Feb. 2001;19(2):148-52.

Li X, Zhan ZY, Knipe R, Lynn DG. "DNA-catalyzed polymerization". J Am Chem Soc. Feb. 6, 2002;124(5):746-7.

Czlapinski, JI and Sheppard, TL. "Nucleic acid template-directed assembly of metallosalen-DNA conjugates". J Am Chem Soc. Sep. 5, 2001;123(35):8618-9 published on the web Aug. 10, 2001.

Leitzel JC, Lynn DG "Template-directed ligation: from DNA towards different versatile templates". Chem Rec. 2001;1(1):53-62. Published online Jan. 30, 2001.

Schmidt JG, Nielsen PE, Orgel LE. "Information transfer from peptide nucleic acids to RNA by template-directed syntheses". Nucleic Acids Res. Dec. 1, 1997;25(23):4797-802.

Dower, WJ et al. "In vitro selection as a powerful tool for the applied evolution of proteins and peptides".Current Opinion in Chemical Biology, 2002, 6:390-398.

Brenner, S and Lerner, RA . "Encoded combinatorial chemistry" Proc. Natl. Acad. Sci. USA. vol. 89, p. 5381-3, Jun. 1992.

Gartner, Z; Liu, DR "The generality of DNA-templated synthesis as a basis for evolving non-natural small molecules". J Am Chem Soc. Jul. 18, 2001;123(28):6961-3.

Gartner, et al.,"Expanding the reaction scope of DNA-templated synthesis Angew". Chem. Int. Ed. 2002, 41, No. 10 pp. 1796-1800. Published May 15, 2002.

Gartner, ZJ et al. "Multistep small-molecule synthesis programmed by DNA templates". J. Am. Chem. Soc. vol. 124, No. 35, 2002, 10304-10306.

(56) References Cited

OTHER PUBLICATIONS

Calderone, CT et al. "Directing otherwise incompatible reactions in a single solution by using DNA-templated organic synthesis". Angew Chem Int Ed, 2002, 41, No. 21. 4104-4108.
Bittker, JA; Phillips, KJ and Liu, DR "Recent advances in the in vitro evolution of nucleic acids". Curr Opin Chem Biol. Jun. 2002;6(3):367-74. Review. Pub. on the web Mar. 20, 2002.
Summerer,D and Marx, A "DNA-templated synthesis: more versatile than expected". Angew Chem Int Ed Engl. Jan. 4, 2002;41(1):89-90. Review.
Gartner, ZJ et al. "Two enabling architectures for DNA-templated organic synthesis ". Angew. Chem Int. Ed. 2003, 42, No. 12, 1370-1375.
Rosenbaum, DM et al. "Efficient and sequence-specific DNA-templated polymerization of peptide nucleic acid aldehydes". J. Am. Chem. Soc. vol. 1251 No. 46, 2003, 13924-13925.
Li, X et al. "Stereoselectivity in DNA-templated organic synthesis and its origins". J. Am. Chem. Soc. vol. 125, No. 34, 2003, 10188-10189.
Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994.
Otto, S et al. S"Recent developments in dynamic combinatorial chemistry". Current opinion in Chemical Biology 2002, 6: 321-327.
Pavia, MR. "The Chemical generation of molecular diversity". http://www.netsci.org/Science/Combichem/feature01.html [Date accessed Nov. 2, 2004].
Braun, E, et al. "DNA-templated assembly and electrode attachment of a conducting silver wire". Nature, vol. 391, Feb. 19, 1998, 775-778.
Tanaka, K et al. "Synthesis of a novel nucleoside for alternative DNA base pairing through metal complexation" J. Org. Chem. 1999, 64, 5002-5003.
Beger, M et al. "Universal bases for hybridization, replication and chain termination", Nucleic acids research, Aug. 1, 2000, vol. 28, No. 15, pub., p. 2911-2914.
Weizman, H et al. "2,2'-Bipyridine ligandoside: a novel building block for modifying DNA with intra-duplex metal complexes". J. Am. Chem. Soc. 2001, 123, 3375-3376.
Frutos, AG et al. "Demonstration of a word design strategy for DNA computing on surfaces". Nucleic Acids Research, 1997, vol. 25, No. 23, 4748-4757.
Loweth, CJ et al. "DNA-based assembly of gold nanocrystals". Angew. Chem. Int. Ed. 1999, 38, No. 12. 1808-1812.
Elghanian, R et al. "Selective colorimetric detection of polynucleotides based on the distance-dependent optical properties of gold nanoparticles". Science, vol. 277, Aug. 22, 1997.
Storhoff, JJ and Mirkin, CA. "Programmed Materials Synthesis with DNA". Chem Rev. Jul. 14, 1999;99(7):1849-1862.
Mirkin CA. "Programming the assembly of two- and three-dimensional architectures with DNA and nanoscale inorganic building blocks". Inorg Chem. May 29, 2000;39(11):2258-72.
Waybright SM, Singleton CP, Wachter K, Murphy CJ, Bunz UH. "Oligonucleotide- directed assembly of materials: defined oligomers". J Am Chem Soc. Mar. 7, 2001;123(9):1828-33. Pub. on web Feb. 7, 2001.
Smith, Bruce and Krummenacker, Markus, "DNA-guided assembly pathway to an assembler" (http://www.wadsworth.org/albcon97/abstract/krummena.htm) [Date accessed Apr. 27, 2004] The 1997 Albany Conference: Biomolecular Motors and Nanomachines.
DeWitt, SH et al. "Diversomers": an approach to nonpeptide, nonoligomeric chemical diversity. Proc. Natl. Acad. Sci, USA, vol. 90, pp. 6909-6913.
Nielsen, J et al. "Synthetic methods for the implementation of encoded combinatorial chemistry". J. Am. Chem. Soc. 1993, 115, 9812-9813.
Ohlmeyer, MHJ et al. "Complex synthetic chemical libraries indexed with molecular tags". Proc. Natl. Acad, Sci, USA, vol. 90, pp. 10922-10926, Dec. 1993, Chemistry.

Zuckermann, RN et al. "Discovery of nanomolar ligands for 7-transmembrane G-protein-coupled receptors from a diverse N-(substituted) glycine peptoid library". J. Med. Chem. 1994, 37, 2678-2685.
Luo, P. et al. "Analysis of the structure and stability of a backbone-modified oligonucleotide: implications for avoiding product inhibition in catalytic template-directed synthesis". J. Am. Chem. Soc. 1998, 120, 3019-3031.
Luther, A et al. "Surface-promoted replication and exponential amplification of DNA analogues". Nature, Nov. 19, 1998, vol. 396, 245-248.
Klekota, B et al. "Selection of DNA-Binding Compounds via Multistage Molecular Evolution". Tetrahedron 55 (1999) 11687-11697.
Furlan, RLE et al. "Molecular amplification in a dynamic combinatorial library using non-covalent interactions". Chem. Commun., 2000, 1761-1762.
Ramström, O et al. "In situ generation and screening of a dynamic combinatorial carbohydrate library against concanavalin a". ChemBioChem, 2000, 1, 41-48.
Cousins, GRL et al. "Identification and Isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.
Roberts, SL et al. "Simultaneous selection, amplification and isolation of a pseudo-peptide receptor by an immobilised N-methyl ammonium ion template". Chem. Commun., 2002, 938-939.
Doyon, J.B et al. "Highly sensitive in vitro selections for DNA-linked synthetic small molecules with protein binding affinity and specificity" J. Am. Chem. Soc, Sep. 16, 2003.
Kanan, M.W et al. "Reaction discovery enabled by DNA-templated synthesis and in vitro selection" Nature, vol. 431, Sep. 30, 2004.
"Finding reactions in a haystack: Try'em all, see what works" Meeting American Chemical Society, Sep. 10, 2004, vol. 305, Science, p. 1558.
"The Nucleus", Jan. 2004, vol. LXXXII, No. 5, R. Grubina; "Summer Research Report: R. Grubina on DNA Templated Synthesis for Small Molecule Library", p. 10-14.
Nazarenko et al., "A closed tube format for amplification and detection of DNA based on energy transfer", Nucleic Acids Research, 1997, vol. 25, No. 12, p. 2516-2521.
Chan et al., "Intra-tRNA distance measurements for nucleocapsid protein-dependent tRNA unwinding during priming of HIV reverse transcription", PNAS vol. 96, p. 459-464, Jan. 1999.
Liu DR, Gartner ZJ, Kanan MW, Calderone CT, DNA-templated synthesis as a basis for the evolution of synthetic molecules. Abstracts of Papers of the American Chemical Society, 225: 612-ORGN , Part 2, Mar. 2003.
Rodriguez et al., "Template-directed extension of a guanosine 5'-phosphate covalently attached to an oligodeoxycytidylate template", J Mol Evol (1991) 33:477-482.
Inoue et al, Oligomerization of (Guanosine 5'-phosphor)-2-methylimidazolide on Poly(C), J. Mol. Biol. (1982), 162, 201-217.
Chen et al., C. B., "Template-directed synthesis on Oligodeoxycytidylate and Polydeoxycytidylate templates" J. Mol. Biol. 1985, 181, 271.
H. Rembold et al., "Single-strand regions of Poly(G) act as templates for oligo (C) synthesis" J. Mol. Evol. 1994, 38, 205.
T. Inoue et al., "A nonenzymatic RNA polymerase model", Science 1983, 219, p. 859-862.
O. L. Acevedo et al., "Non-enzymatic transcription of an oligonucleotide 14 residues long", J. Mol. Biol. 1987, 197, p. 187-193.
C. Böhler et al.,"Template switching between PNA and RNA oligonucleotides", Nature 1995, 376, 578-581.
Acevedo et al., "Template-directed oligonucleotide ligation on hydroxylapatite", Nature vol. 321, Jun. 19, 1986, p. 790-792.
Piccirilli, "RNA seeks its maker", Nature, Aug. 17 1995, vol. 376, p. 548-.
Schwartz, A. W. et al., "Template-directed synthesis of novel, nucleic acid- like structures", Science 1985, 228, 585-7.
Halpin et al.: DNA display III. Solid-phase organic synthesis on unprotected DNA. PLoS Biol. Jul. 2004;2(7):E175. Epub Jun. 22, 2004.

(56) References Cited

OTHER PUBLICATIONS

Halpin et al.: DNA display II. Genetic manipulation of combinatorial chemistry libraries for small-molecule evolution. PLoS Biol. Jul. 2004;2(7):E174. Epub Jun. 22, 2004, pp. 1022-1030.

Halpin et al.: DNA display I. Sequence-encoded routing of DNA populations. PLoS Biol. Jul. 2004;2(7):E173. Epub Jun. 22, 2004.

Doyon, J. B.; Snyder, T. M.; Liu, D. R., "Highly Sensitive in Vitro Selections for DNA-Linked Synthetic Small Molecules with Protein Binding Affinity and Specificity" J. Am. Chem. Soc. 125, 12372-12373 (2003).

X.; Gartner, Z. J.; Tse, B. N.; Liu, D. R., "Translation of DNA into Synthetic N-Acyloxazolidines", J. Am. Chem. Soc. 126, 5090-5092 (2004).

Li, X.; Liu, D. R.,"DNA-Templated Organic Synthesis: Nature's Strategy for Controlling Chemical Reactivity Applied to Synthetic Molecules", Angew. Chem. Int. Ed. 43, 4848-4870 (2004).

Gartner, Z. J.; Tse, B. N.; Grubina, R.; Doyon, J. B.; Snyder, T. M.; Liu, R., "DNA-Templated Organic Synthesis and Selection of a Library of Macrocycles", Science 305, 1601-1605 (2004).

Calderone, C. T. And Liu, D. R., "Nucleic Acid-Templated Synthesis as a Model System for Ancient Translation", Curr. Opin. Chem. Biol. 8, 645-653 (2004).

Sakurai, K.; Snyder, T. M.; Liu, D. R., "DNA-Templated Functional Group Transformations Enable Sequence-Programmed Synthesis Using Small-Molecule Reagents", J. Am. Chem. Soc. 127, 1660-1661 (2005).

David R. Liu, "Translating DNA into synthetic Molecules", PLoS Biology, Jul. 2004, vol. 2, Iss. 7, p. 905-906.

David R. Liu, "The Development of Amplifiable and Evolvable Unnatural Molecules", Harvard Univ. Cambridge Ma Dept of Chemistry and Chemical Biology, Report dated Aug. 4, 2003 No. A104614.

Website of Prof. David R. Liu, publicly available Mar. 11, 2000, http://web.archive.org/web/20000311112631/http://evolve.harvard.edu/, date accessed Jan. 3, 2005.

Website of Prof. David R. Liu, publicly available Oct. 15, 2000, http://web.archive.org/web/20001015144553/http://evolve.harvard.edu/, date accessed Jul. 3, 2005.

Website of Prof. David R. Liu, publicly available Mar. 1, 2001, http://web.archive.org/web/20010301175107/http://evolve.harvard.edu/, date accessed Jan. 3, 2005.

Website of Prof. David R. Liu, publicly available Apr. 19, 2001, http://web.archive.org/web/20010419064232/http://evolve.harvard.edu/, date accessed Jan. 3, 2005.

Website of Prof. David R. Liu, publicly available Sep. 23, 2001, http://web.archive.org/web/20010923021615/http://evolve.harvard.edu/, date Jan. 3, 2005.

Website of Prof. David R. Liu, publicly available Sep. 24, 2002, http://web.archive.org/web/20020924154032/http://evolve.harvard.edu/, date accessed Jul. 3, 2005.

Website of Prof. David R. Liu, publicly available Nov. 20, 2002, http://web.archive.org/web/20021120104204/http://evolve.harvard.edu/, date accessed Jan. 3, 2005

Website of Prof. David R. Liu, publicly available Oct. 15, 2003, http://web.archive.org/web/20031015114255/http://evolve.harvard.edu/, date accessed Nov. 3, 2005.

Fredriksson et al., "Protein detection using proximity-dependent DNA ligation assays", Nature Biotechnology, vol. 20, p. 473-477, May 2002.

Lowe et al, "Combinatorial Libraries for Studying Molecule Recognition", URL: http://www.iupac.org/symposia/proceedings/phuket97/lowe.html, downloaded in Jun. 2005.

Czarnik et al., "Encoding methods for combinatorial chemistry", Current Opinion in Chemical Biology, Jun. 1997, vol. 1, Iss. 1, p. 60-66.

Battersby et al., "Optical encoding of micro-beads for gene screening: alternatives to micro-arrays", Drug Discovery Today, Jun. 1, 2001, vol. 6, Supp 1, p. 19-26.

Shchepinov et al., "Trityl tags for encoding in combinatorial synthesis", Tetrahedron 56 (2000) 2713-2724.

Geysen et al., "Combinatorial Compound Libraries for Drug Discovery: An Ongoing Challenge", Nature Reviews,. Drug Discovery, Mar. 2003, vol. 2, p. 222-230.

Abravaya et al. "Detection of point mutation with a modified ligase chain reaction (GAP-LCR)", Nucleic Acids Research, vol. 23, No. 4, 675-682 (1995).

Acinas et al. "PCR-Induced Sequence Artifacts and Bias: Insights from Comparison of Two 16S rRNA Clone Libraries Constructed from the same Sample", Applied and Environmental Microbiology, vol. 71, No. 12, 8966-8969, (2005).

Agarwal, et al. "Total Synthesis of the gene for an alanine transfer ribonucleic acid from yeast", Abstract only, Nature, 227, 27-34 (1970).

Anonymous. "Preparing Oligonucleotides for Antisensen Experiments", Glen Research Report, vol. 10, 3 (Dec. 1997-issue).

Anonymous. "Cytofectin GSV Transfection Protocol", Glen Research Report, vol. 10, 4-6 (Dec. 1997-issue).

Anonymous. "New Fluorescent Reagents—Tamra CPG, Fluorescein-dt", Glen Research Report, vol. 10, 7 (Dec. 1997-issue).

Anonymous. "Universal Support Replaces Individual Columns", Glen Research Report, vol. 10, 8 (Dec. 1997-issue).

Anonymous. "Q-Supports Reduce Cleavage Time to 2 Minutes", Glen Research Report, vol. 10, 9 (Dec. 1997-issue).

Anonymous. "5,6-Dihydro-Pyrimidines, 2'-Phosphoramidites", Glen Research Report, vol. 10, 11 (Dec. 1997-issue).

Anonymous. "Non-enzymatic Ligation of Single-Stranded and Duplex DNA", Glen Research Report, vol. 10, 12 (Dec. 1997-issue).

Anonymous. "More Novel Monomers—4-Thio-dU, 5'-Amino-dT, 2'-F-Pyrimidines", Glen Research Report, vol. 10, 10 (Dec. 1997-issue).

Anonymous. "DCI—A Logical Alternative Aviator", Glen Research Report, vol. 10, No. 1 (1997).

Australian Patents Act 19909—Section 32 Regulation 3.6, (Request for a Determination of Dispute between Applicants) and 3.7 Applications to Commissioner for Declaration of an Eligible Person.

Baldwin, "Design, Synthesis and use of binary encoded synthetic chemical libraries", Molecular Diversity, 2, 81-88 (1996).

Baldwin, JJ et al. "Synthesis of a Small Molecule Combinatorial Library Encoded with Molecular Tags", J. Am. Chem. Soc. 117, 5588-5589 (1995).

Baran et al. "Total Synthesis of Marine natural products without using protecting groups", Nature, vol. 446, 404-408 (2007).

Barany, "Genetic disease detection and DNA amplification using cloned thermostable ligase", Proc. Natl. Acad., vol. 88, 189-193 (1991).

Barany, F. "The ligase chain reaction in a PCR world", Genome Res. vol. 1, 5-16 (1991).

Barany, F. "The Taql star reaction: strand preferences reveal hydrogen-bond donor and acceptor sites in canonical sequence recognition", Gene vol. 65 149-165 (1988).

Bayer, E. et al. "Liquid Phase Synthesis of Peptides", Nature vol. 237; 30 (Jun. 1972).

Bittker, et al. "Nucleic Acid Evolution and Minimization by Nonhomologous Random Recombination", Nature Biotechnology 20, 1024-1029 (2002).

Bonora, et al. "Large Scale, PEG-supported DNA Synthesis"; Nucleosides & Nucleotides, 10 (1-3), (1991).

Borman, "Combinatorial chemists focus on small molecules, molecular recognition, and automation", Chemical & Engineering News, Feb. 12, 1996.

Braasch, et al. "Locked nucleic acids (LNA): fine-tuning the recognition of DNA and RNA", Elsevier, Chemistry & Biology, 8, 1-7 (2001).

Brennan, et al. "Using T4 RNA Ligase with DNA Substrates", Methods in enzymology, vol. 100, pp. 38-52.

Broude, Natalie E. "Stem-loop oligonucleotides: a robust tool for molecule biology and biotechnology", Trends in Biotechnology, vol. 20, No. 6, Jun. 2002 (22-06) pp. 249-256.

Buller, F. et al. "Design and synthesis of a novel DNA-encoded chemical library using Diels-Alder cycloadditions", Bioorg Med Chem Lett 18, 5926 (2008).

(56) References Cited

OTHER PUBLICATIONS

Buller, F. et al. "Discovery of TNF inhibitors from an DNA-encoded chemical library based on Diels-Alder cycloaddition", Chem Biol 16, 1075 (2009).
Buller et al., "Drug Discovery with DNA-Encoded Chemical Libraries", Bioconjugate Chem., vol. 21 (9), pp. 1571-1580, (2010).
Bunin et al., "[26] Synthesis and Evaluation of 1, 4-Benzodiazepine Libraries," Mthods in Enzymology, vol. 267, pp. 448-465, (1996).
Bunin, et al. "The combinatorial synthesis and chemical and biological evaluation of a 1,4-benzodiazepine library", Proc. Natl. Acad. Sci. USA, vol. 91, pp. 4708-4712 (May 1994).
Buskirk, et al. "Engineering a Ligand-Dependent RNA Transcriptional Activator", Chem. Biol. 11, 1157-1163 (2004), This work is featured in a Research Highlight in Nature Methods 1, 6-7 (2004).
Canne et al. "Chemical Protein Synthesis by Solid Phase Ligation of Unprotected Peptide Segments", J. Am. Chem. Soc., 121, 8720-8727 (1999).
Chen, et al. "Enzyme Engineering for Nonaqueous Solvents: Random Mutagenesis to Enchance Activity of Subtilisin E in Polar Organic Media"; Bio/Technology 9, 1073-1077 (1991)—Abstract.
Chen, et al. "Enzymes in Nonaqueous Solvents; Applications in Carbohydrate and Peptide Preparation", Methods in Biotechnology, vol. 15, 373-374 (2001).
Chu et al. "Ligation of oligonucleotides to nucleic acids or proteins via disulfide bonds." Nucleic Acids Research. vol. 16. No. 9. pp. 3671-3691 (1998).
Clark et al. "Design, synthesis and selection of DNA-encoded small-molecule libraries", Nat Chem Biol 5, 647 (2009).
Clark, Matthew A. "Selecting chemicals: the emerging utility of DNA-encoded libraries", Molecular Discovery Research, GlaxoSmithKline, Waltham, MA, USA. Current Opinion in Chemical Biology, 14(3), 396-403, (2010). Publisher: Elsevier B.V.
Colombo, R. et al. "Synthesis of leucin-enkephalin and methionineenkephalin . . . ", Hoppe-Seyler's Z.Physiol.Chem. vol. 363 (1981).
Cotton, et al. "Reactivity of cytosine and thymine in single-base-pair mismatches with hydroxylamine and osmium tetroxide and its application to the study of mutations", Proc Natl Acad Sci (US), 85, 4397-401 (1988).
Constantino, L et al. "Privileged structures as leads in medicinal chemistry", Curr Med Chem 13, 65, (2006).
Czarnik, A. W. "Encoding strategies in combinatorial chemistry", Proc. Natl. Acad. Sci. USA, vol. 94, pp. 12738-12739 (Nov. 1997).
Degn, Hans, et al. "Enzyme Activity in Organic Solvent as a Function of Water Activity Determined by Membrane Inlet Mass Spectometry"; Biotechnology Techniques vol. 6; No. 2; pp. 161-164 (Mar./Apr. 1992).
Denapoli, et al. "PEG-supported Synthesis of Cyclic Oligodeoxyribonucleotides", Nucleosides & Nucleotides, vol. 12, No. 1 (1993).
"DNA Phosphoramidites & CPG's"; http://www.qualitysystems. com.tw/proligo/dna%20phosphoamidites%20&%20cpg's.htm Dec. 2, 2010.
"Dokl Akad Nauk SSSR", vol. 258, 1242-1245, Krynetskya NF Tumanov YV (1981).
Dolinnaya, et al. "Chemical ligation as a method for the assembly of double-stranded nucleic acids: Modifications and local structure studies", Russian Chemical Bulletin, vol. 45, No. 8 (1996).
Dolinnaya, et al. "Structural and kinetic aspects of chemical reactions in DNA duplexes. Information on DNA local structure obtained from chemical ligation data", Nucleic Acids Research, vol. 19, No. 11, 3073-3080 (1991).
Douglas, et al. "Polymer-supported solution synthesis of oligosaccharides", J. Am. Chem. Soc., vol. 113 (1991).
Drabovich, et al. "Selection of Smart Small-Molecule Ligands: The Proof of Principle", Analytical Chemistry, vol. 81, No. 1, 490-494 (2009).
Drews "Drug Discovery: A Historical Perspective", Science vol. 287, pp. 1960-1964 (2000).

Dreyer, et al. "Enzyme Catalysis in Nonaqueous Media: Past, Present and Future" in Patel (ed.), "Biocatalysis in the Pharmaceutical and Biotechnology Industries", 819-820 (2006).
Ecker, David J, et al. "Rational screening of oligonucleotide combinatorial libraries for drug discovery", Nucleic Acids Research, vol. 21, No. 8, pp. 1853-1856 (1993).
Fack, Fred, et al. "Heteroduplex mobility assay (HMA) pre-screening: An improved strategy for the rapid identification of inserts selected from phage-displayed peptide libraries", Molecular Diversity, vol. 5, No. 1; pp. 7-12 (2000).
Ficht, Simon, et al. "As Fast and Selective as Enzymatic Ligations: Upaired Nucleobases Increase the Selectivity of DNA-Controlled Native Chemical PNA Ligation"; ChemBioChem: vol. 6, Issue 11, pp. 2098-2103 (2005).
Fegan et al. "Rigid cyanine dye nucleic acid labels", Chem Commun May 7; (17) 2004-6 (2008).
Furka, A, "Combinatorial Chemistry: 20 years on . . . ", Drug Discovery today vol. 7, No. 1, p. 1-4 (2002).
Furka, et al. "Combinatorial Libraries by Portioning and Mixing", Combinatorial Chemistry & High Throughput Screening, 2, 105-122 (1999).
Gorin, et al. "Reactivity-Dependent PCR: Direct, Solution-Phase in Vitro Selection for Bond Formation", J. Am. Chem. Soc. 131, pp. 9189-9191 (2009).
Grange, et al. "Detection of point mutations in type I collagen by RNase digestion of RNA/RNA hybrids", Nucleic Acids Research 18: 4227-36 (1990).
Gruen, et al. "An In Vivo Selection System for Homing Endonuclease Activity", Nucleic Acids Research 30, e29 (2002).
Gumport, et al. "T4 RNA Ligase as a Nucleic Acids Synthesis and Modification Reagent", Elsevier North Holland, Inc., 314-345 (1981).
Guo, T. et al. "Preparation of Encoded Combinatorial Libraries for Drug Discovery", Methods in Molecular Biology, Combinatorial Library Methods and Protocols, pp. 23-39 (2002).
Hansen, M. "A Yoctoliter-scale DNA reactor for small-molecule evolution", J Am Chem Soc. 131, 1322 (2009).
Harada, et al. "Unexpected substrate specificity of T4 DNA ligase revealed by in vitro selection", Nucleic Acids Research, vol. 21, No. 10, 2287-2291 (1993).
Harada "In vitro selection of optimal DNS substrates for ligation by a water-soluble carbodiimide", J Mol Evol., 38, 6, 558-560 (1994).
Harada, et al. "In vitro selection of optimal DNA substrates for t4 RNA ligase", Proc. Natl. Acad. Sci. USA, vol. 90, pp. 1576-1579 (Feb. 1993).
Herpin, et al. "Synthesis of a 10000 member 1, 5-Benzodiazepine-2-one Library by the Directed Sorting Method", J. Comb. Chem., 2, 513-521 (2000).
Higgins, et al. "Addition of Oligonucleotides to the 5'-Terminus of DNA by T4 RNA Ligase", Nucleic Acids Research, 6(3): 1013-1024 (1979).
Higgins, et al. "DNA-joining Enzymes: A Review", Methods in Enzymology, vol. 68, pp. 50-71 (1979).
Hinton, et al. "T4 RNA Ligase Joins 2'-Deoxyribonucleoside 3', 5'-Bisphosphates to Oligodeoxyribonucleotides", Biochemistry vol. 17, No. 24, pp. 5091-5097 (1978).
Holmes, CP "Model Studies for New o-Nitrobenzyl Photolabile Linkers: Substituent Effects on the Rates of Photochemical Cleavage", J. Org. Chem. 62, 2370-2380 (1997).
Housby, Nicholas J, et al. "Fidelity of DNA ligation: a novel experimental approach based on the polymerisation of libraries of oligonucleotides", Nucleic Acids Research, vol. 26, No. 18, pp. 4259-4266 (1998).
Hsu "Detection of DNA point mutations with DNA mismatch repair enzymes" Carcinogenesis 15:1657-62 (1994).
Ito et al. Tag-reporter and Resin Capture ± Release Strategy in Oligosaccharide Synthesis. Chemistry—A European Journal 8(14):3077-3084 (2002).
James, Kenneth D. et al. "The Fidelity of Template-Directed Oligonucleotide Ligation and the Inevitability of Polymerase Function", Origins of Life and Evolution of the Biosphere 29, Kluwer Academic Publishers; pp. 375-390, (1999).

(56) References Cited

OTHER PUBLICATIONS

Janda, Kim D. "Tagged versus untagged libraries: Methods for the generation and screening of combinatorial chemical libraries", *Proc. Natl. Acad. Sci. USA*, vol. 91, pp. 10779-10785 (Nov. 1994).

Jäschke, Andres, et al. "Evolution of DNA and RNA as catalysts for chemical reactions"; Current Opinion in Chemical Biology 4; pp. 257-262 (2000).

Jäschke, et al. "Synthesis and properties of oligodeoxyribonucleotide—polyethylene glycol conjugates", *Nucleic Acids Research*, vol. 22, No. 22, pp. 4810-4817 (1994).

Jones, et al. "Enzymes in organic synthesis 22. Effects of organic solvents on horse liver alcohol dehydrogense-catalyzed reduction"; *Can. J. Chem.* 60 pp. 335-338 (1982).

Kahn, Jason "DNA-ligases": http://adnadn.umd.edu/biochem/kahn/molmachines/replication/DNA%20ligase.htm downloaded Dec. 10, 2009.

Kanagawa, Takahiro Bias and Artifacts in Multitemplate Polymerase Chain Reactions (PCR), *Journal of Bioscience and Bioengineering*, vol. 96, No. 4, pp. 317-323 (2003).

Kanan, et al. "Reaction Discovery Enabled by DNA-Templated Synthesis and In Vitro Selection", Supplementary Information, pp. 1-20.

Kerr, JM et al. "Encoded Combinatorial Peptide Libraries Containing Non-Natural Amino Acids", *J. Am. Chem. Soc.* 115, 2529-2531 (1993).

Kinoshita, et al. "Enzymatic Synthesis of Code Regions for Encoded Combinatorial Chemistry", *Nucleic Acids Symposium Series*, 34: 201-202 (1995).

Kinoshita, Y. et al. "Strand ligation in a double-stranded DNA by T4 RNA ligase", *Department of Functional Materials Science*, Saitama University, Urawa, Japan. Chemistry Letters (9), 797-798 (1996).

Klibanov, Alexander M. "Why are enzymes less active in organic solvent than water?"; *Trends in Biotechnology*; vol. 15, Issue 3, 97-101; 1 (Mar. 1997)—Abstract.

Krishna, Sajja Hari "Developments and trends in enzyme catalysis in nonconventional media", *Biotechnology Advances*; vol. 20; Issues 3-4; pp. 239-267 (Nov. 2002)—Abstract.

Krug, et al. "Reversal of T4 RNA Ligase", *Biochemistry* vol. 21, No. 8, pp. 1858-1864 (1982).

Kurz, M. et al. "cDNA—protein fusions: covalent protein—gene conjugates for the in vitro selection of peptides and proteins", *Chembiochem—A European Journal of Chemical Biology*, Wiley VCH, Weinheim, DE, vol. 2, No. 9, Sep. 3, 2001, pp. 666-672, XP002332971, ISSN: 1439-4227.

Lebl, Michal "Parallel Personal Comments on "Classical" Papers in Combinatorial Chemistry", *J. Comb. Chem.* 1, pp. 3-24 (1999).

Lehman, I.R. "DNA ligase: Structure, Mechanism, and Function; The joining of DNA chains by DNA ligase is an essential component of DNA repair, replication, and recombination", *Science* vol. 186; pp. 790-797 (1974).

"Ligase", Answers.com: http://www.answers.com/topic/ligase, [accessed Dec. 10, 2009].

Lim, Carols S. et al. "Syntehsis of DNA Dumbbells: Chemical vs. Enzymatic Ligation of Self-Complementary Oligonucleotides", Abstract only, Nucleotides and Nucleic Acids; vol. 16, Issue 1 & 2; pp. 41-51 (Jan. 1997).

Lindström, Ulf M. et al. "An orthogonal oligonucleotide protecting group strategy that enables assembly of repetitive or highly structured DNAs"; *Nucleic Acids Research* 30(19), e101; 2002 Oxford University Press (Oct. 1, 2002).

Liu, D.R. "Development of Amplifiable and Evolvable Unnatural Molecules", website of Dr. D. R. Liu, publicly available Mar. 11, 2000. http://web.archive.org/web/20000311112631/http://evolve.havard.edu.

Liu, D.R. "The Chemistry and Chemical Biology of Molecular Evolution," website of Dr. D.R. Liu, publicly available Mar. 1, 2001. http://web.archive.org/web/20010301175107/http://evolve.havard.edu.

Liu, D.R. "The Chemistry and Chemical Biology of Molecular Evolution," website of Dr. D.R. Liu, publicly available Oct. 15, 2003. http://web.archive.org/web/20031216020734/http://evolve.havard.edu.

Liu, D.R. "The Chemistry and Chemical Biology of Molecular Evolution," website of Dr. D.R. Liu, publicly available Nov. 20, 2002. http://web.archive.org/web/20021129131743/http://evolve.havard.edu.

Liu, D.R. "The Chemistry of Molecular Evolution," website of Dr. D.R. Liu, publicly available Oct. 15, 2000. http://web.archive.org/web/20001015144553/http://evolve.havard.edu.

Liu, W, et al. "Denaturing high performance liquid chromatography (DHPLC) used in the detection of germline and somatic mutations" Nucleic Acids Research. vol. 26. pp. 1396-1400 (1998).

Liu, D.R. "The Chemistry and Chemical Biology of molecular Evolution", Liu Group Research Summary from the website of Professor David R. Liu, obtained from the website in Feb. 2005.

Lobanov *Trends in Biotechnology*, vol. 20, No. 2, pp. 86-87 (Feb. 2002).

Lockhart, et al. "Expression monitoring by hybridization to high-density oligonucleotide arrays", Bio/Technology, Nature publishing co., New York, US, vol. 14, No. 13, p. 1675-1680 (Dec. 1, 1996).

Loughlin, Wendy A. "Biotransformations in organic synthesis"; Bioresource Technology 74, pp. 49-62 (2000).

Luebke, Kevin J. et al. "Nonenzymatic ligation of double-helical DNA by alternate-strand triple helix formation"; Nucleic Acids Research; vol. 20, No. 12; pp. 3005-3009 (1992).

Maclean, Derek, et al. "Encoded Combinatorial Chemistry: Synthesis and screening of a library of highly functionalized pyrrolidines", Proc. Natl. Acad. Sci. USA, vol. 94, pp. 2805-2810 (Apr. 1997).

Magliery, et al. "Expanding the Genetic Code In Vitro and In Vivo", The Genetic Code and the Origin of Life, Ed. Ribas de Pouplana, L. Landes Bioscience, In Press (2004).

Makara, Gergely M. et al. "Improving Success rates for lead generation using affinity binding technologies", Current Opinion in Biotechnology 16:666-673 (2005).

Mannocci, L. "DNA-Encoded affinity maturation libraries", Proc Natl Acad Sci USA 105, 17670 (2008).

Mannocci, Lucca "DNA-Encoded Chemical Libraries", Diss. ETH No. 18153 (2009).

Margulies, M. et al., "Genome sequencing in microfabricated high-density picolitre reactors", Nature 437, 376 (2005).

Mashal, et al. "Detection of mutations by cleavage of DNA heteroduplexes with bacteriophage resolvases", Nature Genetics 9:177-83 (1995).

Matsuda, et al. "Low Fidelity DNA Synthesis by Human DNA Polymerase—?", *Nature*, 404: 1011-1013 (Apr. 27, 2000).

Matsuura, K., et al. "Construction of glyco-clusters by self-organization of site-specifically glycosylated oligonucleotides and their cooperative amplification of lectin-recognition." *Journal of the American Chemical Society*, vol. 123, No. 2, pp. 357-358 (Jan. 17, 2001).

McCoy et al. "T4 Ribonucleic Acid Ligase Joins Single-Strand Oligo(deoxyribonucleotides)", *Biochemistry* vol. 19, No. 4, 635-642 (1980).

McGregor, et al. "Interaction-Dependent PCR: Identification of Ligand-Target Pairs from Libraries of Ligands and Libraries of Targets in a Single Solution-Phase Experiment", *J. Am. Chem. Soc.* 132, pp. 15522-15524 (2010).

Melkko, Samu. et al. "Lead discovery by DNA-encoded chemical libraries", *Drug Discovery Today*, vol. 12, No. 11/12, pp. 465-471 (Jun. 2007).

Mendel, D. "Site-directed mutagenesis with an expanded genetic code." *Annu. Rev. Biophys. Biomol. Struc.* vol. 24, pp. 435-462. (1995).

Miller, Scott J. "DNA as a template for reaction discovery", *Nature Biotechnology*, vol. 22, No. 11, pp. 1378-1379 (Nov. 2004).

Mudrakovskaya, et al. "Solid-Phase Enzymatic Synthesis of Oligoribonucleotides", *Bioorg Khim* vol. 17, No. 6, pp. 469-472 (1991).

Mutter, M. et al. "Functionalized polyethylene glycols and polypeptides in organic synthesis and catalysis", Reactive Polymers, vol. 6, pp. 99-107 (1987).

(56) References Cited

OTHER PUBLICATIONS

Myers, et al. "Detection of single base substitutions by ribonuclease cleavage at mismatches in RNA:DNA duplexes" *Science* 230: 1242-6 (1985).
Needels, CM, et al. "Generation and screening of an oligonucleotide-encoded synthetic peptide library", *Proc. Natl. Acad. Sci., USA*, vol. 90, pp. 10700-10704. (Nov. 1993).
Nestler, HP et al. "A General Method for Molecular Tagging of Encoded Combinatorial Chemistry Libraries", *J. Org. Chem.*, 59, 4723-4724 (1994).
Nielsen "Combinatorial chemistry and automation", DDT, vol. 1, No. 11, pp. 458-460 (Nov. 1996).
Nikolaiev, V et al. "Peptide-Encoding for structure determination of nonsequenceable polymers within libraries synthesized and tested on solid-phase supports", *Peptide Research*, vol. 6, No. 3, pp. 161-170 (1993).
Nishigaki, Koichi, et al. "Y-ligation: an efficient method for ligating single stranded DNAs and RNAs with T4 RNA ligase", Department of Functional Materials Science, Saitama University, Urawa, Japan. *Molecular Diversity* vol. 4(3), 187-190 (2000).
O'Donovan MC, et al. "Blind analysis of denaturing high-perfomance liquid chromatography as a tool for mutation detection", *Genomics*. 52:4449 (1998).
"Organic Chemistry", Wikipedia, [accessed Dec. 10, 2009]: http://en.wikipedia.org/wiki/organic_chemistry (10 pages).
"Orthogonal Protection Protecting Group", Wikipedia: http://en.Wikipedia.org/wiki/protecting_group#Orthogonal_protection [accessed Apr. 15, 2010].
Persichetti, et al. "Cross-Linked Enzyme Crystals (CLECs) of Thermolysin in the Synthesis of Peptides", *Journal of the American Chemical Society*, 117: 2732-2737 (1995).
Pochet, et al. "Solid-Supported Ligation Primer", *Nucleic Acids Research*, 16(4): 1619 (1988).
Polsky-Cynkin et al. "Use of DNA immobilized on platic and agarose supports to detect DNA by sandwich hybridization", Clin. Chem. 31(9): 1438-43 (Sep. 1985).
Porco, Jr. "Synthesis Undressed", *Nature* 446, 383-5 (Mar. 22, 2007).
Purmal, Andrei A., et al. "A new affinity reagent for the site-specific, covalent attachment of DNA to active-site nucleophiles: application to the EcoRI and Rsrl restriction and modification enzymes", *Nucleic Acids Research*; vol. 20, No. 14; Oxford University Press; pp. 3713-3719 (1992).
Robertson, Dan "Direct Evolution Process for Robust Enzyme Catalysis in Organic Solvents"; Report date: Sep. 1996. pp. 1-14.
Robinson "A Synthesis of Tropinone", *Journal of the Chemical Society Transactions*, vol. 111, pp. 762-768, (1917).
Romaniuk, et al. "Joining of RNA molecules with RNA ligase", *Methods in Enzymology*, vol. 100, pp. 52-59, (1983).
Saiki et al. "Genetic analysis of amplified DNA with immobilized sequence-specific oligonucleotide probes" *PNAS* 86(16): 6230-6234 (1989).
Sarmento, et al. "Cardosins A and B, Two New Enzymes Available for Peptide Synthesis", *Journal of Molecular Catalysis B: Enzymatic*, 5: 327-330 (1998).
Scheuermann, Jörg, et al. "DNA-encoded chemical libraries", *Journal of Biotechnology* 126 568-581 (2006).
Scheuermann, Jörg, et al. "DNA-encoded chemical libraries: A tool for drug discovery and for chemical biology", *ChemBioChem* 0000, 00, 1-8 (2010).
Schmitz, et al. "Solid-Phase Enzymatic Synthesis of Oligonucleotides", *Organic Letters*, 1(11): 1729-1731 (1999).
Schoenleber, R.O. et al. "Photochemical release of amines by C,N-bond cleavage", *Synlett* 501-504 (2003).
Schmidt, JG, et al., "Information transfer from peptide nucleic acids to RNA by template-directed syntheses", *Nucleic Acids Res.*, vol. 25 (23), pp. 4792-4796 (Dec. 1, 1997).
Schultz, et al. "The Combinatorial Library: A Multifunctional Resource", *Biotechnol. Prog.* 12, 729-743 (1996).
Shabarova, et al. "Chemical ligation of DNA: the first non-enzymatic assembly of a biologically active gene", Nucl. Acids Res., 19:4247-51 (1991).
Sharifian, Hoda. "Errors induced during PCR amplification", May 30, 2010.
Shuman, Stewart. "DNA ligases: Progress and Prospects"; jbc.org/content/284/26/17365. full downloaded Feb. 10, 2009.
Snyder, T. "Ordered multistep synthesis in a single solution directed by DNA templates", *Angew Chem* Int Ed Engl 44, 7379 (2005).
Sokolova, N.I., et al. "Chemical reactions within DNA duplexes; Cyanogen bromide as an effective oligodeoxyribonucleotide coupling agent"; *FEBS letters*, vol. 232, No. 1, pp. 153-155 (May 1988).
Still, W. Clark "Career-In-Review (CIR)", BJ Wright, Synthesis Literacy Group, Columbia University Chemistry, Mar. 30, 2007.
Tabor, Stanley "DNA-ligases"; *Current Protocols in Molecular Biology* 3.14.1-3.14.4 (1987).
Takemori, Shigeki, et al. "Stabilization of Enzyme Activity by an Organic Solvent", Abstract only, *Nature* 215, 417-419 (Jul. 22, 1967).
Tan et al. "Natural-product inhibitors of human DNA ligase I", *Biochemical Journal* 314: 993-1000 (1996).
Tan, Derek S. et al. "Ligand discovery using encoded combinatorial libraries", *Current Opinion in Drug Discovery & Development*, 3(4), p. 439-53 (Jul. 2000).
Tessier, et al. "Ligation of Single-Stranded Oligodeoxyribonucleotides by T4 RNA Ligase", *Analytical Biochemistry* 158, 171-178 (1986).
Tse, B. "Translation of DNA into a library of 13,000 synthetic small-molecule macrocycles suitable for in vitro selection", *J Am Chem Soc* 130, 15611 (2008).
Unknown "Science & Technology: Concentrates", *Chem. & Eng. News* 82 [40] 31 (2004).
Uhlenbeck, et al. "T4 RNA Ligase", The Enzymes, vol. XV, pp. 31-58 (1982).
Vágner, et al. "Enzyme-mediated spatial segregation on individual polymeric support beads: Application to generation and screening of encoded combinatorial libraries", *Proc. Natl. Acad. Sci. USA*, vol. 93, pp. 8194-8199, (Aug. 1996).
Vaisman, et al. "Human DNA polymerase, promiscuous mismatch extension", JBC 276: 30615-30622 (2001).
Vratskikh, et al. "Solid-phase synthesis of oligoribonucleotides using T4 RNA ligase and T4 polynucleotide kinase", *Biochimie* 77, 227-232 (1995).
Wagner, et al. "Mutation detection using immobilized mismatch binding protein (MutS)" *Nucleic Acids Research* 22, 3944-3948 (1995).
Walder, JA., et al. "Complementary carrier Peptide Synthesis: General Strategy and Implications for Prebiotic Origin of Peptide Synthesis", *Department of Chemistry, and Department of Biochemistry and Molecular Biology*, Northwestern University, Evanston, Illinois 60201, vol. 76, No. 1, p. 51-55, (1979).
Wang, S., et al. "Circular RNA oligonucleotides. Synthesis, nucleic acid binding properties, and a comparison with circular DNAs"; *Nucleic Acids Research*, 1994, vol. 22, No. 12; Oxford University Press; pp. 2326-2333 (1994).
Washington, et al. "Mismatch extension ability of yeast and human DNA polymerase n", JBC 276: 2263-2266 (2001).
Weiss, et al. "Enzymatic Breakage and Joining of Deoxyribonucleic Acid, I. Repair of Single-Strand Breaks in DNA by an Enzyme System From *Escherichia ccoli* Infected With T4 Bacteriophage*" *PNAS* 57, (4): 1021-1028 (1967).
Whitesides, et al. "Enzymes as Catalysts in Organic Synthesis", *Aldrichimica Acta.*, vol. 16, No. 2, pp. 27-34, (1983).
Winzeler, et al. "Fluorescence-based expression monitoring using microarrays", *Methods Enzymol.* 306: 3-18 (1999).
Wong, Daphne M. et al. "Branch capture reactions: displacers derived from assymmetric PCR"; 1991 Oxford University Press; *Nucleic Acids Research*; vol. 19; No. 9; pp. 2251-2259 (1991).
Xu, Y, et al. "A Novel 5'-lodonucleoside Allows Efficient Non-enzymatic Ligation of Single-Stranded and Duplex DNA", Abstract, *Glen Research Catalog, Tetrahedron Letters* 38:5595-5598 (1997).
Xu, Y, et al. "High sequence fidelity in a non-enzymatic DNA autoligation reaction", *Nucleic Acids Research*, vol. 27, No. 3; pp. 875-881 (1999).

(56) References Cited

OTHER PUBLICATIONS

Zhu, et al. A Primer-dependent Polymerase Function of Pseudomonas aeruginosa AP-dependent DNA ligase (LigD). *Journal of Biological Chemistry* 280(1): 418-427 (2005).
Website of prof. David R. Liu, publicly available Apr. 23, 2003.
Website of prof. David R. Liu, publicly available Aug. 1, 2003.
Website of prof. David R. Liu, publicly available Aug. 2, 2002.
Website of prof. David R. Liu, publicly available Feb. 8, 2003.
Website of prof. David R. Liu, publicly available Feb. 10, 2004.
Website of prof. David R. Liu, publicly available Feb. 15, 2001.
Website of prof. David R. Liu, publicly available Dec. 16, 2003.
Website of prof. David R. Liu, publicly available Jun. 4, 2002.
Website of prof. David R. Liu, publicly available Jun. 6, 2003.
Website of prof. David R. Liu, publicly available Mar. 27, 2003.
Website of prof. David R. Liu, publicly available Mar. 31, 2001.
Website of prof. David R. Liu, publicly available Nov 29, 2002.
Website of prof. David R. Liu, publicly available Nov 30, 2001.
Website of prof. David R. Liu, publicly available Oct 17, 2002.
Decision to Grant from European Application No. EP 02740409.4 dated Jul. 26, 2007.
European Office Action from European Application No. EP 02740409.4 dated Sep. 1, 2005.
Reply to European Office Action from European Application No. EP 02740409.4 dated Jun. 16, 2006.
Intent to Grant from European Application No. EP 02740409.4 printed Oct. 13, 2006.
Extended European Search Report from European Application No. 07114663.3 dated May 25, 2009.
Extended European Search Report from European Application No. 10 18 4311 dated Feb. 28, 2011.
International Preliminary Examination Report from PCT No. PCT/DK02/00419 dated Jan. 28, 2004.
International Search Report from PCT No. PCT/DK02/00419 dated Jun. 25, 2003.
Restriction Requirement from U.S. Appl. No. 10/175,539 mailed Apr. 6, 2005.
Response to Restriction Requirement from U.S. Appl. No. 10/175,539 mailed May 6, 2005.
Office Action (Non-Final Rejection) from U.S. Appl. No. 10/175,539 mailed May 13, 2005.
Response to Office Action (Non-Final Rejection) from U.S. Appl. No. 10/175,539 mailed Apr. 13, 2006.
Office Action (Non-Final Rejection) from U.S. Appl. No. 10/175,539 mailed May 14, 2007.
Response to Office Action (Non-Final Rejection) from U.S. Appl. No. 10/175,539 mailed Sep. 13, 2007.
Office Action (Final Rejection) from U.S. Appl. No. 10/175,539 mailed May 19, 2006.
Notice of Appeal from U.S. Appl. No. 10/175,539 dated Nov. 20, 2006.
Request for Continued Examination from U.S. Appl. No. 10/175,539 dated Feb. 20, 2007.
Office Action (Ex Parte Quayle Action) from U.S. Appl. No. 10/175,539 mailed Nov. 27, 2007.
Response to Ex Parte Quayle Action from U.S. Appl. No. 10/175,539, filed Feb. 27, 2008.
Notice of Allowance from U.S. Appl. No. 10/175,539 mailed May 30, 2008.
Issue Notification U.S. Appl. No. 10/175,539 issued Jun. 1, 2010.
Office Action (Non-Final Rejection) from U.S. Appl. No. 12/330,709 mailed Oct. 27, 2009.
Response to Office Action (Non-Final Rejection) from U.S. Appl. No. 12/330,709, filed Apr. 21, 2010.
Notice of Allowance from U.S. Appl. No. 12/330,709 mailed Mar. 3, 2011.
Request for Continued Examination and supplemental IDS from U.S. Appl. No. 12/330,709, filed Jun. 2, 2011.
Office Action from European Application No. 03709676.5 dated Feb. 23, 2005.
Reply to 1st Office Action from European Application No. 03709676.5 dated Jun. 30, 2005.
2nd Office Action from European Application No. 03709676.5 dated Aug. 26, 2005.
Reply to 2nd Office Action from European Application No. 03709676.5 dated Sep. 13, 2005.
3rd Office Action from European Application No. 03709676.5 date Sep. 30, 2005.
Reply to 3rd Office Action from European Application No. 03709676.5 dated May 19, 2006.
2nd Restriction Requirement from U.S. Appl. No. 10/523,006 mailed Dec. 9, 2009.
Response to 2nd Restriction Requirement from U.S. Appl. No. 10/523,006, filed May 5, 2010.
3rd Restriction Requirement from U.S. Appl. No. 10/523,006 mailed Aug. 3, 2010.
Response to 3rd Restriction Requirement from U.S. Appl. No. 10/523,006, filed Feb. 1, 2011.
Office Action (Non-Final) from U.S. Appl. No. 10/523,006 mailed Mar. 16, 2011.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 6, 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
European Search Report for European Application No. 09 17 7376 dated Feb. 24, 2011.
International Search Report for PCT Application No. PCT/DK03/00921 Jun. 22, 2004.
Restriction Requirement for U.S. Appl. No. 10/539,288 mailed Aug. 2, 2010.
Response to Restriction Requirement for U.S. Appl. No. 10/539,288, filed Jan. 31, 2011.
Office Action (Non-Final) for U.S. Appl. No. 10/539,288 mailed Apr. 25, 2011.
1st Office Action for European Application No. 03729909.6 mailed May 17, 2006.
Reply to 1st Office Action for European Application No. 03729909.6 mailed Mar. 9, 2007.
2nd Office Action for European Application No. 03729909.6 mailed Sep. 22, 2009.
Reply to 2nd Office Action for European Application No. 03729909.6 mailed May 6, 2010.
International Search Report for PCT Application No. PCT/DK03/00417 mailed Feb. 10, 2004.
Restriction Requirement for U.S. Appl. No. 10/518,056 mailed Jan. 4, 2008.
Response to Restriction Requirement for U.S. Appl. No. 10/518,056, filed Jun. 2, 2008.
Office Action (Non-Final) for U.S. Appl. No. 10/518,056 mailed Oct. 8, 2008.
Reply to Office Action for U.S. Appl. No. 10/518,056, filed Feb. 17, 2009.
Office Action (Final Rejection) for U.S. Appl. No. 10/518,056 mailed May 27, 2009.
Notice of Appeal for U.S. Appl. No. 10/518,056 mailed Oct. 27, 2009.
Amendment After Appeal for U.S. Appl. No. 10/518,056, filed Nov. 17, 2009.
Advisory Action for U.S. Appl. No. 10/518,056 mailed Jan. 7, 2010.
Intent to Grant from European Application No. 03709676.5 dated Oct. 10, 2006.
Amendment after Intention to Grant from European Application No. 03709676.5 dated Nov. 16, 2007.

(56) References Cited

OTHER PUBLICATIONS

Decision to Grant from European Application No. 03709676.5 dated Oct. 23, 2008.
European Search Report from European Application No. 08 16 9346 mailed Apr. 13, 2010.
1st Office Action from European Application No. 08169346.7 mailed Apr. 19, 2011.
Response filed in European Application No. 08169346.7 mailed Mar. 23, 2011.
International Search Report for PCT Application No. PCT/DK03/00172 mailed Nov. 3, 2003.
Office Action (Non-Final) for U.S. Appl. No. 10/507,121 mailed Feb. 8, 2007.
Response to Office Action for U.S. Appl. No. 10/507,121 mailed Jun. 7, 2007.
Office Action (Final Rejection) for U.S. Appl. No. 10/507,121 mailed Sep. 7, 2007.
Request for Continued Examination and supplemental amendment for U.S. Appl. No. 10/507,121, filed Feb. 13, 2008.
Notice of Allowance for U.S. Appl. No. 10/507,121 mailed Mar. 20, 2008.
Issue Notification for U.S. Appl. No. 10/507,121 mailed Jul. 30, 2008.
Office Action (Non-Final) from U.S. Appl. No. 12/179,323 mailed Jan. 27, 2010.
Response to Office Action from U.S. Appl. No. 12/179,323, filed Jun. 24, 2010.
Office Action (Final Rejection) for U.S. Appl. No. 12/179,323 mailed Sep. 15, 2010.
Notice of Appeal from U.S. Appl. No. 12/179,323, filed Mar. 15, 2011.
1st Office Action from European Application No. 03766117.0 dated Mar. 24, 2009.
Reply to 1st Office Action from European Application No. 03766117.0 dated Jan. 8, 2010.
2nd Office Action from European Application No. 03766117.0 dated Feb. 16, 2010.
Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Application No. 03766117.0 dated Jun. 9, 2011.
International Search Report from PCT Application No. PCT/DK03/00516 mailed Feb. 18, 2004.
1st Restriction Requirement from U.S. Appl. No. 10/523,006 mailed Apr. 4, 2008.
Response to 1st Restriction Requirement from U.S. Appl. No. 10/523,006, filed Oct. 1, 2008.
Request for Continued Examination and IDS for U.S. Appl. No. 10/518,056, filed Mar. 22, 2010.
1st Office Action for European Application No. 04713515.7 mailed Oct. 19, 2006.
Reply to 1st Office Action for European Application No. 04713515.7 mailed Aug. 20, 2007.
2nd Office Action for European Application No. 04713515.7 mailed Mar. 31, 2008.
Reply to 2nd Office Action for European Application No. 04713515.7 mailed Dec. 5, 2008.
3rd Office Action for European Application No. 04713515.7 mailed Sep. 6, 2010.
Reply to 3rd Office Action for European Application No. 04713515.7 mailed Jun. 21, 2011.
International Search Report for PCT Application No. PCT/DK2004/000116 mailed Aug. 23, 2004.
Office Action (Non-Final) for U.S. Appl. No. 10/545,795 mailed Mar. 31, 2008.
Response filed for U.S. Appl. No. 10/545,795, filed Sep. 30, 2008.
Office Action for U.S. Appl. No. 10/545,795 mailed Jan. 27, 2009.
Notice of Appeal filed for U.S. Appl. No. 10/545,795, filed Jul. 27, 2009.
Amendment after Appeal for U.S. Appl. No. 10/545,795, filed Sep. 28, 2009.
Office Action (Advisory Action) for U.S. Appl. No. 10/545,795 mailed Sep. 29, 2009.
Request for Continued Examination and IDS for U.S. Appl. No. 10/545,795, filed Oct. 27, 2009.
Office Action (Non-Final) for U.S. Appl. No. 10/545,795 mailed Nov. 16, 2009.
Office Action (Non-Final) for U.S. Appl. No. 10/545,795 mailed Mar. 30, 2010.
Office Action (Interview Summary) for U.S. Appl. No. 10/545,795 mailed Jul. 30, 2010.
Response filed for U.S. Appl. No. 10/545,795, filed Aug. 30, 2010.
Office Action (Final rejection) for U.S. Appl. No. 10/545,795 mailed Feb. 1, 2011.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.
International Search Report for International Application No. PCT/DK2004/000117 mailed Aug. 19, 2004.
Restriction Requirement for U.S. Appl. No. 10/546,538 mailed Jul. 31, 2008.
Response to Restriction Requirement for U.S. Appl. No. 10/546,538, filed Dec. 24, 2008.
Office Action (Non-Final) for U.S. Appl. No. 10/546,538 mailed Jun. 10, 2009.
Response to Office Action for U.S. Appl. No. 10/546,538, filed Dec. 9, 2009.
Office Action (Final Rejection) for U.S. Appl. No. 10/546,538 mailed Jun. 8, 2010.
Response to Office Action (Notice of Appeal) for U.S. Appl. No. 10/546,538, filed Dec. 8, 2010.
Office Action (Communication re: Appeal) for U.S. Appl. No. 10/546,538 mailed Jul. 20, 2011.
1st Office Action for European Application No. 04722237.7 dated Mar. 2, 2006.
Reply to 1st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Intent to Grant for European Application No. 04722237.7 dated Jan. 18, 2008.
Amendment to Grant for European Application No. 04722237.7 dated Nov. 11, 2008.
Decision to Grant for European Application No. 04722237.7 dated Feb. 5, 2009.
European Search Report for European Application No. 09154197 mailed Sep. 15, 2010.
International Search Report for International Application No. PCT/DK2004/000195 mailed Dec. 27, 2004.
Restriction Requirement for U.S. Appl. No. 10/549,619 mailed Apr. 21, 2008.
Response to Restriction Requirement for U.S. Appl. No. 10/549,619, filed Sep. 22, 2008.
Office Action (Non-Final) for U.S. Appl. No. 10/549,619 mailed Apr. 28, 2009.
Response to Office Action for U.S. Appl. No. 10/549,619, filed Oct. 26, 2009.
Office Action (Interview Summary) for U.S. Appl. No. 10/549,619 mailed Mar. 3, 2010.
Amendment filed for U.S. Appl. No. 10/549,619, filed Oct. 21, 2010.

(56) References Cited

OTHER PUBLICATIONS

Notice of Allowance for U.S. Appl. No. 10/549,619 mailed Jul. 7, 2010.
Amendment After Allowance for U.S. Appl. No. 10/549,619, filed Oct. 6, 2010.
Issue Notification for U.S. Appl. No. 10/549,619 mailed Mar. 9, 2011.
Australian Application No. 2003273792.
Examination Report for Australian Application No. 2003273792 dated May 6, 2011.
Reply to 1st Office Action for European Application No. 03757752.5 dated Jan. 12, 2006.
Amendment after Esp for European Application No. 03757752.5 dated Feb. 14, 2006.
1st Office Action for European Application No. 03757752.5 dated Mar. 16, 2006.
2nd Office Action for European Application No. 03757752.5 dated Feb. 15, 2007.
Reply to 2nd Office Action for European Application No. 03757752.5 dated Aug. 15, 2007.
Summons for European Application No. 03757752.5 dated Aug. 11, 2008.
Letter for Oral Proceeding for European Application No. 03757752.5 dated Dec. 15, 2008.
Telephone Summary for European Application No. 03757752.5 dated Dec. 23, 2008.
Letter for Oral Proceeding for European Application No. 03757752.5 dated Jan. 2, 2009.
Oral Proceedings for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intent to Grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Office Action for Japanese Application No. 2005-501801 dated Apr. 6, 2010.
Office Action for Japanese Application No. 2005-501801 dated May 31, 2011.
International Search Report for International Application No. PCT/DK03/00739 mailed Aug. 30, 2004.
Restriction Requirement for U.S. Appl. No. 10/525,817 mailed May 9, 2007.
Response to Restriction Requirement for U.S. Appl. No. 10/525,817, filed Sep. 10, 2007.
Restriction Requirement for U.S. Appl. No. 10/525,817 mailed Nov. 28, 2007.
Response to Restriction Requirement for U.S. Appl. No. 10/525,817, filed Feb. 28, 2008.
Restriction Requirement for U.S. Appl. No. 10/525,817 mailed Jul. 7, 2009.
Response to Restriction Requirement for U.S. Appl. No. 10/525,817, filed Oct. 5, 2009.
Office Action (Non-Final) for U.S. Appl. No. 10/525,817 mailed Apr. 1, 2010.
Supplemental Office Action for U.S. Appl. No. 10/525,817 mailed Apr. 5, 2010.
Response filed for U.S. Appl. No. 10/525,817, filed Jul. 27, 2010.
Office Action (Non-Final) for U.S. Appl. No. 10/525,817 mailed Jan. 5, 2011.
Office Action (Interview Summary) for U.S. Appl. No. 10/525,817 mailed Jul. 1, 2011.
Response filed for U.S. Appl. No. 10/525,817, filed Jul. 5, 2011.
Restriction Requirement for U.S. Appl. No. 11/402,957 mailed Jun. 25, 2008.
Response to Restriction Requirement for U.S. Appl. No. 11/402,957, filed Aug. 25, 2008.
Office Action (Non-Final) for U.S. Appl. No. 11/402,957 mailed Nov. 28, 2008.
Response filed for U.S. Appl. No. 11/402,957, filed May 15, 2009.
Office Action (Non-Final) for U.S. Appl. No. 11/402,957 mailed Jul. 6, 2009.
Response filed for U.S. Appl. No. 11/402,957, filed Dec. 7, 2009.
Office Action (Final Rejection) for U.S. Appl. No. 11/402,957 mailed Feb. 16, 2010.
Response filed for U.S. Appl. No. 11/402,957, filed Jul. 28, 2010.
Notice of Appeal filed for U.S. Appl. No. 11/402,957, filed Aug. 16, 2010.
Notice of Allowance for U.S. Appl. No. 11/402,957 mailed Sep. 2, 2010.
Request for Continued Examination filed for U.S. Appl. No. 11/402,957, filed Dec. 2, 2010.
Second Notice of Allowance for U.S. Appl. No. 11/402,957 mailed Apr. 29, 2011.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to 2nd Office Action for European Application No. 04762850.8 dated Sep. 2, 2008.
Intent to Grant for European Application No. 04762850.8 dated Dec. 10, 2008.
Decision to Grant for European Application No. 04762850.8 dated Oct. 8, 2009.
Amendment after Grant for European Application No. 04762850.8 dated Jul. 17, 2009.
International Search Report for PCT/DK2004/000630 mailed Feb. 14, 2005.
Restriction Requirement for U.S. Appl. No. 10/572,644 dated Feb. 4, 2009.
Response to Restriction Requirement for U.S. Appl. No. 10/572,644 dated Jul. 29, 2009.
Restriction Requirement for U.S. Appl. No. 10/572,644 dated Jul. 21, 2010.
Response to Restriction Requirement for U.S. Appl. No. 10/572,644, filed Jan. 19, 2011.
Office Action (Non-Final) for U.S. Appl. No. 10/572,644 dated Oct. 29, 2009.
Response to Office Action for U.S. Appl. No. 10/572,644, filed Apr. 28, 2010.
Office Action (Non-Final) for U.S. Appl. No. 10/572,644 dated Mar. 31, 2011.
1st Office Action for European Application No. 05715120.1 dated Apr. 12, 2007.
Reply to 1st Office Action for European Application No. 05715120.1 dated Feb. 1, 2008.
2nd Office Action for European Application No. 05715120.1 dated Mar. 25, 2008.
Reply to 2nd Office Action for European Application No. 05715120.1 dated Jan. 9, 2009.
Intent to Grant for European Application No. 05715120.1 dated May 7, 2009.
Amendment after Grant for European Application No. 05715120.1 dated Sep. 3, 2009.
Decision to Grant for European Application No. 05715120.1 dated Oct. 1, 2009.
International Search Report for International Application No. PCT/DK2005/000199 mailed Jan. 23, 2006.
Office Action for U.S. Appl. No. 10/593,868 mailed Mar. 30, 2009.
Response to Office Action for U.S. Appl. No. 10/593,868, filed Jul. 28, 2009.
Notice of Allowance for U.S. Appl. No. 10/593,868 mailed Nov. 16, 2009.
Amendment after Allowance for US U.S. Appl. No. 10/593,868 filed 16 Feb. 2010.

(56) References Cited

OTHER PUBLICATIONS

Issue Notification for US U.S. Appl. No. 10/593,868 mailed 7 Apr. 2010.
1st Office Action for European Application No. 05700655.3 dated Jun. 19, 2007.
Reply to 1st Office Action for European Application No. 05700655.3 dated Apr. 11, 2008.
2nd Office Action for European Application No. 05700655.3 dated Sep. 12, 2008.
Reply to 2nd Office Action for European Application No. 05700655.3 dated Jul. 9, 2009.
3rd Office Action for European Application No. 05700655.3 dated Aug. 12, 2009.
Reply to 3rd Office Action for European Application No. 05700655.3 dated Feb. 9, 2010.
Intent to Grant for European Application No. 05700655.3 dated Mar. 31, 2010.
Amendment after Grant for European Application No. 05700655.3 dated Nov. 11, 2010.
Decision to Grant for European Application No. 05700655.3 dated Dec. 2, 2010.
International Search Report for International Application No. PCT/DK2005/000106 mailed Sep. 12, 2005.
Restriction Requirement for U.S. Appl. No. 10/589,551 mailed Apr. 7, 2011.
1st Office Action for European Application No. 06818144.5 dated Dec. 11, 2008.
Reply to 1st Office Action for European Application No. 06818144.5 dated Oct. 30, 2009.
Intent to Grant for European Application No. 06818144.5 dated Feb. 23, 2010.
Amendment after Grant for European Application No. 06818144.5 dated Oct. 7, 2010.
Decision to Grant European Application No. 06818144.5 dated Nov. 5, 2010.
European Search Report for European Application No. 10 19 2716 mailed May 24, 2011.
Invitation to Identify Subject Matter for European Application No. 10 192 717.6 dated Jun. 1, 2011.
International Search Report for International Application No. PCT/DK2006/000685 mailed Jun. 14, 2007.
Communication pursuant to Rule 161(1) and 162 for European Application No. 09765460.2 dated Mar. 14, 2011.
Response to Rule 161(1) and 162 for European Application No. 09765460.2 dated Apr. 18, 2011.
International Search Report for International Application No. PCT/DK2009/050129 mailed Aug. 21, 2009.
Annex I: Vipergen Technology Paper—The YoctoReactor drug discovery technology platform. 2 pages.
Annex II: Vipergen Technology Paper—The YoctoReactor drug discovery technology platform. 2 pages. Aug. 2008.
Millward, S.W. et al. "A General Route for Post-Translational Cyclization of mRNA Display Libraries", *Journal of the American Chemical Society*: vol. 127, 14142-14143, (2005).
Millward, S.W. et al. "Design of Cyclic Peptides That Bind Protein Surfaces with Antibody-Like Affinity", *ACS Chemical Biology*: vol. 2, No. 9, 625-634, (2007).
Giebel, L.B. et al. "Screening of Cyclic Peptide Phage Libraries Identifies Ligands That Bind Streptavidin with High Affinities", *Biochemistry*: vol. 34, No. 47; 15430-15435, (1995).
Ladner, R.C. "Constrained peptides as binding entities", *Elsevier Science Ltd., Trends in Biotechnology*: vol. 13, 426-430, (1995).
Koivunen, E. et al. "Phage Libraries Displaying Cyclic Peptides with Different Ring Sizes: Ligand Specificities of the RGD-Directed Integrins", *Bio/Technology*: vol. 13, 265-270, (1995).
Office Action in European patent application No. 10184311.8, dated Mar. 19, 2012, with Annex.
Office Action in Israel patent application No. 207672, dated Jan. 15, 2012, with English translation.
Response to OA in Israel patent application No. 207672, dated Jun. 14, 2012.
Office Action in Israel patent application No. 207673, dated Jan. 15, 2012, with English translation.
Response to OA in Israel patent application No. 207673, dated Jun. 14, 2012.
Response to OA in Canadian patent application No. 2,544,153, dated Mar. 26, 2012.
Appeal filed for Indian patent application No. 178/MUMNP/2007, dated Nov. 15, 2011.
Office Action in Chinese patent application No. 200380104764.5, dated Feb. 29, 2012, with translation of text of notification.
Response to OA in Chinese patent application No. 200380104764.5, dated Jul. 16, 2012.
Office Action in Japanese patent application No. P2010-226107, dated Jul. 10, 2012, with English translation.
Office Action in European patent application No. 10192716.8, dated Jul. 30, 2012.
Response to OA in European patent application No. 07114663.3, dated Jul. 4, 2012.
Office Action in European patent application No. 07114663.3, dated Jul. 23, 2012.
Official Communication in European patent application No. 09154197.9, dated Aug. 7, 2012.
Response to Office Action in EP 07114663.3 dated May 17, 2013.
3rd Office Action in European patent application No. 07114663.3 dated Jun. 3, 2013.
Office Action from European Application No. 03766117.0 dated Mar. 26, 2013.
Response dated Apr. 12, 2013 to European Search Report issued in European Patent Application No. 10184069.2.
1st Office Action for European Patent Application No. 10184069.2 dated Jul. 3, 2013.
Office Action in European patent application No. 10192716.8 dated Jul. 3, 2013.
Response to office action re 09765460.2 submitted Feb. 22, 2013.
Office Action in Israeli patent application No. 207672 dated May 28, 2013.
Office Action in Israeli patent application No. 207673 dated May 28, 2013.
Office Action of Jan. 29, 2013 re Japanese patent application No. 2010-226107.
Restriction Requirement dated Apr. 6, 2005 re U.S. Appl. No. 10/175,539.
Response to Restriction Requirement submitted May 6, 2005 re U.S. Appl. No. 10/175,539.
Non-final Rejection dated Oct. 13, 2005 re U.S. Appl. No. 101175,539.
Response submitted Apr. 13, 2006 to Non-final Rejection re U.S. Appl. No. 10/175,539.
Final Rejection dated May 19, 2006 re U.S. Appl. No. 10/175,539.
Notice of Appeal filed Nov. 20, 2006 re U.S. Appl. No. 10/175,539.
RCE submitted Feb. 20, 2007 re U.S. Appl. No. 10/175,539.
Non-final Rejection dated May 14, 2007 re U.S. Appl. No. 10/175,539.
Response submitted Sep. 13, 2007 to Non-final Rejection to U.S. Appl. No. 10/175,539.
Quayle Action dated Nov. 27, 2007 re U.S. Appl. No. 10/175,539.
Response submitted Feb. 27, 2008 to Quayle Action re U.S. Appl. No. 10/175,539.
Notice of Allowance dated May 30, 2008 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Issue Notification dated May 12, 2010 re U.S. Appl. No. 10/75,539.
Non-final Rejection dated Oct. 27, 2009 re U.S. Appl. No. 12/330,709.
Response submitted Apr. 21, 2010 to Non-final Rejection re U.S. Appl. No. 12/330,709.
Supplemental response submitted Jun. 2, 2010 re U.S. Appl. No. 12/330,709.

(56) References Cited

OTHER PUBLICATIONS

Ex parte Quyale Action dated Jul. 27, 2010 re U.S. Appl. No. 12/330,709.
Response of Jan. 10, 2011 to Ex parte Quayle Action re U.S. Appl. No. 12/330,709.
Notice of Allowance dated Mar. 3, 2011 re U.S. Appl. No. 12/330,709.
RCE filed Jun. 2, 2011 re U.S. Appl. No. 12/330,709.
Office Action dated Sep. 17, 2012 re U.S. Appl. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
Non-final Rejection dated Feb. 8, 2007 re U.S. Appl. No. 10/507,121.
Response submitted Jun. 7, 2007 to Non-final Rejection re U.S. Appl. No. 10/507,121.
Final Rejection dated Sep. 7, 2007 re U.S. Appl. No. 10/507,121.
RCE filed Feb. 13, 2008 re U.S. Appl. No. 10/507,121.
Notice of Allowance dated Mar. 20, 2008 re U.S. Appl. No. 10/507,121.
Issue Notification for U.S. Appl. No. 10/507,121 dated Jul. 30, 2008.
Non-final Rejection dated Jan. 27, 2010 re U.S. Appl. No. 12/179,323.
Response submitted Jun. 24, 2010 to Non-final Rejection re U.S. Appl. No. 12/179,323.
Final Rejection dated Sep. 15, 2010 re U.S. Appl. No. 12/179,323.
Notice of Appeal submitted Mar. 15, 2011 re U.S. Appl. No. 12/179,323.
RCE submitted Oct. 17, 2011 re U.S. Appl. No. 12/179,323.
Non-final Rejection dated Jul. 3, 2013 re U.S. Appl. No. 12/179,323.
First Restriction Requirement dated Apr. 4, 2008 re U.S. Appl. No. 10/523,006.
Notice of Allowance re U.S. Appl. No. 10/549,619.
Amendments after Notice of Allowance Oct., 2010 re U.S. Appl. No. 10/549,619.
Second amendment after Notice of Allowance Oct. 21, 2012 re U.S. Appl. No. 10/549,619.
Issue Notification of Mar. 9, 2011 re U.S. Appl. No. 10/549,619.
First Restriction Requirement dated May 9, 2007 re U.S. Appl. No. 10/525,817.
Response submitted to First Restriction Requirement Sep. 10, 2007 re U.S. Appl. No. 10/525,817.
Second Restriction Requirement dated Nov. 28, 2007 re U.S. Appl. No. 10/525,817.
Response to second Restriction Requirement submitted Feb. 28, 2008 re U.S. Appl. No. 10/525,817.
Third Restriction Requirement dated Jul. 7, 2009 re U.S. Appl. No. 10/525,817.
Response to third Restriction Requirement submitted Oct. 5, 2009 re U.S. Appl. No. 10/525,817.
Non-final rejection dated Mar. 29, 2010 re U.S. Appl. No. 10/525,817.
Supplemental Non-final Action dated Apr. 1, 2010 re U.S. Appl. No. 10/525,817.
Response submitted Jul. 27, 2010 to Non-final Action Apr. 5, 2010 re U.S. Appl. No. 10/525,817.
Non-final rejection Jan. 5, 2011 re U.S. Appl. No. 10/525,817.
Interview Summary dated Jul. 1, 2011 re U.S. Appl. No. 10/525,817 and Interview Summary dated Jun. 22, 2011 Re U.S. Appl. No. 10/525,817.
Response submitted Jul. 5, 2011 to Non-final Action re U.S. Appl. No. 10/525,817.
Examiner's amendment communication dated Dec. 5, 2011 re U.S. Appl. No. 10/525,817.
Notice of Allowance dated Oct. 14, 2011 re U.S. Appl. No. 10/525,817.
Notice of Allowance dated Jan. 19, 2012 re U.S. Appl. No. 10/525,817.
Rce dated Mar. 21, 2012 re U.S. Appl. No. 10/525,817.
Notice of Allowance dated Mar. 30, 2012 re U.S. Appl. No. 10/525,817.
Issue Notification dated Jun. 6, 2012 re U.S. Appl. No. 10/525,817.
Restriction Requirement of Jun. 25, 2008 re U.S. Appl. No. 11/402,957.
Response submitted Aug. 25, 2008 to Restriction Requirement re U.S. Appl. No. 11/402,957.
Non-final Rejection dated Nov. 28, 2008 re U.S. Appl. No. 11/402,957.
Response submitted May 15, 2009 to Non-final Rejection re U.S. Appl. No. 11/402,957.
Non-final Rejection dated Jul. 6, 2009 re U.S. Appl. No. 11/402,957.
Response submitted Dec. 7, 2009 to Non-final Rejection re U.S. Appl. No. 11/402,957.
Final Rejection dated Feb. 16, 2010 re U.S. Appl. No. 11/402,957.
Response submitted Jul. 28, 2010 to Final Rejection re U.S. Appl. No. 11/402,957.
Notice of Appeal dated Aug. 16, 2010 re U.S. Appl. No. 11/402,957.
Notice of Allowance dated Sep. 2, 2010 re U.S. Appl. No. 11/402,957.
Rce dated Dec. 2, 2010 re U.S. Appl. No. 11/402,957.
Second Notice of Allowance dated Apr. 29, 2011 re U.S. Appl. No. 11/402,957.
Rce dated Jul. 28, 2011 re U.S. Appl. No. 11/402,957.
Third Notice of Allowance dated Oct. 31, 2011 re U.S. Appl. No. 11/402,957.
Rce dated Dec. 13, 2011 re U.S. Appl. No. 11/402,957.
Preliminary amendment Nov. 21, 2012 re U.S. Appl. No. 11/402,957.
Non-final Rejection dated May 22, 2013 re U.S. Appl. No. 11/402,957.
Restriction Requirement dated May 14, 2013 re U.S. Appl. No. 13/455,223.
Response submitted Aug. 14, 2013 to Restriction Requirement re U.S. Appl. No. 13/455,223.
First Restriction Requirement dated Feb. 4, 2009 re U.S. Appl. No. 10/572,644.
Reponse submitted Jul. 29, 2009 to First Restriction Requirement re U.S. Appl. No. 10/572,644.
Non-final rejection dated Oct. 29, 2009 re U.S. Appl. No. 10/572,644.
Response submitted Apr. 28, 2010 to Non-final rejection re U.S. Appl. No. 10/572,644.
Second Restriction Requirement dated Jul. 21, 2010 re U.S. Appl. No. 10/572,644.
Response submitted Jan. 19, 2011 to Second Restriction Requirement re U.S. Appl. No. 10/572,644.
Non-final rejection dated Mar. 31, 2011 re U.S. Appl. No. 10/572,644.
Response submitted Sep. 30, 2011 to Non final rejection re U.S. Appl. No. 10/572,644.
Notice of Appeal filed Jul. 6, 2012 re U.S. Appl. No. 10/572,644.
Adang et al., "The Contribution of Combinatorial Chemistry to Lead Generation: An Interim Analysis", Current Medicinal Chemistry 2001, 8, 985-998.
Affleck, "Solutions for library encoding to create collections of discrete compounds", Current Opinion in Chemical Biology, 2001, 5:257-263.
Bain et al., "Biosynthetic site-specific incorporation of a non-natural amino acid into a polypeptide", J. Am. Chem. Soc., 1989, 111, 8013-8014.
Barnes, et al., "Recent developments in the encoding and deconvolution of combinatorial libraries", Chemical Biology 2000, 4:346-350.
Chen et al., "Total Synthesis of Naturally Occurring Prostaglandin F2a on a Non-Cross-Linked Polystyrene Support", Tetrahedron Letters 39 (1998) pp. 3943-3946.
Coe et al., "Solution-phase combinatorial chemistry", Molecular Diversity, 4: 31-38, 1999.
Dolle, "Comprehensive Survey of Combinatorial Library Synthesis: 2000", Journal of Combinatorial Chemistry, 2001, vol. 3, No. 6, pp. 477-517.
Dolle, "Comprehensive Survey of Combinatorial Library Synthesis: 2001", Journal of Combinatorial Chemistry, 2002, vol. 4, No. 5, pp. 369-418.

(56) References Cited

OTHER PUBLICATIONS

Dolle, "Comprehensive Survey of Combinatorial Library Synthesis: 2002", Journal of Combinatorial Chemistry, 2003, vol. 5, No. 6, pp. 693-753.
Furka et al., "General method for rapid synthesis of multicomponent peptide mixtures", Int. J. Peptide Protein Res., 37, 1991, 487-493.
Gallop et al., "Applications of Combinatorial Technologies to Drug Discovery. 1. Background and Peptide Combinatorial Libraries", Journal of Medicinal Chemistry, 1994, vol. 37, No. 9, pp. 1233-1251.
Guillen Schlippe et al.,"In Vitro Selection of Highly Modified Cyclic Peptides That Act as Tight Binding Inhibitors", J. Am. Chem. Soc. 2012, 134, 10469-10477.
Han et al., "Liquid-phase combinatorial synthesis", Proc. Natl. Acad. Sci. USA, vol. 92, pp. 6419-6423, Jul. 1995.
Kleiner et al., "Small-molecule discovery from DNA-encoded chemical libraries", Chem. Soc. Rev., 2011, 40, pp. 5707-5717.
Li et al., "Kinetics of RNA Degradation by specific base catalysis of transesterification involving the 2'-hydroxyl group", J. Am. Chem. Soc., 1999, 121, pp. 5364-5372.
Lipinski et al., "Experimental and computational approaches to estimate solubility and permeability in drug discovery and development settings", Adv. Drug Deliv. Rev., vol. 46 (1-3), 2001, pp. 3-26.
Lipinski, "Lead- and drug-like compounds: the rule-of-five revolution", Drug Discovery Today: Technologies, vol. 1, No. 4, 2004, pp. 337-341.
Ma et al., "In Vitro Selection of Unnatural Cyclic Peptide Libraries via mRNA Display", Book Ribosome Display and Related Technologies: Methods and Protocols, ch. 21, pp. 367-390.
MacLean et al., "Glossary of terms used in combinatorial chemistry", Pure Appl. Chem., vol. 71, No. 12, pp. 2349-2365, 1999.
Meier et al, "Combinatorial Methods, Automated Synthesis and High-Throughput Screening in Polymer Research: The Evolution Continues", Macromol. Rapid Commun. 2004, 25, 21-33.
Needels et al., "Generation and screening of an oligonucleotide-encoded synthetic peptide library", Proc. Natl. Acad. Sci. USA, vol. 90, pp. 10700-10704, Nov. 1993.
Ni et al., "Versatile Approach to Encoding Combinatorial Organic Syntheses Using Chemically Robust Secondary Amine Tags", J. Med. Chem. 1996, 39, 1601-1608.
Nicolaou et al., "Radiofrequency Encoded Combinatorial Chemistry", Angew. Chem. Int. Ed. Engl., 1995, 34, No. 20, pp. 2289-2291.
Noren et al., "A general method for site-specific incorporation of unnatural aminoacids into protein", Science, American Association for the advancement of science, Washington, DC, vol. 244, 1989, pp. 182-188.
Starck et al., "The puromycin route to assess stereo- and regiochemical constraints on peptide bond formation in eukaryotic ribosomes", J. Am. Chem. Soc., 2003, 125, 8090-8091.
Studer et al., "Fluorous Synthesis: A Fluorous-Phase Strategy for Improving Separation Efficiency in Organic Synthesis", 1997, Science 275, pp. 823-826.
Terrett et al., "Combinatorial synthesis the design of compound libraries and their application to drug discovery", Tetrahedron, 1995, vol. 51, No. 30., pp. 8135-8173.
Website: "Combinatorial chemistry", http://www.ukessays.co.uk/essays/chemistry/combinatorial-chemistry.php, Oct. 29, 2012, pp. 1-11.
Website—Thompson C. M., Medicinal Chemistry, lecture 14, Pharmaceutical Sciences 621 & Chemistry 569 http://www2.umt.edu/medchem/teaching/medchem/mclect14.htm.
Website—http://en.wikipedia.org/wiki/DNA-encoded chemical library, Oct. 2, 2012, pp. 1-12.
Wermuth et al., "Glossary of terms used in medical chemistry", Pure & Appl. Chem, 1998, vol. 70, No. 5, pp. 1129-1143.
Ymane et al., "Discrimination between D- and L-Tyrosyl transfer ribonucleic acids in peptide chain elongation", American Chemical Society, vol. 20, No. 25, Dec. 8, 1981, pp. 7059-7064.
Balkenhohl et al., "Combinatorial synthesis of small organic molecules", Angew Chem Int Ed Engl. 1996, 35, pp. 2288-2337.
Chorghade, "Drug discovery and development", 2006, ISBN-13: 978-0-471-39848-6, Published by John Wiley & Sons, Inc., Hoboken, New Jersey.
1st Office Action of Mar. 2, 2013 re EP 10183942.1.
2nd Office Action of Feb. 6, 2013 re EP 10184311.8.
3rd Office Action of Jan. 29, 2013 re EP 08169346.7.
5th Office Action of May 31, 2012 re EP 03766117.0.
Communication pursuant to Rules 161(1) and 162 of Dec. 12, 2012 re EP No. 11720372.9.
European search report jun. 6, 2012 re EP 10184069.2.
Office Action of May 7, 2012 re EP 09765460.2.
Response to 1st Office Action submitted Jan. 18, 2013 10184311.8.
Response to 2nd Office Action re EP 08169346.7 submitted Dec. 21, 2012.
Response to 4th Office Action of Jun. 9, 2011 re EP 03766117.0 submitted Mar. 14, 2012.
Response to ESR of Jan. 25, 2012 re EP 10192717.6 submitted Dec. 5, 2012.
Response to ESR of 2012 re EP 10183942.1 submitted Jan. 9, 2013.
Response to oppositions against EP 1558744 submitted Dec. 5, 2012.
Notice of Acceptance dated Jun. 22, 2011 re Australian app. No. 2003273792.
Notification of Allowance re Chinese patent app. No. 200380104764.5.
Office action of Aug. 20, 2012 re Canadian application No. 2544153.
RCE of Sep. 6, 2012 re U.S. Appl. No. 10/572,644.
Non-final rejection dated Mar. 30, 2009 re U.S. Appl. No. 10/593,868.
Response submitted Jul. 28, 2009 to Non-final rejection re U.S. Appl. No. 10/593,868.
Notice of Allowance dated Nov. 16, 2009 re U.S. Appl. No. 10/593,868.
Amendments after Notice of Allowance Feb. 16, 2010 re U.S. Appl. No. 10/593,868.
Issue Notification dated Apr. 7, 2010 re U.S. Appl. No. 10/593,868.
Restriction Requirement dated Apr. 7, 2011 re U.S. Appl. No. 10/589,551.
Response submitted Oct. 7, 2011 to Restriction Requirement re U.S. Appl. No. 10/589,551.
Non-final rejection dated Oct. 26, 2011 re U.S. Appl. No. 10/589,551.
1st Restriction requirement of Oct. 5, 2011 re U.S. Appl. No. 12/095,778.
Response dated Mar. 5, 2012 to 1st Restriction Requirement re U.S. Appl. No. 12/095,778.
2nd Restriction requirement dated Jun. 27, 2012 re U.S. Appl. No. 12/095,778.
Response submitted Dec. 27, 2012 to 2nd Restriction Requirement re U.S. Appl. No. 12/095,778.
Office Action dated Apr. 15, 2013 re U.S. Appl. No. 12/095,778.
Response dated May 15, 2013 to Restriction Requirement re U.S. Appl. No. 12/095,778.
Decision of dismissal of amendment dated Aug. 14, 2013 re Japanese patent application No. 2010-226107.
Strachan, "Human Molecular Genetics", 2nd edition, textbook published by Wiley-Liss, 1999.
Office Action dated Jul. 16, 2013 re European patent application No. 10192717.6.
Response to Non-final rejection submitted Sep. 16, 2013 re U.S. Appl. No. 10/539,288.
Response to Non-final rejection submitted Sep. 23, 2013 re U.S. Appl. No. 11/402,957.
Written submissions re EP 1558744 submitted Sep. 11, 2013 by proprietor.
Written submissions re EP 1558744 submitted Sep. 11, 2013 by opponent.
Bain et al., "Regioselective Ligation of Oligoribonucleotides using DNA Splints", Nucl. Acids Res., vol. 20, No. 16, 4372, 1992.
Boger & Goldberg "Chapter 10: Multi-step Solution Phase Combinatorial Synthesis " in Combinatorial Chemistry, ed. Hicham Fenniri, Oxford University Press (Oxford, England), 2000, pp. 303-326.

(56) References Cited

OTHER PUBLICATIONS

Cheng et al., "Novel Solution Phase Strategy for the Synthesis of Chemical Libraries Containing Small Organic Molecules", J. Am. Chem. Soc., vol. 118, 2567-2573, 1996.
Clark et al., "Design, Synthesis and Selection of DNA-encoded Small-molecule Libraries", Nat. Chem. Biol., vol. 5, No. 9, 647-772, 2009.
Curran, "Strategy-Level Separations in Organic Synthesis: From Planning to Practice", Angew. Chem. Int. Ed., vol. 37, 1174-1196, 1998.
Declaration by DR. Dennis Benjamin (including curriculum vitae).
Frutos et al., "Enzymatic Ligation Reactions of DNA 'Words' on Surfaces for DNA Computing", J. Am. Chem. Soc., vol. 120, No. 40, 10277-10282, 1998.
Gait, "Chapter 1: An Introduction to Modern Methods of DNA Synthesis": Van Boom & Wreesman, "Chapter 7: Chemical Synthesis of Small Oligoribonucleotides in solution"; and Beckett & Uhlenbeck, "Chapter 8: Enzymatic Synthesis of Oligoribonucleotides", in Oligonucleotide Synthesis: A Practical Approach, ed. M.J. Gait, IRL Press (Oxford, England and Washington, DC), 1984, pp. 1-22, 153-183, and 185-197.
Gartner et al., "Expanding the Reaction Scope of DNA-Templated Synthesis", Angew. Chem. Int. Ed., vol. 41, No. 10, 1796-1800, 2002.
Gartner et al., "Multistep Small-Molecule Synthesis Programmed by DNA Templates", J. Am. Chem. Soc., vol. 124, No. 35, 10304-10306 (including Supporting Information, pp. 1-4).
Glen Research Report, "Advances in RNA Synthesis and Structural Analysis", vol. 11, No. 2, 1998 (December).
Harrison et al., "Synthesis and Hybridization Analysis of a Smal Library of Peptide-oligonucleotide Conjugates", Nucl. Acids Res., vol. 26, No. 13, 3136-3145, 1998.
Hausch et al., "Libraries of Multifunctional RNA Conjugates for the Selection of New RNA Catalysts", Bioconjugate Chem., vol. 8, 885-890, 1997.
Hill et al., "Diels-Alder Bioconjugation of Diene-Modified Oligonucleotides", J. Org. Chem., vol. 66, 5352-5358, 2001.
Itakura et al., "Expression in *Escherichia coli* of a Chemically Synthesized Gene for the Hormone Somatostatin", Science, vol. 198, 1056-1063, 1977.
Janda, "Tagged Versus Untagged Libraries: Methods for the Generation and Screening of Combinatorial Chemical Libraries, " PNAS USA, vol. 91, 10779-10785, 1994.
Kelemen et al., "Hypersensitive Substrate for Ribonucleases", Nucl. Acids. Res., vol. 27, No. 18, 3696-3701, 1999.
Kempe et al., "Chemical and Enzymatic Biotin-labeling of Oligodeoxyribonucleotides", Nucl. Acids Res., vol. 13, No. 1, 45-57, 1985.
Kinoshita et al., "Enzymatic Synthesis of Sequencing Primers Based on a Library of Tetramers", Chem. Express, No. 7, 149-152, 1992.
Kinoshita et al., "Strand Ligation in a double-stranded DNA by T4 RNA Ligase", Chem. Lett., No. 9, 797-798, 1996.
Kitamura et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura et al., "Development of Systemic in vitro Evolution and Its Application to Generation of Peptide-Aptamer-Based Inhibitors of Cathepsin E", J. Mol. Biol., vol. 387, 1186-1198, 2009.
Moore et al. "Site-specific Modification of Pre-mRAN: the 2'-hydroxyl Groups at the Splice Sites", Science, vol. 256, 992-997, 1992.
Nielsen et al., "Synthetic Methods for the Implementation of Encoded Combinatorial Chemistry", J. Am. Chem. Soc., vol. 115, 9812-9813, 1993 with supplementary Materials (pp. 1-7).
Nielsen et al., "Toward Chemical Implementation of Encoded Combinatorial Libraries", Methods: A Companion to Meth: Enzymol., vol. 6, 361-371, 1994.
Roux et al., "Optimization and troubleshooting in PCR", PCR Methods Appl., vol. 4, S185-S194, 1995.
Schmitz et al., "Solid-phase Enzymatic Synthesis of Oligonucleotides", Org. Lett., vol. 1, 1729-1731, 1999.
Seelig et al., "Site-Specific Modification of Enzymatically Synthesized RNA: Transcription Initiation and Diels-Alder Reaction, " Tetrahed. Lett., vol. 38, 7729-7732, 1997.
Response to first Restriction Requirement submitted Oct. 1, 2008 re U.S. Appl. No. 10/523,006.
Second Restriction Requirement dated Dec. 9, 2009 re U.S. Appl. No. 10/523,006.
Response to second Restriction Requirement submitted May 5, 2010 re U.S. Appl. No. 10/523,006.
Third Restriction Requirement dated Aug. 3, 2010 re U.S. Appl. No. 10/523,006.
Response to third Restriction Requirement submitted Feb. 1, 2011 re U.S. Appl. No. 10/523,006.
Non-final Rejection dated Mar. 16, 2011 re U.S. Appl. No. 10/523,006.
Response submitted Sep. 16, 2011 to non-final rejection re U.S. Appl. No. 10/523,006.
Final rejection dated Feb. 6, 2012 re U.S. Appl. No. 10/523,006.
Restriction Requirement dated Jan. 4, 2008 re U.S. Appl. No. 10/518,056.
Response to Restriction Requirement submitted Jun. 2, 2008 re U.S. Appl. No. 10/518,056.
Non-final Rejection dated Oct. 8, 2008 re U.S. Appl. No. 10/518,056.
Response after Non-final Rejection submitted Feb. 17, 2009 re U.S. Appl. No. 10/518,056.
Final Rejection dated May 27, 2009 re U.S. Appl. No. 10/518,056.
Notice of Appeal filed Oct. 27, 2009 re U.S. Appl. No. 10/518,056.
Amendments after Notice of Appeal submitted Nov. 17, 2009 re U.S. Appl. No. 10/518,056.
Advisory Action dated Jan. 7, 2010 re U.S. Appl. No. 10/518,056.
RCE filed Mar. 22, 2010 re U.S. Appl. No. 10/518,056.
Non-final Rejection mailed Mar. 31, 2008 re U.S. Appl. No. 10/545,795.
Response after Non-final Rejection submitted Sep. 30, 2008 Re U.S. Appl. No. 10/545,795.
Final Rejection dated Jan. 27, 2009 re U.S. Appl. No. 10/545,795.
Notice of Appeal filed Jul. 27, 2009 re U.S. Appl. No. 10/545,795.
Amendments after Notice of Appeal submitted Sep. 28, 2009 re U.S. Appl. No. 10/545,795.
Advisory Action dated Sep. 29, 2009 re U.S. Appl. No. 10/545,795.
Second amendment after Notice of Appeal submitted Oct. 28, 2009 re U.S. Appl. No. 10/545,795.
Advisory Action dated Oct. 21, 2009 re U.S. Appl. No. 10/545,795.
Rce submitted Oct. 27, 2009 re U.S. Appl. No. 10/545,795.
Non-final Rejection dated Nov. 16, 2009 re U.S. Appl. No. 10/545,795.
Non-final Rejection dated Mar. 30, 2010 re U.S. Appl. No. 10/545,795.
Interview summary dated Jul. 15, 2010 re U.S. Appl. No. 10/545,795.
Interview summary dated Jul. 30, 2010 re U.S. Appl. No. 10/545,795.
Response after Non-final Rejection dated Aug. 30, 2010 re U.S. Appl. No. 10/545,795.
Final Rejection dated Feb. 1, 2011 re U.S. Appl. No. 10/545,795.
Notice of Appeal filed Jul. 27, 2011 re U.S. Appl. No. 10/545,795.
Restriction Requirement dated Jul. 31, 2008 re U.S. Appl. No. 10/546,538.
Response to Restriction Requirement filed Dec. 24, 2008 re U.S. Appl. No. 10/546,538.
Non-final Rejection dated Jun. 10, 2009 re U.S. Appl. No. 10/546,538.
Response after Non-final Rejection submitted Dec. 9, 2009 re U.S. Appl. No. 10/546,538.
Final Rejection dated Jun. 8, 2010 re U.S. Appl. No. 10/546,538.
Notice of Appeal filed Dec. 8, 2010 re U.S. Appl. No. 10/546,538.
Appeal dismissed dated Jul. 20, 2011 re U.S. Appl. No. 10/546,538.
Restriction requirement mailed Apr. 24, 2012 re U.S. Appl. No. 13/179,283.
Response submitted Jul. 23, 2012 to restriction requirement re U.S. Appl. No. 13/179,283.
Non-final rejection dated Jul. 31, 2012 re U.S. Appl. No. 13/179,283.
Response of Jan. 30, 2013 to Non final rejection re U.S. Appl. No. 13/179,283.
Final rejection dated Apr. 11, 2013 re U.S. Appl. No. 13/179,283.

(56) References Cited

OTHER PUBLICATIONS

Restriction Requirement of Apr. 21, 2008 re U.S. Appl. No. 10/549,619.
Response filed Sep. 22, 2009 to Restriction Requirement re U.S. Appl. No. 10/549,619.
Non-final Rejection Apr. 28, 2009 re U.S. Appl. No. 10/549,619.
Response after Non-final Rejection submitted Oct. 26, 2009 re U.S. Appl. No. 10/549,619.
Interview summary Mar. 3, 2010 re U.S. Appl. No. 10/549,619.
Seo et al., "Click Chemistry to Construct Fluorescent Oligonucelotides for DNA sequencing", J. Org. Chem., vol. 68, 609-612, 2003.
Sherlin et al., "Chemical and Enzymatic Synthesis of tRNAs for High-throughput Crystallization", RNA, vol. 7, No. 11, 1671-1678, 2001.
Tabuchi et al., "An Efficient Ligation Method in the Making of an in vitro Virus for in vitro Protein Evolution," Biol., Proced. Online, vol. 4, No. 1, 49-54, 2002.
Verma et al., "Modified Oligonucleotides: Synthesis and Strategy for Users", Annu. Rev. Biochem., vol. 67, 99-134, 1998.
Woiwode et al., "Synthetic Compound Libraries Displayed on the Surface of Encoded Bacteriophage", Chem. Biol., vol. 10, 847-858, (Sep. 2003).
Wojczewski et al., "Fluorescent Oligonucleotides—Versatile Tools as Probes and Primers for DNA and RNA Analysis", Synlett, No. 10, 1667-1678, 1999.
Wong & Whitesides, "Enzymes in Synthetic Organic Chemistry", Tetrahedron Organic Chemistry Series vol. 12, Pergamon, Elsevier Science Lrd. (Oxford, England) 1994, pp. Xiii-Xv, 1-40, and 329-334.
Zhang et al., "Solution-Phase Preparation of a 560-Compound Library of Individual Pure Mappicine Analogous by Fluorous Mixture Synthesis", J. Am. Chem. Soc., vol. 124, 10443-10450, 2002.
Barrio et al., "Synthesis of modified nucleoside 3',5'-bisphophates and their incorporation into oligoribonucleotides with T4 RNA Ligase", Biochemistry, vol. 17, No. 11, 1978.
Chan et al., "Altered DNA ligase I activity in Bloom's syndrome cells", Nature, vol. 325, pp. 357-359, 1987.
Cranston et al., "Studies on ribonucleic acid ligase", J.Biol.Chem., vol. 249, No. 23, pp. 7447-7456, 1974.
England et al., "Enzymatic oligoribonucleotide synthesis with T4 RNA ligase", American Chemical Society, vol. 17, No. 11, 1978.
Gassen et al., "Synthesis by polymer-bound ribonuclease of the termination codons U-A-A, U-A-G, and U-G-A" Biochemical and biophysical research communications, vol. 44, No. 6, pp. 1410-1415, 1971.
Haseth et al., "Interaction of *Escherichia coli* host factor protein with oligoriboadenylates", Biochemistry, 19, pp. 6138-6446, 1980.
Hoffman et al., "Polynucleotide phosphorylase covalently bound to cellulose and ith use in the preparation of homopolynucleotides", Biochemical and biophysical research communications, vol. 41, No. 3, pp. 710-714, 1970.
Kiebom, "Enzymes that do not work in organic solvents: Too polar substrates give too tight enzyme-product complexes", Recl. Tray. Chim. Pays-Bas, 107, pp. 347-348, 1988.
Middleton et al., "Synthesis and purification of oligoribonucleotides using T4 RNA ligase and reverse-phase chromatography", Analytical Biochemistry, 144, pp. 110-117, 1985.
Narang, "DNA synthesis", Tetrahedron, vol. 39, No. 1, pp. 3-22, 1983.
Neilson et al., "Synthesis of biologically active portions of an intercistronic region by use of a new 3'-phosphate incorporation method to protect 3'-OH and their binding to ribosomes", Eur. J. Biochem., 99, pp. 429-437, 1979.
Ochoa et al., "Enzymatic synthesis of polynucleotides", J.Biol. Chem., vol. 236, 12, pp. 3303-3311, 1961.
Willis et al., "DNA ligase I deficiency in Bloom's syndrome", Nature, vol. 325, pp. 355-357, 1987.
Decision to Grant dated Oct. 10, 2013 re European patent appliction No. 09154197.9.
Decision to Grant EP 10183942.1 dated Nov. 14, 2013.
d'Angelo et al., "HIV-1 integrase: the next target for AIDS therapy?", Pathol. Biol. 2001, 49, pp. 237-246.
P101US01 Final rejection dated Oct. 28, 2013 re U.S. Appl. No. 12/330,709.
P104US00 RCE submitted Aug. 6, 2012 re U.S. Appl. No. 10/523,006.
P104US00 Response submitted Oct. 11, 2013 re U.S. Appl. No. 10/523,006.
P119US01 Notice of Appeal filed Sep. 11, 2013 re U.S. Appl. No. 13/179,283.
P123US02 Non-final rejection dated Nov. 15, 2013 re U.S. Appl. No. 13/455,223.
Non-final rejection dated Oct. 8, 2013 re U.S. Appl. No. 12/095,778.
Kurz et al. "Psoralen photo-crosslinked mRNA puromycin conjugates: a novel template for the rapid and facile preparation of mRNA-protein fusions." Nucleic Acids Res. 2000, 28(18): E83.
Balasubramanian, "Solid phase chemical technologies for combinatorial chemistry", J. Cell. Biochem. Suppl., 37, 2001, pp. 28-33.
Balasubramanian, "The science of chemical discovery: probing the unknown with new technologies", DDT, vol. 5, No. 12, Dec. 2000, pp. 533-534.
piercenet.com/method/avidin-biotin-interaction retrieved Nov. 5, 2013.
Schreiber, "The small-molecule approach to biology—Chemical genetics and diversity-oriented organic synthesis make possible the systematic exploration of biology", C&EN, Mar. 3, 2003, pp. 51-61.
Wills et al., "Recent developments in linker design and application", Current Opinion in Chemical Biology, 2003, 7, pp. 346-352.
Office Action in European application No. 07114663.3, dated Sep. 12, 2011.
Response to European Search Report in European application No. 10184311.8, dated Feb. 6, 2012.
Response to Office Action in European application No. 08169346.7, dated Feb. 10, 2012.
Office Action in European application No. 08169346.7, dated Feb. 24, 2012.
Annex to Office Action in European application No. 08169346.7, dated Feb. 24, 2012.
Response to Office Action in European application No. 09154197.9, dated Aug. 5, 2011.
Office Action in European application No. 09154197.9, dated Sep. 12, 2011.
Annex to Office Action in European application No. 09154197.9, dated Sep. 12, 2011.
European Search Report in European application No. 10183942.1, dated Feb. 6, 2012.
European Search Opinion in European application No. 10183942.1 dated Feb. 6, 2012.
Communication re partial European Search Report in European application No. 10184069.2, dated Feb. 10, 2012.
Partial European Search Report in European application No. 10184069.2, dated Feb. 3, 2012.
Response to Invitation in European application No. 10192717.6, dated Aug. 5, 2011.
Communication re European Search Report in European application No. 10192717.6, dated Oct. 7, 2011.
Partial European Search Report in European application No. 10192717.6, dated Sep. 8, 2011.
Response to Partial European Search Report in European application No. 10192717.6, dated Dec. 8, 2011.
European Search Report in European application No. 10192717.6, dated Jan. 16, 2012.
European Search Opinion in European application No. 10192717.6, dated Jan. 25, 2012.
International Search Report in PCT/DK2011/000031, dated Aug. 23, 2011.
Opposition against EP 1558744 filed by Strawman Limited on Mar. 12, 2012.
Opposition against EP 1558744 filed by HGF on Mar. 14, 2012.

\* cited by examiner

Fig. 1 Examples of Complementary Connector Polynucleotides (CCPN's)

Fig. 2   Library Formation, Screening and Analysis

Various CCPN/CPN complexes

Fig. 4 (continued)
E  n = 3   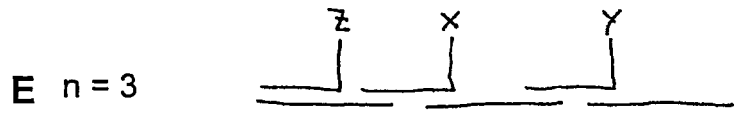
F  n = 3   
　　　　　　　　　　　　　　　　　　　　n = 4
G  n = 3   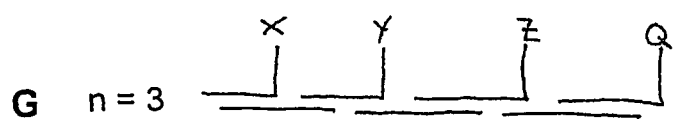
H  n = 3   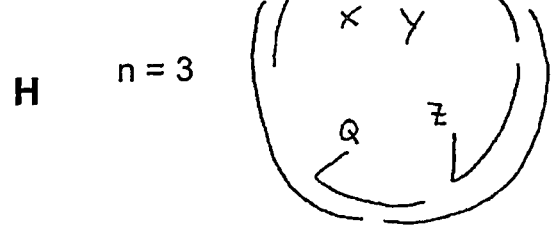

Fig. 4 (continued)
I  n = 2
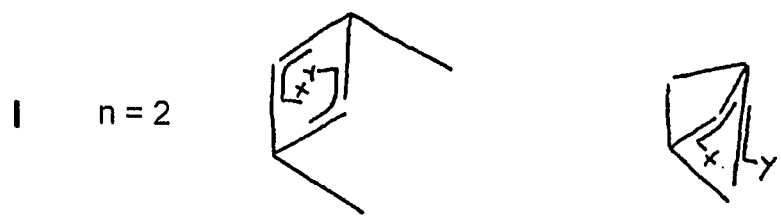
J  n = 2
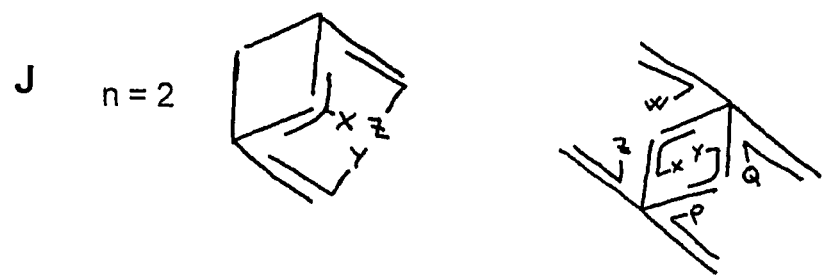
K  n = 3-4
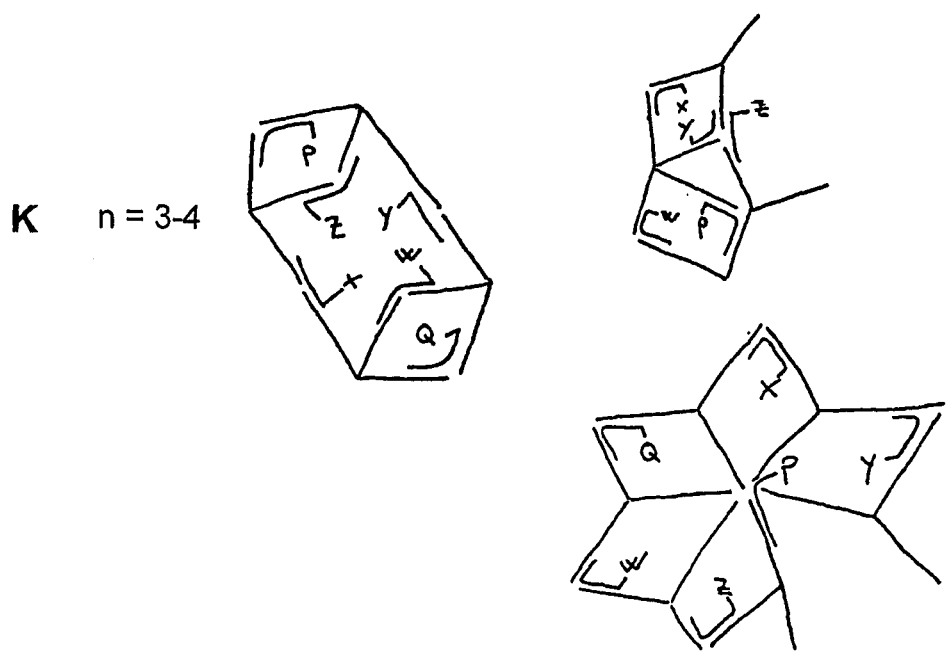

Fig. 5   Examples of Complementary Connector Polynucleotides

Fig. 6 Library formation, Screening and Analysis

Fig. 7 Library formation, Screening and Analysis

Fig. 8  Library formation, Screening and Analysis

Fig. 9  Library formation, Screening and Analysis

Fig. 10 Library formation, Screening and Analysis

Fig. 11  Library formation, Screening and Analysis

Fig. 12    Library formation, Screening and Analysis

Fig. 13  Library formation, Screening and Analysis

Fig. 14  Library formation, Screening and Analysis

Fig. 15    Example Library

Fig. 16　Different complexes of CCPN's and CPN's

Fig. 17 Different complexes of CCPN's and CPN's

Fig. 18  Different complexes of CCPN's and CPN's

Fig. 19  Different complexes of CCPN's and CPN's

Fig. 20 Different complexes of CCPN's and CPN's, wherein CPN's carry reactive groups or functional entities comprising functional entity reactive groups

Fig. 21 Zipperbox

Fig. 22 Library formation. Selfassembly of CPN and CCPN complexes

Fig. 23. Reaction types allowing simultaneous reaction and linker cleavage.

Nucleophilic substitution using activation of electrophiles

A. Acylating monomer building blocks - principle

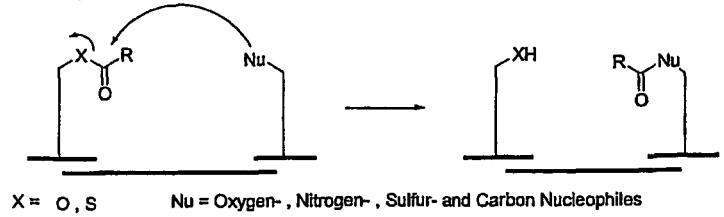

X = O, S    Nu = Oxygen-, Nitrogen-, Sulfur- and Carbon Nucleophiles

B. Acylation
Amide formation by reaction of amines with activated esters

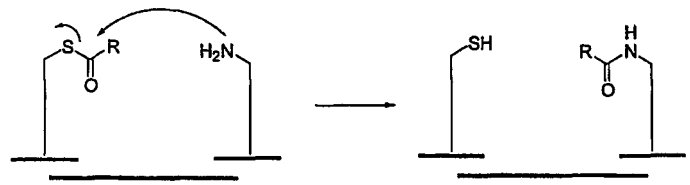

C. Acylation
Pyrazolone formation by reaction of hydrazines with β-Ketoesters

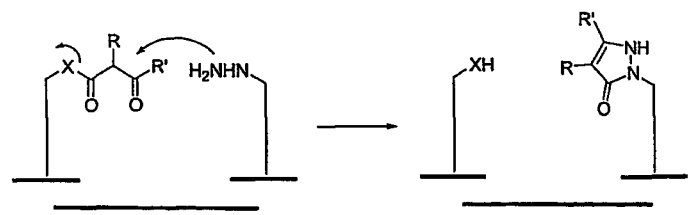

D. Acylation
Isoxazolone formation by reaction of hydroxylamines with β-Ketoesters

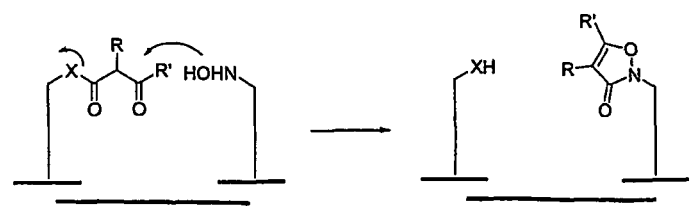

Fig. 23 (continued)
Reaction types allowing simultaneous reaction and linker cleavage. Continued.

E. Acylation
Pyrimidine formation by reaction of thioureas with β–Ketoesters

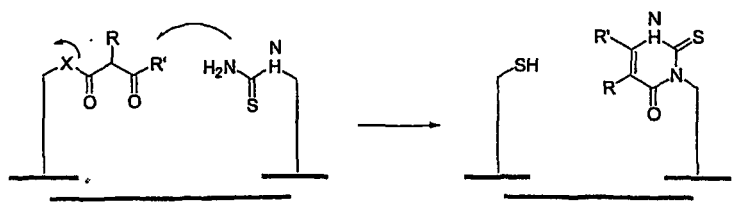

F. Acylation
Pyrimidine formation by reaction of ureas with Malonates

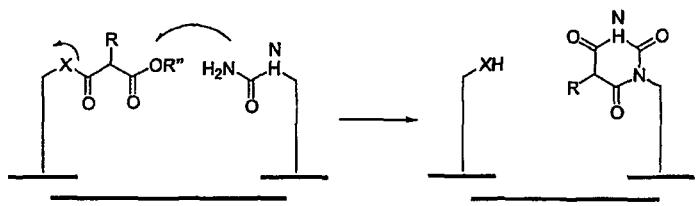

G. Acylation
Coumarine or quinolinon formation by a Heck reaction followed by a nucleophilic substitution

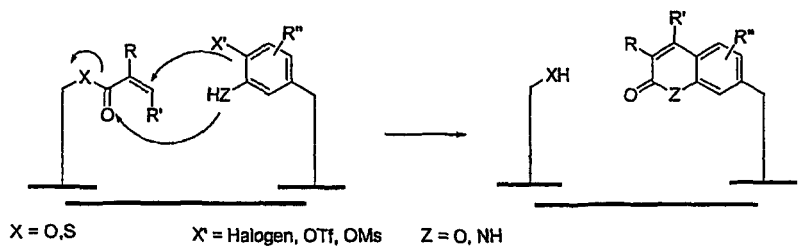

X = O,S    X' = Halogen, OTf, OMs    Z = O, NH

Fig. 23 (continued)
Reaction types allowing simultaneous reaction and linker cleavage. Continued.
H. Acylation
Phthalhydrazide formation by reaction of Hydrazines and Phthalimides
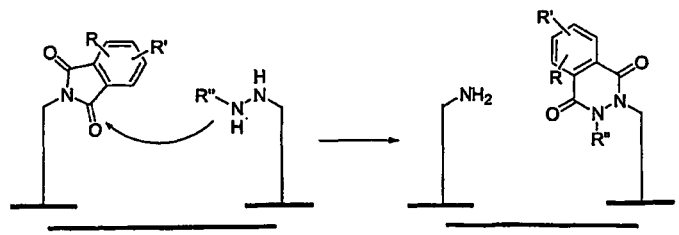
I. Acylation
Diketopiperazine formation by reaction of Amino Acid Esters
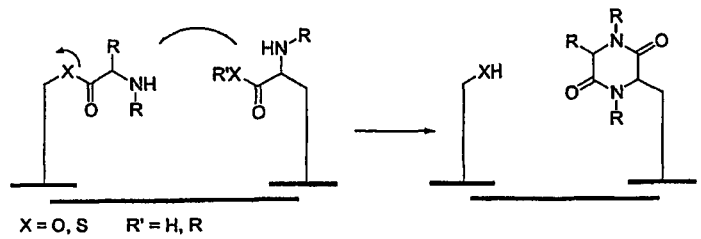
X = O, S   R' = H, R
J. Acylation
Hydantoin formation by reaction of Urea and α-substituted Esters
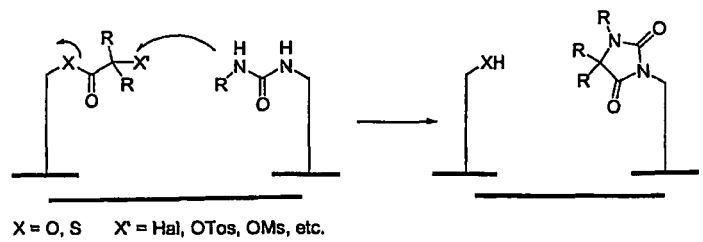
X = O, S   X' = Hal, OTos, OMs, etc.

Fig. 23 (continued)

Reaction types allowing simultaneous reaction and linker cleavage. Continued.

K. Alkylating monomer building blocks - principle
Alkylated compounds by reaction of Sulfonates with Nucleofiles

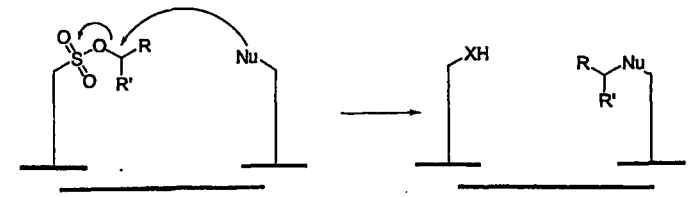

Nu = Oxygen-, Nitrogen-, Sulfur- and Carbon Nucleophiles

L. Vinylating monomer building blocks - principle

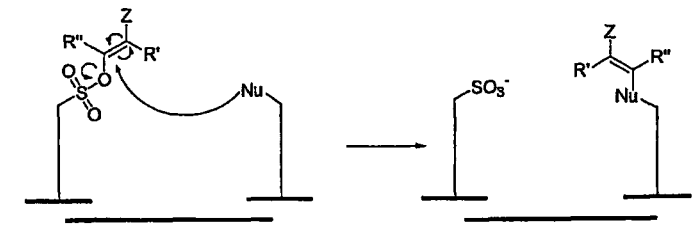

Z = CN, COOR, COR, $NO_2$, $SO_2R$, S(=O)R, $SO_2NR_2$, F
Nu = Oxygen-, Nitrogen-, Sulfur- and Carbon Nucleophiles

M. Heteroatom electrophiles
Disulfide formation by reaction of Pyridyl disulfide with mercaptanes

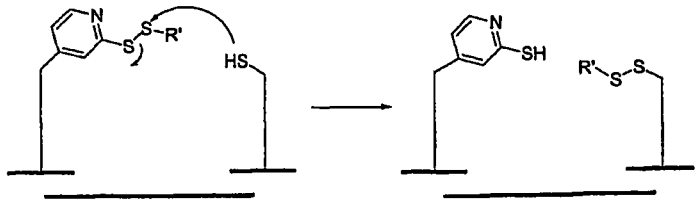

Fig. 23 (continued)

Reaction types allowing simultaneous reaction and linker cleavage. Continued.

N. Acylation
Benzodiazepinone formation by reaction of Amino Acid Esters and Amino Ketones

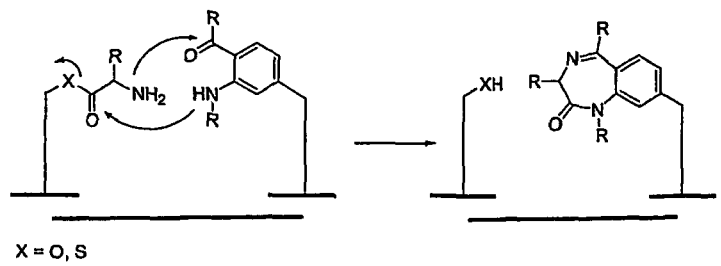

X = O, S

Addition to carbon-hetero multiple bonds

O. Wittig/Horner-Wittig-Emmons reagents
Substituted alkene formation by reaction of Phosphonates with Aldehydes or Ketones

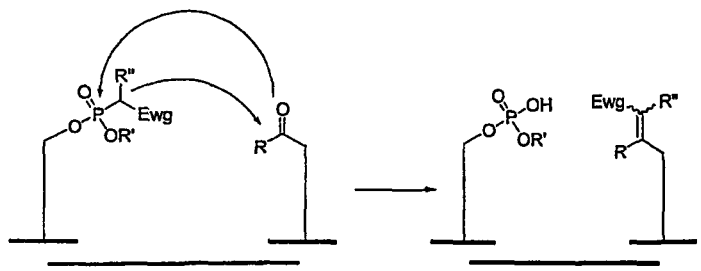

Ewg = CN, COOR, COR, $NO_2$, $SO_2R$, S(=O)R, $SO_2NR_2$, F etc.

P. Wittig/Horner-Wittig-Emmons reagents
Substituted alkene formation by reaction of Phosphonates with Aldehydes or Ketones

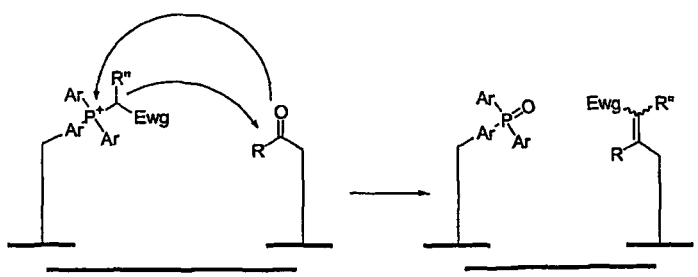

Ewg = CN, COOR, COR, $NO_2$, $SO_2R$, S(=O)R, $SO_2NR_2$, F etc.
Ar = aryl, hetaryl

Fig. 23 (continued)

Reaction types allowing simultaneous reaction and linker cleavage. Continued.

Transition metal catalysed reactions

Q. Transition metal cat. Arylations

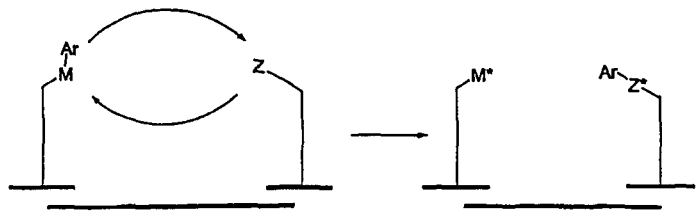

Z = haloaryl, halohetaryl, ArOMs, ArOTf, ArOTos or NHR or OH or SH etc.
Z* = Aryl, hetaryl, NR or O or S etc
M = e.g. BR, $BR_2^-$, $SnR_2$ etc.
R = H, alkyl, aryl, hetaryl, OR, $NR_2$
M* = e.g. B(OH)R, $B(OH)R_2^-$, $Sn(OH)R_2$ etc.

R. Arylation
Biaryl formation by the reaction of Borates with Aryls or Heteroaryls

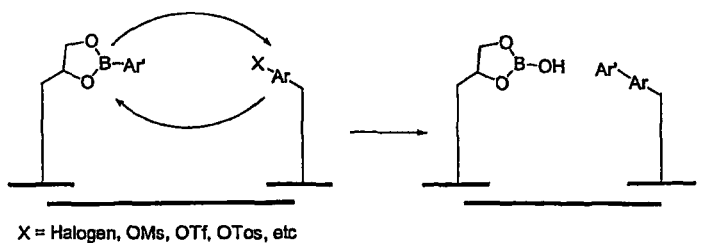

X = Halogen, OMs, OTf, OTos, etc

S. Arylation
Biaryl formation by the reaction of Boronates with Aryls or Heteroaryls

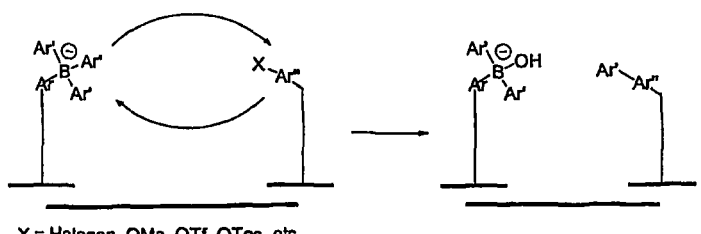

X = Halogen, OMs, OTf, OTos, etc
Ar = aryl, hetaryl

Fig. 23 (continued)
Reaction types allowing simultaneous reaction and linker cleavage. Continued.
T. Arylation
Biaryl formation by the reaction of Boronates with Aryls or Heteroaryls
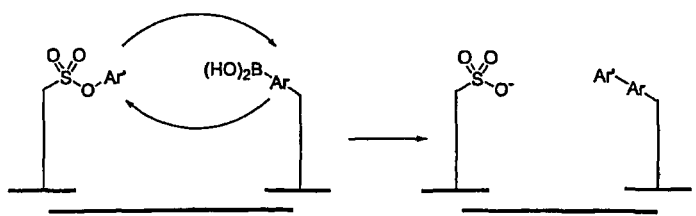
U. Arylation
Arylamine formation by the reaction of amines with activated Aryls or Heteroaryls
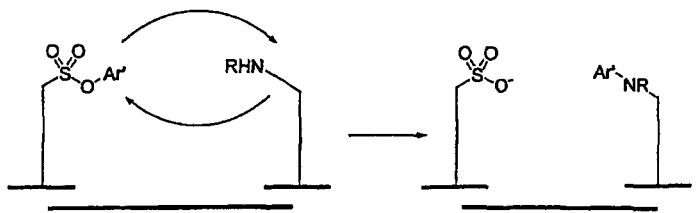
V. Arylation
Arylamine formation by the reaction of amines with hypervalent iodonium salts
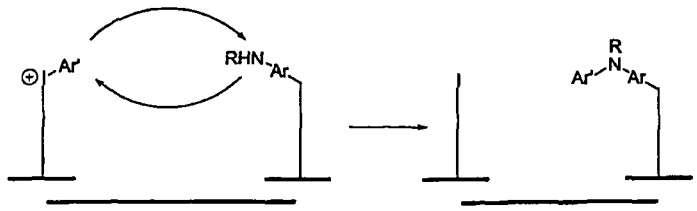

Fig. 23 (continued)

Reaction types allowing simultaneous reaction and linker cleavage. Continued.

X. Arylation
Vinylarene formation by the reaction of alkenes with Aryls or Heteroaryls

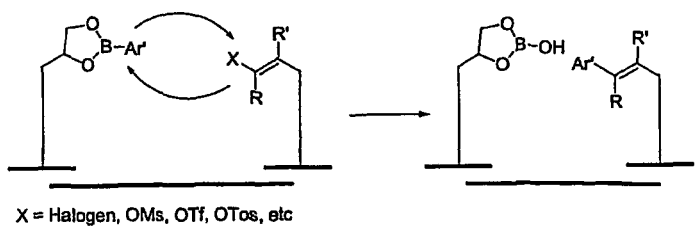

X = Halogen, OMs, OTf, OTos, etc

Y. Alkylation
Alkylation of arenes/hetarens by the reaction with Alkyl boronates

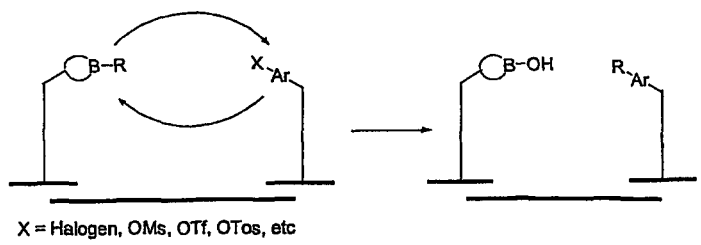

X = Halogen, OMs, OTf, OTos, etc

Z. Alkylation
Alkylation of arenes/hetarenes by reaction with enolethers

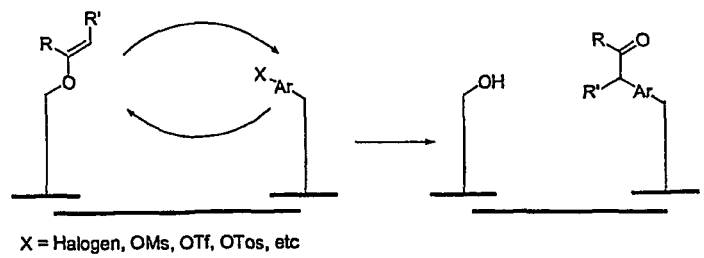

X = Halogen, OMs, OTf, OTos, etc

Fig. 23 (continued)

Reaction types allowing simultaneous reaction and linker cleavage. Continued.

Nucleophilic substitution using activation of nucleophiles

AA. Condensations
Alkylation of aldehydes with enolethers or enamines

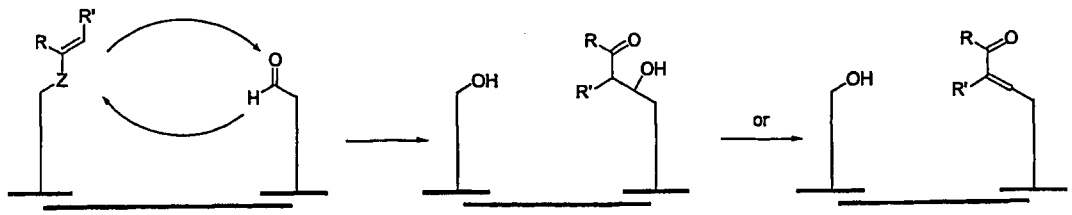

Z = NR, O; X = Halogen, OMs, OTf, OTos, etc

AB. Alkylation
Alkylation of aliphatic halides or tosylates with enolethers or enamines

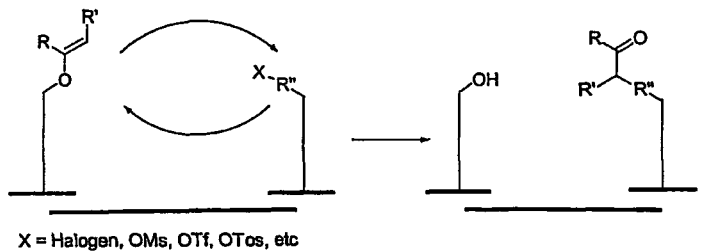

X = Halogen, OMs, OTf, OTos, etc

Cycloadditions

AC. [2+4] Cycloadditions

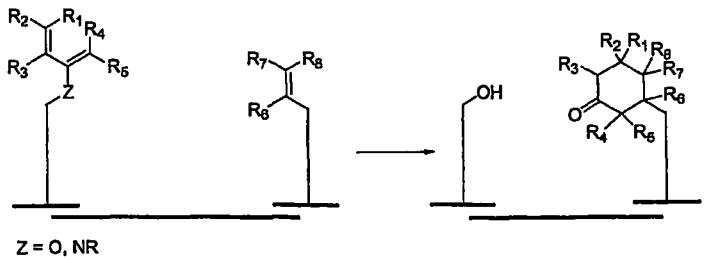

Z = O, NR

Fig. 23 (continued)
Reaction types allowing simultaneous reaction and linker cleavage. Continued.
AD. [2+4] Cycloadditions
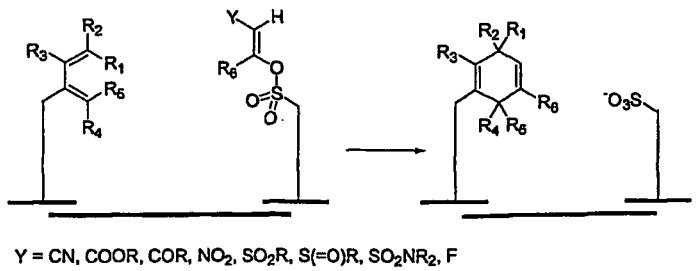
Y = CN, COOR, COR, $NO_2$, $SO_2R$, $S(=O)R$, $SO_2NR_2$, F
AE. [3+2] Cycloadditions
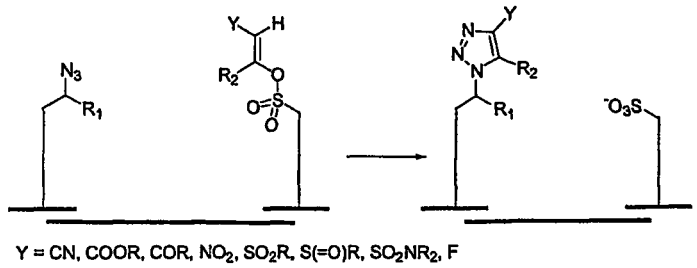
Y = CN, COOR, COR, $NO_2$, $SO_2R$, $S(=O)R$, $SO_2NR_2$, F
AF. [3+2] Cycloadditions
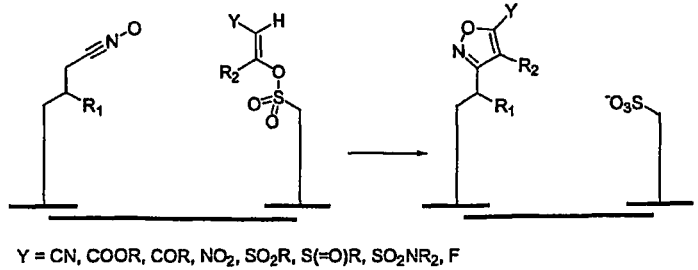
Y = CN, COOR, COR, $NO_2$, $SO_2R$, $S(=O)R$, $SO_2NR_2$, F Fig. 24.
Pairs of reactive groups X,Y and the resulting bond XY.
Nucleophilic substitution reaction
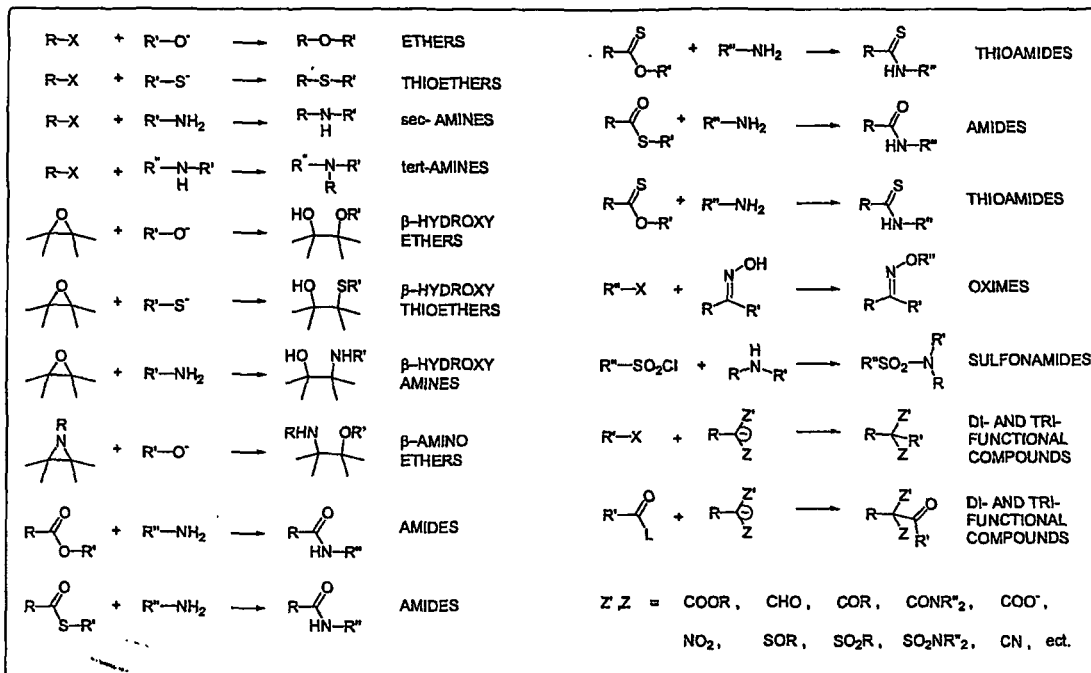
Aromatic nucleophilic substitution
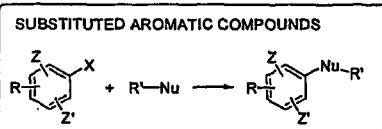
Nu = Oxygen-, Nitrogen-, Sulfur- and Carbon Nucleophiles
X = F, Cl, Br, I, $OSO_2CH_3$, $OSO_2CF_3$, $OSO_2TOL$,,, etc.
Z',Z = COOR, CHO, COR, $CONR''_2$, COO⁻, CN,
$NO_2$, SOR, $SO_2R$, $SO_2NR''_2$,, ect.
Transition metal catalysed reactions
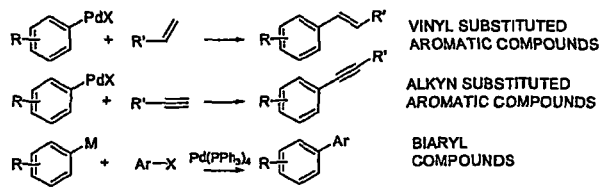

Fig. 24. (continued)
Pairs of reactive groups X,Y and the resulting bond XY. Continued.
Addition to carbon-carbon multiplebonds
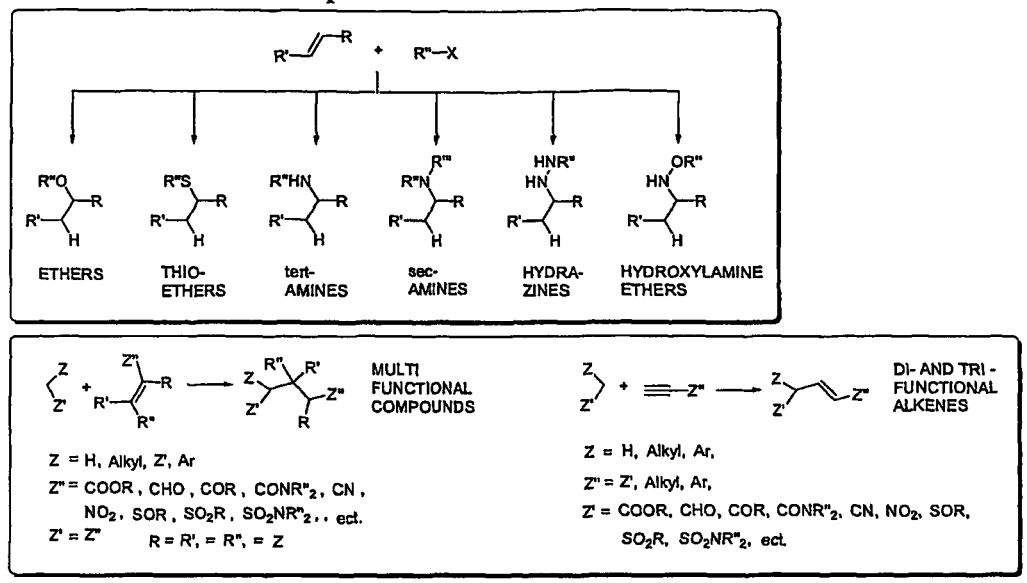
Cycloaddition to multiple bounds
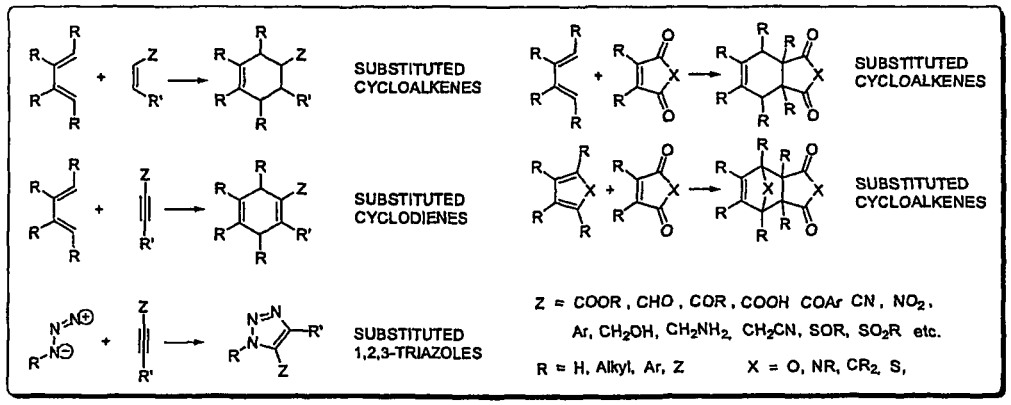

Pairs of reactive groups X,Y and the resulting bond XY. Continued.

Addition to carbon-hetero multiple bonds

Fig. 25. Cleavable Linkers

A. Linker for the formation of Ketones, Aldehydes, Amides and Acids

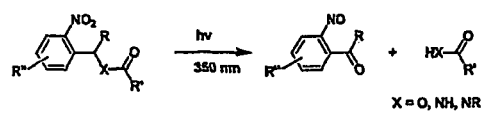

B. Linker for the formation of Ketones, Amides and Acids

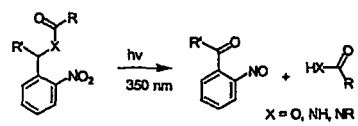

C. Linker for the formation of Aldehydes and Ketones

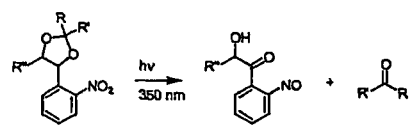

D. Linker for the formation of Alcohols and Acids

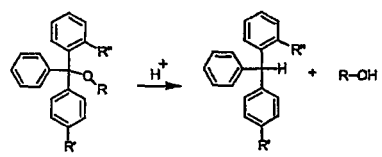

E. Linker for the formation of Amines and Alcohols

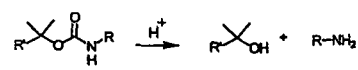

F. Linker for the formation of Esters, Thioesters, Amides and Alcohols

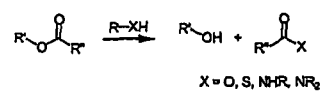

G. Linker for the formation of Sulfonamides and Alcohols

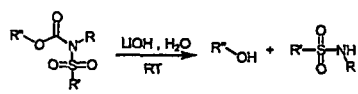

H. Linker for the formation of Ketones, Amines and Alcohols

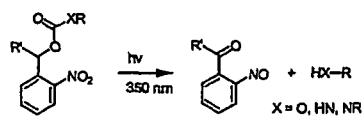

Fig. 25 (continued)

Cleavable Linkers

I. Linker for the formation of Ketones, Amines, Alcohols and Mercaptanes

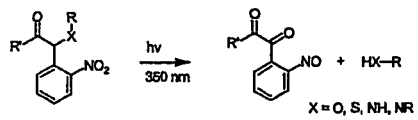

X = O, S, NH, NR

J. Linker for the formation of Biaryl and Bihetaryl

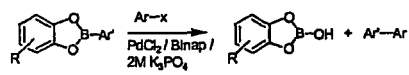

K. Linker for the formation of Benzyles, Amines, Anilins Alcohols and Phenoles

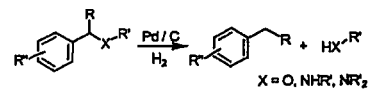

X = O, NHR', NR'$_2$

L. Linker for the formation of Mercaptanes

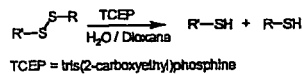

TCEP = tris(2-carboxyethyl)phosphine

M. Linker for the formation of Glycosides

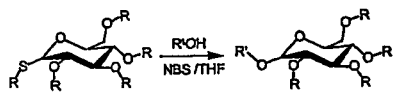

N. Linker for the formation of Aldehydes and Glyoxylamides

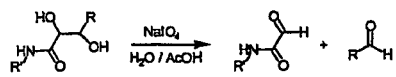

O. Linker for the formation of Aldehydes, Ketones and Aminoalcohols

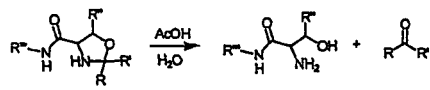

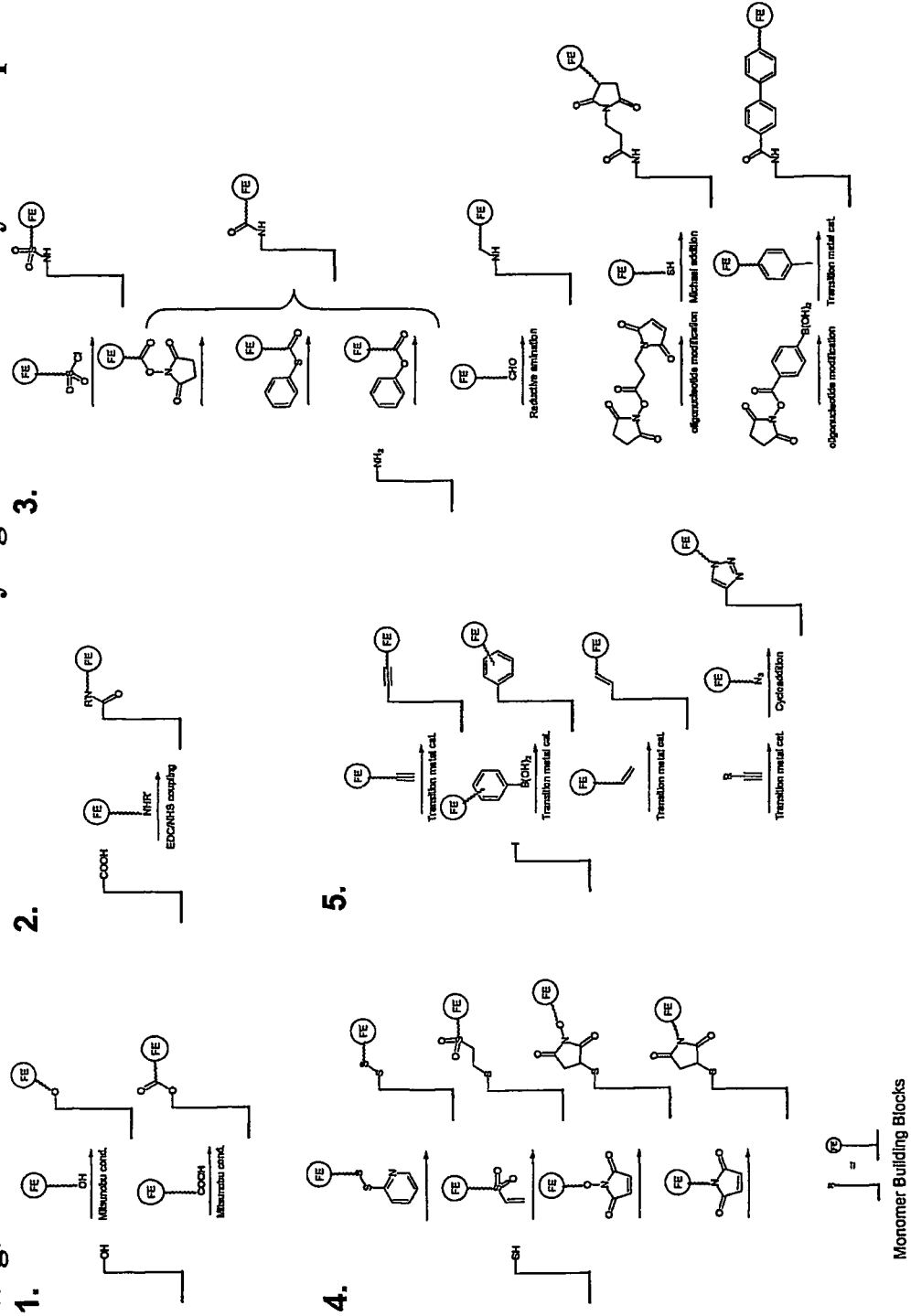
Fig. 26 Formation of CCPN's carrying a functional entity – Examples

SEQUENCE LISTING

```
<160> NUMBER OF SEQ ID NOS: 79

<210> SEQ ID NO 1
<211> LENGTH: 12
<212> TYPE: DNA
<213> ORGANISM: Artificial Sequence
<220> FEATURE:
<223> OTHER INFORMATION: The oligonucleotides were prepared by
      conventional phosphoramidite synthesis.
<220> FEATURE:
<221> NAME/KEY: misc_feature
<222> LOCATION: (5)..(8)
<223> OTHER INFORMATION: N denotes a random nucleobase, preferably
      selected from G, A, C, T, or U
```

```
<400> SEQUENCE: 1
gcggnnnncg cg                                                              12

<210> SEQ ID NO 2
<211> LENGTH: 12
<212> TYPE: DNA
<213> ORGANISM: Artificial Sequence
<220> FEATURE:
<223> OTHER INFORMATION: Scaffold like CCPN's type A's

<400> SEQUENCE: 2
gcggattacg cg                                                              12

<210> SEQ ID NO 3
<211> LENGTH: 12
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 3
gcggaattcg cg                                                              12

<210> SEQ ID NO 4
<211> LENGTH: 12
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (5)..(8)
<223> OTHER INFORMATION: N denotes a random nucleobase, preferably
      selected from G, A, C, T, or U

<400> SEQUENCE: 4
taatnnnntt aa                                                              12

<210> SEQ ID NO 5
<211> LENGTH: 12
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 5
taatgccgtt aa                                                              12

<210> SEQ ID NO 6
<211> LENGTH: 12
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 6
taatgggctt aa                                                              12

<210> SEQ ID NO 7
<211> LENGTH: 22
<212> TYPE: DNA
<213> ORGANISM: Artificial Sequence
<220> FEATURE:
```

<223> OTHER INFORMATION: The oligonucleotides were prepared by
      conventional phosphoramidite synthesis
<220> FEATURE:
<221> NAME/KEY: misc_feature
<222> LOCATION: (10)..(13)
<223> OTHER INFORMATION: N denotes a random nucleobase, preferably
      selected from G, A, C, T, or U

<400> SEQUENCE: 7
tttttggaan nnnagagttt tt                                            22

<210> SEQ ID NO 8
<211> LENGTH: 22
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 8
tttttggaac cttagagttt tt                                            22

<210> SEQ ID NO 9
<211> LENGTH: 22
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 9
tttttggaac ttcagagttt tt                                            22

<210> SEQ ID NO 10
<211> LENGTH: 12
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (5)..(8)
<223> OTHER INFORMATION: N denotes a random nucleobase, preferably
      selected from G, A, C, T, or U

<400> SEQUENCE: 10
ggttnnnngt tg                                                       12

<210> SEQ ID NO 11
<211> LENGTH: 12
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (5)..(8)
<223> OTHER INFORMATION: N denotes a random nucleobase, preferably
      selected from G, A, C, T, or U

<400> SEQUENCE: 11
accannnncc aa                                                       12

<210> SEQ ID NO 12
<211> LENGTH: 12
<212> TYPE: DNA
<213> ORGANISM: Artificial Sequence

```
<220> FEATURE:
<223> OTHER INFORMATION: All nucleotides herein are prepared by
      conventional phosphoramidite synthesis
<220> FEATURE:
<221> NAME/KEY: misc_feature
<222> LOCATION: (5)..(8)
<223> OTHER INFORMATION: N denotes a random nucleobase, preferably
      selected from G, A, C, T, or U

<400> SEQUENCE: 12
tctcnnnncc tt                                                              12

<210> SEQ ID NO 13
<211> LENGTH: 25
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (5)..(8)
<223> OTHER INFORMATION: N denotes a random nucleobase, preferably
      selected from G, A, C, T, or U
<220> FEATURE:
<221> NAME/KEY: misc_feature
<222> LOCATION: (22)..(25)
<223> OTHER INFORMATION: N denotes a random nucleobase, preferably
      selected from G, A, C, T, or U

<400> SEQUENCE: 13
cgcgnnnncc gcaaaaactc tnnnn                                                25

<210> SEQ ID NO 14
<211> LENGTH: 25
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 14
cgcgtaatcc gcaaaaactc taagg                                                25

<210> SEQ ID NO 15
<211> LENGTH: 33
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (14)..(17)
<223> OTHER INFORMATION: N denotes a random nucleobase, preferably
      selected from G, A, C, T, or U
<220> FEATURE:
<221> NAME/KEY: misc_feature
<222> LOCATION: (26)..(29)
<223> OTHER INFORMATION: N denotes a random nucleobase, preferably
      selected from G, A, C, T, or U

<400> SEQUENCE: 15
ttccaaaaac aacnnnnaac cttggnnnnt ggt                                       33

<210> SEQ ID NO 16
<211> LENGTH: 21
<212> TYPE: DNA
<213> ORGANISM: Artificial Sequence
<220> FEATURE:
<223> OTHER INFORMATION: The oligonucleotides were prepared by
```

```
      conventional phosphoramidite synthesis
<220> FEATURE:
<221> NAME/KEY: misc_feature
<222> LOCATION: (14)..(17)
<223> OTHER INFORMATION: N denotes a random nucleobase, preferably
      selected from G, A, C, T, or U

<400> SEQUENCE: 16
ttccaaaaac aacnnnnaac c                                              21

<210> SEQ ID NO 17
<211> LENGTH: 10
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)

<400> SEQUENCE: 17 ntntntggtg                                                           10

<210> SEQ ID NO 18
<211> LENGTH: 10
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)

<400> SEQUENCE: 18 ntntntgggt                                                           10

<210> SEQ ID NO 19
<211> LENGTH: 20
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
```

```
<222> LOCATION: (5)..(5)
<223> OTHER INFORMATION: n represents inosine (I)
<220> FEATURE:
<221> NAME/KEY: misc_feature
<222> LOCATION: (13)..(13)
<223> OTHER INFORMATION: n represents inosine (I)
<220> FEATURE:
<221> NAME/KEY: misc_feature
<222> LOCATION: (15)..(15)
<223> OTHER INFORMATION: n represents inosine (I)
<220> FEATURE:
<221> NAME/KEY: misc_feature
<222> LOCATION: (18)..(18)
<223> OTHER INFORMATION: n represents inosine (I)

<400> SEQUENCE: 19
ntntntggtt ttntnttntg                                              20

<210> SEQ ID NO 20
<211> LENGTH: 20
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (13)..(13)
<223> OTHER INFORMATION: n represents inosine (I)
<220> FEATURE:
<221> NAME/KEY: misc_feature
<222> LOCATION: (15)..(15)
<223> OTHER INFORMATION: n represents inosine (I)
<220> FEATURE:
<221> NAME/KEY: misc_feature
<222> LOCATION: (18)..(18)
<223> OTHER INFORMATION: n represents inosine (I)

<400> SEQUENCE: 20
ntntntgggg ggntnttntg                                              20

<210> SEQ ID NO 21
<211> LENGTH: 20
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (13)..(13)
<223> OTHER INFORMATION: n represents inosine (I)
<220> FEATURE:
<221> NAME/KEY: misc_feature
<222> LOCATION: (15)..(15)
```

```
<223> OTHER INFORMATION: n represents inosine (I)
<220> FEATURE:
<221> NAME/KEY: misc_feature
<222> LOCATION: (18)..(18)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)

<400> SEQUENCE: 21
ntntntggtg tgntnttntg                                                   20

<210> SEQ ID NO 22
<211> LENGTH: 10
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (8)..(8)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)

<400> SEQUENCE: 22 gtntnttntg                                                              10

<210> SEQ ID NO 23
<211> LENGTH: 10
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (8)..(8)
<223> OTHER INFORMATION: n represents inosine (I)

<400> SEQUENCE: 23 ttntnttntg                                                              10

<210> SEQ ID NO 24
<211> LENGTH: 20
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (1)..(1)
<223> OTHER INFORMATION: N denotes a random nucleobase
<220> FEATURE:
<221> NAME/KEY: misc_feature
<222> LOCATION: (2)..(2)
```

```
<223> OTHER INFORMATION: N denotes a random nucleobase
<220> FEATURE:
<221> NAME/KEY: misc_feature
<222> LOCATION: (19)..(19)
<223> OTHER INFORMATION: N denotes a random nucleobase
<220> FEATURE:
<221> NAME/KEY: misc_feature
<222> LOCATION: (20)..(20)
<223> OTHER INFORMATION: N denotes a random nucleobase

<400> SEQUENCE: 24
nnccacacac cacaacacnn                                                     20

<210> SEQ ID NO 25
<211> LENGTH: 10
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (1)..(1)
<223> OTHER INFORMATION: N denotes a random nucleobase
<220> FEATURE:
<221> NAME/KEY: misc_feature
<222> LOCATION: (2)..(2)
<223> OTHER INFORMATION: N denotes a random nucleobase

<400> SEQUENCE: 25 nnccacacac                                                                10

<210> SEQ ID NO 26
<211> LENGTH: 10
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (1)..(2)
<223> OTHER INFORMATION: N denotes a random nucleobase
<220> FEATURE:
<221> NAME/KEY: misc_feature
<222> LOCATION: (3)..(3)
<223> OTHER INFORMATION: N denotes inosine (I)
<220> FEATURE:
<221> NAME/KEY: misc_feature
<222> LOCATION: (5)..(5)
<223> OTHER INFORMATION: N denotes inosine (I)
<220> FEATURE:
<221> NAME/KEY: misc_feature
<222> LOCATION: (8)..(8)
<223> OTHER INFORMATION: N denotes inosine (I)

<400> SEQUENCE: 26 nnntnttntg                                                                10

<210> SEQ ID NO 27
<211> LENGTH: 50
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (3)..(7)
<223> OTHER INFORMATION: N denotes a random nucleobase
<220> FEATURE:
<221> NAME/KEY: misc_feature
<222> LOCATION: (14)..(17)
```

```
<223> OTHER INFORMATION: N denotes a random nucleobase
<220> FEATURE:
<221> NAME/KEY: misc_feature
<222> LOCATION: (24)..(27)
<223> OTHER INFORMATION: N denotes a random nucleobase
<220> FEATURE:
<221> NAME/KEY: misc_feature
<222> LOCATION: (34)..(37)
<223> OTHER INFORMATION: N denotes a random nucleobase
<220> FEATURE:
<221> NAME/KEY: misc_feature
<222> LOCATION: (44)..(48)
<223> OTHER INFORMATION: N denotes a random nucleobase

<400> SEQUENCE: 27
gcnnnnnacg cgannnntac gtannnntgt cacnnnntcg tcannnnngc         50

<210> SEQ ID NO 28
<211> LENGTH: 30
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: misc_feature
<222> LOCATION: (3)..(7)
<223> OTHER INFORMATION: N denotes a random nucleobase
<220> FEATURE:
<221> NAME/KEY: misc_feature
<222> LOCATION: (14)..(17)
<223> OTHER INFORMATION: N denotes a random nucleobase
<220> FEATURE:
<221> NAME/KEY: misc_feature
<222> LOCATION: (24)..(28)
<223> OTHER INFORMATION: N denotes a random nucleobase

<400> SEQUENCE: 28
gcnnnnntca tctnnnngcg tacnnnnngc                               30

<210> SEQ ID NO 29
<211> LENGTH: 20
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 29
gcctatgtga cgaatctgtg                                          20

<210> SEQ ID NO 30
<211> LENGTH: 5
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (5)..(5)
<223> OTHER INFORMATION: 3'-amino-group, Glen research cat#20-2958-01

<400> SEQUENCE: 30 gattc                                                           5

<210> SEQ ID NO 31
<211> LENGTH: 5
<212> TYPE: DNA
<213> ORGANISM: Artificial Sequence
<220> FEATURE:
```

```
<223> OTHER INFORMATION: The oligonucleotides were prepared by
      conventional phosphoramidite synthesis
<220> FEATURE:
<221> NAME/KEY: modified_base
<222> LOCATION: (1)..(1)
<223> OTHER INFORMATION: amino modifier, Glen research cat#10-1905-90
      suitable for attachment of chemical entities.

<400> SEQUENCE: 31 gaatc                                                                      5

<210> SEQ ID NO 32
<211> LENGTH: 20
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (20)..(20)
<223> OTHER INFORMATION: 5'-phosphate

<400> SEQUENCE: 32
atgcgtaccg cgattcatgc                                                     20

<210> SEQ ID NO 33
<211> LENGTH: 5
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (1)..(1)
<223> OTHER INFORMATION: N represents an amino modifier, Glen research
      cat#10-1905-90 suitable for attachment of chemical entities.

<400> SEQUENCE: 33 gaatc                                                                      5

<210> SEQ ID NO 34
<211> LENGTH: 20
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (20)..(20)
<223> OTHER INFORMATION: 5'-phosphate

<400> SEQUENCE: 34
cgctgcaaga tgaattctgc                                                     20

<210> SEQ ID NO 35
<211> LENGTH: 22
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 35
gattcctagg atgcatatta ca                                                  22

<210> SEQ ID NO 36
```

```
<211> LENGTH: 24
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 36
gctgtaatat gcatcctagg aatc                                          24

<210> SEQ ID NO 37
<211> LENGTH: 17
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (1)..(1)
<223> OTHER INFORMATION: 5'-phosphate

<400> SEQUENCE: 37
tgcagtagtc gtaactg                                                  17

<210> SEQ ID NO 38
<211> LENGTH: 19
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 38
cagttacgac tactgcagc                                                19

<210> SEQ ID NO 39
<211> LENGTH: 26
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (1)..(1)
<223> OTHER INFORMATION: modified with biotin, Applied Biosystems
<220> FEATURE:
<221> NAME/KEY: misc_feature
<222> LOCATION: (1)..(2)
<223> OTHER INFORMATION: n denotes inosine (I)

<400> SEQUENCE: 39
nngattccta ggatgcatat tacagc                                        26

<210> SEQ ID NO 40
<211> LENGTH: 19
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 40
cagttacgac tactgcagc                                                19

<210> SEQ ID NO 41
<211> LENGTH: 21
<212> TYPE: DNA
```

```
<213> ORGANISM: Artificial Sequence
<220> FEATURE:
<223> OTHER INFORMATION: The oligonucleotides were prepared by
      conventional phosphoramidite synthesis

<400> SEQUENCE: 41
gattcctagg atgcatatta c                                             21

<210> SEQ ID NO 42
<211> LENGTH: 80
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 42
agctggatgc tcgacaggtc aggtcgatcc gcgttaccag tcttgcctga acgtagtcgt   60
ccgatgcaat ccagaggtcg                                               80

<210> SEQ ID NO 43
<211> LENGTH: 87
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 43
agctggatgc tcgacaggtc aagtaacagg tcgatccgcg ttaccagtct tgcctgaacg   60
tagtcgtccg atgcaatcca gaggtcg                                       87

<210> SEQ ID NO 44
<211> LENGTH: 25
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (25)..(25)
<223> OTHER INFORMATION: carboxy-dT modification, Glenn Research cat.no.
      10-1035-

<400> SEQUENCE: 44
ctggtaacgc ggatcgacct gttac                                         25

<210> SEQ ID NO 45
<211> LENGTH: 20
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (20)..(20)
<223> OTHER INFORMATION: carboxy-dT modification, Glenn Research cat.no.
      10-1035-

<400> SEQUENCE: 45
tctggattgc atcgggttac                                               20

<210> SEQ ID NO 46
<211> LENGTH: 20
<212> TYPE: DNA
```

```
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (20)..(20)
<223> OTHER INFORMATION: modified with a PC-spacer joined to biotin
<220> FEATURE:
<221> NAME/KEY: modified_base
<222> LOCATION: (1)..(1)
<223> OTHER INFORMATION: amino-Modifier C6 dT modification, Glenn
      Research cat.no. 10-1039-

<400> SEQUENCE: 46
gacctgtcga gcatccagct                                              20

<210> SEQ ID NO 47
<211> LENGTH: 25
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (1)..(1)
<223> OTHER INFORMATION: Amino-Modifier 5 Glenn Research cat. no.
      10-1905

<400> SEQUENCE: 47
gtaacgacct gtcgagcatc cagct                                        25

<210> SEQ ID NO 48
<211> LENGTH: 25
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (25)..(25)
<223> OTHER INFORMATION: carboxy-dT modification, Glenn Research cat.no.
      10-1035-

<400> SEQUENCE: 48
acgactacgt tcaggcaaga gttac                                        25

<210> SEQ ID NO 49
<211> LENGTH: 82
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 49
agctggatgc tcgacaggtc aagtaacagg tcgatccgcg ttatatcgtt tacggcatta  60
ccgcccatag cttgcggctt gc                                           82

<210> SEQ ID NO 50
<211> LENGTH: 44
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 50
```
ggcatggtcc atcgactgca atatgcaagc cgcaagctat gggc                44

<210> SEQ ID NO 51
<211> LENGTH: 50
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 51
ggcatggtcc atcgactgca atatcgtata gcaagccgca agctatgggc          50

<210> SEQ ID NO 52
<211> LENGTH: 60
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 52
ggcatggtcc atcgactgca atatcgttta cggcattacc gcaagccgca agctatgggc   60

<210> SEQ ID NO 53
<211> LENGTH: 80
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 53
ggcatggtcc atcgactgca atatcgttta cggcattacc atatcgttta cggcattacc   60
gcaagccgca agctatgggc                                              80

<210> SEQ ID NO 54
<211> LENGTH: 100
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 54
ggcatggtcc atcgactgca atatcgttta cggcattacc atatcgttta cggcattacc   60
atatcgttta cggcattacc gcaagccgca agctatgggc                        100

<210> SEQ ID NO 55
<211> LENGTH: 40
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 55
ggcatggtcc atcgactgca gcaagccgca agctatgggc                        40

<210> SEQ ID NO 56
<211> LENGTH: 60
<212> TYPE: DNA
<213> ORGANISM: Artificial Sequence
<220> FEATURE:
<223> OTHER INFORMATION: The oligonucleotides were prepared by conventional phosphoramidite synthesis

<400> SEQUENCE: 56
cttatacctt gttgtagccg tcttgcctga acgtagtcgt ccgatgcaat ccagaggtcg    60

<210> SEQ ID NO 57
<211> LENGTH: 62
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 57
cttatacctt gttgtagccg tcttgcctga acgtagtcgt ttccgatgca atccagaggt    60
cg                                                                  62

<210> SEQ ID NO 58
<211> LENGTH: 64
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 58
cttatacctt gttgtagccg tcttgcctga acgtagtcgt acttccgatg caatccagag    60
gtcg                                                                64

<210> SEQ ID NO 59
<211> LENGTH: 66
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 59
cttatacctt gttgtagccg tcttgcctga acgtagtcgt tgacttccga tgcaatccag    60
aggtcg                                                              66

<210> SEQ ID NO 60
<211> LENGTH: 68
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 60
cttatacctt gttgtagccg tcttgcctga acgtagtcgt ggtgacttcc gatgcaatcc    60
agaggtcg                                                            68

<210> SEQ ID NO 61
<211> LENGTH: 70
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 61
cggctacaac aaggtataag aaaaacatcg taggattctt tcctacgatg gcaagccgca    60
agctatgggc 70

<210> SEQ ID NO 62
<211> LENGTH: 60
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 62
cggctacaac aaggtataag aaaaacagga ttctttcctg gcaagccgca agctatgggc    60

<210> SEQ ID NO 63
<211> LENGTH: 70
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 63
cttatacctt gttgtagccg tcttgcctga acgtagtcgt ggtgacttgg ccgatgcaat    60
ccagaggtcg                                                          70

<210> SEQ ID NO 64
<211> LENGTH: 72
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 64
cttatacctt gttgtagccg tcttgcctga acgtagtcgt ggtgacttgg tgccgatgca    60
atccagaggt cg                                                       72

<210> SEQ ID NO 65
<211> LENGTH: 74
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 65
cttatacctt gttgtagccg tcttgcctga acgtagtcgt ggtgacttgg tgacccgatg    60
caatccagag gtcg                                                     74

<210> SEQ ID NO 66
<211> LENGTH: 76
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 66
cttatacctt gttgtagccg tcttgcctga acgtagtcgt ggtgacttgg tgacttccga    60
tgcaatccag aggtcg                                                   76

<210> SEQ ID NO 67
<211> LENGTH: 78
<212> TYPE: DNA

<213> ORGANISM: Artificial Sequence
<220> FEATURE:
<223> OTHER INFORMATION: The oligonucleotides were prepared by
      conventional phosphoramidite synthesis

<400> SEQUENCE: 67 cttataccttt gttgtagccg tcttgcctga acgtagtcgt ggtgacttgg tgacttggcc    60
gatgcaatcc agaggtcg                                                  78

<210> SEQ ID NO 68
<211> LENGTH: 62
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 68
tgcagtcgat ggaccatgcc agctggatgc tcgacaggtc aaccgatgca atccagaggt    60
cg                                                                   62

<210> SEQ ID NO 69
<211> LENGTH: 70
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 69
tgcagtcgat ggaccatgcc agctggatgc tcgacaggtc aatcaggctg ccgatgcaat    60
ccagaggtcg                                                           70

<210> SEQ ID NO 70
<211> LENGTH: 72
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 70
cggttgaggt acaggtcgat ccgcgttacc agtcttgcct gaacgtagtc gtgcccatag    60
cttgcggctt gc                                                        72

<210> SEQ ID NO 71
<211> LENGTH: 37
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (1)..(1)
<223> OTHER INFORMATION: Spacer 9  Glenn Research cat. no. 10-1909,
      joined to Amino-Modifier 5 Glenn Research cat. no. 10-1905

<400> SEQUENCE: 71
gtaacgtacc tcaaccggac ctgtcgagca tccagct                             37

<210> SEQ ID NO 72
<211> LENGTH: 65
<212> TYPE: DNA
<213> ORGANISM: Artificial Sequence

```
<220> FEATURE:
<223> OTHER INFORMATION: The oligonucleotides were prepared by
      conventional phosphoramidite synthesis

<400> SEQUENCE: 72
ggtacaggtc gatccgcgtt accagtcttg cctgaacgta gtcgtgccca tagcttgcgg      60
cttgc                                                                 65

<210> SEQ ID NO 73
<211> LENGTH: 70
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 73
ggtacaggtc gatccgcgtt accagggtac tcttgcctga acgtagtcgt gcccatagct      60
tgcggcttgc                                                            70

<210> SEQ ID NO 74
<211> LENGTH: 70
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 74
gttgaggtac aggtcgatcc gcgttaccag tcttgcctga acgtagtcgt gcccatagct      60
tgcggcttgc                                                            70

<210> SEQ ID NO 75
<211> LENGTH: 68
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 75
tgaggtacag gtcgatccgc gttaccagtc ttgcctgaac gtagtcgtgc ccatagcttg      60
cggcttgc                                                              68

<210> SEQ ID NO 76
<211> LENGTH: 66
<212> TYPE: DNA
<213> ORGANISM: Artificial Sequence
<220> FEATURE:
<223> OTHER INFORMATION: The oligonucleotides were prepared by
      conventional phosphoramidite synthesis

<400> SEQUENCE: 76
aggtacaggt cgatccgcgt taccagtctt gcctgaacgt agtcgtgccc atagcttgcg      60
gcttgc                                                                66

<210> SEQ ID NO 77
<211> LENGTH: 25
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
```

```
<221> NAME/KEY: modified_base
<222> LOCATION: (25)..(25)
<223> OTHER INFORMATION: amino-Modifier C6 dT, Glenn Research cat.no.
      10-1039-

<400> SEQUENCE: 77
cgacctctgg attgcatcgg gttac                                            25

<210> SEQ ID NO 78
<211> LENGTH: 25
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (25)..(25)
<223> OTHER INFORMATION: amino-Modifier C6 dT, Glenn Research cat.no.
      10-1039-

<400> SEQUENCE: 78
acgactacgt tcaggcaaga gttac                                            25

<210> SEQ ID NO 79
<211> LENGTH: 25
<212> TYPE: DNA
<213> ORGANISM: Artificial Sequence
<220> FEATURE:
<223> OTHER INFORMATION: The oligonucleotides were prepared by
      conventional phosphoramidite synthesis
<220> FEATURE:
<221> NAME/KEY: modified_base
<222> LOCATION: (25)..(25)
<223> OTHER INFORMATION: amino-Modifier C6 dT, Glenn Research cat.no.
      10-1039-

<400> SEQUENCE: 79
ctggtaacgc ggatcgacct gttac                                            25
```

QUASIRANDOM STRUCTURE AND FUNCTION GUIDED SYNTHESIS METHODS

TECHNICAL FIELD OF THE INVENTION

One aspect of the present invention is directed to methods for the synthesis of molecules in which the steps of synthesising the molecule from a plurality of reactants or functional entities is guided by connector polynucleotides (CPNs) capable of hybridizing to complementary connector polynucleotides (CCPNs) harbouring at least one functional entity comprising at least one reactive group.

As at least one of said CCPNs hybridize to at least two CPNs, it will be possible to bring together at least two CPNs to which further CCPNs can hybridize. Accordingly, each CPN will "call" for one or more CCPNs capable of hybridising to the CPN.

Following the formation in the above-described way of a supramolecular hybridization complex comprising a plurality of CPNs and a plurality of CCPNs, the reaction of reactants or functional entity reactive groups result in the formation of at least one molecule comprising the reaction product generated by the reacted reactants, such as e.g. a molecule comprising covalently linked functional entities.

The formation of the molecule involves reacting the plurality of reactants, said reactions resulting e.g. in the transfer of functional entities from one or more "donor CCPNs" to at least one "acceptor CCPN" with which the transferred functional entities were not covalently associated prior to the transfer.

Transferring at least one functional entity from one CCPN to another CCPN and reacting the reactants can in one embodiment result in the formation of a molecule e.g. comprising covalently linked functional entities without the "donor CCPNs" being covalently linked once the molecule has been generated. Accordingly, in one embodiment, once the reactants have reacted and the molecule has been formed, the "donor CCPN's" are not covalently linked e.g. by covalent bonds between functional entities constituting the molecule. In this embodiment, the cleavage of covalent bonds between reactants, or functional entities, and "donor CCPNs", also prevent the "donor CCPNs" from being covalently linked to each other.

Both the CPNs and the CCPNs comprise a polynucleotide part. The formation of the molecule comprising reacted reactants, such as e.g. covalently linked functional entities, does not involve a step of cleaving the polynucleotide part of a CPN or a CCPN. In this way the methods of the present invention are different from state of the art polynucleotide ligation and restriction reactions.

BACKGROUND OF THE INVENTION

Ribosome mediated translation involves hybridising the anti-codon of tRNAs to a mRNA template and generating a bond between the amino acid residues harboured by the tRNAs. Only 2 reactive groups are reacted in order to generate the peptide bond between neighbouring amino acid residues in the growing peptide chain. Ribosome mediated translation employs the principle of template directed synthesis and does not involve hybridization of a plurality of connector polynucleotides (CPNs) to a plurality of complementary connector polynucleotides (CCPNs). Another difference between ribosome mediated translation and the method of the present invention is that in the present method for synthesising at least one molecule, at least 1 CCPN hybridizes to at least 2 CPNs.

Additional examples of template directed synthesis methods are disclosed in WO 93/03172 (Gold et al.) and WO 02/074929 (Liu et al.). The methods of the present invention are not related to template directed synthesis as no templates are employed in the methods of the present invention.

Enzymatic ligation and chemical ligation are processes well known in the art. In some cases only 2 reactive groups react in order to generate a product. An example is a reaction between e.g. a 5'-phosphate group of a nucleotide and a 3'-hydroxy group of another nucleotide.

In one embodiment of the present invention, the synthesis and formation of a molecule in accordance with the methods of the present invention does not result in polynucleotides being covalently linked once the molecule has been formed. Rather, the plurality of CCPNs having donated functional entities to the synthesis of the molecule comprising reacted reactants, such as e.g. covalently linked functional entities, remain hybridised to one or more CPNs and do not become covalently linked once the molecule comprising covalently linked functional entities has been generated.

SUMMARY OF THE INVENTION

The present invention alleviates a number of short-comings associated with prior art methods and solves a number of problems related to the limited applicability of template directed synthesis methods used for generating large libraries of molecules.

Template directed synthesis employs a single template of covalently linked nucleotides for the synthesis of a molecule. Once the template is defined by its sequence the number and kind of anti-codons or transfer units capable of hybridizing to the codons of the template have de facto also been defined. This is not the case with the quasirandom structure and function guided synthesis methods of the present invention in which a connector polynucleotide (CPN) guides the synthesis of a molecule by calling for complementary connector polynucleotides (CCPNs) capable of hybridizing to the CPN. This is illustrated in FIG. 2.

Unlike template directed synthesis methods in which the sequence of codons of the template determines the sequence of anti-codons or transfer units hybridizing to the template, the final structure of a supramolecular complex comprising a plurality a CPNs and a plurality of CCPNs cannot readily be predicted in all cases prior to carrying out the quasirandom structure and function guided synthesis methods of the present invention.

The quasirandom structure and function guided synthesis methods of the present invention—being less deterministic than template directed synthesis methods relying exclusively on a predetermined codon sequence—has a number of advantages over template directed synthesis methods.

The individual molecules of the present invention are generated during or after the formation of a higher order polynucleotide complex comprising a plurality of connector polynucleotides (CPN's) and a plurality of complementary connector polynucleotides (CCPN's) of which at least some CPN's and/or CCPN's are carrying reactants such as e.g. functional entities/chemical moieties, wherein said reactants are either precursor components to be used in the synthesis of the molecule (i.e. components which can be reacted, act as catalysers, be spatially rearranged, or otherwise altered in structure and/or function) and/or components which can otherwise be integrated into the synthesized molecule.

The association of two complementary connector polynucleotides through a connector polynucleotide ensures one or more of the following desirable characteristics:

A high reactivity between functional entities present on different CCPN's (because of a high proximity/local concentration of reactants such as functional entity reactive groups), a controllable reactant reactivity (i.e. functional entity reactive groups of complementary connector polynucleotides of a complex react with each other, and not with functional entity reactive groups of complementary connector polynucleotides of other complexes), and an efficient selection of desirable molecules is ensured through iterative cycles of screening and amplification of connector polynucleotides, optionally including one or more "shuffling" steps ("shuffling" in this context includes mixing of connector polynucleotides to obtain complexes e.g. comprising the same connector polynucleotides, but in new combinations, or located in different positions).

Further advantages of the present invention relate to desirable features of higher order hybridization complexes comprising a plurality of connector polynucleotides (CPN's) and complementary connector polynucleotides (CCPN's). The advantages include, among other things:

A desirable variability in the number of reactants which can be provided for the synthesis, i.e. the ability to vary the number of complementary connectors (CCPN's) for each molecule within a library, thus providing a high degree of flexibility in the generation of libraries of chemical compounds.

Libraries of e.g. $10^8$ or more chemical compounds can be generated with a relatively low diversity of CCPN's—unlike libraries of a similar size generated from template directed methods, which require a much higher number of anti-codons or transfer units to be used, as no variability can be achieved for the template directed methods.

A high variation in the degree of functionalization of scaffolds is possible, i.e. allowing diversification of branching degree.

It is possible to generate a library—and to further evolve the library—by exploiting CCPN "cross-talk", i.e. the ability of one CCPN reactant to preferably react with a subset of all available CCPN reactants.

The methods can employ a large set of scaffolds and allow a diverse set of attachments chemistries to be used for diversifying scaffolds or libraries of chemical compounds.

Inherent shuffling steps can be used for evolving scaffolds and chemical libraries, including steps in which connector polynucleotides are mixed to obtain complexes e.g. comprising the same connector polynucleotides, but in new combinations, or located in different positions.

Short oligonucleotides can be used in the methods of the present invention. This offers a cost effective means for generating large libraries. The oligonucleotides used in the methods of the present invention are much shorter than the often very long oligonucleotides used in prior art methods exploiting template directed synthesis of chemical compounds.

In a first aspect there is provided a method for synthesising a molecule comprising the steps of
i) providing a plurality of connector polynucleotides each capable of hybridizing to at least 1 complementary connector polynucleotide,
ii) providing a plurality of complementary connector polynucleotides selected from the group consisting of
  a) complementary connector polynucleotides comprising at least 1 functional entity comprising at least 1 reactive group,
  b) complementary connector polynucleotides comprising at least 1 reactive group,
  c) complementary connector polynucleotides comprising at least 1 spacer region,
iii) hybridizing at least 2 complementary connector polynucleotides to at least 2 connector polynucleotides,
  wherein at least 2 of said complementary connector polynucleotides comprise at least 1 functional entity comprising at least 1 reactive group,
  wherein at least 1 of said complementary connector polynucleotides hybridizes to at least 2 connector polynucleotides, and
iv) reacting at least 2, such as 3 or more functional entity reactive groups by reacting at least 1 reactive group of each functional entity,
  wherein the reaction of said functional entity reactive groups results in the formation of the molecule by covalently linking at least 2 functional entities provided by separate complementary connector polynucleotides.

In a further aspect there is provided a method for synthesising one or more molecule(s) comprising the steps of
i) providing a plurality of connector polynucleotides each capable of hybridizing to at least 1 complementary connector polynucleotide,
ii) providing a plurality of complementary connector polynucleotides selected from the group consisting of
  a) complementary connector polynucleotides comprising at least 1 functional entity comprising at least 1 reactive group,
  b) complementary connector polynucleotides comprising at least 1 reactive group,
  c) complementary connector polynucleotides comprising at least 1 spacer region,
iii) hybridizing at least 2 complementary connector polynucleotides to at least 2 connector polynucleotides,
  wherein at least 2 of said complementary connector polynucleotides comprise at least 1 functional entity comprising at least 1 reactive group,
  wherein at least 1 of said complementary connector polynucleotides hybridizes to at least 2 connector polynucleotides, and
iv) reacting at least 2, such as 3 or more functional entity reactive groups by reacting at least 1 reactive group of each functional entity,
  wherein the reaction of said functional entity reactive groups results in the formation of the molecule by covalently linking at least 2 functional entities provided by separate complementary connector polynucleotides,
  wherein the molecule comprising covalently linked functional entities is linked to a the polynucleotide part of a complementary connector polynucleotide,
  wherein the molecule does not comprise the linker and the polynucleotide part of said complementary connector polynucleotide,
  wherein complementary connector polynucleotides hybridized to connector polynucleotides are not linked by covalent bonds,
  wherein connector polynucleotides hybridized to complementary connector polynucleotides are not linked by covalent bonds, and
  wherein the method does not involve ribosome mediated translation.

In a still further aspect there is provided a method for synthesising at least one molecule comprising the steps of
i) providing a plurality of connector polynucleotides each capable of hybridizing to at least 1 complementary connector polynucleotide,
ii) providing a plurality of complementary connector polynucleotides selected from the group consisting of a) complementary connector polynucleotides comprising at least 1 reactant comprising at least 1 reactive group
b) complementary connector polynucleotides comprising at least 1 reactive group,
c) complementary connector polynucleotides comprising at least 1 spacer region,
iii) hybridizing at least 2 complementary connector polynucleotides to at least 2 connector polynucleotides,
wherein at least 2 of said complementary connector polynucleotides comprise at least 1 reactant comprising at least 1 reactive group,
wherein at least 1 of said complementary connector polynucleotides hybridizes to at least 2 connector polynucleotides, and
iv) synthesising the at least one molecule by reacting at least 2 reactants.

In a further aspect there is provided a method for synthesising at least one molecule comprising the steps of
i) providing a plurality of building block polynucleotides each capable of hybridizing to at least 1 other building block polynucleotide,
wherein said building block polynucleotides are selected from the group consisting of
a) building block polynucleotides comprising at least 1 reactant comprising at least 1 reactive group
b) building block polynucleotides comprising at least 1 reactive group,
c) building block polynucleotides comprising at least 1 spacer region,
ii) forming a hybridization complex comprising at least 4 building block polynucleotides,
wherein at least 2 of said building block polynucleotides comprise at least 1 reactant comprising at least 1 reactive group,
wherein at least 1 of said building block polynucleotide hybridizes to at least 2 other building block polynucleotides, and
iii) synthesising the at least one molecule by reacting at least 2 reactants.

In a still further aspect there is provided a method for synthesising a plurality of different molecules, said method comprising the steps of
i) providing a plurality of connector polynucleotides each capable of hybridizing to at least 1 complementary connector polynucleotide,
ii) providing a plurality of complementary connector polynucleotides selected from the group consisting of
a) complementary connector polynucleotides comprising at least 1 functional entity comprising at least 1 reactive group,
b) complementary connector polynucleotides comprising at least 1 reactive group,
c) complementary connector polynucleotides comprising at least 1 spacer region,
iii) hybridizing the plurality of connector polynucleotides and complementary connector polynucleotides, thereby forming a plurality of different hybridisation complexes, each hybridisation complex comprising at least 2 complementary connector polynucleotides and at least 2 connector polynucleotides,
wherein, for each of said hybridisation complexes,
at least 2 of said complementary connector polynucleotides comprise at least 1 functional entity comprising at least 1 reactive group, and
at least 1 of said complementary connector polynucleotides hybridizes to at least 2 connector polynucleotides, and
iv) reacting at least 2 functional entity reactive groups of each complex by reacting at least 1 reactive group of each functional entity,
wherein, for each hybridisation complex, the reaction of said functional entity reactive groups results in the formation of a different molecule by covalently linking at least 2 functional entities provided by separate complementary connector polynucleotides, thereby synthesising a plurality of different molecules.

In a still further aspect there is provided a method for identification of at least one molecule having desirable characteristics, said method comprising the steps of
i) targeting a plurality of different molecules to a potential binding partner, wherein the plurality of different molecules are a) synthesised by any of the methods cited herein for synthesising at least one molecule, or b) synthesised by the below mentioned method steps iii) and iv),
ii) selecting at least one of said molecules having an affinity for said binding partner,
iii) isolating connector polynucleotides from the selected molecules of step ii),
iv) optionally, hybridizing the connector polynucleotides isolated in step iii) to a plurality of complementary connector polynucleotides selected from the group consisting of
a) complementary connector polynucleotides comprising at least 1 functional entity comprising at least 1 reactive group,
b) complementary connector polynucleotides comprising at least 1 reactive group,
c) complementary connector polynucleotides comprising at least 1 spacer region,
reacting the functional entity reactive groups, thereby generating at least one molecule by linking at least 2 functional entities provided by separate complementary connector polynucleotides, and
performing steps i), ii), and iii) above for the at least one molecule generated in step iv), and
v) decoding the nucleic acid sequence of isolated connector polynucleotides to reveal the identity of functional entities that have participated in the formation of the molecule(s) having an affinity for said binding partner.

In a still further aspect there is provided a method for selecting at least one bifunctional molecule comprising a hybridisation complex linked to at least one molecule part comprising reacted reactants, such as covalently linked functional entities, wherein each complex comprises a plurality of connector polynucleotides (CPNs) and a plurality of complementary connector polynucleotides (CCPNs) having guided the synthesis of the molecule, wherein at least 2 of said CPNs and/or said CCPNs have each donated at least one reactant, such as at least one functional entity, to the method for synthesising the at least one molecule, wherein the complex comprises as least 1 CCPN hybridized to at least 2 CPNs, said method comprising the steps of targeting a plurality of the bifunctional molecules to a potential binding partner for the at least one molecule part of the bifunctional molecule linked by at least one linker to a CPN and/or a CCPN of the hybridization complex, wherein said binding partner has an affinity for the molecule part of the bifunctional molecule, and selecting at least one of said bifunctional molecules comprising at least one molecule part having an affinity for said binding partner. The method optionally comprises the further step of decoding the hybridisation complex, preferably by identifying the CPNs and/or the CCPNs forming the hybridisation complex, or part thereof, of the bifunctional molecule, and thereby identifying the molecule part of the bifunctional molecule. The decoding can involve ligating individual CPNs and/or ligating individual CCPNs of the hybridisation complex, optionally a ligation preceded by a polynucleotide extension reaction filling in any gaps between hybridised CPNs and/or hybridised CCPNs, amplifying the ligated CPNs and/or the ligated CCPNs, or amplifying at least part of the polynucleotide part of the ligated CPNs and/or the ligated CCPNs, sequencing the amplified part(s), and thereby determining the identity of the CPNs and/or CCPNs forming part of the hybridisation complex, or determining at least part of said identity allowing a conclusive identification of the individual CPNs and/or the individual CCPNs.

In yet another aspect there is provided a method for evolving a plurality of bifunctional molecules comprising a hybridisation complex linked to at least one molecule part comprising reacted reactants, such as covalently linked functional entities, wherein each complex comprises a plurality of connector polynucleotides (CPNs) and a plurality of complementary connector polynucleotides (CCPNs) having guided the synthesis of the molecule, wherein at least 2 of said CPNs and/or said CCPNs have each donated at least one functional entity to the method for synthesising the of at least one molecule, wherein each complex comprises as least 1 CCPN hybridized to at least 2 CPNs, said method comprising the steps of selecting at least one bifunctional molecule, optionally by performing the immediately above-cited method for selecting at least one bifunctional molecule, isolating CPNs from said complex, optionally by ligating the CPNs and cleaving the ligation product with suitable restriction nucleases, thereby obtaining isolated CPNs, further optionally by performing a polynucleotide extension reaction prior to performing the ligation reaction in order to close any gaps between the CPNs, providing a plurality of CCPNs at least some of which comprise a reactant, such as a functional entity comprising a reactive group, hybridising said isolated CPNs and said plurality of provided CCPNs, reacting reactants, such as reacting functional entity reactive groups of said CCPNs comprising such groups, optionally repeating any one or more of the aforementioned steps, and evolving a plurality of different bifunctional molecules.

In a further aspect of the invention there is provided a bifunctional molecule obtainable by any of the methods of the invention and comprising a molecule part formed by reaction of reactants, such as functional entities, and a nucleic acid part formed by hybridisation between at least 2 complementary connector polynucleotides and at least 2 connector polynucleotides, including a nucleic acid part formed by hybridisation between at least the polynucleotide entity of 2 complementary connector polynucleotides and at least the polynucleotide entity of 2 connector polynucleotides.

In yet another aspect there is provided a composition of bifunctional molecules obtainable by any of the methods of the invention, wherein each member of the composition comprises a molecule part formed by reaction of reactants, such as functional entities, and a nucleic acid part comprising a hybridisation complex between at least the polynucleotide entity of 2 complementary connector polynucleotides and at least the polynucleotide entity of 2 connector polynucleotides.

There is also provided a hybridization complex comprising a plurality of connector polynucleotides and a plurality of complementary connector polynucleotides, wherein the complex comprises as least 2 complementary connector polynucleotides hybridized to at least 2 connector polynucleotides. The hybridisation complex can be regarded as an intermediate product in the process of generating the above-mentioned bifunctional molecule(s). Accordingly, a hybridisation complex can be present prior to or during molecule synthesis, but once the molecule has been synthesised, it forms part of a bifunctional molecule further comprising the CPNs and CCPNs forming part of the hybridisation complex of the bifunctional molecule.

In yet another aspect there is provided a supramolecular complex comprising at least one molecule comprising covalently linked functional entities and a plurality of connector polynucleotides (CPNs) and a plurality of complementary connector polynucleotides (CCPNs), wherein at least some of said CPNs and/or CCPNs have donated functional entities to the synthesis of the at least one molecule, wherein the complex comprises as least 1 CCPN hybridized to at least 2 CPNs. In a further aspect there is provided a plurality of such supramolecular complexes.

DEFINITIONS

At least 1 single complementary connector polynucleotide (CCPN) hybridizes to at least 2 connector polynucleotides (CPN): The hybridization events leading to the formation of the supramolecular complex can occur simultaneously or sequentially in any order as illustrated in FIG. 2.

A bifunctional molecule comprises a (final) molecule part and a hybridisation complex part. The hybridisation complex part of the bifunctional molecule comprises at least 2 CCPNs the polynucleotide part of which (individual CCPN) is hybridised to the polynucleotide part of at least 1 CPN, wherein at least some of said hybridised CPNs and/or CCPNs have provided their reactants, such as functional groups, to the method for synthesising the at least one molecule linked to the hybridisation complex of the bifunctional molecule.

Branched CPN: Connector polynucleotide comprising one or more branching points connecting linear or branched polynucleotides.

Building block polynucleotide: Generic term for a polynucleotide part linked to either a) a reactant such as a functional entity comprising at least one reactive group (type I BBPN), or b) a reactive group (in the absence of a reactant or functional entity) (type II BBPN), or the BBPN can simply comprise a polynucleotide part comprising a spacer region for spacing e.g. functional entities of other BBPNs (type III BBPN). The term building block polynucleotide thus includes CPNs and CCPNs irrespective of their type.

Complementary connector polynucleotide (CCPN): Part of a supramolecular complex comprising a plurality of CPNs and a plurality of CCPNs as illustrated in FIG. 2. A CCPN comprises a polynucleotide part which can be linked to either a) a reactant such as a functional entity comprising at least one reactive group (type I CCPN), or b) a reactive group (in the absence of a reactant or functional entity) (type II CCPN), or the CCPN can simply comprise a polynucleotide part comprising a spacer region for spacing e.g. functional entities of other CCPNs (type III CCPN). When the polynucleotide part of a CCPN is linked to a reactant, such as a functional entity comprising at least one reactive group, or in the functional entity being covalently linked to another functional entity, or part thereof, the CCPN acts as a "donor CCPN" or as an "acceptor CCPN" and thus takes part in the method for synthesising the at least one molecule. In some embodiments, some CCPNs will be "donor CCPNs" donating functional entities to the synthesis of a molecule comprising covalently linked functional entities, whereas at least one other CCPN will be an "acceptor CCPN", or a CPN will be an "acceptor CPN". A method for synthesising at least one molecule exploiting one or more "donor CCPNs" comprising at least one reactant, such as at least one functional group, does not exclude using—in the same method—at least one "donor CPN" comprising at least one reactant, such as at least one functional group. The covalent or non-covalent bond between a functional entity and a polynucleotide part of a "donor CCPN" can be cleaved before, during, or after the synthesis and formation of the molecule comprising reacted reactants, such as covalently linked functional entities. A covalent bond will be generated between reactants or functional entities associated with an acceptor CCPN, or an acceptor CPN, during the synthesis of the molecule comprising reacted reactants, such as covalently linked functional entities. The synthesis and formation of molecules each comprising covalently linked functional entities is thus in one embodiment a result of both i) formation of covalent bonds linking functional entities present on acceptor CCPNs, and ii) cleavage of covalent bonds linking functional entities and polynucleotides of donor CCPNs. Once a molecule has been synthesised in this fashion, bonds will link individual donor CCPNs and an acceptor CCPN.

Connector polynucleotide: Part of a supramolecular complex comprising a plurality of CPNs and a plurality of CCPNs as illustrated in FIG. 2. A CPN guides the synthesis of a molecule comprising covalently linked functional entities by "calling" for CCPNs capable of hybridizing to the CPN. In some embodiments, it is preferred that the CPNs comprise only a polynucleotide part, and no reactant (or functional entity) or reactive group(s) (CPN type III). However, in other embodiments, the polynucleotide part of a CPN can be linked to at least one reactant (or functional entity) comprising at least one reactive group (CPN type 1), or the polynucleotide part of a CPN can be linked to a reactive group (in the absence of a reactant or functional entity) (CPN type II).

Decoding: The nucleic acid part of a CPN or a CCPN harbours information as to the identity of the corresponding reactant or functional entity linked to the nucleic acid part of the CPN or the CCPN. Following a selection step the functional entities which have participated in the formation of the encoded molecule can be identified. The identity of a molecule can be determined if information on the chemical entities, the synthesis conditions and the order of incorporation can be established.

The nucleic acid part of the CCPNs or CPNs of successful hybridization complexes can be decoded separately, or the various nucleic acid strands can be ligated together prior to decoding. In one embodiment of the invention individual CPNs are ligated together prior to decoding to ease the handling of the various informative nucleic acid strands, i.e. the polynucleotide part of the individual CPNs having participated in the synthesis of the at least one molecule. A ligation product between individual CPNs, or between individual CCPNs, of a selected bifunctional molecule is referred to below as an identifier sequence. It may be sufficient to obtain information on the chemical structure of the various functional entities that have participated in the synthesis of the at least one molecule in order to deduce the full structure of the molecule, as structural constraints during the formation can aide the identification process. As an example, the use of different kinds of attachment chemistries may ensure that a chemical entity on a building block can only be transferred to a certain position on a scaffold. Another kind of chemical constrains may be present due to steric hindrance on the scaffold molecule or the functional entity to be transferred. In general however, it is preferred that information can be inferred from the identifier sequence that enable the identification of each of the functional entities that have participated in the formation of the encoded molecule along with the point in time in the synthesis history when the chemical entities have been incorporated in the (nascent or intermediate) molecule.

Although conventional DNA sequencing methods are readily available and useful for this determination, the amount and quality of isolated bifunctional molecule hybridisation complexes linked to a molecule having the desired property may require additional manipulations prior to a sequencing reaction. Where the amount is low, it is preferred to increase the amount of the identifier sequence by polymerase chain reaction (PCR) using PCR primers directed to primer binding sites present in the identifier sequence. In addition, the quality of the library may be such that multiple species of different bifunctional molecules are co-isolated by virtue of similar capacities for binding to a target. In cases where more than one species of bifunctional molecule are isolated, the different isolated species can suitably be separated prior to sequencing of the identifier oligonucleotide.

Thus in one embodiment, the different identifier sequences of the isolated bifunctional complexes are cloned into separate sequencing vectors prior to determining their sequence by DNA sequencing methods. This is typically accomplished by amplifying all of the different identifier sequences by PCR, and then using unique restriction endonuclease site(s) on the amplified product to directionally clone the amplified fragments into sequencing vectors. The cloning and sequencing of the amplified fragments is a routine procedure that can be carried out by any of a number of molecular biological methods known in the art.

Alternatively, the bifunctional complex or the PCR amplified identifier sequence can be analysed in a microarray. The array may be designed to analyse the presence of a single codon or multiple codons in a identifier sequence.

Functional entity: Part of a CPN or a CCPN. Functional entities comprise at least one reactive group. The functional entity comprises a part or an intermediate of the molecule to be synthesised. A functional entity can also comprise the product of a reaction having previously taken place between separate functional entities, i.e. the term also applies to intermediate products being generated prior to or during the synthesis of the molecule.

The functional entity of a CPN or CCPN serves the function of being a precursor for the structural entity eventually appearing on the encoded molecule. Therefore, when it is stated in the present application that a functional entity is linked to another functional entity through the reaction of the reactive groups of respective functional entities, it is to be understood that not necessarily all the atoms of the original functional entity is to be found on the final molecule having been synthesised. Also, as a consequence of the reactions involved in the linking, the structure of the functional entity can be changed when it appears on the encoded molecule. Especially, the cleavage resulting in the release of the functional entity may generate reactive group(s) which in a subsequent reaction can participate in the formation of a connection between the (nascent or intermediate) molecule and a further functional entity. Furthermore, two or more functional entities may generate an intermediate which can be reacted with a third (or further) functional entity to form a nascent or final molecule.

The connection or linking between functional entities or, alternatively, a functional entity and a nascent encoded molecule, is aided by one or more reactive groups of the functional entities. The reactive groups may be protected by any suitable protecting groups which need to be removed prior to the linking of the functional entities. Dependent on the reaction conditions used, the reactive groups may also need to be activated. A functional entity featuring a single reactive group may suitably be used i.a. in the end positions of polymers or to be reacted with a scaffold, whereas functional entities having two or more reactive groups intended for the formation of linkage between functional entities, are typically present as scaffolds or in the body part of a polymer. A scaffold is a core structure, which forms the basis for creating multiple variants of molecules based on the same set of functional entities to be reacted in different combinations in order to generate the variants. The variant forms of the scaffold is typically formed through reaction of reactive groups of the scaffold with reactive groups of other functional entities, optionally mediated by fill-in groups or catalysts, under the creation of a covalent linkage.

Functional entity reactive group: Each functional entity comprises at least one reactive group the reaction of which with a reactive group of a separate functional entity results in the formation of covalently linked functional entities, or part thereof.

A reactive group of a functional entity may be capable of forming a direct linkage to a reactive group of another functional entity, or a nascent or intermediate molecule, or a reactive group of a functional entity may be capable of forming a connection to a reactive group of another functional entity through a bridging fill-in group. It is to be understood that not all the atoms of a reactive group are necessarily maintained in the connection formed. Rather the reactive groups are to be regarded as precursors for the linkage formed.

Hybridization complex: Plurality of CPN's hybridised to a plurality of CCPN's, wherein one or more reactants or functional entities or intermediate molecules can be linked to one or more CPN's and/or CCPN's. Accordingly, a single intermediate molecule can be linked to either a CPN and/or a CCPN, and different reactants or functional entities or intermediate molecules can be linked to the same or different CPN(s) or CCPN(s). Once the final molecule has been formed, the term hybridisation complex is no longer used, instead, the term bifunctional molecule comprising a (final) molecule part and a hybridization complex part is used. The overlap of complementary polynucleotides of CPNs and CCPNs hybridising to one another is preferably 4 or more nucleotides, such as e.g. 6 nucleotide overlaps, for example overlaps of 10-12 nucleotides.

Linear CPN: CPN comprising a sequence of covalently linked nucleotides.

Molecule: Molecule comprising covalently linked functional entities, or the molecule being the reaction product when reactive groups of different (i.e. separate) functional entities are reacted and functional entities are joined together or linked to a scaffold. The molecule can be linked to the polynucleotide part of a CCPN by a linker. In one embodiment, neither the linker nor the polynucleotide part of the CCPN forms part of the molecule. The formation of a molecule involves in one embodiment the transfer of at least one functional entity, or part thereof, a) from one or more CCPN(s) to one or more separate CCPN(s), and/or b) from one or more CPN(s) to one or more separate CPN(s), and/or c) from one or more CPN(s) to one or more CCPN(s), and/or d) from one or more CCPN(s) to one or more CPN(s), preferably by reacting at least 2, such as at least 3, 4, 5, 6, 7, 8, 9, 10, 11, 12, 13, 14, 15, 16, 17, 18, 19, functional entity reactive groups in order to synthesise the molecule. Either before, during, or after the transfer of the at least one functional entity from one building block polynucleotide to another, a covalent bond between the at least one functional entity and the polynucleotide of the donor CCPNs is cleaved. Once a molecule has been synthesised in this fashion, no donor CCPNs will be linked to each other by covalent bonds, and no covalent bonds will link individual donor CCPNs and an acceptor CCPN.

Other reactive groups: Groups the reaction of which does not result in the formation of a molecule comprising covalently linked functional entities. The reaction of other reactive groups does not involve the donation of a functional entity or a part thereof from one CCPN to another CCPN.

Plurality: At least 2, such as 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, such as 45, 50, 55, 60, 65, 70, 75, 80, 85, 90, 95, 100, for example, 200, 300, 400, 500, 600, 700, 800, 900, 1000, such as more than 1000.

Reactant: Precursor moiety for a structural unit in the synthesised molecule. The reaction of reactants result in the formation of at least one molecule in accordance with the methods of the present invention.

Reacting functional entity reactive groups: A molecule is generated by reactions involving functional entity reactive groups. Reacting functional entity reactive groups of separate functional entities results in linking the functional entities or a part thereof by covalent bonds. Types of reactive groups and types of reactions involving such reactive groups are listed in FIG. 23. The listing is merely exemplifying and not exhaustive.

Reactive group: Activatable part of e.g. a reactant, such as a functional entity, i.e. a (reactive) group forming part of, being integrated into, being linked to, or otherwise associated with, a building block polynucleotide of type I as designated herein. A reactive group, such as e.g. a catalyst, can also occur on its own without forming part of, being integrated into, being linked to, or otherwise associated with, a reactant, such as a functional entity. In the latter case the reactive group is linked to the polynucleotide part of a building block polynucleotide of type II as designated herein.

Spacer region: Region on a CPN or CCPN capable of separating and/or spatially organising functional entities located on adjacently positioned CPNs or CCPNs in a hybridisation complex. In one embodiment the spacer region is the region of a building block polynucleotide not hybridised to another building block polynucleotide. The polynucleotide part of both CPNs and CCPNs can comprise a spacer region, optionally in the absence of a functional entity or a reactive group linked to said polynucleotide part. In some embodiments, a building block polynucleotide comprising a spacer region in the polynucleotide part of the building block polynucleotide does not comprise a reactant or a functional entity or a reactive group (participating in molecule formation) linked to said polynucleotide part of said building block polynucleotide. However, building block polynucleotides comprising such reactants or functional entities or reactive groups linked to the polynucleotide part of the building block polynucleotide may further comprise a spacer region, such as e.g. a region of the polynucleotide part of the building block polynucleotide which does not hybridise to the polynucleotide part of other building block polynucleotides. In such embodiments, it will be understood that CPNs of type III and CCPNs or type III (as designated herein elsewhere) do not also comprise one or more reactants, or one or more functional entities, or one or more reactive groups participating in molecule formation. Spacer regions can be designed so that they are capable of self-hybridization and hair-pin structure formation. Preferred "spacer regions" are polynucleotides to which no functional entities and no reactive groups are attached.

Zipper box: Linkers linking functional entities to e.g. the polynucleotide part of a CPN or a CCPN can comprise a "zipper box". Two linkers may be provided with a zipper box, i.e. a first linker comprises a first part of a molecule pair being capable of reversible interaction with a second linker comprising the second part of the molecule pair. Typically, the molecule pair comprises nucleic acids, such as two complementary sequences of nucleic acids or nucleic acid analogs. In a certain aspect, the zipper domain polarity of the CCPN harbouring the first linker attached to the first functional entity is reverse compared to the zipper domain polarity of the CCPN harbouring the second functional entity. Usually, the zipping domain is proximal to the functional entity to allow for a close proximity of the functional entities. In preferred embodiments, the zipping domain is spaced form the functional entity with no more than 2 nucleic acid monomers. Typically, the zipping domain sequence comprises 3 to 20 nucleic acid monomers, such as 4 to 16, and preferably 5 to 10, depending on the conditions used.

The annealing temperature between the nucleic acid part of the CCPN and a CPN is usually higher than the annealing temperature of the zipper box molecule pair to maintain the hybridisation complex during the reaction. Usually, the difference between the annealing temperatures is 10° C., such as 25° C., or above. In a certain embodiment of the invention, the conditions during assembling of the hybridisation complex includes a concentration of the CCPN and CPN which is higher than the concentration during reaction to allow for optimal dimerisation conditions for the two parts of the molecule pair. The concentration during the assembly of the hybridisation complex is in a preferred aspect at least 10 times higher compared to the concentration used for dimerisation of the to parts of the molecule pair. In a certain aspect, the reaction step is performed by altering the temperature below and above the annealing temperature of the zipping domain, however ensuring that the hybridisation complex retains its integrity.

Figure 1:
FIG. 1.

The figure illustrates different examples of complementary connector polynucleotides (CCPN's).

A.) A CCPN containing an oligonucleotide/polynucleotide sequence, a linker and a functional entity carrying one or more reactive groups. The linker may optionally be cleavable and may comprise an oligonucleotide, a natural or unnatural peptide or a polyethyleneglycol (PEG), a combination thereof or other linkers generally used in organic synthesis, combinatorial chemistry or solid phase synthesis.

B.) Similar to A with a different positioning of the reactive group.

C.) A combination of type A and type B.

D.) This CCPN only contains a reactive group and not a functional entity in the sense of types A, B and C.

E.) A spacer CCPN without functional entity.

FIG. 2.

The figure illustrates the overall concept of the present invention. A set of CCPN's are mixed either sequentially or simultaneously with a set of CPN's, whereby at least two complementary connector polynucleotides hybridize to at least two connector polynucleotides, wherein at least two of said complementary connector polynucleotides comprise at least one functional entity comprising at least one reactive group, and wherein at least one of said complementary connector polynucleotides hybridizes to at least two connector polynucleotides.

In the next step, reaction occurs between reactive groups on functional entities, whereby a molecule is obtained by linking at least two functional entities, each provided by a separate complementary connector polynucleotide, by reacting at least one reactive group of each functional entity. If a number of such hybridization complexes are formed a number of molecules will be synthesized. If this is performed in one tube, a mixed library of compounds is prepared. Such molecules, attached to a CCPN or a number of CCPN's, form together with the CPN's, to which they hybridize, a complex.

The library of compounds/complexes may then be assayed for specific properties such as e.g. affinity or catalytic activity, and compounds/complexes with such activity may be isolated. The CPN's and/or CCPN's of such complexes may be isolated and amplified. Such amplified CPN's may go into further rounds of library generation, whereby a new library of compounds/complexes will be formed, a library which is enriched in molecules with properties corresponding to the properties assayed for.

FIG. 3.

The figure illustrates a set of different molecules which may be formed by the process of the present invention through the steps described above for FIG. 2. The figure serves only for illustrative purposes and is not in any way intended to limit the scope of the present invention.

FIG. 4.

The figure illustrates various hybridisation complexes comprising CPNs and CCPNs. Reactants or functional entities the reaction of which generates the at least one molecule is illustrated by capital letters (X, Y, Z, etc.). For illustration purposes the functional entities remain associated with the "donor CCPNs" (or "donor CPNs"), however, the reactants can react prior to, during or after the formation of the hybridisation complexes indicated in the figure. Once the reactants have reacted and the molecule has been generated, a bifunctional molecule is formed. The reaction of reactive groups can involve e.g. reacting at least one reactive group of each reactant or functional entity, or it can involve reacting one reactive group of a plurality of reactants with a plurality of reactive groups of a single reactant, typically a scaffold moiety. The hybridization complexes can be linear or circular as illustrated in the figure. The CPNs and/or the CCPNs can be linear or branched. The circular symbol with an x indicates a CPN/CCPN in an orientation perpendicular to the plane of the paper.

FIG. 5.

The figure illustrates a further set of examples of CCPN's, wherein the linker maybe placed at one end of the polynucleotide sequence. In examples E. and F. the CCPN's neither carries a functional entity nor a reactive group. In example E. the CCPN may be capable of self association e.g. through complementary nucleotide sequences, whereby hybridization can occur. In example F., part of the CCPN loops out upon association such as e.g. hybridization with a CPN. In this example no self association occurs.

FIG. 6.

Figure 2:
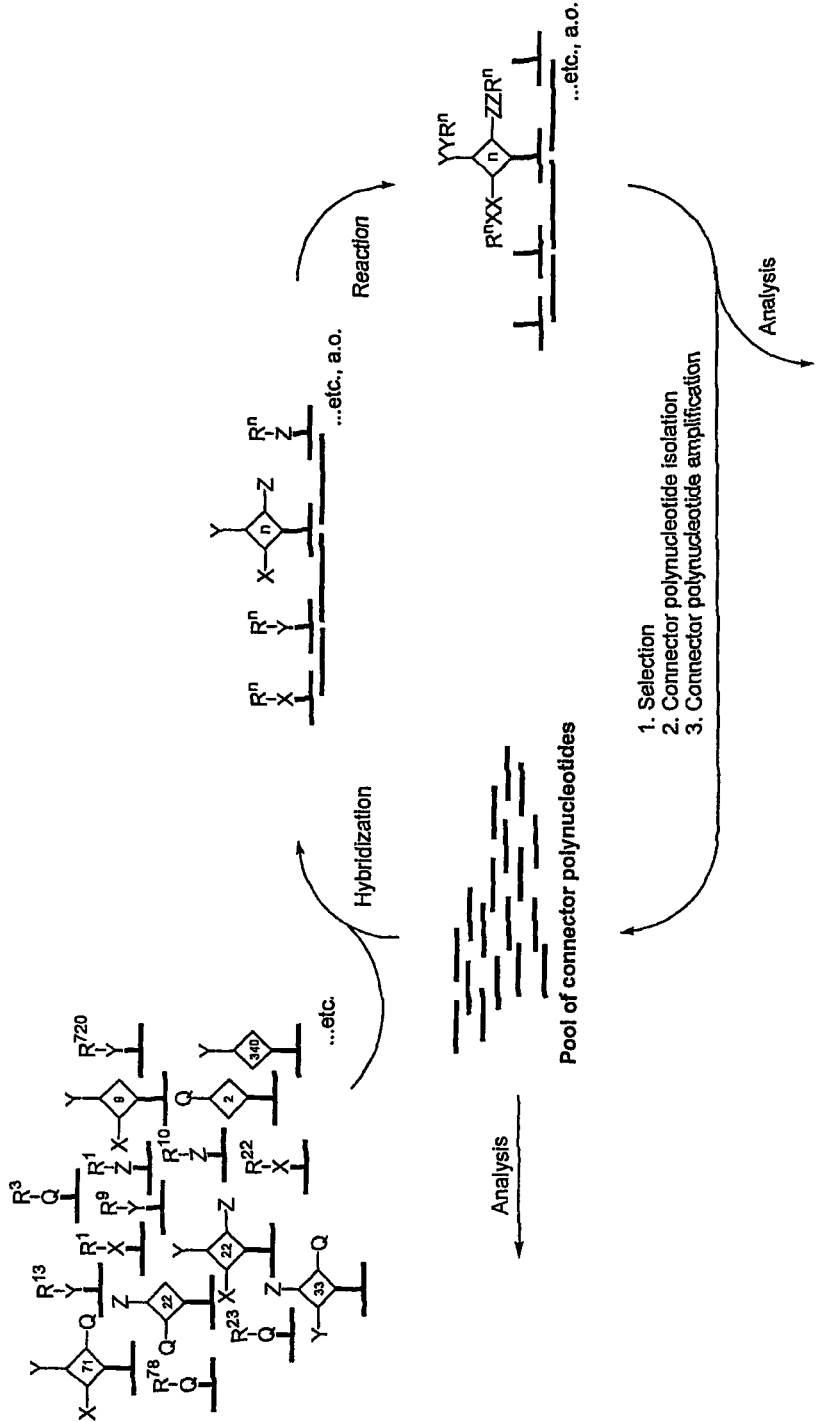

The figure illustrates one embodiment of the concept described and shown in FIG. 2. In this embodiment some or all polynucleotides of CCPN's are ligated together and some or all polynucleotides of CPN's are ligated together. Depending on the number of CCPN's and CPN's in each individual complex formed, different lengths of ligated CPN's may be isolated. Alternatively, the ligated products are not isolated, but rather is followed by an amplification step by e.g. PCR, which will selectively amplify the ligated CPNs. These ligated CPN's may undergo PCR and be analysed by e.g. sequencing. The ligated CPN's may be fragmentalised again, e.g. through the use of restriction enzymes.

FIG. 7.

Figure 6:
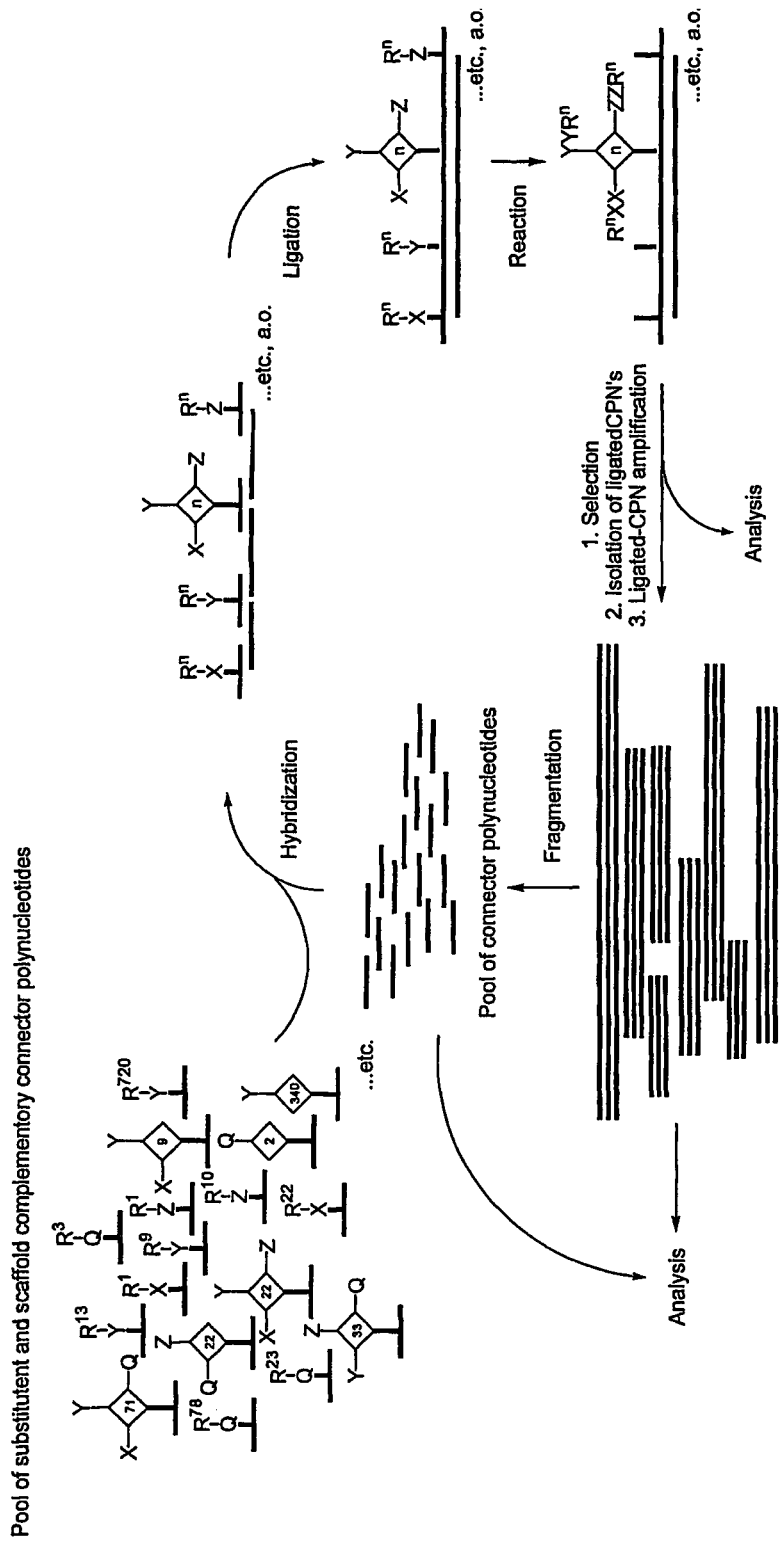
Figure 7:
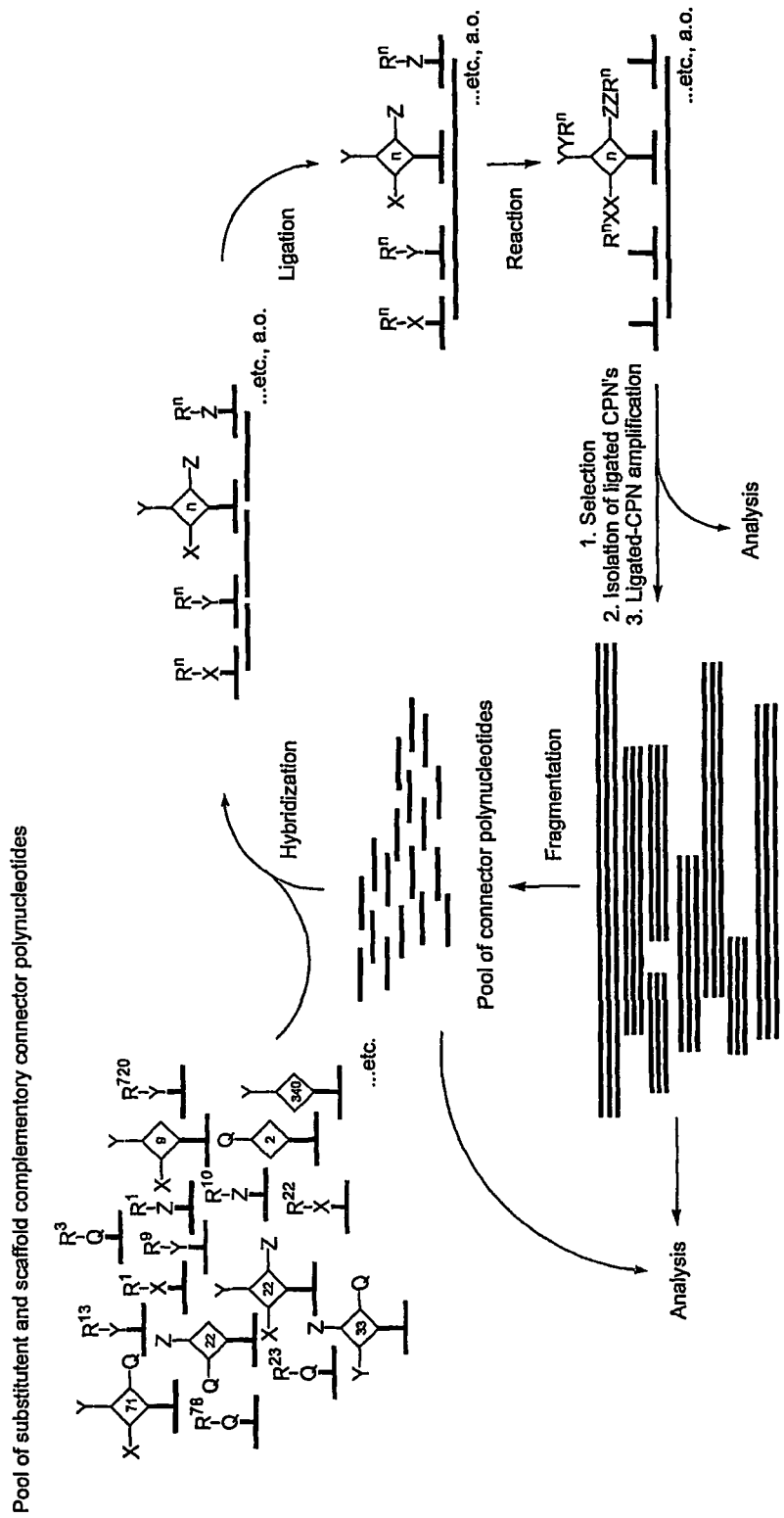

As in FIG. 6 wherein some or all the CPN's in each complex are ligated together whereas the CCPN's are not. This may be achieved e.g. if a gap between the polynucleotide sequences of CCPN's exists.

FIG. 8.

As in FIG. 6 wherein some or all the CCPN's in each complex are ligated together whereas the CPN's are not. This may be achieved e.g. if a gap between the polynucleotide sequences of CPN's exists. In this embodiment fragmentalisation of ligated CPN's is not performed during the process.

FIG. 9.

Figure 9:
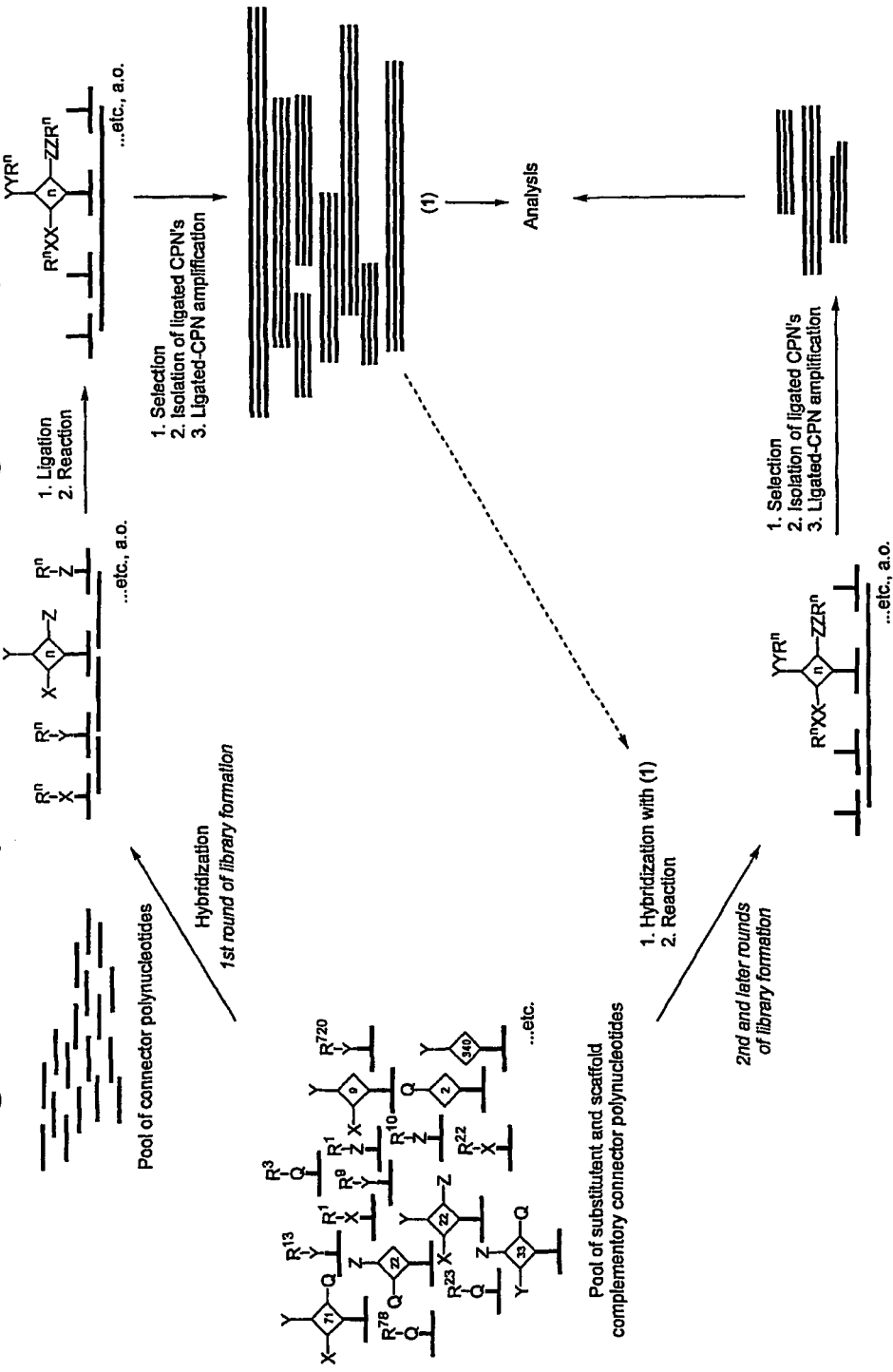
Figure 10:
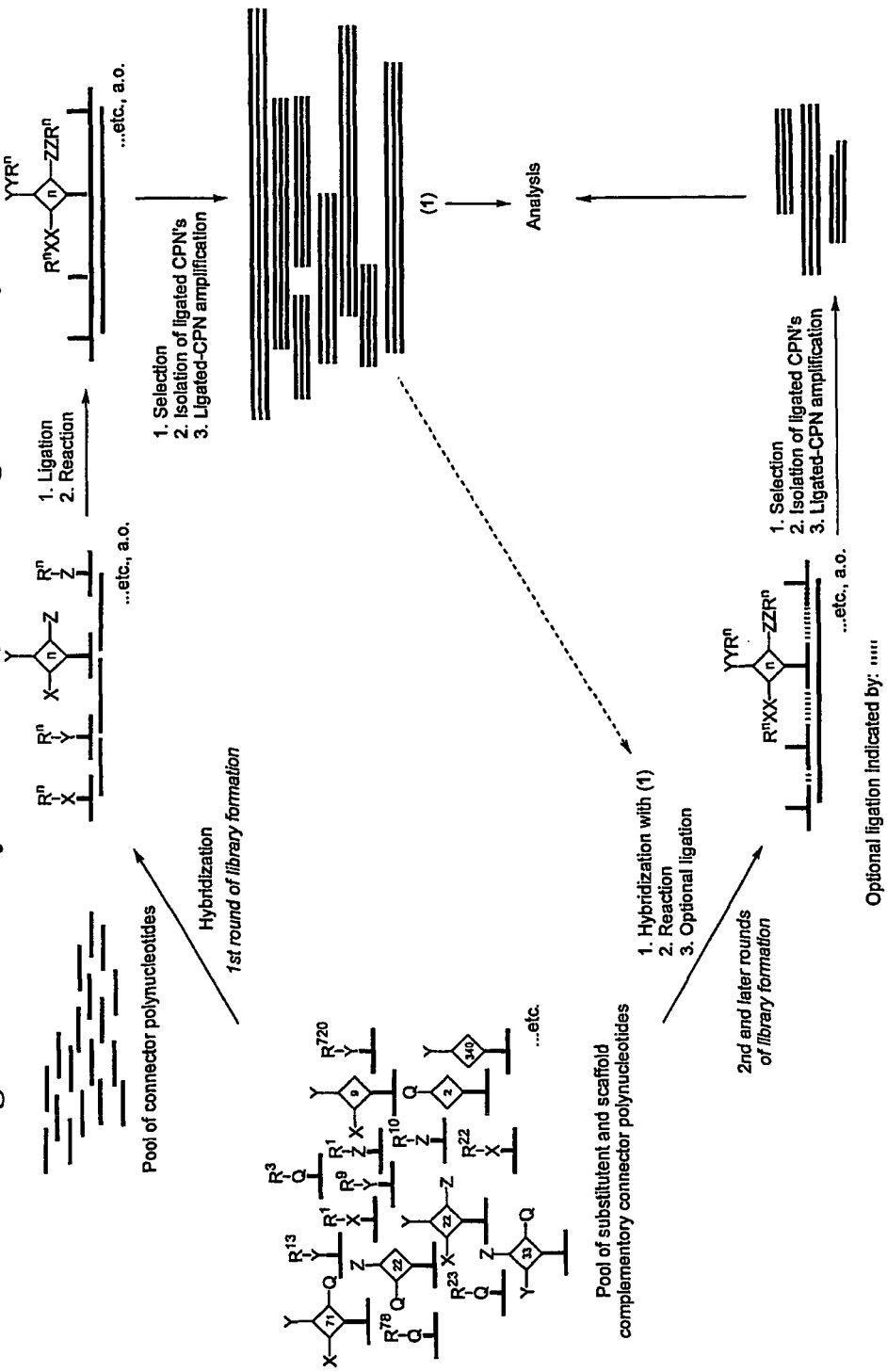

FIG. 9 illustrates a method for the formation, screening and analysis of a library.

FIG. 10.

As in FIG. 6 for the first round of library formation, however, with the optional omission of fragmentalisation of ligated CPN's in second and later rounds of library formation and with the optional ligation of CCPN's in the second and later rounds of library formation. If fragmentalization (not shown) is performed during rounds libraries will be formed in such rounds as shown for the $1^{st}$ round of library formation.

FIG. 11.

As in FIG. 6, except that the steps of ligation and reaction of functional entities have been interchanged, such that reaction of functional entities occurs prior to ligation. Here, the ligation serves as an introductory step for the amplification of the CPNs and CCPNs (by e.g. PCR). Alternatively, a "ligated-CPN product" and its amplification may also be obtained by performing a PCR after the reaction step, without the addition of primers. This will lead to the assembly of the various CPNs into one strand; the product can then be amplified by the addition of external primers.

FIG. 12.

Figure 11:
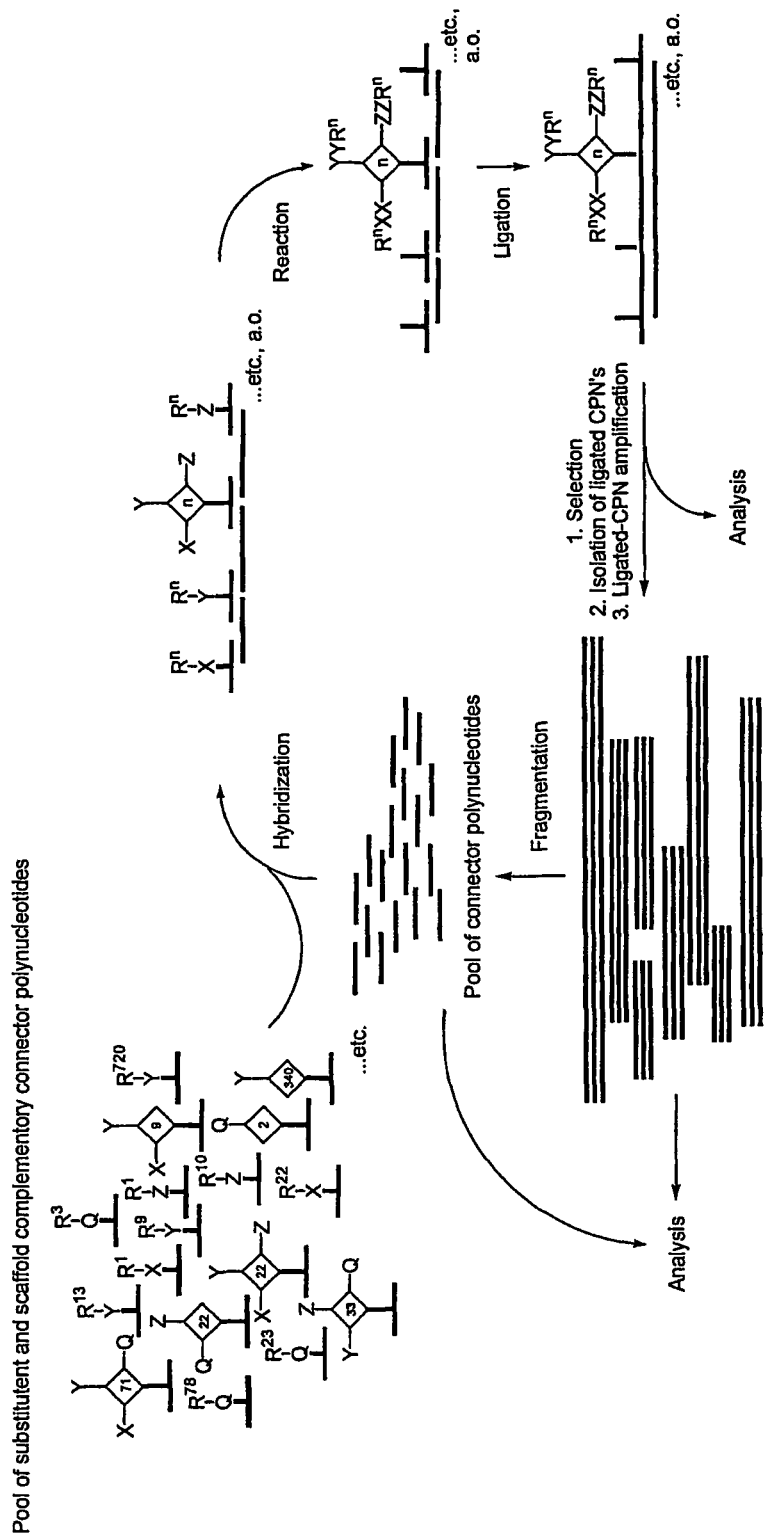
Figure 12:
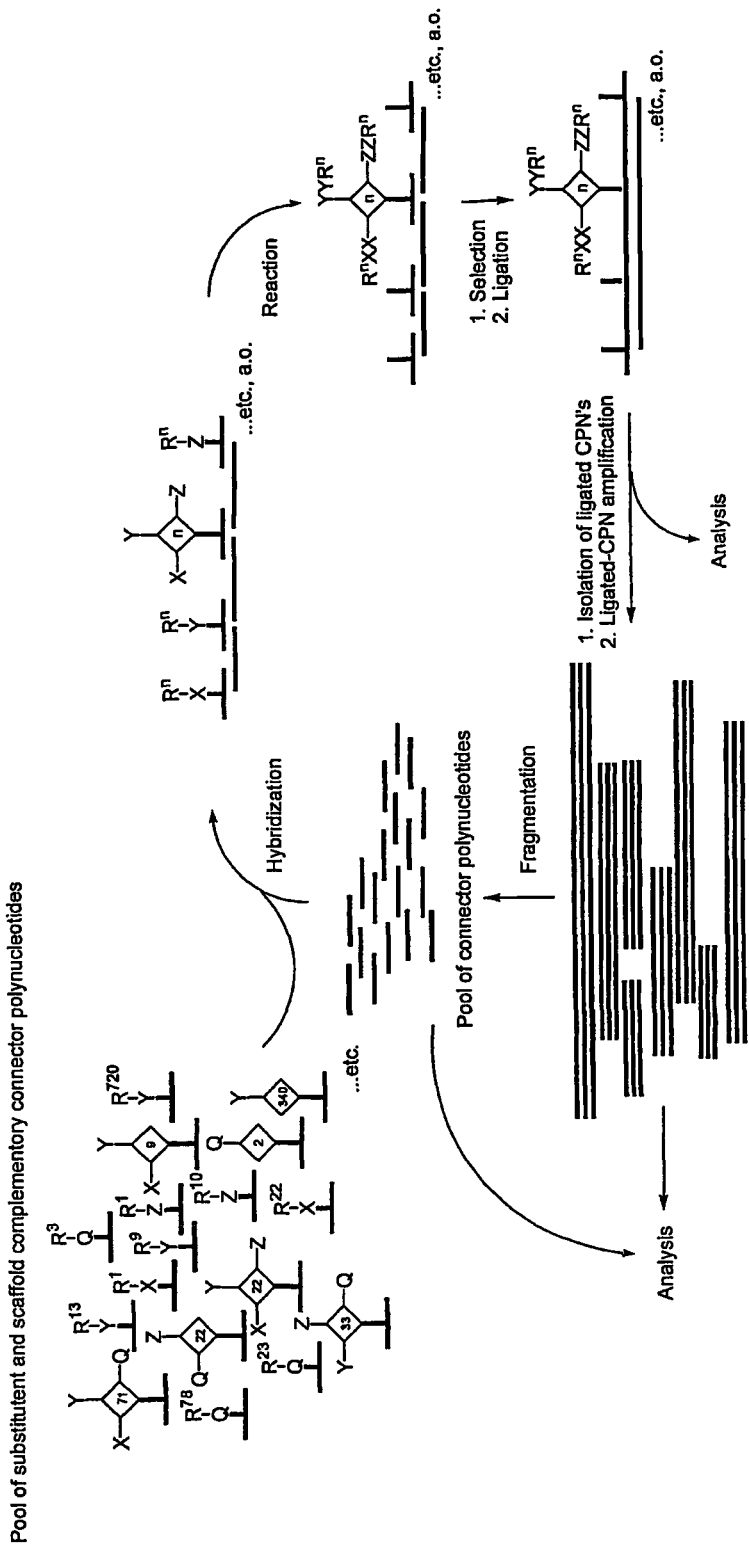
Figure 13:
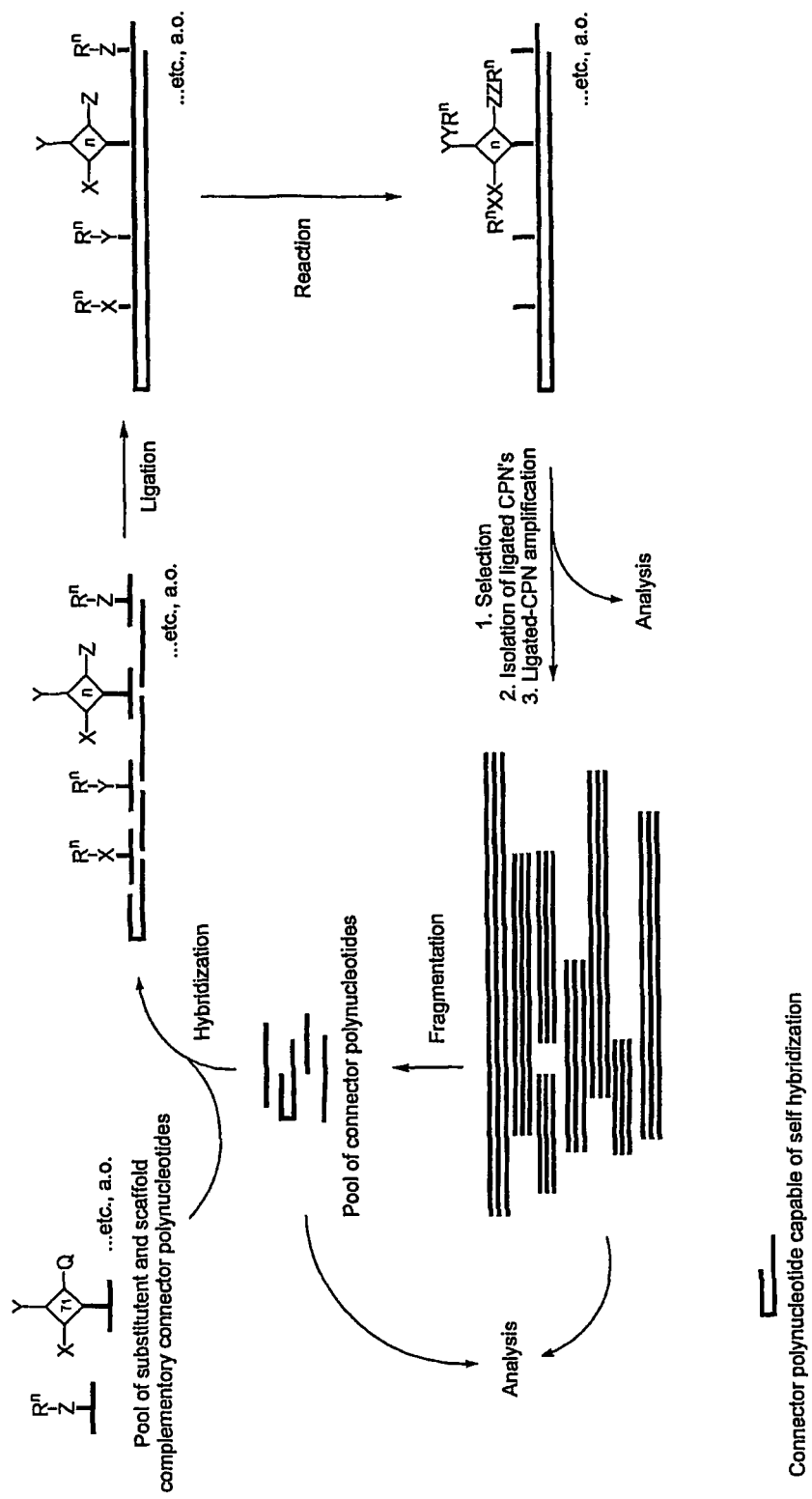
Figure 14:
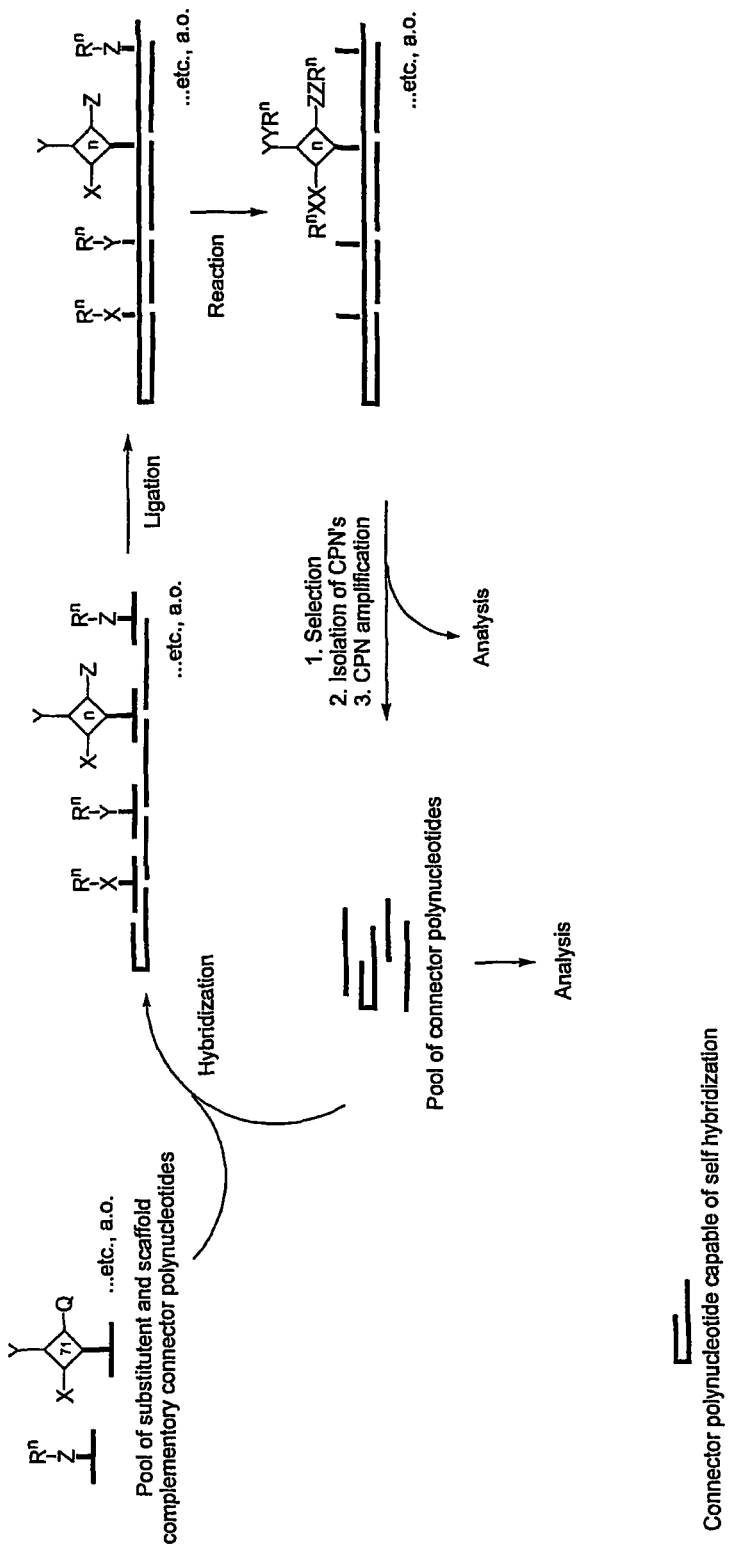
Figure 15:
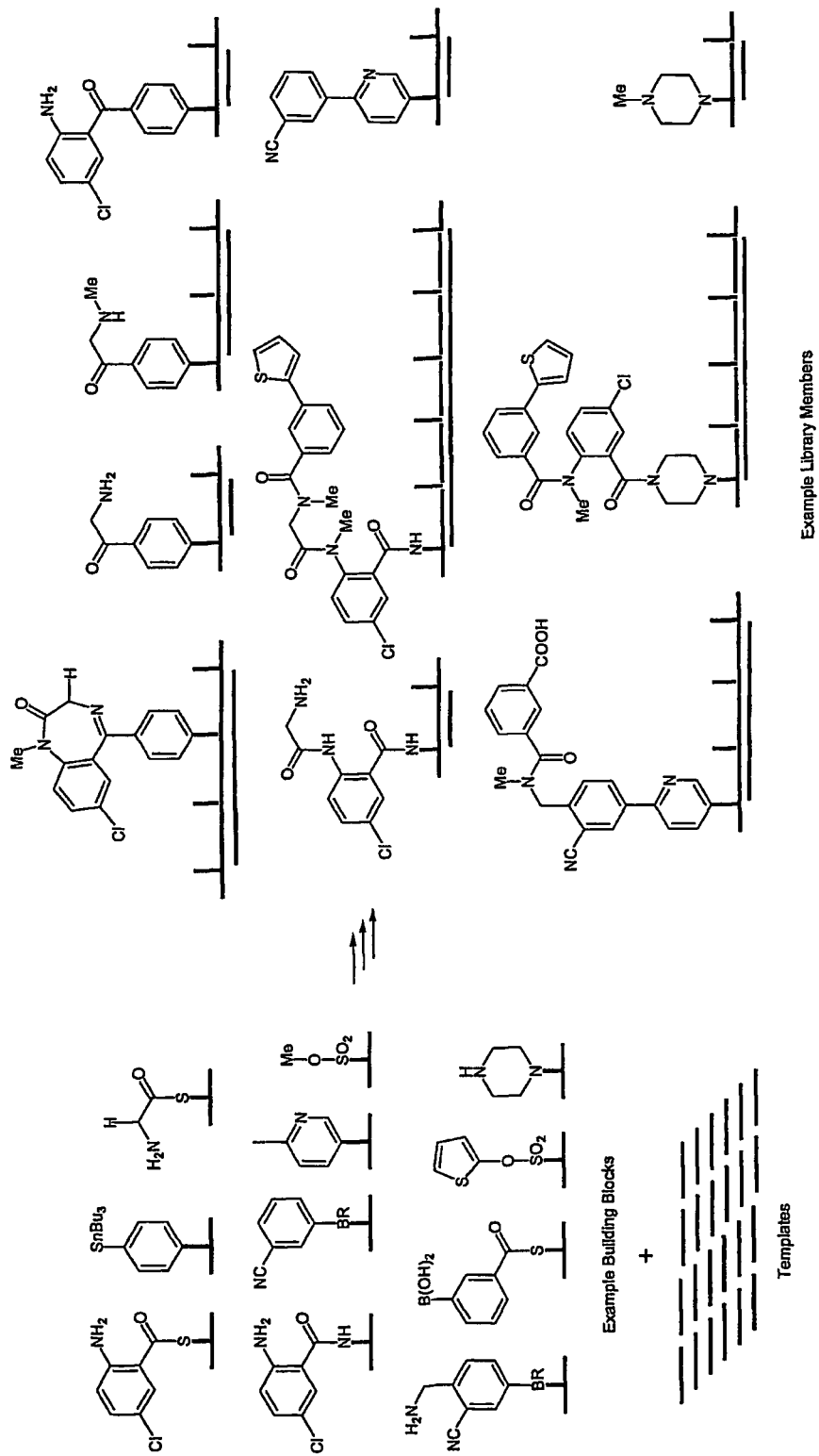
Figure 16:
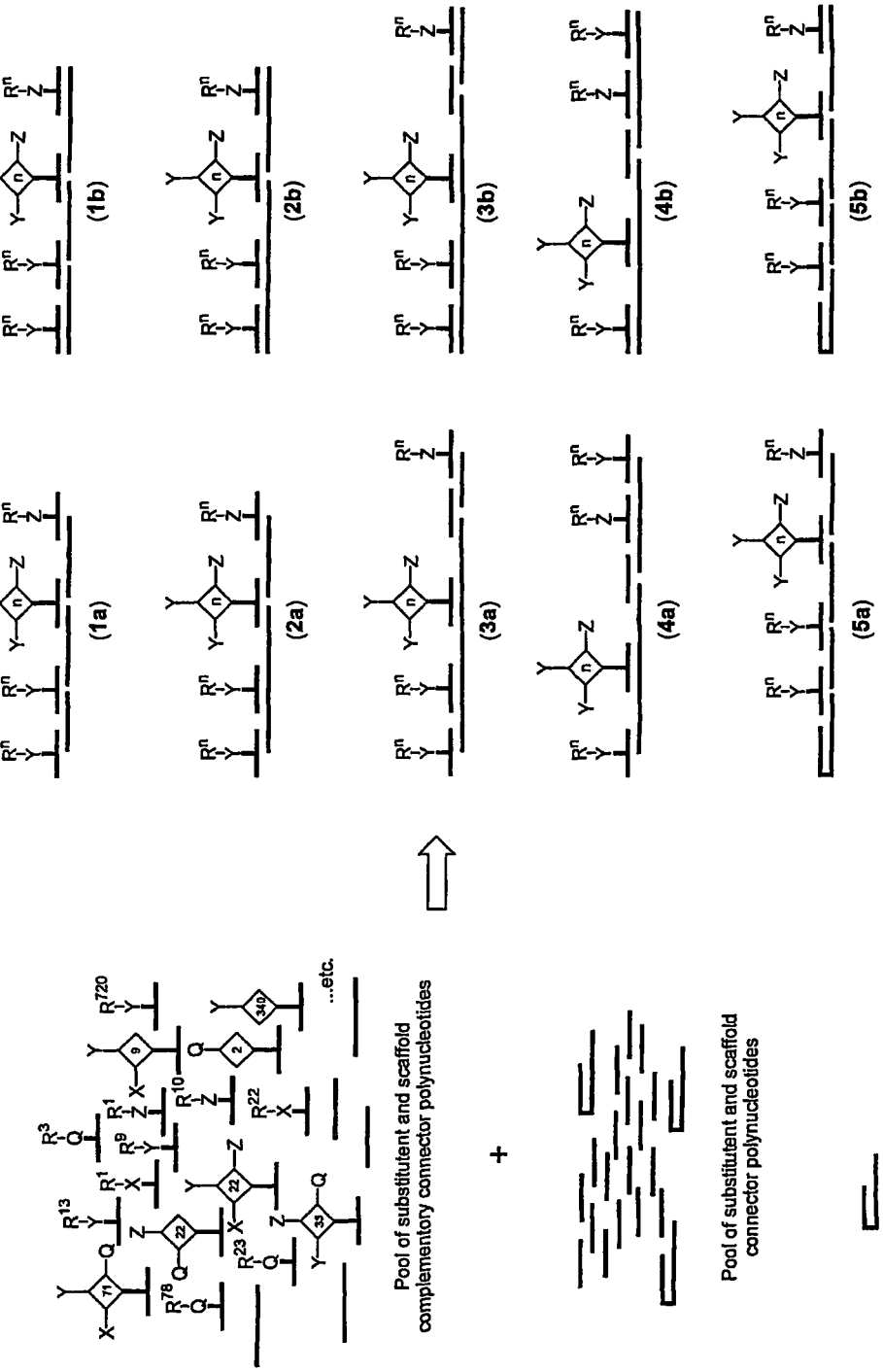
Figure 17:
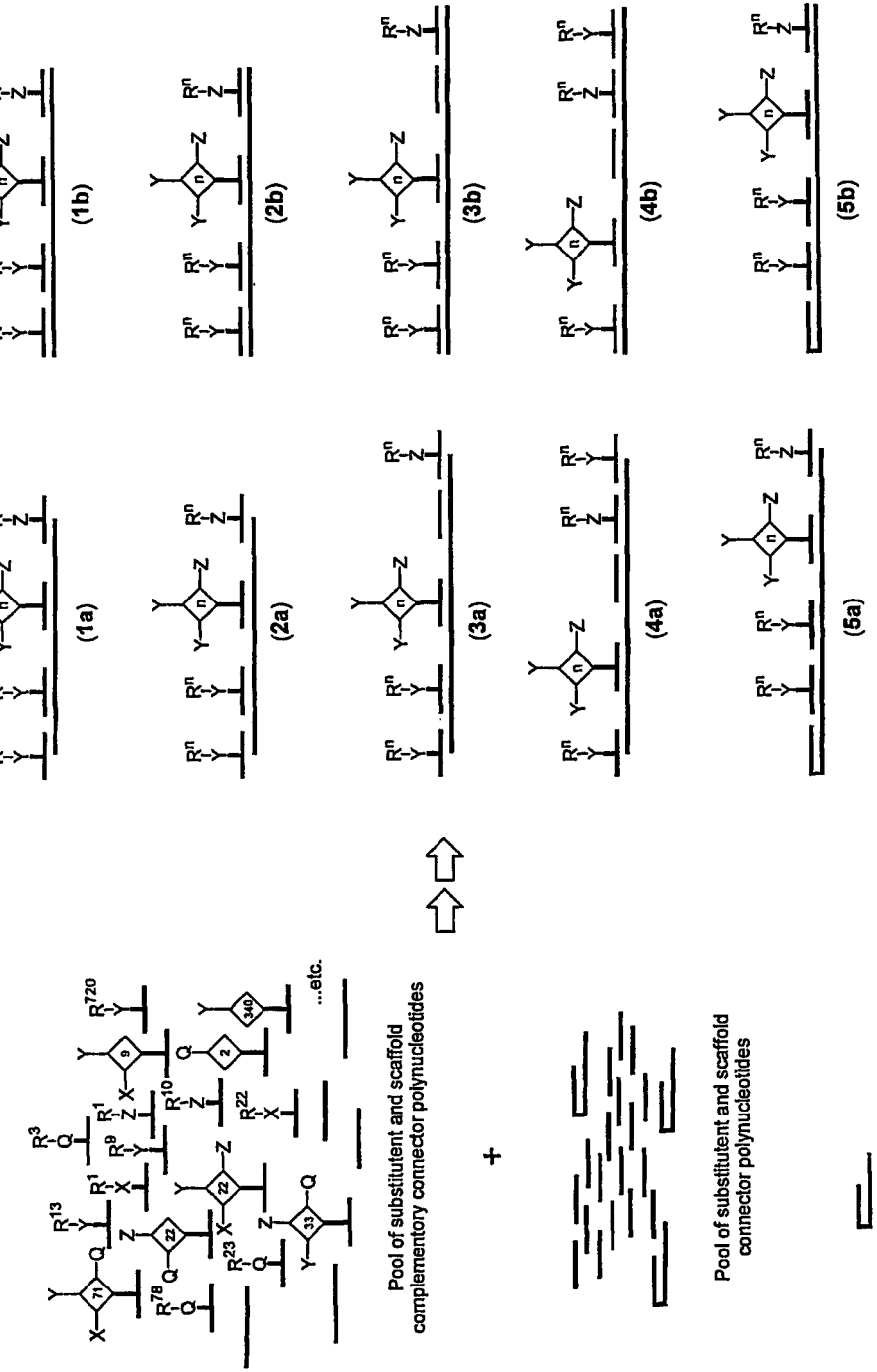
Figure 18:
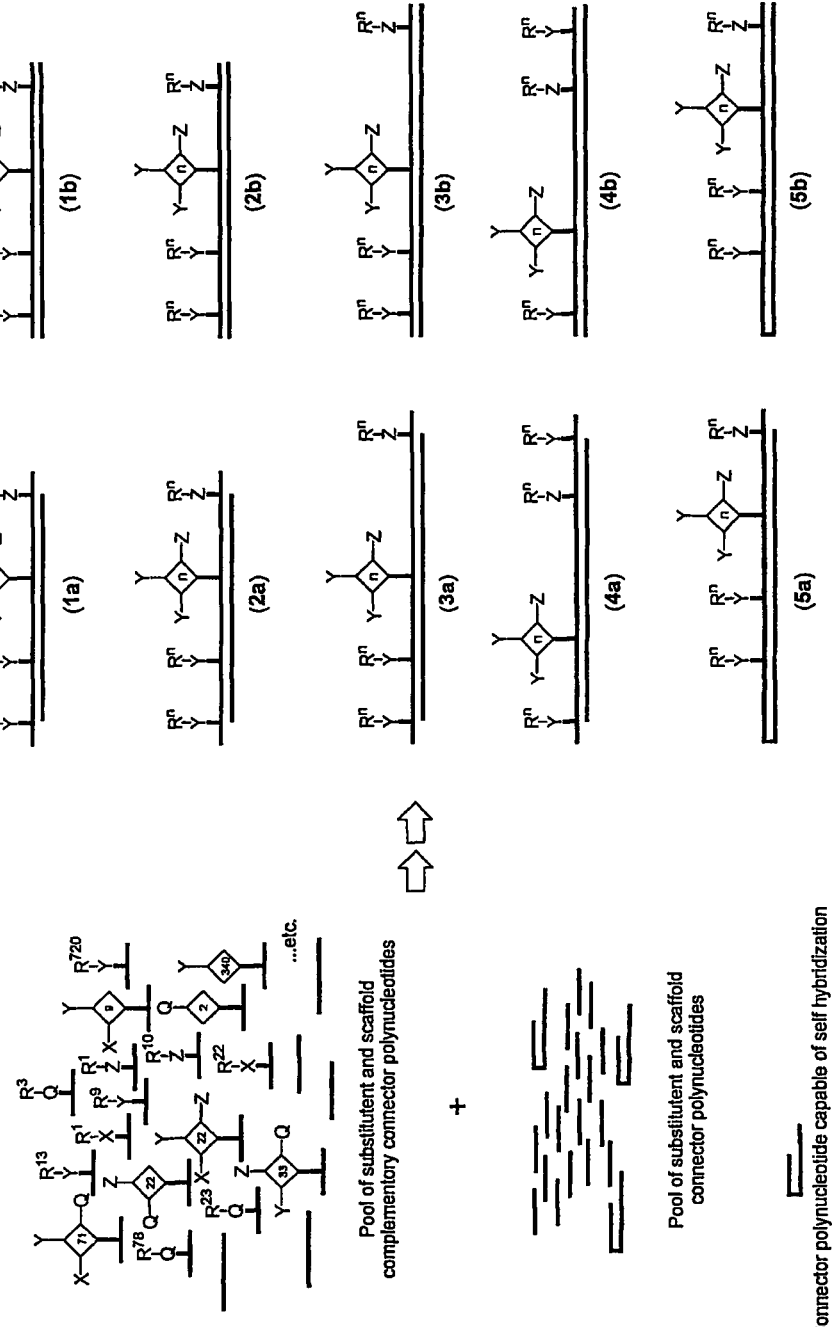
Figure 19:
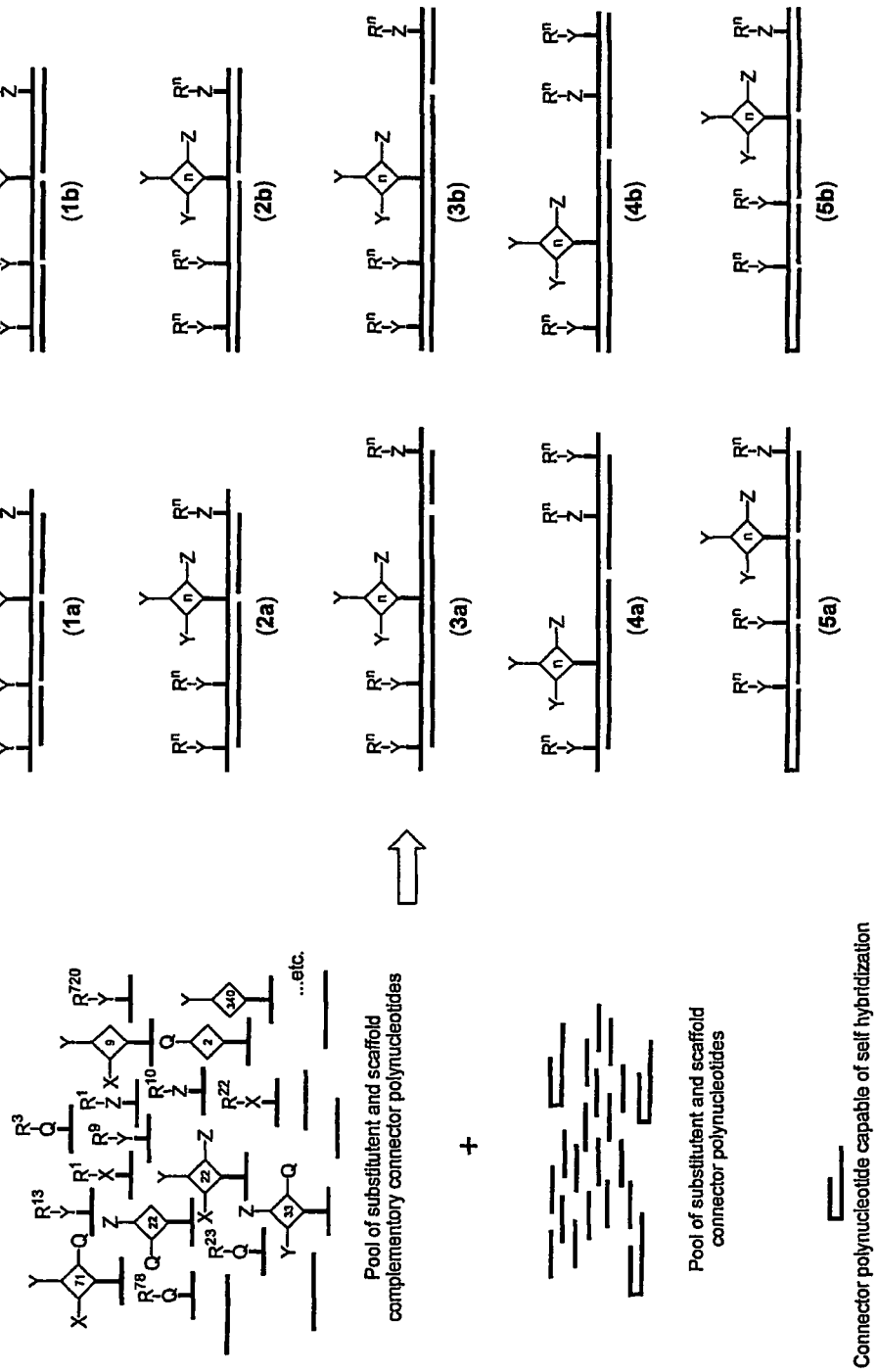
Figure 20:
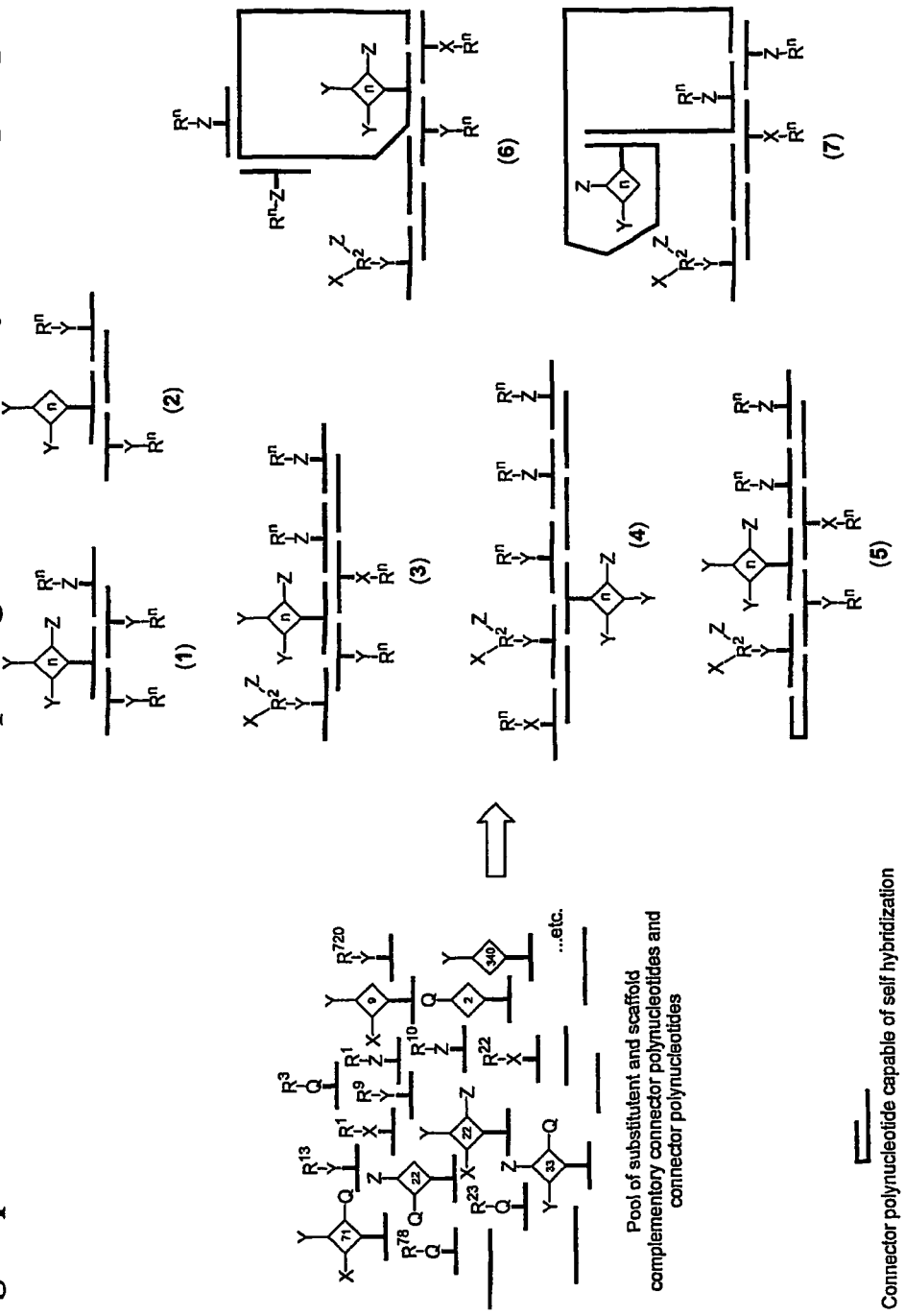

As in FIG. 6, wherein the steps of ligation and selection have been changed, such that selection occurs prior to ligation. As in FIG. 11, instead of ligating, PCR without external primers can be performed, followed by PCR including external primers.

FIG. 13.

As in FIG. 6, wherein some CPN's are capable of self hybridization, whereby CCPN's and CPN's in each complex may be linked. The ligation product following selection may optionally be treated with e.g. restriction enzymes to allow the ligated CPN's to be isolated or non-ligated CPN's to be isolated through partial or total fragmentalisation.

FIG. 14.

Figure 8:
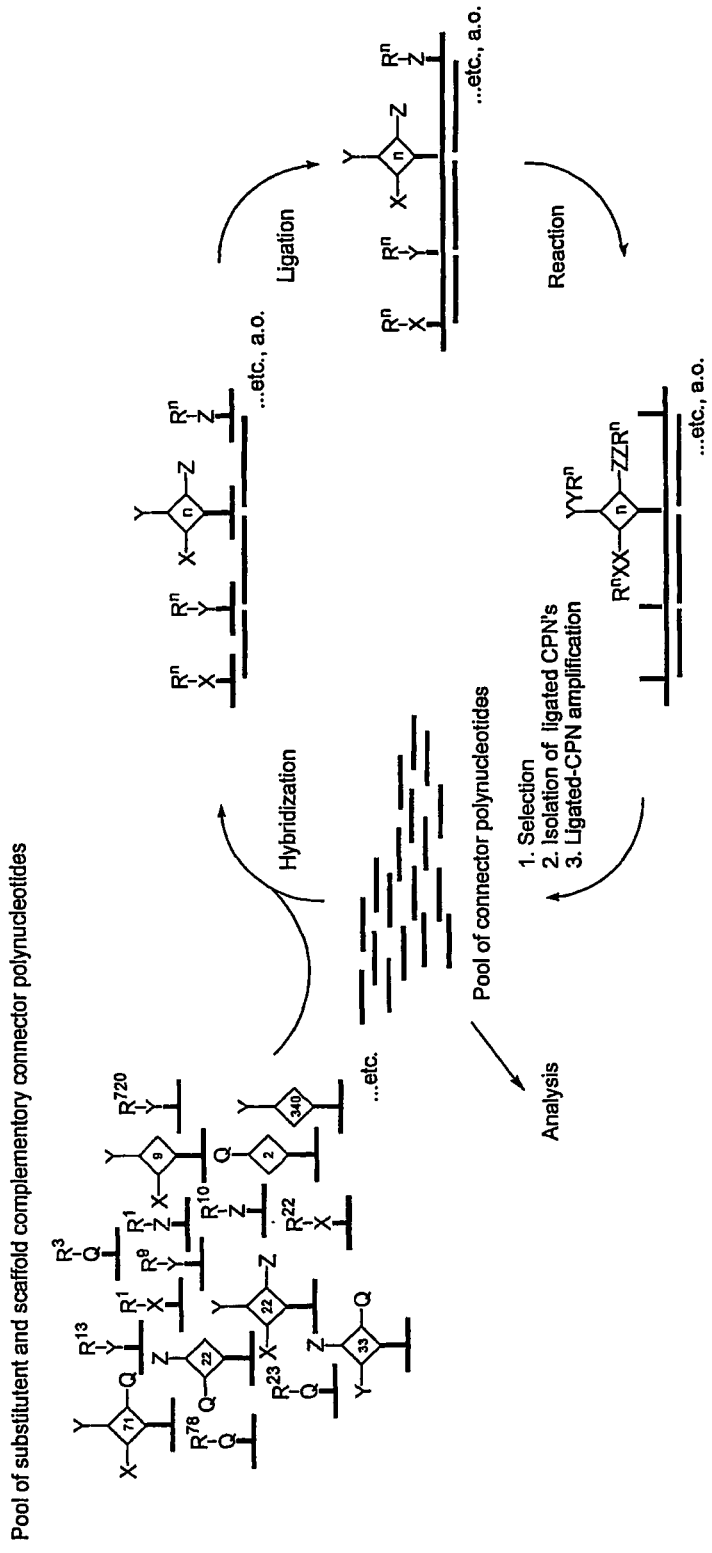

As in FIG. 8, wherein at least one CPN in each complex is capable of self hybridization, whereby CCPN's and some or all CPN's in each complex may be linked. In this example only one terminal CPN is capable of self hybridization and is ligated to the CCPN's. This setting may allow an easy separation of CPN's from CCPN's.

FIG. 15.

The figure illustrates a set of different molecules which may be formed by the process of the present invention through the steps described above. In this example where CPN's have been ligated together and CCPN's have been ligated together. The figure serves only for illustrative purposes and is not in any way intended to limit the scope of the present invention.

FIG. 16-19.

The figures illustrates further examples of CPN and CCPN complexes with or without ligational steps and with (a) and without (b) terminal oligonucleotide overhangs.

FIG. 20.

The figure illustrates different CPN/CCPN complexes, wherein the some or all CPN's carry a reactive group or a functional entity comprising one or more reactive groups.

FIG. 21.

The figure illustrates the principle of a zipperbox. The zipperbox is a region optionally comprising an oligonucleotide sequence where said region is capable of hybridizing to another zipperbox, wherein this second zipperbox optionally comprises an oligonucleotide sequence complementary to the first zipperbox. The zipperbox may be situated on a CPN or a CCPN. Upon hybridization of two zipperboxes, the proximity between functional entity reactive groups increases, whereby the reaction is enhanced.

By operating at a temperature that allows transient interaction of complementary zipperboxes, functional entity reactive groups are brought into close proximity during multiple annealing events, which has the effect of reactive groups in close proximity in a larger fraction of the time than otherwise achievable. Alternatively, one may cycle the temperature between a low temperature (where the zipper boxes pairwise interacts stably), and a higher temperature (where the zipper boxes are apart, but where the CCPN/CPN complex remains stable. By cycling between the high and low temperature several times, a given reactive group is exposed to several reactive groups, and eventually will react to form a bond between two function entities through their reactive groups.

FIG. 22.

The figure illustrates how different CPN and CCPN complexes may form by a self assembly process through cross talk between CPN's and CCPN's. The figure only illustrates two paths, but the illustration is not intended to limit the invention hereto. The complexes may form through the mixing of all components in one step or through the stepwise addition of CPN's and CCPN's in each step,

FIG. 23.

The figure illustrates reaction types allowing simultaneous reaction and linker cleavage. Different classes of reactions are shown which mediate translocation of a functional group from one CCPN (or CPN (not illustrated)) to another, or to an anchorage CCPN. The reactions illustrated are compatible with simultaneous reaction and linker cleavage, i.e. one functional entity is transferred (translocated) directly from one CCPN (or CPN (not illustrated)) onto another CCPN (or CPN (not illustrated)) without the need of subsequent and separate linker cleavage through the application of further new conditions allowing for such.

(A) Reaction of nucleophiles with carbonyls. As a result of the nucleophilic substitution, the functional group (entity) R is translocated to the CCPN initially carrying the nucleophile.

(B) Nucleophilic attack by the amine on the thioester leads to formation of an amide bond, in effect translocating the functional group R of the thioester to the other CCPN.

(C) Reaction between hydrazine and β-ketoester leads to formation of pyrazolone, in effect translocating the R and R' functional groups to the other CCPN.

(D) Reaction of hydroxylamine with β-ketoester leads to formation of the isooxazolone, thereby translocating the R and R' groups to the other CCPN.

(E) Reaction of thiourea with β-ketoester leads to formation of the pyrimidine, thereby translocating the R and R' groups to the other CCPN.

(F) Reaction of urea with malonate leads to formation of pyrimidine, thereby translocating the R group to the other CCPN.
(G) Depending on whether Z=O or Z=NH, a Heck reaction followed by a nucleophilic substitution leads to formation of coumarin or quinolinone, thereby translocating the R and R' groups to the other CCPN.
(H) Reaction of hydrazine and phthalimides leads to formation of phthalhydrazide, thereby translocating the R and R' groups to the other CCPN.
(I) Reaction of amino acid esters leads to formation of diketopiperazine, thereby translocating the R group to the other CCPN.
(J) Reaction of urea with α-substituted esters leads to formation of hydantoin, and translocation of the R and R' groups to the other CCPN.
(K) Alkylation may be achieved by reaction of various nucleophiles with sulfonates. This translocates the functional groups R and R' to the other CCPN.
(L) Reaction of a di-activated alkene containing an electron withdrawing and a leaving group, whereby the alkene is translocated to the nucleophile carrying CCPN.
(M) Reaction of disulfide with mercaptan leads to formation of a disulfide, thereby translocating the R' group to the other CCPN.
(N) Reaction of amino acid esters and amino ketones leads to formation of benzodiazepinone, thereby translocating the R group to the other CCPN.
(O) Reaction of phosphonium salts with aldehydes or ketones leads to formation of substituted alkenes, thereby translocating the R" group to the other CCPN.
(P) Reaction of phosphonates with aldehydes or ketones leads to formation of substituted alkenes, thereby translocating the R" group to the other CCPN.
(O) The principle of translocation of e.g. aryl groups from one CCPN to another CCPN.
(R) Reaction of boronates with aryls or heteroaryls results in transfer of an aryl group to the other CCPN (to form a biaryl).
(S) Reaction arylsulfonates with aryl groups bound as Boron derivatives leads to transfer of the aryl group.
(T) Biaryl formation through translocation of one aryl group to another CCPN.
(U) Arylamine formation (e.g. Hartwig/Buchwald type of chemistry) through N-arylation, i.e. transfer of aryl groups to CCPN's carrying amino groups.
(V) As U using hypervalent iodonium derivatives.
(X) Reaction of boronates with vinyls (or alkynes) results in transfer of an aryl group to the other CCPN to form a vinylarene (or alkynylarene).
(Y) Reaction between aliphatic boronates and arylhalides, whereby the alkyl group is translocated to yield an alkylarene.
(Z) Transition metal catalysed alpha-alkylation through reaction between an enolether and an arylhallide, thereby translocating the aliphatic part.
(AA) Condensations between e.g. enamines or enolethers with aldehydes leading to formation of alpha-hydroxy carbonyls or alpha, beta-unsaturated carbonyls. The reaction translocates the nucleophilic part.
(AB) Alkylation of alkylhalides by e.g. enamines or enolethers. The reaction translocates the nucleophilic part.
(AC) [2+4]cycloadditions, translocating the diene-part.
(AD) [2+4]cycloadditions, translocating the ene-part.
(AE) [3+2]cycloadditions between azides and alkenes, leading to triazoles by translocation of the ene-part.
(AF) [3+2]cycloadditions between nitriloxides and alkenes, leading to isoxazoles by translocation of the ene-part.

Figure 24:
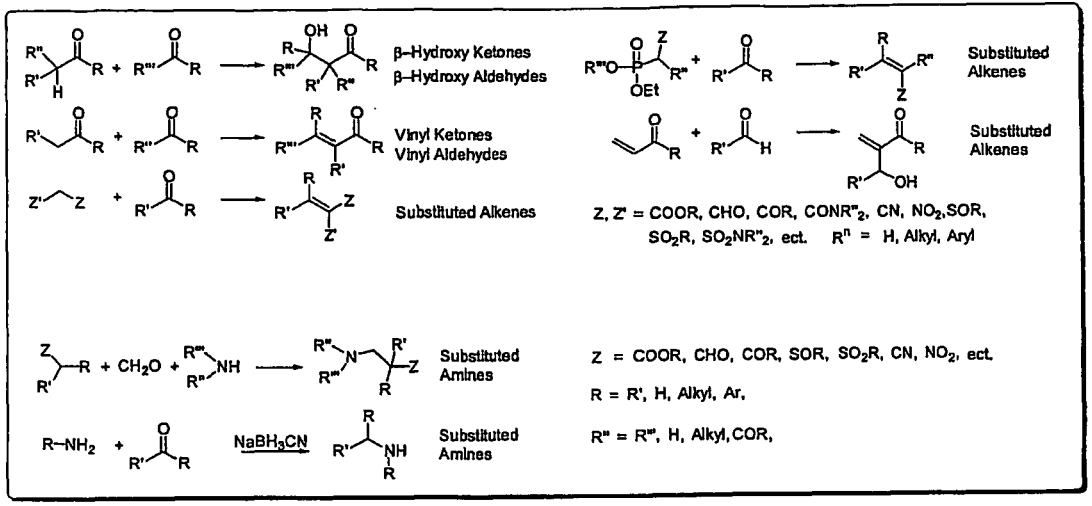

FIG. 24.
The figure illustrates pairs of reactive groups (X) and (Y), and the resulting bond (XY).
A collection of reactive groups and functional entity reactive groups that may be used for the synthesis of molecules are shown, along with the bonds formed upon their reaction. After reaction, linker cleavage may be applied to release one of the functional entities, whereby the transfer of one functional entity from one CCPN to another is effectuated.

FIG. 25.
The composition of linker may be include derivatives of the following, but is not limited hereto:
Carbohydrides and substituted carbohydrides
Vinyl, polyvinyl and substituted polyvinyl
Acetylene, polyacetylene
Aryl/Hetaryl, polyaryl/hetaryl and substituted polyaryl/polyhetaryl
Ethers, polyethers such as e.g. polyethyleneglycol and substituted polyethers
Amines, polyamines and substituted polyamines
Double stranded, single stranded or partially double or single stranded natural and unnatural polynucleotides and substituted double stranded, single stranded or partially double stranded natural and unnatural polynucleotides such as but limited to DNA, RNA, LNA, PNA, TNA
Polyamides and natural and unnatural polypeptides and substituted polyamides and natural and unnatural polypeptides
Phosphate containing linkers
Any combination of the above
Linkers may be cleavable or non-cleavable. The figure illustrates cleavable linkers, conditions for their cleavage, and the resulting products are shown.

FIG. 26.
The figure illustrates different examples of the formation of CCPN's carrying functional entities. Reactions and reagents are shown that may be used for the coupling of functional entities to modified oligonucleotides (modified with thiol, carboxylic acid, halide, or amine), without significant reaction with the unmodified part of the oligonucleotide or alternatively, connective reactions for linkage of linkers to complementing elements. Commercially, mononucleotides are available for the production of starting oligonucleotides with the modifications mentioned.

Figure 27:
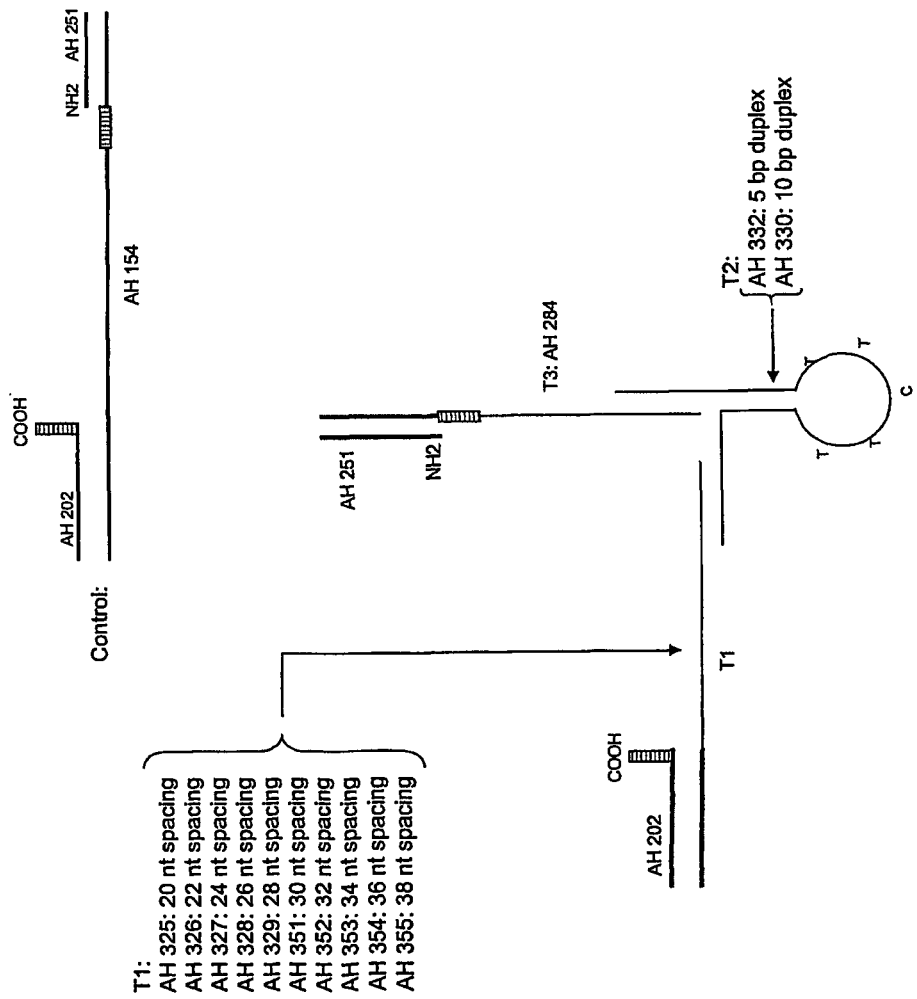

FIG. 27.
The figure illustrates the hair-pin oligo set-up.

Figure 28:
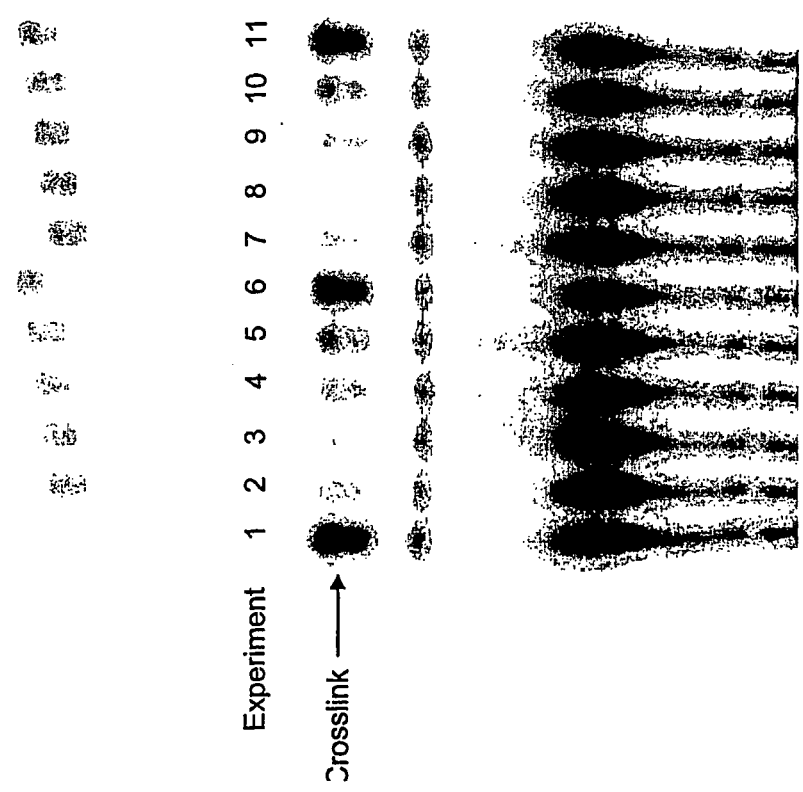

FIG. 28.
The figure illustrates the polyacrylamide gel analysis described in more detail in example 2A. The arrow indicates the cross-link product of the AH251 oligo and the radioactively labelled AH202 oligo. The cross-linked product has slower mobility in the gel than the labelled, non-reacted AH202 oligo.

Figure 29:
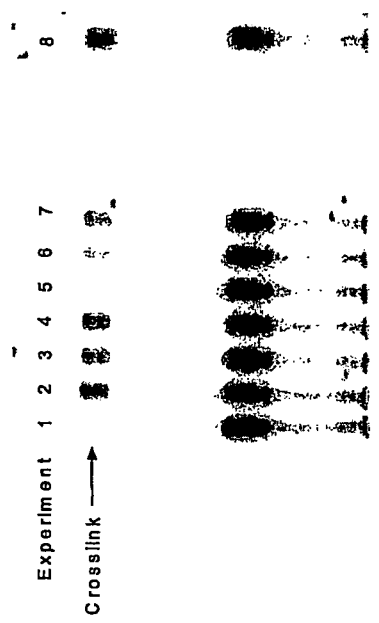

FIG. 29.
The figure illustrates the polyacrylamide gel analysis described in more detail in example 2B. The arrow indicates the cross-link product of the AH251 oligo and the radioactively labelled AH202 oligo. The cross-linked product has slower mobility in the gel than the labelled, non-reacted AH202 oligo.

Figure 30:
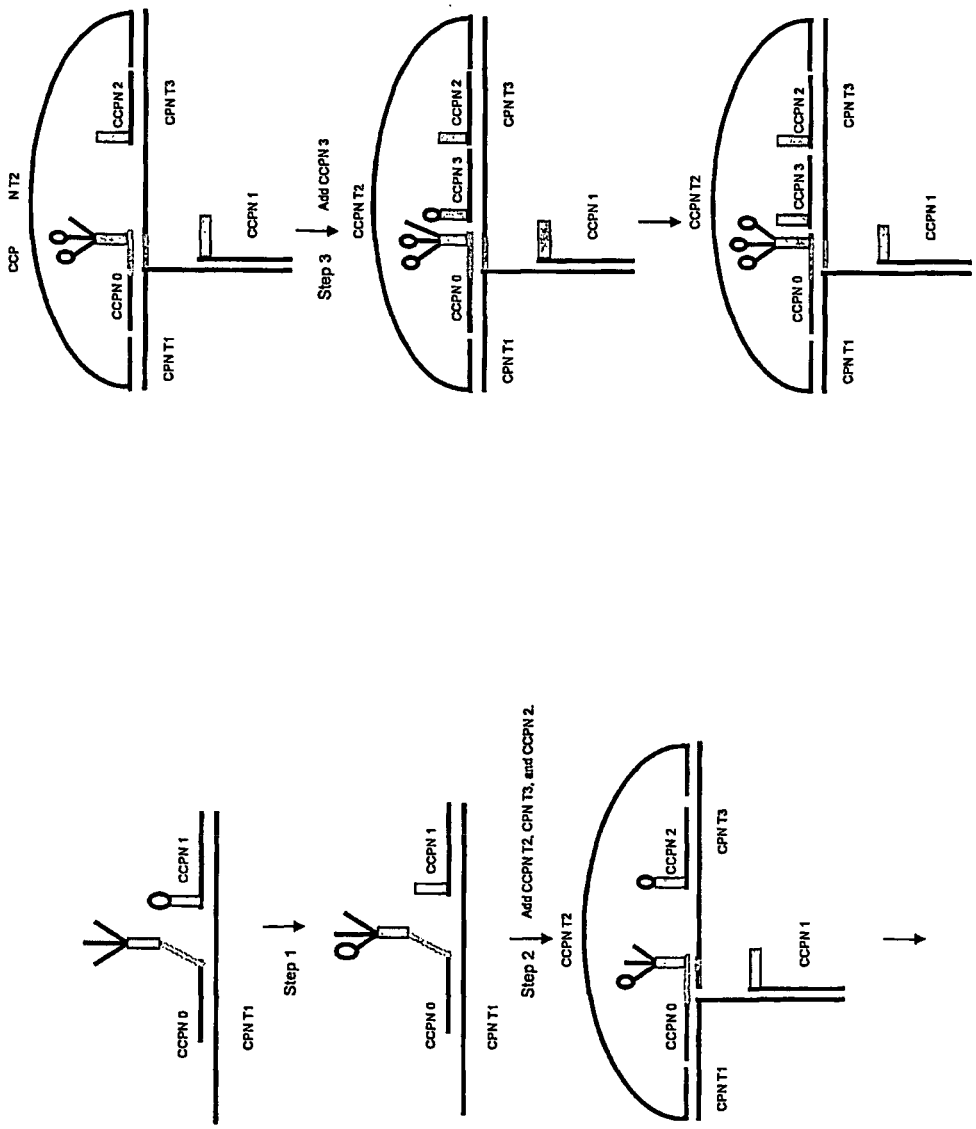

FIG. 30.
Encoding scheme for the synthesis of a small molecule from four encoded units (corresponding to CCPN0, CCPN1, CCPN2, and CCPN3), using a circular oligonucleotide CCPN/CPN-complex. This scheme is employed in example 2H; the first part of the scheme is employed in example 2G.

Figure 31:
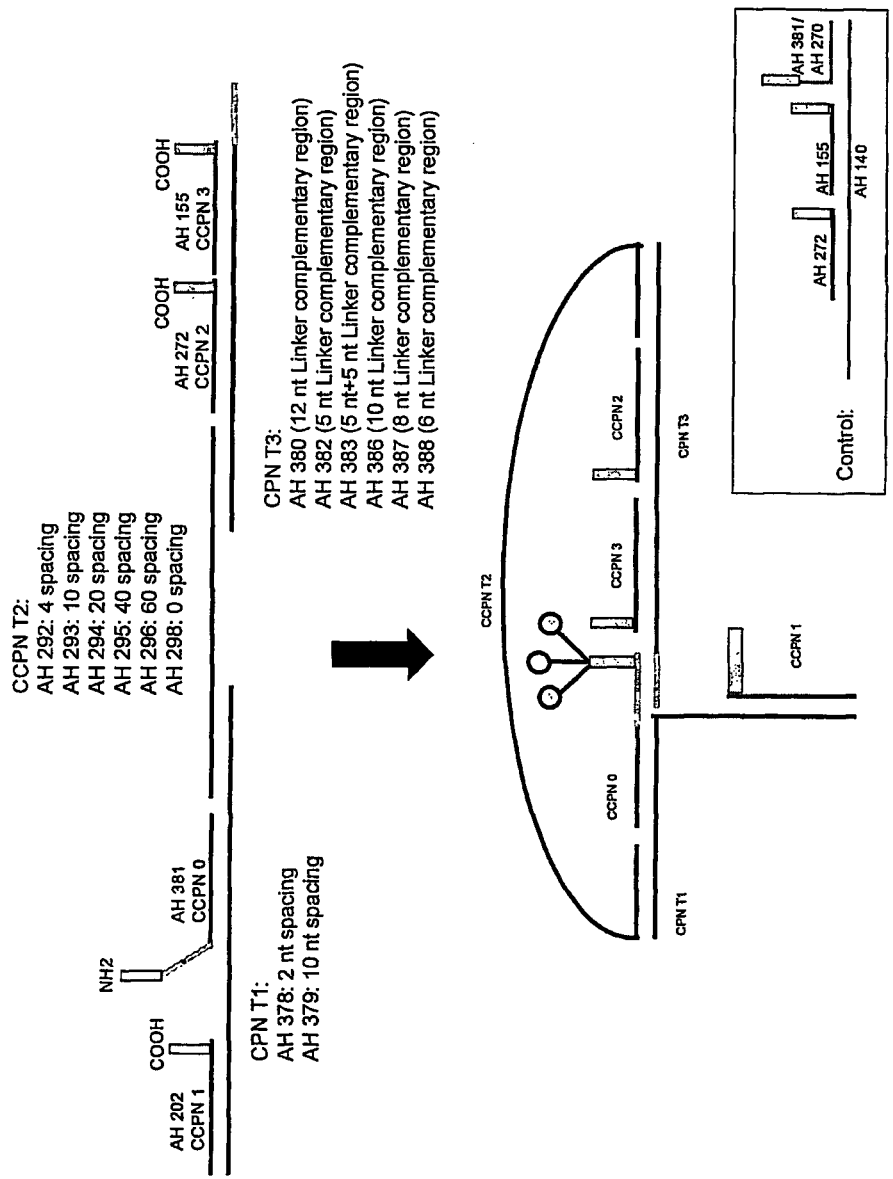

FIG. 31. This figure shows the proposed circular structure, as well as gives an overview of the different oligos CPN T1, CCPN T2 and CPN T3 used in examples 2C-2H, and the CCPN0, CCPN1, CCPN2 and CCPN3 oligos carrying the functional entities. The insert shows the oligo set-ups used in the positive control reaction.

Figure 32:
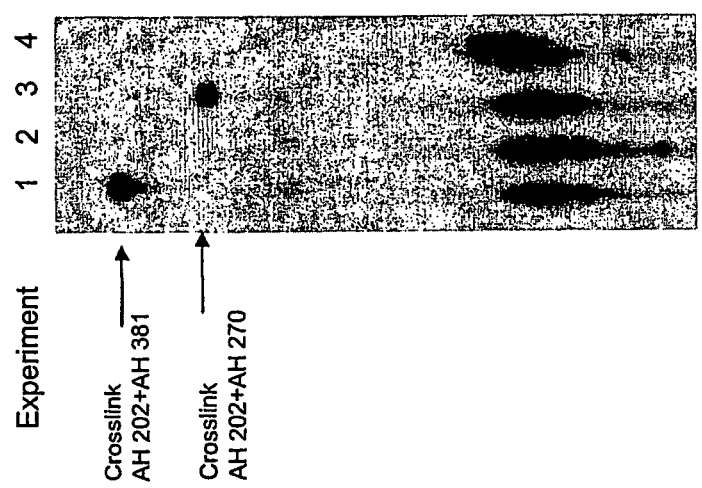

FIG. 32. The polyacrylamide gel analysis of example 2C.
The arrow indicates the cross-link product of the AH381 or AH270 oligo with the radioactively labelled AH202 oligo. The cross-linked product has slower mobility in the gel than the labelled, non-reacted AH202 oligo.

Figure 33:
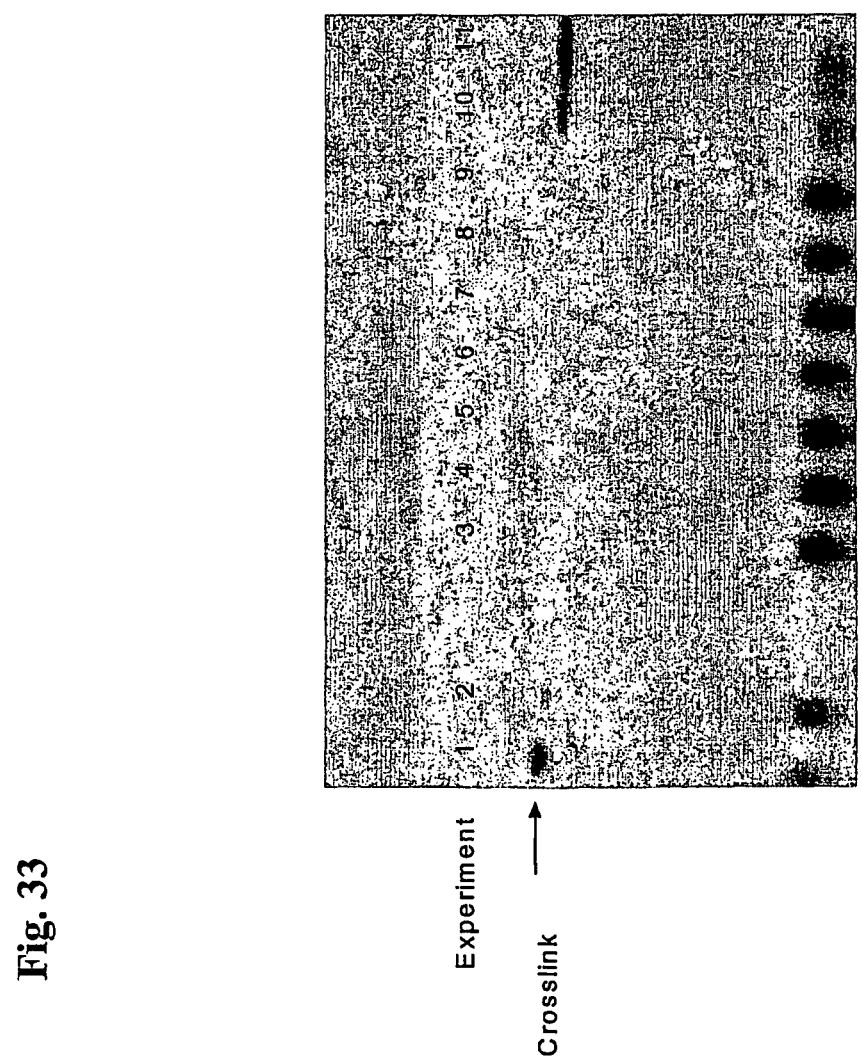

FIG. 33. The polyacrylamide gel analysis of example 2D.
The arrow indicates the cross-link product of the AH381 oligo with the radioactively labelled AH155 or AH272 oligos. The cross-linked product has slower mobility in the gel than the labelled, non-reacted AH155 or AH272 oligos.

Figure 34:
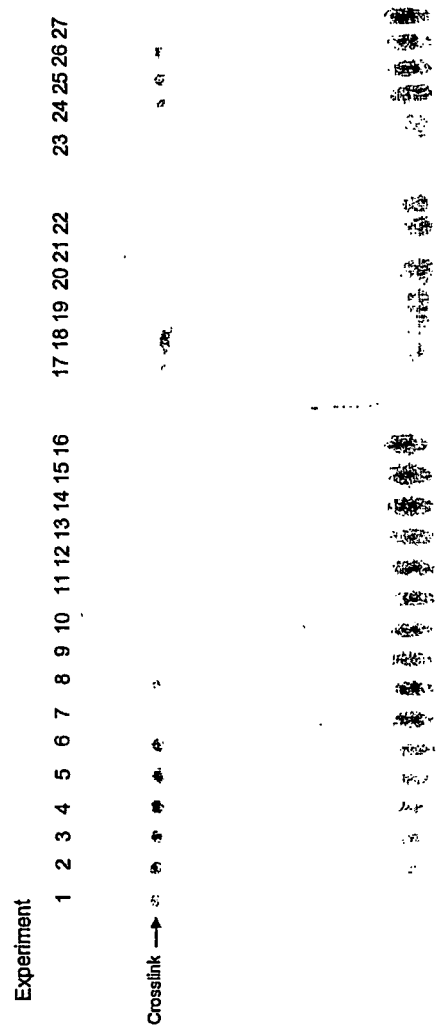

FIG. 34. The polyacrylamide gel analysis of example 2E.
The arrow indicates the cross-link product of the AH381 oligo with the radioactively labelled AH155 or AH272 oligos. The cross-linked product has slower mobility in the gel than the labelled, non-reacted AH155 or AH272 oligos.

Figure 35:
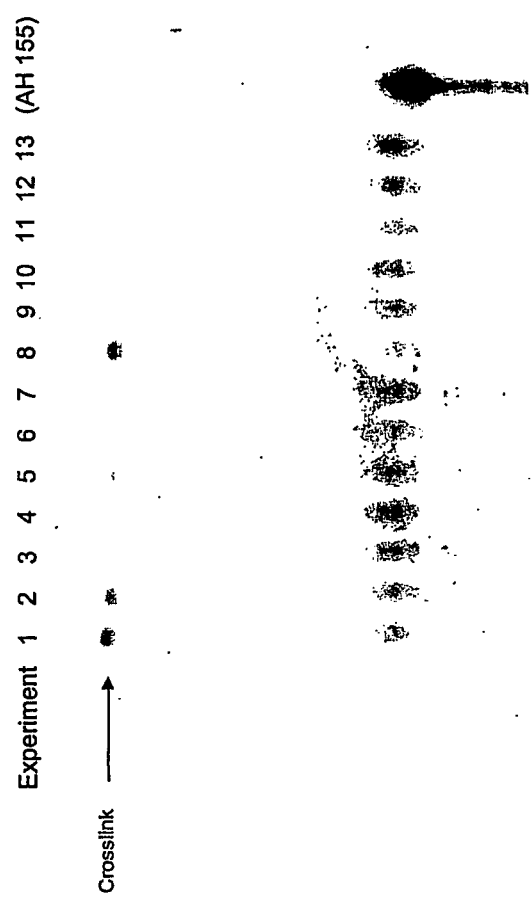

FIG. 35. The polyacrylamide gel analysis of example 2F.
The arrow indicates the cross-link product of the AH381 oligo with the radioactively labelled AH155 oligo. The cross-linked product has slower mobility in the gel than the labelled, non-reacted AH155 oligo.

Figure 36:
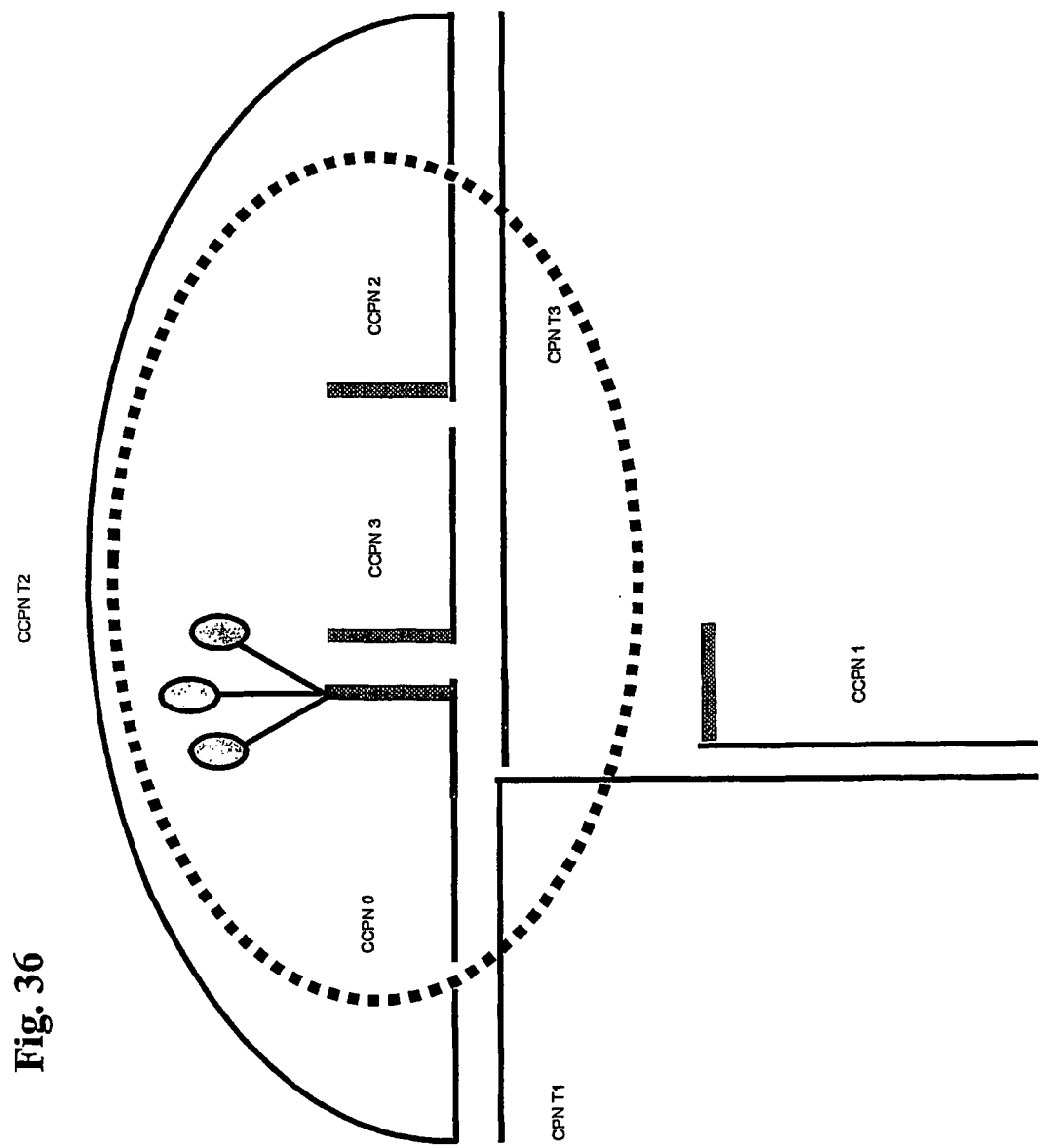

FIG. 36. The figure shows the proposed complex of example 2H.
The dotted circle highlights a part of the structure, consisting of 3 CCPNs and 2 CPNs, where one CCPN carries a functional entity and anneals to two CPNs.

Figure 37:
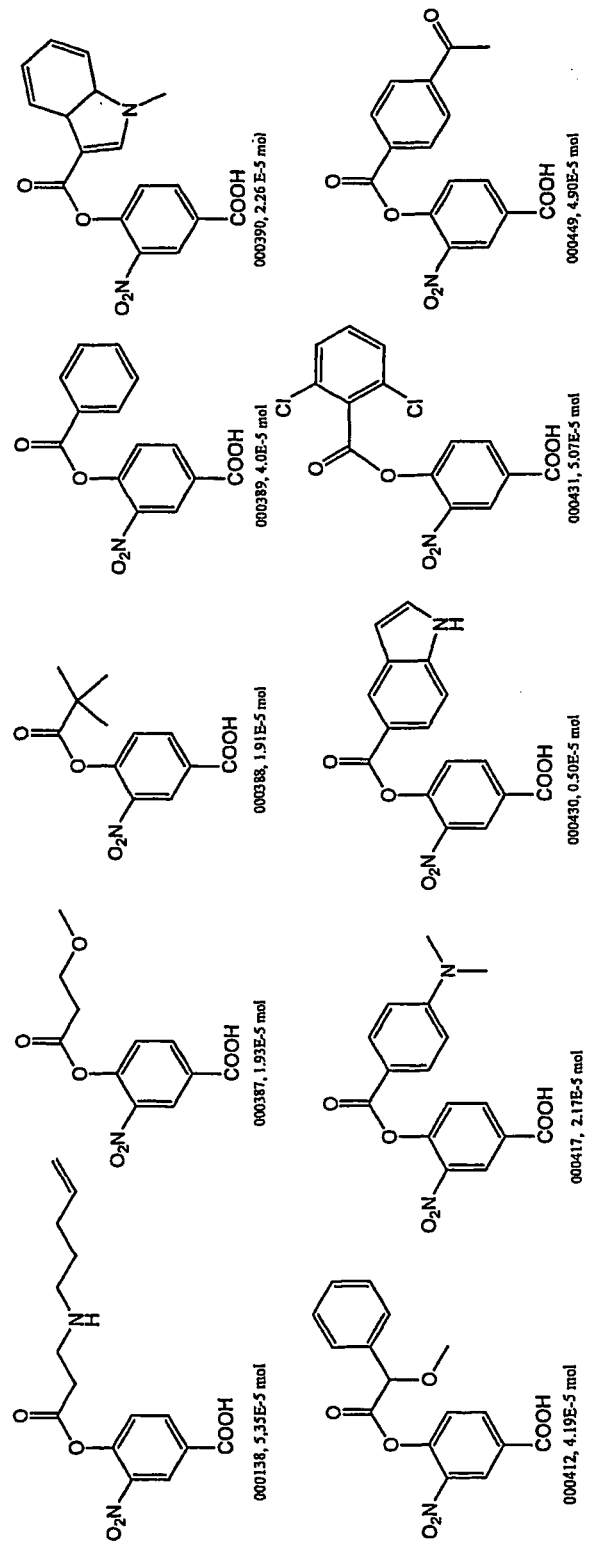

FIG. 37. Nitro phenol esters used in example 2G and 2H. Structures and yields are given.

DETAILED DESCRIPTION OF THE INVENTION

The method of the present invention have several advantages over template directed synthesis methods. As described below the methods of the present invention can be distinguished from well known methods such as e.g. ribosome mediated translation and ligation of polynucleotides.

In one embodiment of the present invention, the methods for synthesizing at least one molecule does not employ—for the purpose of synthesising the at least one molecule—the formation of a double stranded polynucleotide comprising complementary nucleotide stands obtained by joining or ligating end-positioned nucleotides by enzymatic reaction(s) or by chemical ligation using other reactive groups than 5'-phophate groups and 3'-hydroxy groups employed by e.g. ligase catalysed reactions disclosed in standard text books (for chemical ligation, see e.g. by Bruick et al. (1997) and Gryaznov and Letsinger (1993)).

Rather, the method is directed to reacting functional entity reactive groups and thereby generating at least one small molecule, or a polymer molecule, by transferring functional entities or parts thereof from one or more donor CCPNs and/or donor CPNs to at least one acceptor CCPN or at least one acceptor CPN. A plurality of functional entities are preferably transferred from a plurality of donor CPPNs to a single (ultimate) acceptor CPPN. Functional entity reactive groups can react chemically or be enzymatically catalysed.

The end-product of the synthesis methods of the present invention is in one embodiment a molecule consisting of functional entities initially carried by CPN's and/or CCPN's.

The molecule can also be obtained by reacting reactants provided by donor CPPNs and/or donor CPNs. The molecule is in one embodiment linked to the polynucleotide part of a CPN or a CCPN.

When the methods of the invention relate to functional entities carried primarily by CCPNs, a single functional entity can e.g. be transferred from each of a plurality of donor CPPNs to at least one acceptor CPPN, or more than one functional entity can be transferred from some or all of said donor CPPNs to an acceptor CPPN. When reactants or functional entities are donated to a scaffold, a plurality of reactive groups of said scaffold (e.g. a plurality of reactive groups of a single reactant or a single functional entity) will react with one or more reactive groups of the plurality of reactants or functional entities taking place in the formation of the scaffolded molecule.

The plurality of scaffold reactive groups involved in the formation of a scaffolded molecule can be e.g. at least 2, such as 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or more reactive groups. In one embodiment, the number of reactants or functional entities capable of reacting with the scaffold reactive groups is limited to the total number of scaffold reactive groups available for reaction with said reactants or functional entities linked to the polynucleotide part of donor CCPNs or donor CPNs. Independently of the number of scaffold reactive groups, at least 2, such as e.g. 3, 4, 5, 6, 7, 8, 9, 10, 11, 12, 13, 14, 15, 16, 17, 18, 19, or 20 reactants can react with the scaffold reactive groups when a scaffolded molecule is being formed in accordance with the methods of the present invention, wherein each reactant is preferably donated (provided) by a separate donor building block polynucleotide.

Independently of the number of scaffold reactive groups and independently of the number of reactants reacted, the number of donor building block polynucleotides in the hybridisation complex having provided reactants—directly or indirectly (i.e. several reactions having already taken place before a once or twice or further reacted reactant reacts with a scaffold reactive group)—for the synthesis of the scaffolded molecule can be anything in the range of from 2 to 25, such as from 2 to 20, for example from 2 to 15, such as from 2 to 10, for example from 2 to 8, such as from 2 to 6, for example from 2 to 5, such as from 2 to 4, for example from 3 to 25, such as from 3 to 20, for example from 3 to 15, such as from 3 to 10, for example from 3 to 8, such as from 3 to 6, for example from 3 to 5, such as 3 or 4. The total number of different donor building block polynucleotides present for the synthesis of different scaffolded molecules can of course be many times higher that these figures. Typically, the number of different donor building block polynucleotides donating/providing a reactant, such as a functional entity, to the synthesis of a library of different scaffolded molecules, will be in the order of at least 100, such as at least 1000, for example at least 10000, such as at least 100000 different donor building block polynucleotides (selected from donor CPNs and/or donor CCPNs).

The hybridisation complex allowing the above-mentioned formation of a scaffolded molecule to take place preferably comprises at least n CPNs, n being an integer of from 2 to 10, preferably from 2 to 8, such as from 2 to 6, for example from 2 to 5, such as from 3 to 10, preferably from 3 to 8, such as from 3 to 6, for example from 3 to 5, and at least n CCPNs, such as at least n+1 CCPNs, for example at least n+2 CCPNs, such as at least n+3 CCPNs, for example at least n+4 CCPNs, such as at least n+5 CCPNs, for example at least n+6 CCPNs, such as at least n+7 CCPNs, for example at least n+8 CCPNs, such as at least n+9 CCPNs, for example at least n+10 CCPNs, such as at least n+11 CCPNs, for example at least n+12 CCPNs, such as at least n+13 CCPNs, for example at least n+14 CCPNs, such as at least n+15 CCPNs.

Covalent bonds between donor CPPNs (or donor CPNs) and their functional entities can be cleaved before, during or after the synthesis of the molecule.

The molecule formed on an acceptor CCPN does not comprise the linker or the polynucleotide part of the acceptor CCPN. Accordingly, the generation of a molecule does not result from a covalent addition of nucleotide(s) to the polynucleotide of the CCPN to which the molecule is linked when the functional entity reactive group reactions have taken place and covalent bonds cleaved between functional entities and donor CCPNs.

Also, in one embodiment the synthesis methods of the present invention do not result in the formation of a double-stranded polynucleotide molecule in the form of joined or ligated nucleotides of CPNs or CCPNs after the small molecule or polymer has been formed.

Accordingly, the at least one molecule being synthesised by the methods of the invention are distinct from molecules obtained by ligating or joining nucleotide fragments, including double stranded nucleotide fragments.

Furthermore, the methods of the present invention do not involve ribosome mediated translation and prior art methods employing ribosomes for translation purposes are therefore not pertinent to the present invention and are disclaimed as such.

Accordingly, the at least one molecule is generated when, in one embodiment, functional entities on separate complementary connector polynucleotides (CCPNs) are joined by reactions involving functional entity reactive groups. The formation of the molecule is a result of the formation of covalent bonds formed between functional entities constituting the molecule as well as the cleavage of covalent bonds between at least some of the functional entities and the polynucleotide part of the CCPN having donated a particular functional entity, or a part thereof, to the molecule.

The methods of the invention are preferably carried out without cleaving the polynucleotide sequence(s) of CPNs or CCPNs during the synthesis and formation of the molecule.

Accordingly, reactions involving functional entity reactive groups can lead to the formation of a molecule comprising covalently linked functional entities donated by separate CCPNs from which functional entities have been cleaved. The cleavage of the functional entities results in the donor CCPNs not being covalently linked to the molecule. The donation of any single functional entity can occur in a single step or sequentially in one or more steps, and the donation of a plurality of functional entities can occur simultaneously or sequentially in one or more steps.

When reactive groups of a CCPN are located in one embodiment at both (or all) termini of the polynucleotide of a CCPN, functional entity reactive groups of at least some CCPNs participating in the synthesis of the molecule are preferably located only at one of said terminal positions of the polynucleotide. It is such functional entity reactive groups the reaction of which result in the formation of the molecule. However, other reactive groups can be present in the terminal position(s) not occupied by the functional entity comprising functional entity reactive groups. Such reactive groups are different from functional entity reactive groups in so far as these "other" reactive groups do not participate in the synthesis and formation of the molecule.

One example of such "other" reactive groups is e.g. a natural 5'-phosphate group of the polynucleotide of a CCPN comprising a functional entity comprising at least one reactive group at its 3'-terminal end. Another example of a reactive group which is not regarded as a functional entity reactive group is e.g. the natural 3'-hydroxy group of the polynucleotide of a CCPN comprising a functional entity comprising at least one reactive group at its 5'-terminal end.

Accordingly, in one embodiment a functional entity comprising functional entity reactive group(s) is preferably located at one of the terminal end(s) of a CCPN and only functional entity reactive groups are reacted in order to generate a molecule comprising covalently linked functional entities donated by separate CCPNs without said functional entity donation ultimately (i.e. after the molecule has been formed) resulting in CCPNs being covalently linked to each other.

Preferably, at least one functional entity reactive group reaction involving e.g. 2, 3, 4, or more functional entity reactive groups preferably does not result in a CCPN being joined to other polynucleotides or CCPNs at both the 5'-terminal end and the 3'-terminal end of the polynucleotide of the CCPN at the time the molecule has been generated by covalently linking functional entities donated by separate CCPNs.

Accordingly, there is provided in one embodiment methods wherein at least some CCPNs comprise both functional entity reactive groups and other reactive groups, and wherein reactions at both (or all) terminal positions of the polynucleotide of such CCPNs are not all functional entity reactive group reactions. Only reactive groups the reaction of which results in the formation of the molecule comprising covalently linked functional entities are functional entity reactive groups.

When functional entity reactive groups and other reactive groups are located within the same CCPN, the different kinds of reactive groups will most often be located at different terminal ends of the polynucleotide of the CCPN. Accordingly, functional entity reactive group(s) will generally be separated from other reactive groups of a CCPN by a nucleotide or a nucleobase or a phosphate group.

Preferred aspects of the methods for the synthesis of at least one molecule, or for the synthesis of a plurality of different molecules, are described herein elsewhere.

In one embodiment, the at least one molecule comprising covalently linked functional entities is linked to the polynucleotide part of a complementary connector polynucleotide, but the molecule does not comprise the linker and the polynucleotide part of said complementary connector polynucleotide.

In one embodiment, when the at least one molecule has been formed and covalent bonds created between the functional entities of the molecule, said functional entities are no longer covalently linked to the (donor) CCPNs having donated functional entities or parts thereof to the molecule. The functional entity of a CCPN is preferably attached to a nucleobase by means of a cleavable linker. Such linkers can be cleaved e.g. by acid, base, a chemical agent, light, electromagnetic radiation, an enzyme, or a catalyst.

Accordingly, in one embodiment of the invention, following molecule formation, complementary connector polynucleotides hybridized to connector polynucleotides are not linked by covalent bonds. Also, in another embodiment, connector polynucleotides (CPNS) hybridized to complementary connector polynucleotides are not linked by covalent bonds. Consequently, such methods are distinct from both ribosome mediated translation of a single template of covalently linked nucleotides and from methods involving nucleotide synthesis and/or ligation as the latter methods result in the formation of ligation products in which nucleotides become covalently linked to each other.

The CCPN polynucleotides can comprise hybridizable nucleotide sequences such as e.g. natural and/or unnatural polynucleotides such as e.g. DNA, RNA, LNA, PNA, and morpholino sequences. The CPN polynucleotides are preferably amplifiable polynucleotides and more preferably polynucleotides comprising DNA and/or RNA. One or more CPNs can be bound to a solic support.

The number or CPNs and/or CCPNs provided for the synthesis of a single molecule can be from 2 to 200, for example from 2 to 100, such as from 2 to 80, for example from 2 to 60, such as from 2 to 40, for example from 2 to 30, such as from 2 to 20, for example from 2 to 15, such as from 2 to 10, such as from 2 to 8, for example from 2 to 6, such as from 2 to 4, for example 2, such as from 3 to 100, for example from 3 to 80, such as from 3 to 60, such as from 3 to 40, for example from 3 to 30, such as from 3 to 20, such as from 3 to 15, for example from 3 to 15, such as from 3 to 10, such as from 3 to 8, for example from 3 to 6, such as from 3 to 4, for example 3, such as from 4 to 100, for example from 4 to 80, such as from 4 to 60, such as from 4 to 40, for example from 4 to 30, such as from 4 to 20, such as from 4 to 15, for example from 4 to 10, such as from 4 to 8, such as from 4 to 6, for example 4, for example from 5 to 100, such as from 5 to 80, for example from 5 to 60, such as from 5 to 40, for example from 5 to 30, such as from 5 to 20, for example from 5 to 15, such as from 5 to 10, such as from 5 to 8, for example from 5 to 6, for example 5, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100.

Although it is preferred in some embodiments to react at least 3 or more functional entity reactive groups when synthesizing the at least one molecule, in certain other embodiments only 2 reactive groups need to be reacted. The number of reactive groups reacted will depend on the number of functional entities used for the synthesis of the molecule.

When the present invention in one embodiment provides a method for synthesising at least one molecule comprising the steps of
  i) providing a plurality of connector polynucleotides each capable of hybridizing to at least 1 complementary connector polynucleotide,
  ii) providing a plurality of complementary connector polynucleotides selected from the group consisting of
    a) complementary connector polynucleotides comprising at least 1 reactant, such as a functional entity comprising at least 1 reactive group,
    b) complementary connector polynucleotides comprising at least 1 reactive group,
    c) complementary connector polynucleotides comprising at least 1 spacer region,
  iii) hybridizing at least 2 complementary connector polynucleotides to at least 2 connector polynucleotides,
    wherein at least 2 of said complementary connector polynucleotides comprise at least 1 reactant, such, as a functional entity comprising at least 1 reactive group,
    wherein at least 1 of said complementary connector polynucleotides hybridizes to at least 2 connector polynucleotides, and
  iv) reacting at least 2 reactants or functional entity reactive groups by reacting at least 1 reactive group of each reactant or functional entity,
    wherein the reaction of said reactants or functional entity reactive groups results in the formation of the molecule by reacting the reactive groups of the reactants, or by covalently linking at least 2 functional entities provided by separate complementary connector polynucleotides.
  Step iv) can e.g. comprise an embodiment wherein at least 3 reactants or functional entity reactive groups, such as at least 4 reactants or functional entity reactive groups, for example at least 5 reactants or functional entity reactive groups, such as at least 6, such as at least 8, for example at least 10 reactants or functional entity reactive groups, by reacting at least 1 reactive group of each reactant or functional entity.

In one embodiment the method preferably comprises in steps iii) and iv),
  iii) hybridizing at least 3 complementary connector polynucleotides to at least 2 connector polynucleotides,
    wherein at least 3 of said complementary connector polynucleotides comprise at least 1 reactant, such as a functional entity comprising at least 1 reactive group,
    wherein at least 1 of said complementary connector polynucleotides hybridizes to at least 2 connector polynucleotides,
    and
  iv) reacting at least 3 reactants or functional entity reactive groups by reacting at least 1 reactive group of each reactant or functional entity, wherein the reaction of said reactants or functional entity reactive groups results in the formation of the molecule by reacting the reactive groups of the reactants, or by covalently linking at least 3 functional entities provided by separate complementary connector polynucleotides.

Step iv) can e.g. comprise an embodiment wherein at least 4 reactants or functional entity reactive groups are reacted, such as at least 5 reactants or functional entity reactive groups are reacted, for example at least 6 reactants or functional entity reactive groups are reacted, such as at least 8 reactants or functional entity reactive groups, such as at least 10, for example at least 12 reactants or functional entity reactive groups are reacted, by reacting at least 1 reactive group of each reactant or functional entity.

In one embodiment the method preferably comprises in steps iii) and iv),
iii) hybridizing at least 4 complementary connector polynucleotides to at least 2 connector polynucleotides,
  wherein at least 4 of said complementary connector polynucleotides comprise at least 1 reactant such as a functional entity comprising at least 1 reactive group,
  wherein at least 1 of said complementary connector polynucleotides hybridizes to at least 2 connector polynucleotides,
  and
iv) reacting at least 4 reactants or functional entity reactive groups by reacting at least 1 reactive group of each reactant or functional entity,
  wherein the reaction of said reactants or functional entity reactive groups results in the formation of the molecule by reacting the reactive groups of the reactants, or by covalently linking at least 4 functional entities provided by separate complementary connector polynucleotides.

Step iv) can e.g. comprise an embodiment wherein at least 5 reactants or functional entity reactive groups are reacted, such as at least 6 reactants or functional entity reactive groups are reacted, for example at least 8 reactants or functional entity reactive groups are reacted, such as at least 10 reactants or functional entity reactive groups are reacted, for example at least 12 reactants or functional entity reactive groups are reacted, such as at least 14 reactants or functional entity reactive groups are reacted, by reacting at least 1 reactive group of each reactant or functional entity.

In one embodiment the method preferably comprises in steps iii) and iv),
iii) hybridizing at least 5 complementary connector polynucleotides to at least 2 connector polynucleotides,
  wherein at least 5 of said complementary connector polynucleotides comprise at least 1 reactants, such as a functional entity comprising at least 1 reactive group,
  wherein at least 1 of said complementary connector polynucleotides hybridizes to at least 2 connector polynucleotides,
  and
iv) reacting at least 5 reactants or functional entity reactive groups by reacting at least 1 reactive group of each reactant or functional entity,
  wherein the reaction of said reactants or functional entity reactive groups results in the formation of the molecule by reacting the reactive groups of the reactants, or by covalently linking at least 5 functional entities provided by separate complementary connector polynucleotides.

Step iv) can e.g. comprise an embodiment wherein at least 6 reactants or functional entity reactive groups are reacted, such as at least 7 reactants or functional entity reactive groups are reacted, for example at least 8 reactants or functional entity reactive groups are reacted, such as at least 10 reactants or functional entity reactive groups are reacted, for example at least 12 reactants or functional entity reactive groups are reacted, such as at least 14 reactants or functional entity reactive groups are reacted, for example at least 16 reactants or functional entity reactive groups are reacted, such as at least 18 reactants or functional entity reactive groups are reacted, by reacting at least 1 reactive group of each reactant or functional entity.

The above method of can comprise the further step(s) of hybridizing at least 1 further complementary polynucleotide selected from the group consisting of
  a) complementary connector polynucleotides comprising at least 1 functional entity comprising at least 1 reactive group,
  b) complementary connector polynucleotides comprising at least 1 reactive group,
  c) complementary connector polynucleotides comprising at least 1 spacer region,
to the hybridization complex of step iii), such as to at least 1 connector polynucleotide hybridized to a complementary connector polynucleotide in this complex
and/or the further step(s) of hybridizing at least 1 further connector polynucleotide to the hybridization complex of step iii), such as to at least 1 complementary connector polynucleotide hybridized to a connector polynucleotide in this complex.

The above further step(s) can be repeated as often as required and at least e.g. 2 or 3 times, such as 4 or 5 times, for example 6 or 7 times, such as 8 or 9 times, for example 10 or 11 times, such as 12 or 13 times, for example 14 or 15 times, such as 16 or 17 times, for example 18 or 19 times, such as 20 or 21 times, for example 22 or 23 times, such as 24 or 25 times, for example 26 or 27 times, such as 28 or 29 times, for example 30 or 31 times, such as 32 or 33 times, for example 34 or 35 times, such as 36 or 37 times, for example 38 or 39 times, such as 40 or 41 times, for example 42 or 43 times, such as 44 or 45 times, for example 46 or 47 times, such as 48 or 49 times, for example 50 times.

It is also possible to repeat steps iii) and iv) of the above method at least once, such as 2 or 3 times, such as 4 or 5 times, for example 6 or 7 times, such as 8 or 9 times, for example 10 or 11 times, such as 12 or 13 times, for example 14 or 15 times, such as 16 or 17 times, for example 18 or 19 times, such as 20 or 21 times, for example 22 or 23 times, such as 24 or 25 times, for example 26 or 27 times, such as 28 or 29 times, for example 30 or 31 times, such as 32 or 33 times, for example 34 or 35 times, such as 36 or 37 times, for example 38 or 39 times, such as 40 or 41 times, for example 42 or 43 times, such as 44 or 45 times, for example 46 or 47 times, such as 48 or 49 times, for example 50 times.

In some preferred embodiments, at least n connector polynucleotides and at least n−1 complementary connector polynucleotides are provided, n being an integer preferably of from 3 to 6, and each complementary connector polynucleotide hybridizes to at least 2 connector polynucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

Figure 4:
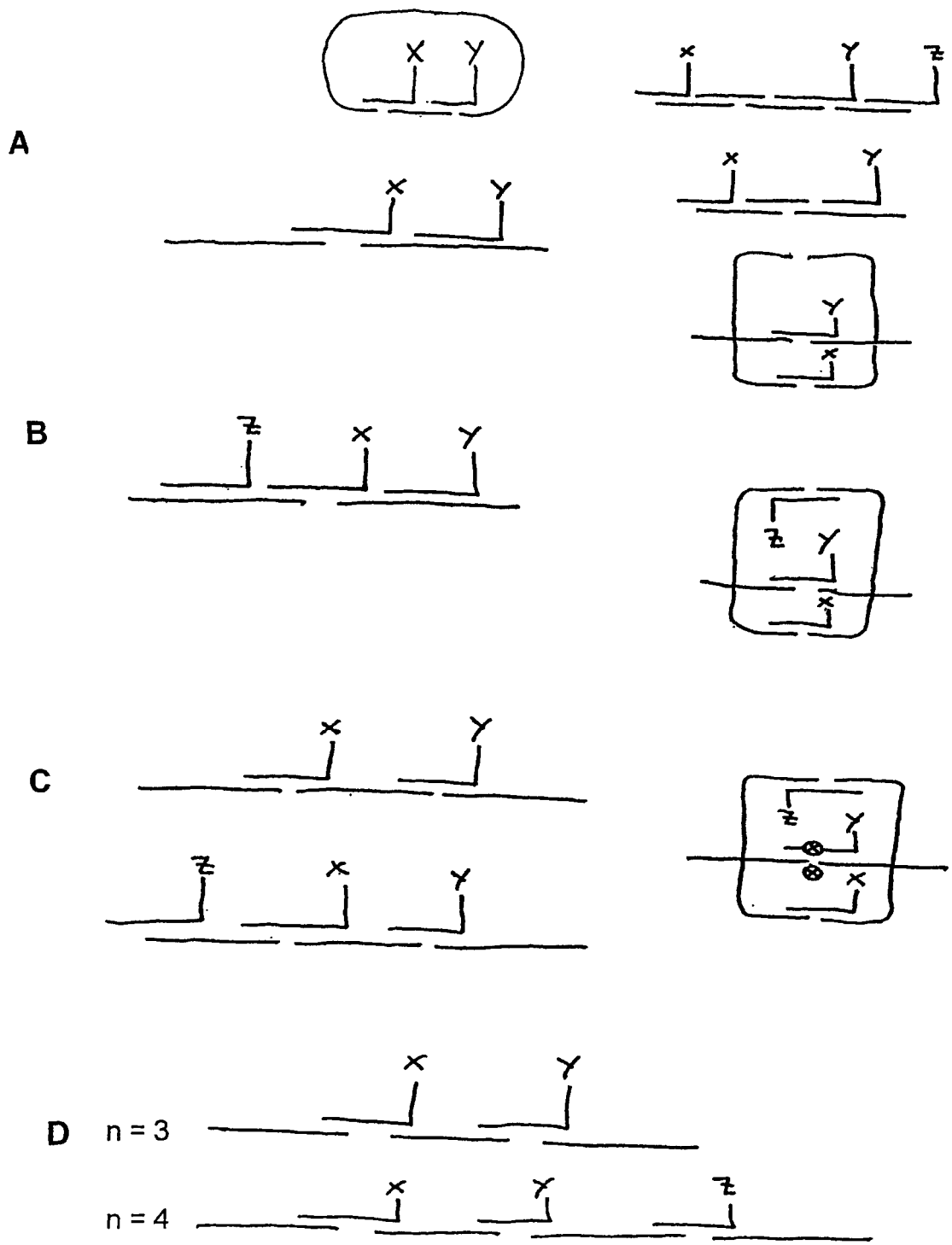
Figure 5:
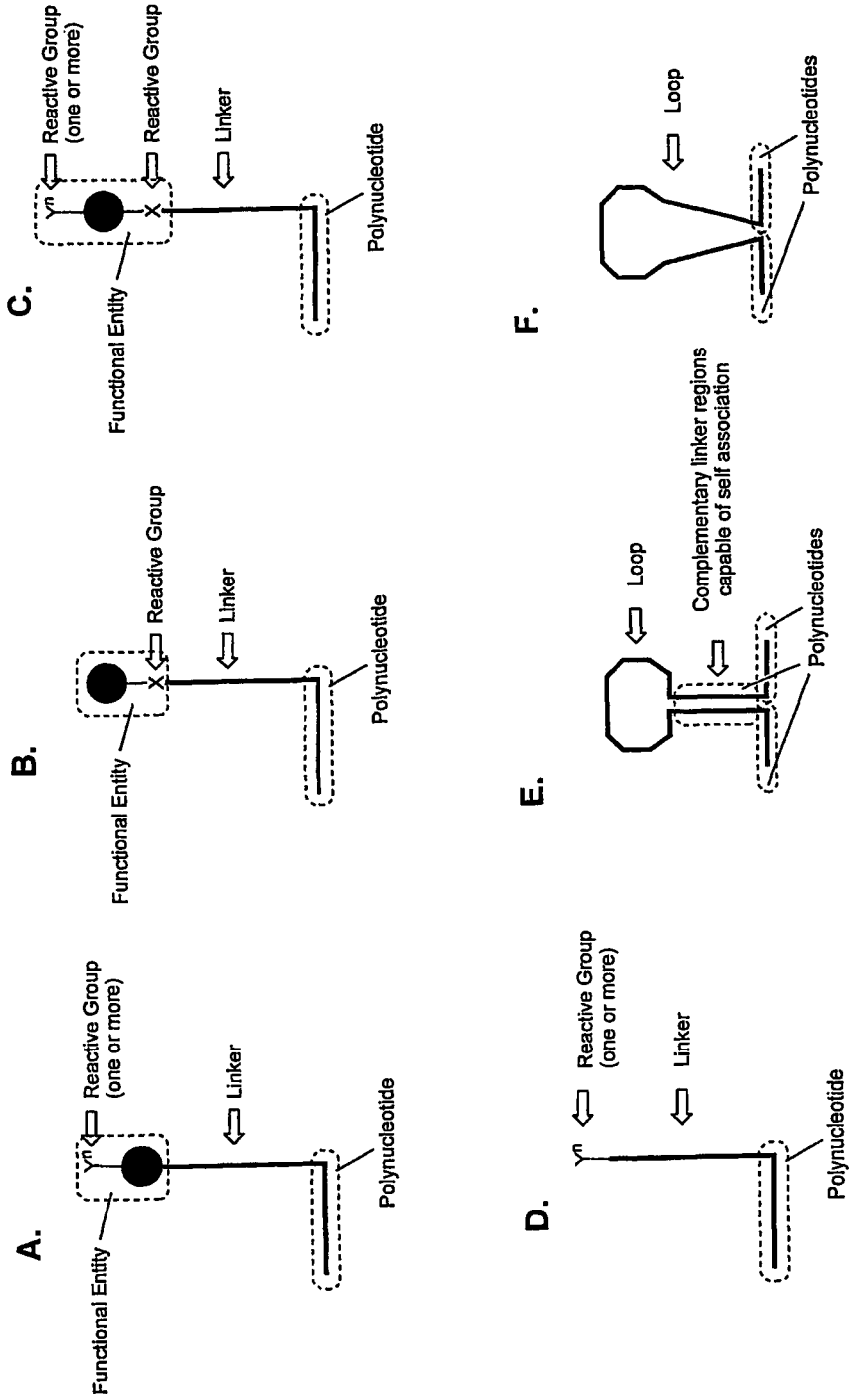

Below is described further embodiments of the methods of the invention for synthesising at least one molecule. The below embodiments are concerned with the provision of different types of hybridisation complexes comprising a plurality of CPNs hybridised to a plurality of CCPNs. The below non-exhaustive examples and embodiments specify some of the possibilities for providing CPNs and CCPNs and forming hybridisation complexes comprising a plurality of CPNs hybridised to a plurality of CCPNs. The examples are illustrated in FIG. 4 herein. It will be understood that all or only some of the CPNs and CCPNs provided can comprise a polynucleotide part linked to a reactant (capital letters in FIG. 4). For all of the below embodiments, the at least one molecule can be generated by reacting reactants positioned on separate CPNs and/or separate CCPNs prior to the formation of the at least one molecule.

In one embodiment, at least n connector polynucleotides and at least n complementary connector polynucleotides are provided, n being an integer of preferably from 3 to 6, and at least n−1 complementary connector polynucleotide hybridize to at least 2 connector polynucleotides. There is also provided a method wherein n complementary connector polynucleotide hybridize to at least 2 connector polynucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In yet another embodiment, at least n connector polynucleotides and at least n+1 complementary connector polynucleotides are provided, n being an integer of preferably from 3 to 6, and at least n−1 complementary connector polynucleotide hybridize to at least 2 connector polynucleotides. It is also possible that n complementary connector polynucleotide hybridize to at least 2 connector polynucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50. There is also provided a method wherein n complementary connector polynucleotide hybridize to at least 2 connector polynucleotides.

In a still further embodiment, at least n connector polynucleotides and at least n+2 complementary connector polynucleotides are provided, n being an integer of preferably from 3 to 6, and at least n−1 complementary connector polynucleotide hybridize to at least 2 connector polynucleotides. It is also possible for n complementary connector polynucleotide to hybridize to at least 2 connector polynucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In yet another embodiment, at least n connector polynucleotides and at least n+3 complementary connector polynucleotides are provided, n being an integer of preferably from 3 to 6, and at least n−1 complementary connector polynucleotide hybridize to at least 2 connector polynucleotides. It is also possible for n complementary connector polynucleotide to hybridize to at least 2 connector polynucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In a further embodiment at least n connector polynucleotides and at least n+4 complementary connector polynucleotides are provided, n being an integer of from preferably 3 to 6, and at least n−1 complementary connector polynucleotide hybridize to at least 2 connector polynucleotides. It is also possible for n complementary connector polynucleotide to hybridize to at least 2 connector polynucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In still further embodiments, there is provided methods wherein n connector polynucleotides and at least n+5, such as at least n+6, for example n+7, such as at least n+8, for example n+9, such as at least n+10, for example n+11, such as at least n+12, for example at least n+13, such as n+14, for example at least n+15, such as n+16, for example at least n+17, such as n+18, for example at least n+19, such as n+20, for example at least n+21, such as at least n+22, for example n+23, such as at least n+24, for example n+25 complementary connector polynucleotides are provided, n being an integer of preferably from 3 to 6, and at least n−1 or n complementary connector polynucleotide hybridize to at least 2 connector polynucleotides. n can also be more than 6, such as e.g. such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In all of the above-mentioned methods it is furthermore possible for any plurality of complementary connector polynucleotides to hybridise to a single connector polynucleotide of the supramolecular complex. Any plurality can be e.g., but not limited to, 2 or 3, for example 4 or 5 or 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

More than one single connector polynucleotide can be hybridized to the above plurality of complementary connector polynucleotides, such as 2 single connector polynucleotides, for example 3 or 4 single connector polynucleotides, such as 5 or 6 single connector polynucleotides, for example 7 or 8 single connector polynucleotides, such as 9 or 10 single connector polynucleotides, for example 11 or 12 single connector polynucleotides, such as 13 or 14 single connector polynucleotides, for example 15 or 16 single connector polynucleotides, such as 17 or 18 single connector polynucleotides, for example 19 or 20 single connector polynucleotides.

The plurality of connector polynucleotides provided can comprise linear and/or branched connector polynucleotides. In one embodiment, the plurality of connector polynucleotides comprise at least n branched connector polynucleotides and at least n complementary connector polynucleotides, n being an integer of preferably from 2 to 6, and wherein at least n−1 complementary connector polynucleotide hybridize to at least 2 branched connector polynucleotides. In other embodiments there is provided at least n+1 complementary connector polynucleotides. Also, it is possible for at least n such as n+1 complementary connector polynucleotides to hybridize to at least 2 branched connector polynucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In one embodiment, a molecule of the invention is formed when functional entities are transferred from donor complementary connector polynucleotides to an acceptor complementary connector polynucleotide. Accordingly, one or more reactive group(s) of at least 1 functional entity of a complementary connector polynucleotide react with one or more reactive group(s) of at least 1 functional entity of at least 1 other complementary connector polynucleotide. The at least 1 functional entity preferably comprise from 1 to 6 reactive groups, such as e.g. 2 or 3 or 4 or 5 reactive groups.

In one preferred embodiment, at least 3 reactive groups of at least 1 functional entity react with at least 1 reactive group of at least 3 other functional entities. The molecule can ultimately be generated on an acceptor complementary connector polynucleotide by covalently linking functional entities, or a part thereof, donated by one or more individual complementary connector polynucleotides (CCPNs) each comprising at least one functional entity, such as 2 or 3 CCPNs, for example 4 or 5 CCPNs, such as 6 or 7 CCPNs, for example 8 or 9 CCPNs, such as 10 or 11 CCPNs, for example 12 or 13 CCPNs, such as 14 or 15 CCPNs, for example 16 or 17 CCPNs, such as 18 or 19 CCPNs, for example 20 or 21 CCPNs, such as 22 or 23 CCPNs, for example 24 or 25 CCPNs.

The plurality of complementary connector polynucleotides preferably comprise at least 2 complementary connector polynucleotides (CCPNs) which are non-identical, such as 10 CCPNs, for example 50 CCPNs, such as 1000 CCPNs, for example 10000 CCPNs, such as 100000 CCPNs which are non-identical.

In one embodiment there is provided a method wherein said plurality of complementary connector polynucleotides comprise at least 2 branched complementary connector polynucleotides.

The plurality of connector polynucleotides preferably comprise connector polynucleotides comprising a sequence of n nucleotides, wherein n is an integer of from 8 to preferably less than 400, such as 300, for example 200, such as 100, for example 50, such as 40, for example 30. The plurality of connector polynucleotides can further comprise connector polynucleotides comprising at least 1 branching point connecting at least three polynucleotide fragments comprising a sequence of n nucleotides, wherein n is an integer of from 8 to preferably less than 400, such as 300, for example 200, such as 100, for example 50, such as 40, for example 30.

In some embodiments of the invention connector polynucleotides can be selected from the group consisting of
a) connector polynucleotides comprising at least 1 functional entity comprising at least 1 reactive group,
b) connector polynucleotides comprising at least 1 reactive group,
c) connector polynucleotides comprising at least 1 spacer region, The plurality of complementary connector polynucleotides can comprise polynucleotides comprising a sequence of n nucleotides, wherein n is an integer of from 8 to preferably less than 400, such as 300, for example 200, such as 100, for example 50, such as 40, for example 30. The plurality of complementary connector polynucleotides can further comprise polynucleotides comprising at least 1 branching point connecting at least three polynucleotide fragments comprising a sequence of n nucleotides, wherein n is an integer of from 8 to preferably less than 400, such as 300, for example 200, such as 100, for example 50, such as 40, for example 30.

In another aspect of the invention there is provided a method for synthesising a plurality of different molecules, said method comprising the steps of performing any of the methods described herein above for each different molecule being synthesised.

Further steps in the method for synthesising a plurality of different molecules are provided herein below. One further step comprises selecting molecules having desirable characteristics, wherein the selection employs a predetermined assaying procedure.

Another further step is amplifying at least part of the individual connector polynucleotides used for the synthesis of a selected molecule. Yet another further step is contacting a population of said amplified connector polynucleotides, or fragments thereof, with a plurality of complementary connector polynucleotides.

It is also possible to perform an additional synthesis round by carrying out the steps of the method using a population of said amplified connector polynucleotides or a population of said amplified connector polynucleotide fragments.

A still further step is characterised by performing a ligation of individual CPNs or individual CCPNs, optionally preceded by a polynucleotide extension reaction for extending gaps and e.g. duplex polynucleotides further comprising a single stranded part selected from the group consisting of a non-hybridizing part of a connector polynucleotide and a non-hybridizing part of a complementary connector polynucleotide.

Further steps pertaining to this method are
a) digesting said ligated and optionally extended duplex polynucleotides,
b) displacing the duplex polynucleotides, thereby generating single polynucleotide strands of extended connector polynucleotides and extended complementary connector polynucleotides, and
c) contacting digested, extended and displaced connector polynucleotides with a plurality of complementary connector polynucleotides, after which it is possible to performing an additional synthesis round by carrying out the steps of the method using a population of said ligated (and optionally extended), digested and displaced connector polynucleotides.

The invention also pertains to bifunctional molecules comprising a molecule part and a hybridisation complex part comprising a plurality of hybridised building block polynucleotides. The molecules capable of being synthesised by the present invention (i.e. the molecule part of bifunctional molecules) are disclosed in detail herein below. It will be understood that the invention also pertains to bifunctional molecules comprises such molecules.

Molecules capable of being synthesised by the methods of the present invention include, but is not limited to molecules comprising a linear sequence of functional entities and branched molecules comprising a branched sequence of functional entities. Molecules comprising a cyclic sequence of functional entities can also be provided.

Yet another example of a molecule capable of being synthesised is an oligomer or a polymer comprising at least one repetitive sequence of functional entities. In one embodiment, the sequence of at least three functional entities is preferably repeated at least twice in the molecule, in another embodiment any sequence of at least three functional entities in the molecule occurs only once.

Preferred molecules comprise or essentially consists of amino acids selected from the group consisting of α-amino acids, β-amino acids, γ-amino acids, co-amino acids, natural amino acid residues, monosubstituted α-amino acids, disubstituted α-amino acids, monosubstituted β-amino acids, disubstituted β-amino acids, trisubstituted amino acids, and tetrasubstituted, amino acids.

The backbone structure of said β-amino acids preferably comprises or essentially consists of a cyclohexane-backbone and/or a cyclopentane-backbone.

Other preferred classes of molecules are molecule comprising or essentially consisting of vinylogous amino acids, and molecule comprises or essentially consists of N-substituted glycines.

Further preferred molecules comprise or essentially consist of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopoly-peptides, polyamides, vinylogous sulfonamide peptide, polysulfonamide, conjugated peptides comprising e.g. prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolidone, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, including any combination thereof.

Yet further preferred molecules are those comprising a scaffold structure comprising a plurality of covalently linked functional entities selected from the group consisting of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopoly-peptides, polyamides, vinylogous sulfonamide peptides, polysulfonamides, conjugated peptides comprising e.g. prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolidones, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, and wherein the plurality of functional entities is preferably from 2 to 200, for example from 2 to 100, such as from 2 to 80, for example from 2 to 60, such as from 2 to 40, for example from 2 to 30, such as from 2 to 20, for example from 2 to 15, such as from 2 to 10, such as from 2 to 8, for example from 2 to 6, such as from 2 to 4, for example 2, such as from 3 to 100, for example from 3 to 80, such as from 3 to 60, such as from 3 to 40, for example from 3 to 30, such as from 3 to 20, such as from 3 to 15, for example from 3 to 15, such as from 3 to 10, such as from 3 to 8, for example from 3 to 6, such as from 3 to 4, for example 3, such as from 4 to 100, for example from 4 to 80, such as from 4 to 60, such as from 4 to 40, for example from 4 to 30, such as from 4 to 20, such as from 4 to 15, for example from 4 to 10, such as from 4 to 8, such as from 4 to 6, for example 4, for example from 5 to 100, such as from 5 to 80, for example from 5 to 60, such as from 5 to 40, for example from 5 to 30, such as from 5 to 20, for example from 5 to 15, such as from 5 to 10, such as from 5 to 8, for example from 5 to 6, for example 5, such as from 6 to 100, such as from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100.

Molecular weights of the molecules to be synthesised in accordance with the present invention are preferably "small molecules", i.e. molecules preferably having a molecular weight (MW) of less than 10000 Daltons, such as less than 8000 Daltons, for example less than 6000 Daltons, such as less than 5000 Daltons, for example less than 4000 Daltons, for example less than 3500 Daltons, such as less than 3000 Daltons, for example less than 2500 Daltons, for example less than 2000 Daltons, such as less than 1800 Daltons, for example less than 1600 Daltons, for example less than 1400 Daltons, such as less than 1200 Daltons, for example less than 1000 Daltons.

The functional entities of the above molecules can be linked by a chemical bond selected from the group of chemical bonds consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

In one embodiment the chemical bond linking at least some of the functional entities of the molecule is preferably formed by a reaction of a nucleophile group of a first functional entity with an ester or thioester of another functional entity. The linker of the functional entity bearing the thioester group is preferably cleaved simultaneously with the formation of the bond resulting in a transfer of the functional entity or a part thereof to the nucleophilic functional entity. The nucleophile group is preferably selected from —$NH_2$, $H_2NHN$—, HOHN—, $H_2N$—C(O)—NH—.

The backbone structure of a molecule synthesised by the methods of the present invention can comprises or essentially consists of one or more molecular group(s) selected from —NHN(R)CO—; —NHB(R)CO—; —NHC(RR')CO—; —NHC(=CHR)CO—; —$NHC_8H_4CO$—; —$NHCH_2CHRCO$—; —$NHCHRCH_2CO$—; —$COCH_2$—; —COS—; —CONR—; —COO—; —CSNH—; —$CH_2NH$—; —$CH_2CH_2$—; —$CH_2S$—; —$CH_2SO$—; —$CH_2SO_2$—; —$CH(CH_3)S$—; —CH=CH—; —NHCO—; —NHCONH—; —CONHO—; —C(=$CH_2$)$CH_2$—; —$PO_2^-NH$—; —$PO_2^-CH_2$; —$PO_2^-CH_2N^+$—; —$SO_2NH^-$—; and lactams.

In accordance with the present invention it is possible to generate a composition comprising a plurality of more than or about $10^3$ different molecules, such as more than or about $10^4$ different molecules, for example more than or about $10^5$ different molecules, such as more than or about $10^6$ different molecules, for example more than or about $10^7$ different molecules, such as more than or about $10^8$ different molecules, for example more than or about $10^9$ different molecules, such as more than or about $10^{10}$ different molecules, for example more than or about $10^{11}$ different molecules, such as more than or about $10^{12}$ different molecules, for example more than or about $10^{13}$ different molecules, such as more than or about $10^{14}$ different molecules, for example more than or about $10^{12}$ different molecules, such as more than or about $10^{16}$ different molecules, for example more than or about $10^{17}$ different molecules, such as more than or about $10^{18}$ different molecules.

The molecules can be targeted to a potential binding partner while still bound to a CCPN or a CPN of a bifunctional molecule, or the molecules can be cleaved from the CPPN to which they are bound following their synthesis. When targeted to a potential binding partner, the present invention also pertains to complexes further comprising a binding partner having an affinity for the molecule. Such binding partners can be e.g. any another molecule selected from the group consisting of DNA, RNA, antibody, peptide, or protein, or derivatives thereof.

Methods for the synthesis and efficient screening of molecules is described herein above. The below sections describe in further detail selected embodiments and different modes for carrying out the present invention.

The methods of the present invention allows molecules to be formed through the reaction of a plurality of reactants, such as e.g. reactions involving the formation of bonds between functional entities i.e. chemical moieties, by the reaction of functional entity reactive groups. The present invention describes the use of connector polynucleotides (CPN's) to bring functional entities in proximity, whereby such bond formations are made possible, leading to the synthesis of molecules such as e.g. small molecules and polymers.

In the present invention, the individual chemical moieties/ functional entities may be carried by oligonucleotides (CCPN's) capable of annealing to said CPN's. The combination and reaction of functional entity reactive groups carried by such complementary connectors polynucleotides, will lead to formation of molecules via complexation to CPN's.

Figure 22:
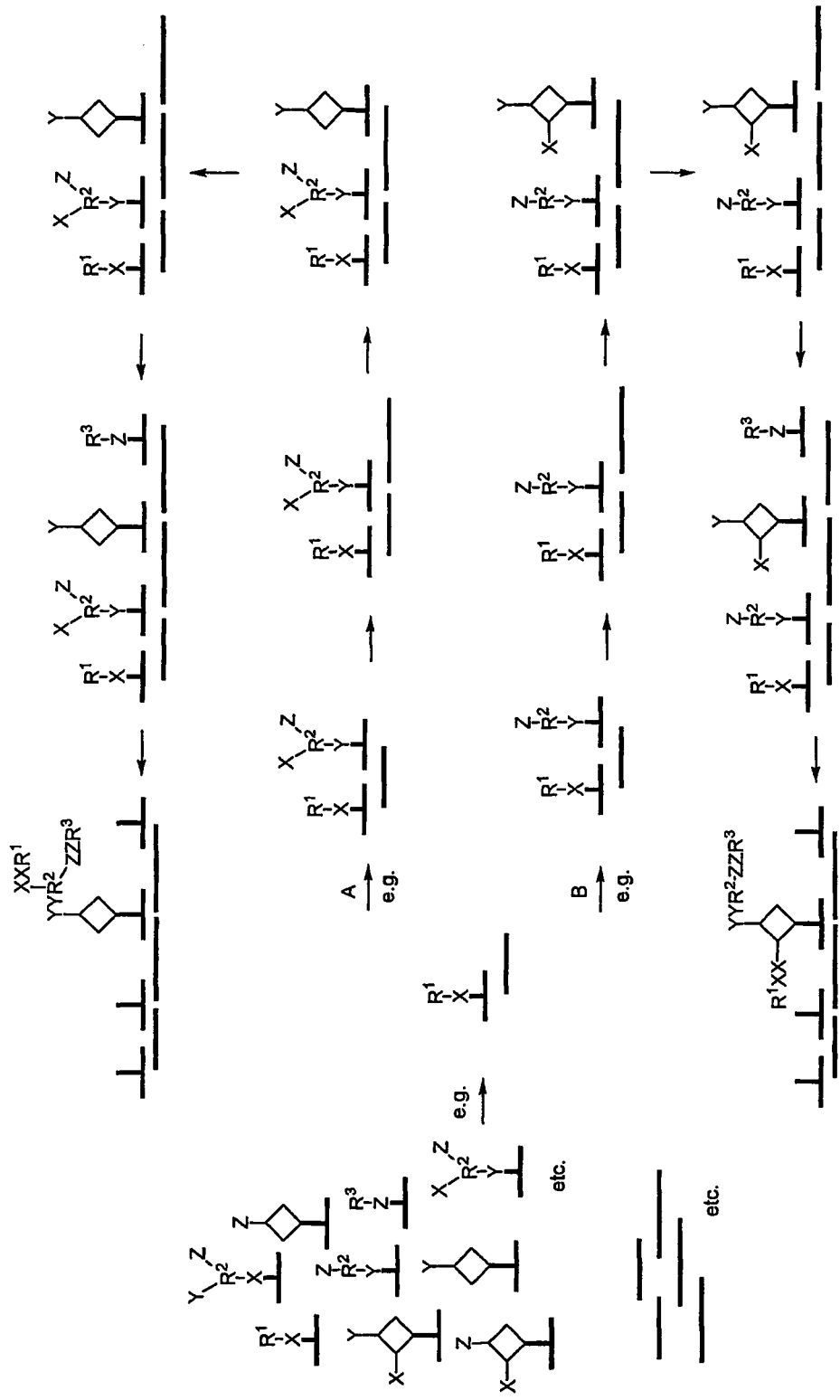

Each CPN may bring two or more CCPN's in proximity, whereby reactions between functional groups on these CCPN's are made more likely to occur. Functional entity reactive groups/reactive moieties/functional groups may be activated scaffolds or activated substituent like moieties etc. Some CCPN's only anneal to one CPN other CCPN's may anneal to two CPN's. In one embodiment of the present invention, a CCPN anneals to a CPN, which CPN allows the annealing of one further CCPN. This second CCPN may then allow the annealing of a second CPN, which may allow annealing of further CCPN's and so forth (See e.g. FIG. 22). Hybridization of multiple CCPN's and CPN's may be either sequentially or simultaneously in either one or multiple tubes. As such all CCPN's and CPN's may be added at once. Alternatively, they may be added sequentially, i.e. e.g. first a set of CPN's, then a set of CCPN's followed by a new set of CPN's or visa versa. In this sequential setting a handling control of CCPN/CPN-complex selfassembly is achieved. In another embodiment, a set of CCPN's forms complexes $A^1$-$A''$ with a set of CPN's in one separate compartment e.g. a tube. In other compartments, other sets of CCPN's forms complexes $B^1$-$B''$ with a set of CPN's etc. These separately formed complexes may be combined and form further new complexes, either directly or through further addition of CCPN's or CPN's. This illustrates still another way of a handling control of CCPN/CPN-complex selfassembly.

The present invention may be used in the formation of a library of compounds. Each member of the library is assembled by the use of a number of CCPN's, which number may be the same or different for different molecules. This will allow the formation of a mixed library of molecules assembled from 2 to n chemical moieties/fragments/functional entities or parts thereof.

Figure 3:
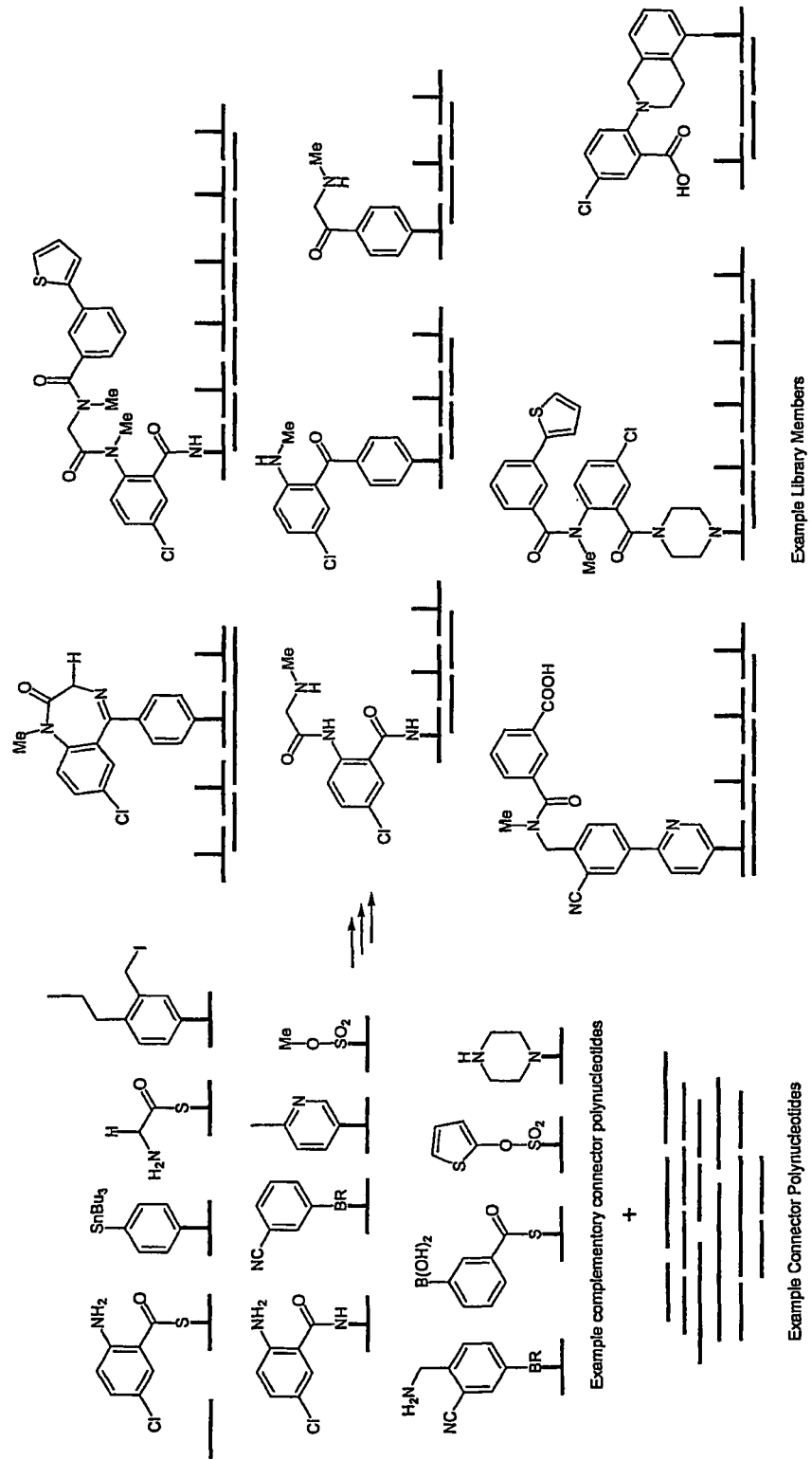

If such a library, e.g. contains molecules assembled from 1-7 functional entities/chemical moieties and 100 different functional entity/moiety types exists, the library would theoretically be a mixture of more than $100^7$ molecules. See FIG. 3.

In one setting, a CCPN may specify for the annealing of a specific type of CPN, a CPN which will specify the annealing of a further specific second CCPN, which functional entity reactive groups are capable of reacting with the functional entity reactive groups of CCPN one. In this setting each CCPN will therefore specify, which CCPN it interacts with via the CPN sequence, i.e. which reaction partner(s) they accept/prefer.

Some CCPN's carrying scaffolds may contain a certain set of functional groups. Other CCPN's carry scaffolds with another set of functional groups and still, each scaffold carrying CCPN may be combined with other CCPN's, which functional entity reactive groups can react with exactly that scaffold in the presence of a number of other types of CCPN's, including e.g. CCPN's which could have reacted but were not allowed to react. Further details are described below. This control of correct/accepted combinations of functional entity reactive groups will allow the formation of a mixed library of highly branched, semi-branched and linear molecules. The CCPN cross talk may also be used to control the properties of library members. E.g. CCPN's carrying large functional entities may only call for CCPN's carrying small functional entities or CCPN's carrying hydrophilic entities may call for CCPN's carrying hydrophilic functional entities or lipophilic functional entities depending on design.

As the chemistries applicable, will be increased by the fact, that CCPN's themselves ensure correct/accepted functional entity reaction partners, a much higher number of scaffolds will become easily available and may co-exist. E.g., it may be that derivatization of one scaffold can only be performed through the use of one specific set of transformation, whereas another scaffold may need another set of transformations. Different reactions and different CCPN's will therefore be needed for derivatization of each of these scaffolds. This is made possible by the present invention. See further details below.

As the total number of theoretically synthesizable molecules may exceed the number of actually synthesized molecules, which can be present in a given tube, shuffling becomes important to ensure a maximum of tested CCPN combinations. If e.g. $10^{17}$ is considered as a potential maximum number of different molecules present in a given reaction tube, then by using 1.000 different CCPN's and allowing formation of molecules assembled from the functional entities of 6 CCPN's, this number will be exceeded. Selection ensures that appropriate CPN's will survive, and shuffling will ensure that the number of combinations tested will be maximized.

In one embodiment of the present invention, a CPN-sequence is designed so as to anneal to one specific CCPN-sequence. This gives a one-to-one relationship between the functional entity descriptor (e.g. a polynucleotide based codon) and encoded functional entity. However, the same effect, a specific functional entity is encoded by specific CPNs and CCPNs, can be obtained by having a set of CPN-sequences that anneal to a set of CCPN-sequences. This would then require that identical functional entities are carried by all the CPNs or CCPNs of a set.

This kind of "codon-randomization" is sometimes advantageous, for example when CPN-sequences and CCPN-sequences are designed so as to allow an expansion of the library size at a later stage. If the coding region of e.g. a CPN is 3 nucleotides (providing 64 different codons), but only 16 different functional entities have been prepared, then the CCPNs may be grouped into 16 groups, for example where the first of the three nucleotide positions is randomized (i.e. 4 different CCPN-sequences carry the same functional entity).

A pseudo-one-to-one relationship is thus preserved, since the identity of the encoded functional entity can be unambiguously identified by identification of the CPN (or CCPN) involved.

Sometimes scrambling, i.e. one CPN or CCPN sequence specifying more than one functional entity, is advantageous. Likewise, under certain conditions it is advantageous to have one CPN or CCPN specify more than one functional entity. This will, however, not lead to a one-to-one or a pseudo-one-to-one relationship. But may be advantageous, for example in cases where the recovered (isolated) entity from a selection can be identified through characterization of for example its mass (rather than its attached polynucleotide complex), as this will sample a larger chemistry space.

The present invention may use short oligonucleotides, which are easily available in high purity.

In the assembly of a molecule, individual CCPN's are connected via CPN's. The functional group composition of each functional entity on the CCPN, determines the shape of the final molecule. Highly branched molecules may as such be assembled by transfer (or cross linkage followed by (linker) cleavage) of functional entities from multiple mono-functionalized functional entities (i.e. comprising one function entity reactive group) of CCPN's (e.g. substituent like) to multi-functionalized functional entities (i.e. comprising multiple functional entity reactive groups) of CCPN's (e.g. scaffolds/anchor like). Which transfer may be conducted in one or more steps. E.g.:

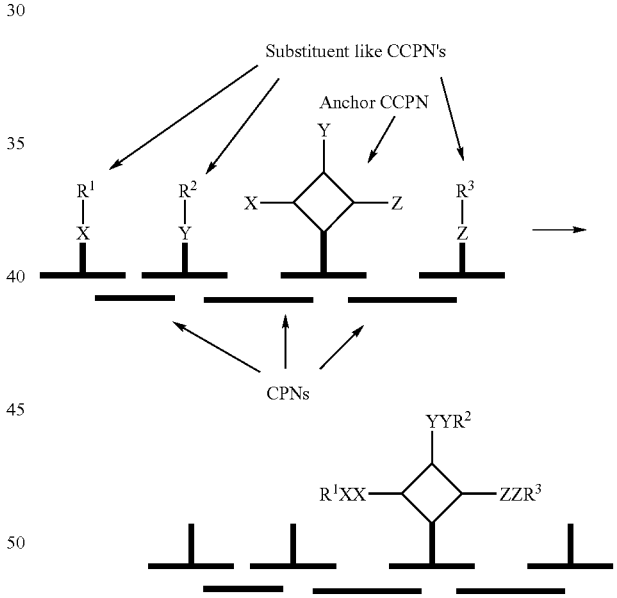

where X, Y and Z denotes functional entity reactive groups capable of reacting with each other, e.g. an amine reacting with an acylating CCPN etc., and R denotes a substituent such e.g. methyl, phenyl etc. E.g.:

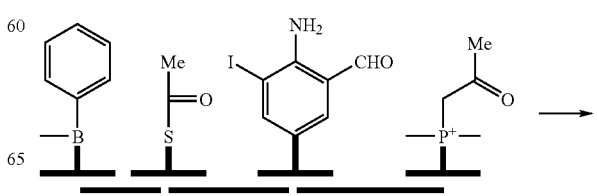

-continued

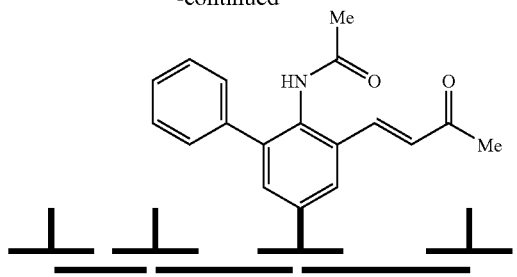

Linear molecules on the other hand, demands that the functional entity of the anchor/scaffold like CCPN contains less activated functionalization (i.e. fewer functional entity reactive groups), and furthermore that the functional entity reactive groups of substituent like CCPN's reacts with each other. E.g.:

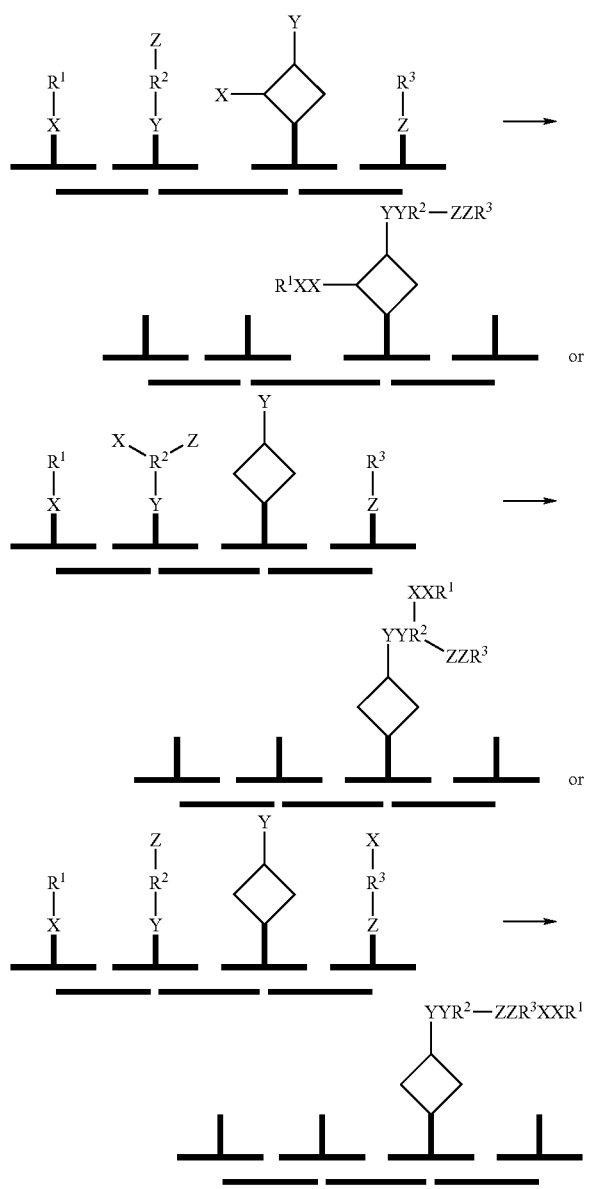

However, in the formation of a library which both contains a mixture of highly branched, less branched and linear molecules, it is important to control, that the number and type of functional groups capable of reacting with each other match.

The use of a plurality of CPN's solves this issue, by allowing only specific combinations of CCPN's in the encoding of each molecule. Each CPN thereby ensures a specific match between the number and type of needed reactions. The simplest CPN, for annealing two CCPN's could be composed like:

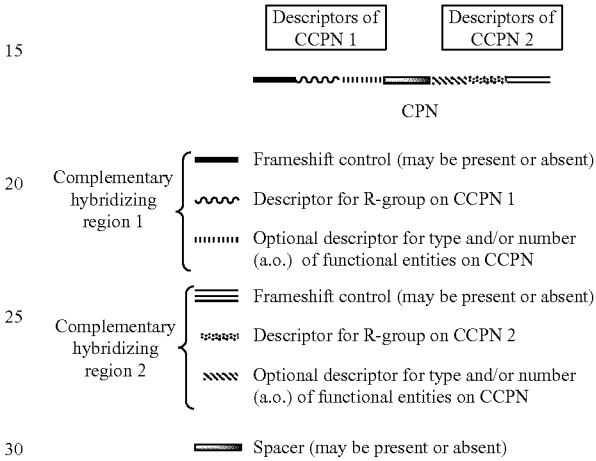

The exact position of domain types may be varied as appropriate.

In the formation of a molecule, a plurality of CPN's is used. In the generation of a library of molecules, each molecule will be assembled through the use of individual combinations of CPN's. A library of molecules may be prepared as individually separated compounds or as a mixture of compounds.

Each set of CPN's will contain variable polynucleotide regions in the domains for the descriptors for R-groups, and each of these variable polynucleotide regions may be combined with different combinations of CCPN annealing capabilities.

Similarly, may CCPN's, in their hybridizing domains specify/signal the need for specific reaction partners.

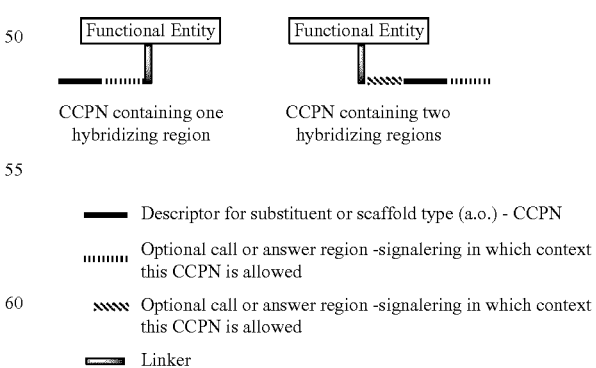

In a very simple setting, the scaffold carrying CCPN1's signals the need for one specific set (type and number) of substituent like CCPN's. E.g.,

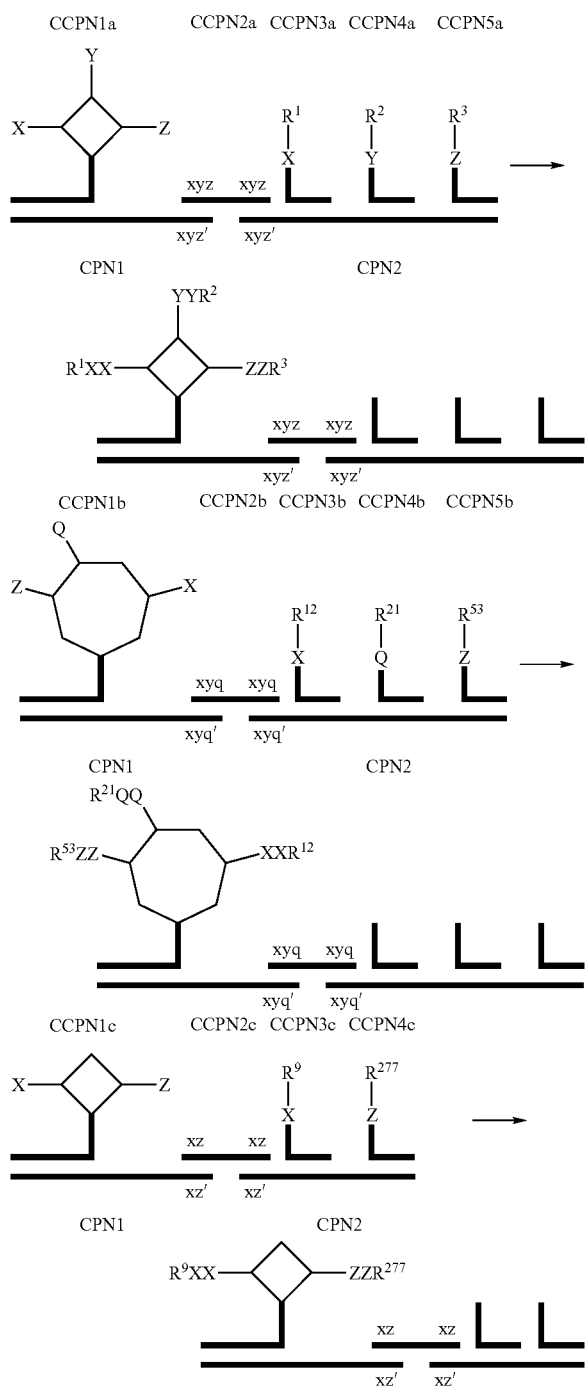

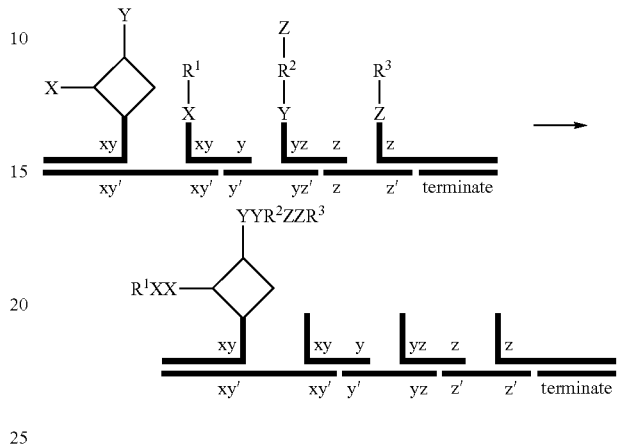

Each scaffold will thereby be derivatized appropriately, according to the needed types and numbers of reaction partners. The CCPN1, i.e. the scaffold like/anchor CCPN signals the need for a set of substituent CCPN's via annealing to an appropriate CPN1. This CPN1 calls for another CCPN2, which in this example corresponds to a spacer. The CCPN2 carry on the call for the appropriate CPN2, carrying the appropriate substituent like CCPN's via annealing of these to that CPN2. In this example, the substituent like CCPN's can only be brought in proximity to the appropriate scaffold/anchor CCPN and thereby allowed to react, if the chemistries fit, which is signaled through CCPN cross talk via CPN's. The complexes of CPN's and CCPN's described in the present invention may optionally contain single stranded regions.

Another extreme would be the setting where each individual CCPN signals its own need for reaction partners. With mono-directional scaffold derivatization one design/embodiment could be like the following:

The anchor/scaffold CCPN carries two functional groups X and Y in the functional entity. It therefore signals the call for X and Y partners. The first substituent like CCPN carries only a functional group X and answers by signaling this, as it furthermore calls for a substituent like CCPN carrying functional entity reactive group Y. These "calls/answers" are mediated via the CPN, without which these two CCPN's would not be brought in proximity and allowed to react.

The second substituent like CCPN answers the call for a functional entity reactive group Y, but since this CCPN also carries a functional entity reactive group Z, it calls for that. The third substituent like CCPN answers the call for a functional entity reactive group Z, but does not call for further CCPN's. A terminator CPN may optionally anneal to the fourth complementary connector. As can be seen, the answer signal may optionally also contains information about, what exactly this CCPN further calls for. In other words, the call signal may be answered by the availability of functional entity reactive groups as well as the one which are further called for.

The CPN's may be amplified at some step in the process or optionally be ligated to yield a one length polynucleotide, which may also be amplified and optionally further manipulated.

After e.g. selection/enrichment of the CPN/CCPN/small molecule complexes with desired characteristics (e.g. binding affinity for a protein target), the CPNs and CCPNs recovered may be amplified before characterization or a further round of selection, by any of several means:

1. Oligonucleotide primers that anneal to the terminal regions of the CPNs and CCPNs are added, and a PCR-reaction performed. This leads to the amplification of the oligonucleotide portion of all the individual CPNs and CCPNs. When the CPNs and CCPNs carry functional entities, these functional entities can be coupled to one of the two primers that anneal to a CPN or CCPN. This will lead to the amplification of this CPN or CCPN with its functional entity.

2. A PCR reaction may be performed without the addition of primers. After a number of PCR cycles (e.g. 20-30 cycles), external primers can be added. This will result in the generation of longer DNA-molecules, spanning the length of the quasirandom complexes. If the CPNs and CCPNs have been appropriately designed, cleavage by restriction nucleases can regenerate the CPNs and CCPNs, ready for a new round of quasirandom complex and small molecule formation.

3. The CPNs or the CCPNs may be ligated together, e.g. using a DNA ligase. This will result in the generation of longer DNA-molecules spanning the length of the quasirandom complexes. If the CPNs and CCPNs have been appropriately designed, cleavage by restriction nucleases can regenerate the CPNs and CCPNs, ready for a new round of quasirandom complex and small molecule formation.

The same scaffold as described above could end up as a more branched molecule in another combination of CCPN's, e.g.:

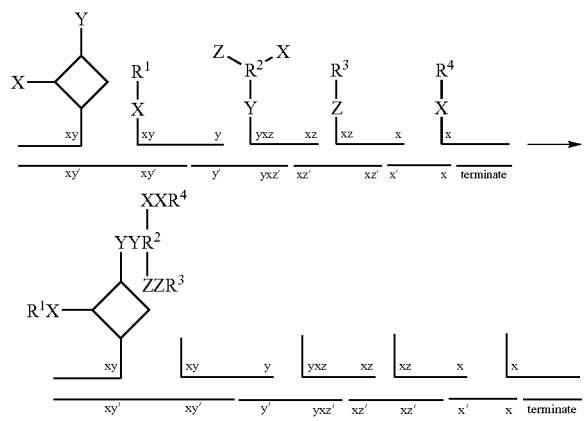

The difference between the two examples being, that the second substituent like CCPN in this setting was different, but still answered the call for a Y substitutent like CCPN from the first X substitutent like CCPN. Another difference being, that this CCPN makes its own call for both a Z and an X functional entity reactive group carrying substitutent like CCPN. In this example scrambling may occur due to the fact that the calls allowed two different X functional entity reactive group carrying substituent like CCPN's to anneal.

In another setting, one may use bi-directional scaffold derivatization, such as e.g.:

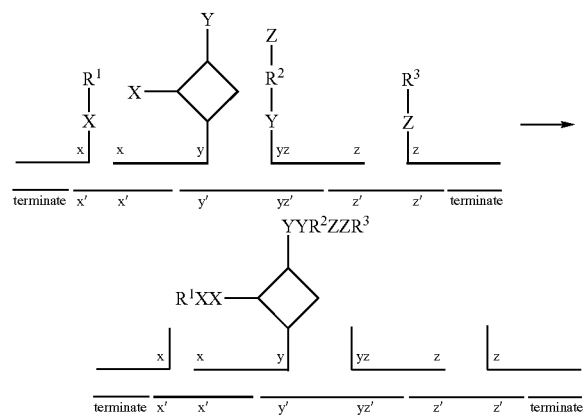

In this setting the scaffold/anchor CCPN contains two call regions, one at each terminus. Such a setting may be useful in a multiple CCPN settings, as substituent CCPN's are brought in higher proximity to the anchor CCPN.

In between settings of the above is also possible, i.e. a combination where some CPN's hybridizes multiple CCPN's, whereas other CPN's only hybridizes one or two CCPN's.

The following example illustrates one example of a setup for the formation of a linear molecule.

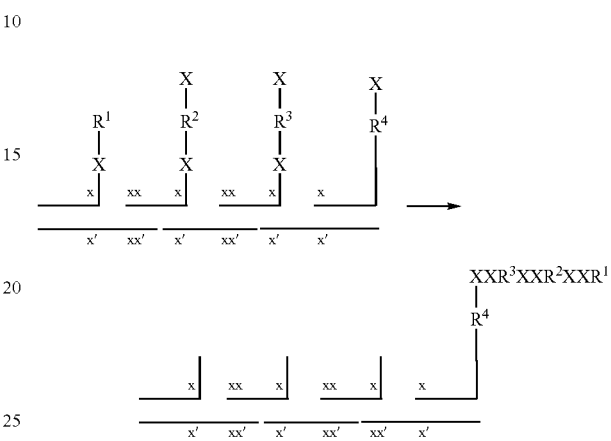

In this setting the first CCPN signals the call to undergo an "x"-reaction, which is answered by CCPN number two, which further signals the call to undergo an "x"-reaction etc. The fourth CCPN does not make any further calls.

The following section describes how hybridization regions may be designed for CCPN's and CPN's. Each region may specify, the needed types/numbers of reaction partners.

The following simple example illustrates one design. Two different scaffold like CCPN's A and B demands different types of functional entity reaction group chemistries.

A. Derivatized by alkylation or acylation

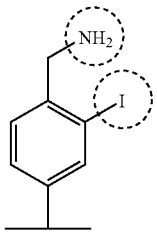

Derivatized by Suzuki or like reaction

B. Derivatized by Suzuki or like reaction

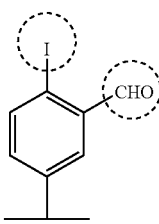

Derivatized by HWE reaction

They are then to be combined with a set of substituent like CCPN's as illustrated e.g. C1-C7.

C.

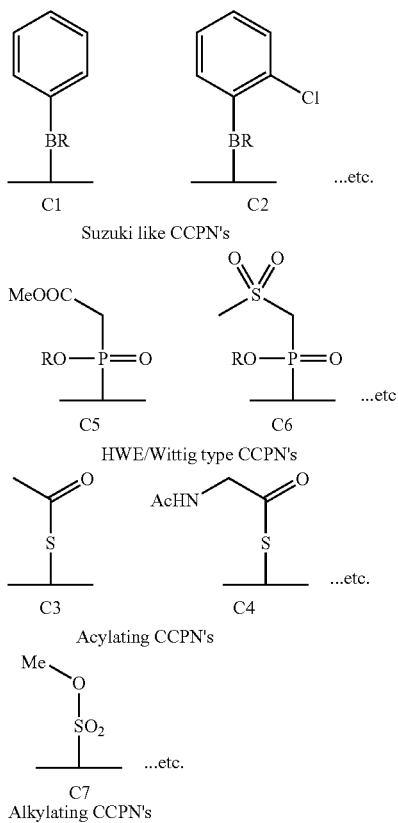

Suzuki like CCPN's

HWE/Wittig type CCPN's

Acylating CCPN's

Alkylating CCPN's

In the very simple setting, the scaffold like CCPN's calls for all the substituents needed, where such substituents are hybridized to e.g. the same CPN, i.e. only two CPN's are used. The four synthesized molecules below illustrate some of the products found in the library.

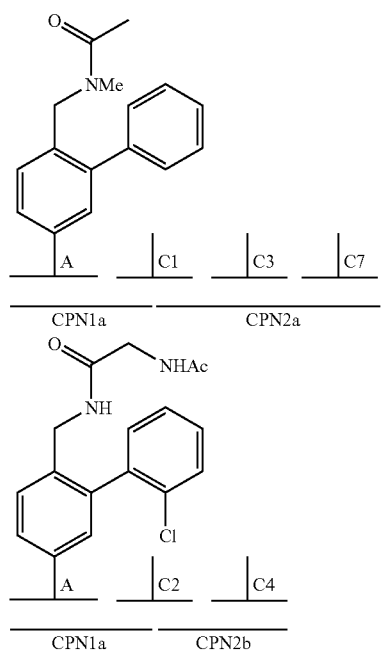

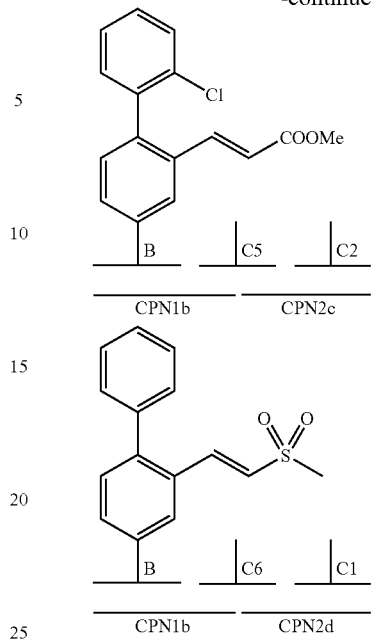

CPN type 1a anneals the scaffold type A and calls for (can only combine with) CCPN's carrying functional entity reactive groups capable of undergoing acylation and/or alkylation and furthermore a CCPN carrying functional entity reactive groups capable of undergoing a Suzuki reaction. This ensures e.g. that CCPN's carrying functional entity reactive groups capable of undergoing e.g. HWE reaction will not be combined with scaffold like CCPN type A.

CPN type 2a carries three CCPN's with functional entity reactive groups capable of undergoing acylation, alkylation and Suzuki type reactions.

CPN type 2b carries only two CCPN's with functional entity reactive groups capable of undergoing acylation and Suzuki type reactions.

CPN type 2a thereby allows further branching, whereas CPN type 2b does not.

CPN type 1b anneals the scaffold type B and calls for (can only combine with) CCPN's carrying functional entity reactive groups capable of undergoing HWE/Wittig reaction and furthermore a CCPN carrying functional entity reactive groups capable of undergoing a Suzuki reaction. This ensures e.g. that CCPN's carrying functional entity reactive groups capable of undergoing e.g. acylation reaction will not be combined with scaffold like CCPN type B.

If all four bases are used in the variable regions of CCPN's a total and e.g. 256 different scaffolds type A, 256 different scaffolds type B, 256 different acylating CCPN's, 256 different alkylating CCPN's, 256 Suzuki type CCPN's and 256 different HWE/Wittig type CCPN's could be used. The following sequences for polynucleotide sequences could be one design to illustrate the principle (wherein N denotes a random nucleobase, preferably selected from G, A, C, T, U):

(SEQ ID NO: 1)
Scaffold like CCPN's type A's: 3'-GCGCNNNNGGCG-5'

One specific scaffold e.g. the one illustrated above could e.g. have the specific sequence: 3'-GCGCATTAGGCG-5'. (SEQ ID NO:2)

Another scaffold type A, demanding the same chemistries but having another skeleton could have the specific sequence: 3'-GCGCTTAAGGCG-5' (SEQ ID NO:3) etc.

```
                                          (SEQ ID NO: 4)
Scaffold like CCPN's type B's: 3'-AATTNNNNTAAT-5'
```

One specific scaffold e.g. the one illustrated above could e.g. have the specific sequence: 3'-AATTGCCGTAAT-5' (SEQ ID NO:5)

Another scaffold type A, demanding the same chemistries but having another skeleton could have the specific sequence: 3'-AATTCGGGTAAT-5' (SEQ ID NO:6) etc.

```
                                          (SEQ ID NO: 7)
Suzuki type CCPN's: 3'-TTTTTGAGANNNNNAAGGTTTTT-5'
```

One specific Suzuki type CCPN e.g. C1 illustrated above could e.g. have the specific sequence: 3'-TTTTTGAGATTC-CAAGGTTTTT-5' (SEQ ID NO:8). Another Suzuki type CCPN could e.g. have the sequence 3'-TTTTTGAGACT-TCAAGGTTTTT-5' (SEQ ID NO:9).

```
Acylation type CCPN's:
                                          (SEQ ID NO: 10)
3'-GTTGNNNN1TGG-5'

Alkylation type CCPN's:
                                          (SEQ ID NO: 11)
3'-AACCNNNNACCA-5'

HWE/Wittig type CCPN's:
                                          (SEQ ID NO: 12)
3'-TTCCNNNNNCTCT-5'

CPN type 1a sequences:
                                          (SEQ ID NO: 13)
3'-NNNNTCTCAAAAACGCCNNNNGCGC-5'
```

One specific type of these would be 3'-GGAATCT-CAAAAACGCCTAATGCGC-5' (SEQ ID NO:14) this CPN would allow the hybridization of CCPN type A and CCPN type C1.

Another specific sequence would allow the hybridization of e.g. C2 instead of C1 but not C3-C7 etc.

In some settings single stranded regions may be applied to increase flexibility of the complex. This may be implemented by increasing e.g. the number of A nucleobases from 5 nucleobases to 7 or 10 or what is found appropriate.

```
CPN type 2a sequences:
                                          (SEQ ID NO: 15)
3'-TGGTNNNNGGTTCCAANNNNCAACAAAAACCTT-5'

CPN type 2b sequences:
                                          (SEQ ID NO: 16)
3'-CCAANNNNCAACAAAAACCTT-5'
```

Sequences for CPN type 1b, 2c and 2d are designed similarly to allow hybridization of CCPN's carrying functional entity reactive groups capable of undergoing HWE reactions rather than acylating and/or alkylating reactions.

If the number of potential combination is to be maximally increased a high number of CPN's may be used and each CCPN may then make use of "cross talk".

In such a setting, the reactions used may be 1. acylations (Ac), 2. alkylations (Al) 3. Cross coupling/Suzuki and like reactions (C) and 4. HWE/Wittig type reactions (W). Each reaction demands a donor and an acceptor, where donor denotes a functional entity reactive group, which upon reaction leads to transfer of the functional entity or a part thereof of that CCPN. Transfer may be directly in one step or sequentially through cross linkage followed by cleavage. An acceptor denotes a functional entity reactive group, which upon reaction accepts the transfer of a functional entity or part thereof from another CCPN.

When designing CCPN hybridization regions, one may bias the library towards specific properties, e.g. if selection is used to identify drug candidates in the library, it is in most cases not appropriate to have aromatic amines presented due to their potential toxic properties, whereas aliphatic amines are in general acceptable. CCPN's carrying aromatic amines may therefore specifically signal the need to be partnered, with a CCPN carrying a functional entity reactive group capable of undergoing acylation reactions and optionally allow a CCPN carrying a functional entity reactive group capable of undergoing alkylating reactions, whereas aliphatic amines may be partnered with both CCPN's carrying functional entity reactive groups capable of undergoing acylation and alkylation reactions. Aromatic hydroxyl groups, on the other hand, should not be acylated due to the generation of another acylating specie, which will generally not be acceptable as drug candidate. Aromatic hydroxyl groups should therefore only be alkylated. Such demands may be entered into hybridization region for a specific CCPN.

If all four reaction types were to be used in one library generation, then the hybridization region of each CCPN could specify, which one of the reaction types, mentioned above, are needed (denoted by "*"), allowed (denoted by "+") and forbidden (denoted by "−").

Plus ("+") sequences may be composed of non-specific hybridizing nucleobases such as e.g. inosine. Minus ("−") sequences may be composed of a nucleobase sequence with one specific sequence and the need of a specific partner will be specified by another specific sequence.

E.g. nucleobase sequence I (inosine)="+"; nucleobase sequence T (thymine)="−", and nucleobase sequence G (guanine)=(*).

|   | "+": Allowed reactive group on CCPN's further downstream | "−": Disallowed reactive group on CCPN's further downstream | "*": Needed reactive group on CCPN's further downstream |
|---|---|---|---|
| CCPN sequence | I | T | G |
| CPN sequence accepted | A or C | A | C |

As the need, acceptance or disallowance of e.g. four different reaction partners is to be signaled, the overall descriptor sequence for type and number of functional entities on a CCPN corresponds to four polynucleotide subregions. In the following illustrations, the regions 1, 2, 3, 4 correspond to the need or acceptance of the partners Ac (1); Al (2); C (3) and W (4). One further nucleobase in that polynucleotide sub-region may optionally indicate whether the functional entity reactive group is of donor or acceptor type. In the following nucleobase T (thymine) indicates a donor, nucleobase G (guanine) indicates an acceptor and nucleobase I (inosine) is used if donor/acceptor type is not specified.

In the design example above, the four regions 1 (Acylation), 2 (Alkylation), 3 (Cross Coupling/Suzuki) and 4 (Wittig/HWE) could be of a total of 8 nucleobases for the call region and 8 nucleobases for the answer region.

One simpler example, using a higher number of CPN's could be the following example. In this example, the call signal specifies only the need/allowed CCPN's and the answer similarly.

The CCPN's in a peptide like library composed of complementary connectors 1-7 could have the following identifier polynucleotide sequences.

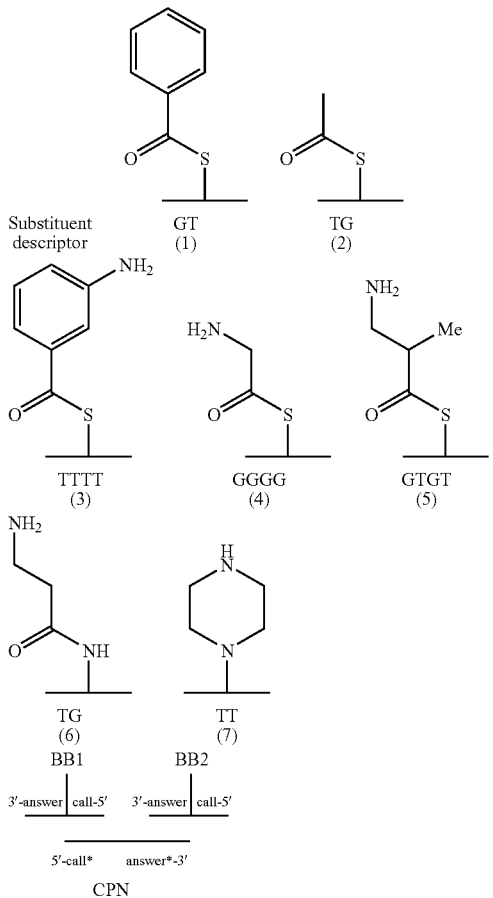

The sequence of the complementary connector polynucleotides could then be:

```
                                             (SEQ ID NO: 17)
CCPN1: 3'-GT-GGTITITI-5'

(SEQ ID NO: 18)
CCPN2: 3'-TG-GGTITITI-5'

(SEQ ID NO: 19)
CCPN3: 3'-GTITTITI-TTTT-GGTITITI-5'

(SEQ ID NO: 20)
CCPN4: 3'-GTITTITI-GGGG-GGTITITI-5'

(SEQ ID NO: 21)
CCPN5: 3'-GTITTITI-GTGT-GGTITITI-5'

(SEQ ID NO: 22)
CCPN6: 3'-GTITTITI-TG-5'

(SEQ ID NO: 23)
CCPN7: 3'-GTITTITI-TT-5'
```

CCPN1 and CCPN2 carries only a call region and calls for acylating acceptors. CCPN3-CCPN5 carries both an answer and a call region. The answer region specifies that it needs an acylating donor but also allows alkylating agents. The call region specifies the call for an acylating acceptor.

CCPN6 and CCPN7 carries only an answer region. The answer region specifies that it needs an acylating donor but also allows alkylating donors.

To generate this library, the following CPN may then fulfill the need:

```
                                             (SEQ ID NO: 24)
CPN1: 3'-NN-CACAACAC-CACACACC-NN-5'
```

Where N denotes a variable nucleobase.

In this library all CCPN's carrying function entity groups of amino type have been specified as allowance for alkylation, but with the need for acylation.

In order to control the degree of supramolecular complex formation, terminator sequences may be added at some point in time. The concentration of which, will determine the mean distribution of how many CCPN's and CPN each complex is made of.

Such terminator sequences could in the example above be:

```
                                             (SEQ ID NO: 25)
Terminator1: 3'-CACACACC-NN-5'

(SEQ ID NO: 26)
Terminator2: 3'-GTITTITI-NN-5'
```

EXAMPLES

The following example illustrates the use and the principle for the synthesis and identification of connector polynucleotide sequences enabling the synthesis of a small peptide.

Example 1

Quasi-Structure Mediated Synthesis of a Small Molecule that Binds Integrin Receptor $\alpha_V/\beta_{III}$ Materials:
Purified human integrin $\alpha_V/\beta_{III}$ (Chemicon Inc.)
Streptavidin Sepharose 6B (AmershamPharmacia)
Nunc ImmunomoduleU8 Maxisorp (Biotecline cat# Nun475078)
Sheared herring DNA (Sigma)
Bovine serum albumin (BSA)(Sigma-Aldrich)
Taq-polymerase (Promega)
Micro Bio-Spin 6 (Bio-Rad cat: 732-6221)
FokI, AvrII and PstI restriction enzymes
T7 Exonuclease
Connector Polynucleotides (CPN's) and Complementary Connector Polynucleotides (CCPN's):

```
CPN1:
                                             (SEQ ID NO: 27)
5'-pGCNNNNNACGCGANNNNNTACGTANNNNTGTCACNNNNTCGTCANNN
NNGC-3'

CPN2:
                                             (SEQ ID NO: 28)
5'-pGCNNNNNTCATCTNNNNGCGTACNNNNNGC-3'

CCPN1:
5'-GCCTATGTGACGAATCTGTG-XXXXX-GATTC-Y-3'
(SEQ ID NO: 29 before XXXXX, SEQ ID NO: 30 after; X
is PEG-linker)

CCPN2:
5'-Z-GAATC-XXXXX-ATGCGTACCGCGATTCATGCp-3'
(SEQ ID NO: 31 before XXXXX, SEQ ID NO: 32 after)

CCPN3:
5'-Z-GAATC-XXXXX-CGCTGCAAGATGAATTCTGCp-3'
(SEQ ID NO: 33 before XXXXX, SEQ ID NO: 34 after)
```

Linker Polynucleotides for CPN Amplification:

```
                                         (SEQ ID NO: 35)
    LP1: 5'-GATTCCTAGGATGCATATTACA (SEQ ID NO: 36)
    LP2: 3'-CTAAGGATCCTACGTATAATGTCG (SEQ ID NO: 37)
    LP3: 3'-GTCAATGCTGATGACGTp (SEQ ID NO: 38)
    LP4: 5'-CAGTTACGACTACTGCAGC
```

Amplification polynucleotides

```
                                         (SEQ ID NO: 39)
    AP1: 5'-B-T_{in}T_{in}GATTCCTAGGATGCATATTACAGC-3'

(SEQ ID NO: 40)
    AP2: 5'-CAGTTACGACTACTGCAGC-3'
```

Underlined sequence=FokI restriction site
Bold sequence=AvrII restriction site
Italic sequence=PstI restriction site
P=5'-phosphate
Sequencing Polynucleotide:

```
                                         (SEQ ID NO: 41)
    SP: 5'-GATTCCTAGGATGCATATTAC
``` where X=PEG-linker, Glen research cat#10-1918-90; B=biotin, Applied Biosystems and Y=3'-amino-group, Glen research cat#20-2958-01, Z=amino modifier, Glen research cat#10-1905-90 suitable for attachment of chemical entities. p=5'-phosphate.

Protocol

In the following protocol, the guanidine functionality of arginine may be appropriately protected if needed. E.g. by use of trifluoroacetyl (which can be removed, when needed, by alkaline treatment), benzyloxycarbonyl (which can be removed, when needed, by catalytic hydrogenation), enzymatically cleavable protecting groups and others known to the person skilled in the art.

Step 1: Loading of Building Block Polynucleotides

CCPN1.

5 nmol of CCPN1 is incubated with 25 mM NHS and 50 mM EDC in 100 mM HEPES-OH buffer pH 7.5 at 30° C. for 30 min. Excess EDC/NHS is removed using spin-column filtration. The NHS-activated CCPN1 is incubated with 20 mM arginine in HEPES-OH buffer at 30° C. for 2 hours. CCPN1 is purified using spin column filtration and loading efficiency is tested using ES-MS (Bruker Inc.)

CCPN2 & CCPN3.

5 nmol of CCPN2 or CCPN3 is incubated with 25 mM TCEP [tricarboxyethyl-phosphine] in 100 mM HEPES-OH at 30° C. for 1 hour producing a terminal SH-group. TCEP and buffer are removed by gel-filtration before addition of 50 mM N-hydroxymaleimide (NHM) in 100 mM HEPES-OH, pH 7.5. The preparations are incubated at 30° C. for 2 hours producing CCPN's comprising a NHS activating unit. Excess NHM is removed by gel-filtration. 100 mM 4-pentanoyl glycine or 4-pentenoyl-OMe aspartate in DMF is pre-activated using equimolar EDC in DMF at 25° C. for 30 minutes. The CCPN-NHS is incubated with 50 mM EDC activated 4-pentanoyl protected glycine or 4-pentenoyl-OMe aspartate, respectively, in a 100 mM MES buffer pH 6.0 at 25° C. for 5 minutes (DMF:H$_2$O=1:4). Excess building block is removed by gel-filtration and activated CCPN is eluted in 100 mM MES buffer pH 6.0.

Scheme 1: Loading of polynucleotides with building blocks

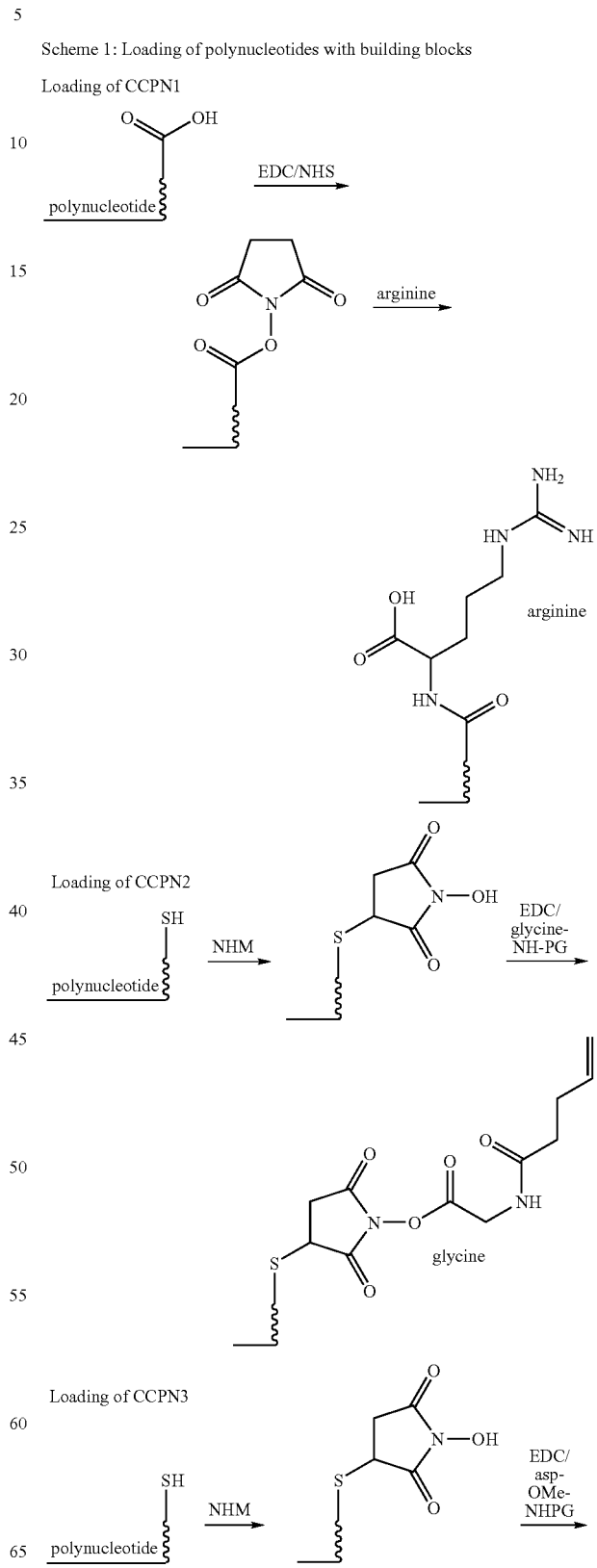

-continued

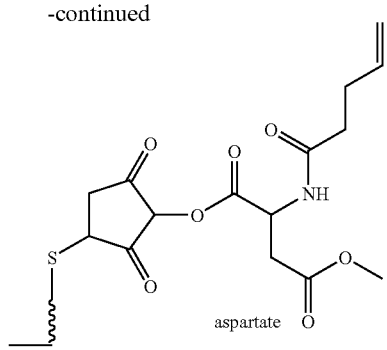

aspartate

Step 2: Formation of Multi-Polynucleotide Complexes and Transfer of Building Blocks.

10 μmol each of activated CCPN1 and CCPN2 from step 1 is incubated with 10 μmol of CPN1 and CPN2 in 100 mM MES buffer pH 6.0 supplemented with 5 mM 12 in THF (for amino-deprotection). The reaction is incubated at 25° C. for 4 hours allowing assembly of multi-polynucleotide complexes and concomitant transfer of the glycine residue (Scheme 2B). Subsequently, 10 μmol of activated CCPN3 is added to the reaction and incubated at 25° C. for an additional 4 hours. Transfer of the O-Methyl aspartate followed by mild alkaline treatment (pH 9.0, 1 h) produce the RGD peptide linked to CCPN1 (Scheme 2C).

Scheme 2: Quasi-structure mediated synthesis of an RGD peptide

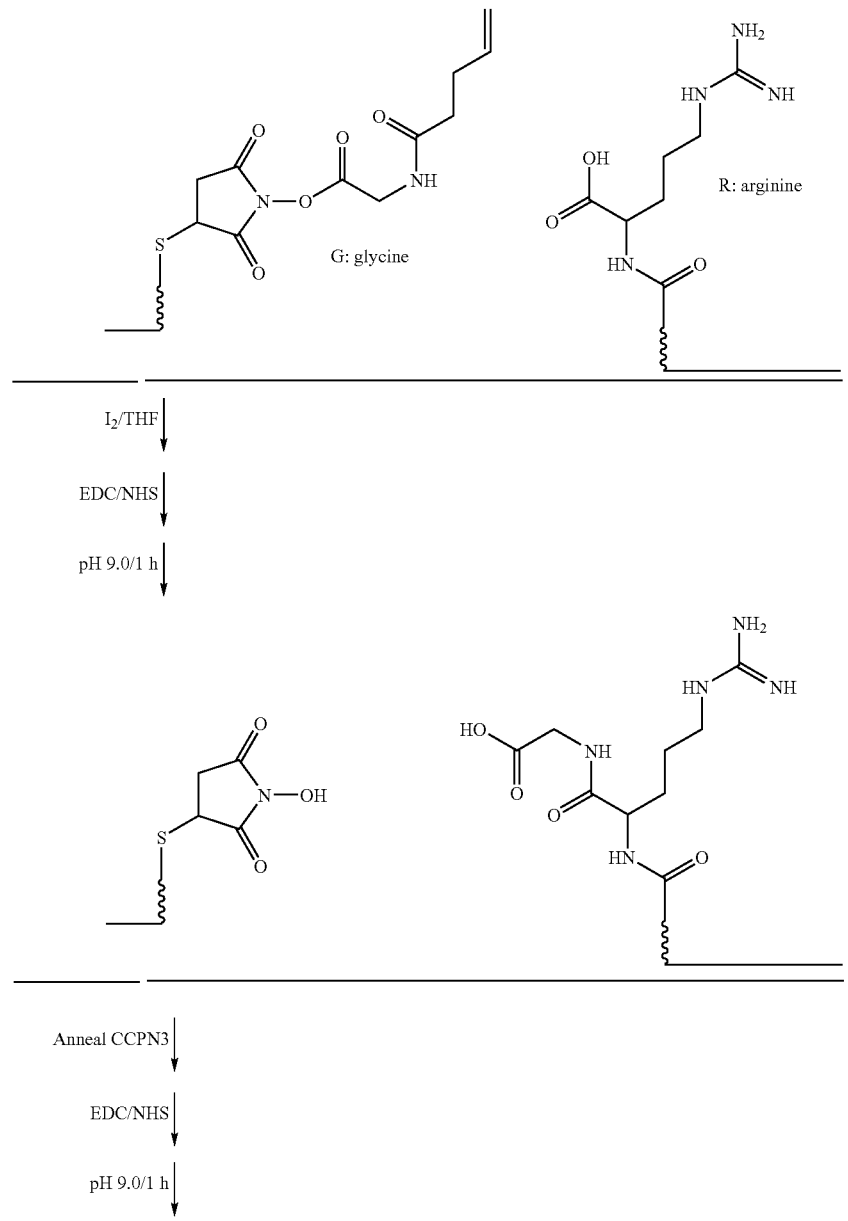

-continued

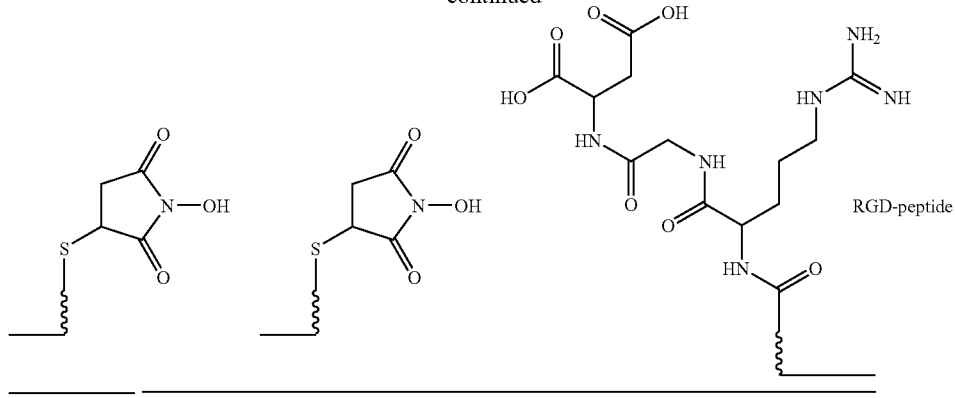

Step 3: Selection of Multi-Polynucleotide Complexes Displaying the RGD Peptide.

A single well of a Nunc-8 plate is incubated overnight with 100 μl of 1 μg/ml of integrin receptor in standard phosphate-buffered saline (PBS). The well is washed five times with 100 μl PBS. The well is blocked using 100 μl 0.5 mg/ml sheared herring DNA in PBS-buffer for 2 h at room temperature.

Finally the well is washed five times using 100 μl Integrin binding buffer [Tris-HCl (pH 7.5), 137 mM NaCl, 1 mM KCl, 1 mM $MgCl_2$, 1 mM $CaCl_2$ and 1 mM $MnCl_2$]. The multi-polynucleotide complexes are added to the immobilised integrin and incubated at 37° C. for 30 min. The supernatant is removed and the immobilised integrin is washed 5 times using 100 μl Integrin binding buffer. The polynucleotide complexes are eluted heating the sample to 80° C. for 5 min. The sample is cooled to room-temperature.

Step 4: Amplification of Polynucleotides

1 μl of the sample from step 3 is used for amplification of polynucleotide fragments using the following protocol (see also Scheme 3):

Scheme 3: Amplification of connector polynucleotides

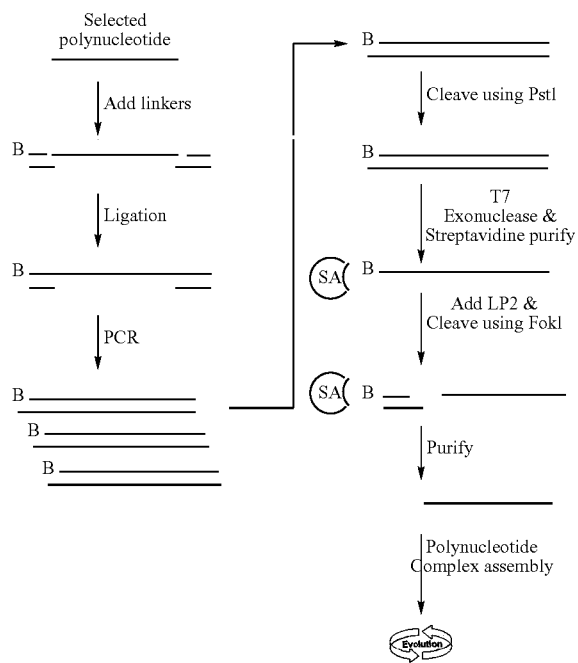

1 μmol each of preformed LP1/LP2 complex and 1 pmol of LP3/LP4 complex is added to the eluted connector polynucleotide fragments in ligation buffer comprising 30 mM Tris-HCl (pH 7.8) 10 mM $MgCl_2$, 10 mM DTT and 1 mM dATP before addition of 10 units of T4 DNA ligase. The sample is incubated at 16° C. for 4 hours before denaturation at 75° C. for 15 min. 1/10 of the sample is used as template in a PCR reaction comprising 10 μmol of the oligonucleotides AP1 and AP2 10 mM Tris-HCl pH 9.0, 50 mM KCl, 1 mM $MgCl_2$, 0.1% Triton X-100, 250 mM each of dATP, dCTP, dGTP and dTTP. The sample is run with initial denaturation at 94° C., for 2 min and 30 cycles using denaturation at 94° C. for 30 seconds, annealing at 44° C. for 30 seconds and elongation at 72° C. for 15 seconds. Finally, the sample is phenol extracted twice before DNA precipitation.

Regeneration of single stranded connector polynucleotides are accomplished by first cleaving the PCR products using 10 units of PstI in a buffer comprising 50 mM Tris-HCl (pH 7.9), 100 mM NaCl, 10 mM $MgCl_2$ and 1 mM DTT at 37° C. for 2 hours in a volume of 50 μl. Following cleavage, the sample is subjected to 5' to 3' digestion using T7 exonuclease at 37° C. for 1 hour in a total volume of 500 μl. Next, the biotinylated strand is purified on streptavidin-sepharose beads using the following procedure:

50 streptavidin-sepharose slurry is washed 4 times using 1 ml of 20 mM $NH_4$-acetate pH 7.5 before addition of digestion sample in a total volume of 500 μl and further incubation at 25° C. for 15 minutes. The streptavidin beads are washed 4 times using 1 ml of $H_2O$. The amplified polynucleotides are regenerated by annealing of 10 μmol of LP2 to the streptavidin bound polynucleotide. Excess LP2 is removed by washing the beads 4 times using $H_2O$, Subsequently, the beads are incubated in 100 μl buffer comprising 20 mM Tris-acetate (pH 7.9), 50 mM K-acetate, 10 mM $MgCl_2$ and 1 mM DTT before addition of 10 units of FokI restriction enzyme and incubation at 37° C. for 2 hours. The eluted polynucleotide is sampled and heated for 80° C. for 5 minutes to denature the restriction enzyme before purification of the polynucleotides using gel-filtration.

Step 5: Repeat Step 2 Using the Amplified Polynucleotides

The new population of single stranded polynucleotides which are enriched for sequences that represent ligands for the integrin αV/β3 receptor are annealed to the library of tagged-peptides from step 1 as described in step 2 and subjected to yet another round of selection and amplification.

The selection and amplification procedure (step 2-5) is repeated for 5 rounds.

Step 6: Identification of Connector Polynucleotide Sequences Involved in the Synthesis of RGD.

The identity of enriched double stranded polynucleotide fragments from step 4 is established by DNA cloning in a M13 mp18 plasmid vector and examining individual clones by sequence analysis.

For statistical purposes more than 50 clones is sequenced to identify sequence bias within the pool of cloned polynucleotides.

Example 2

Figure 21:
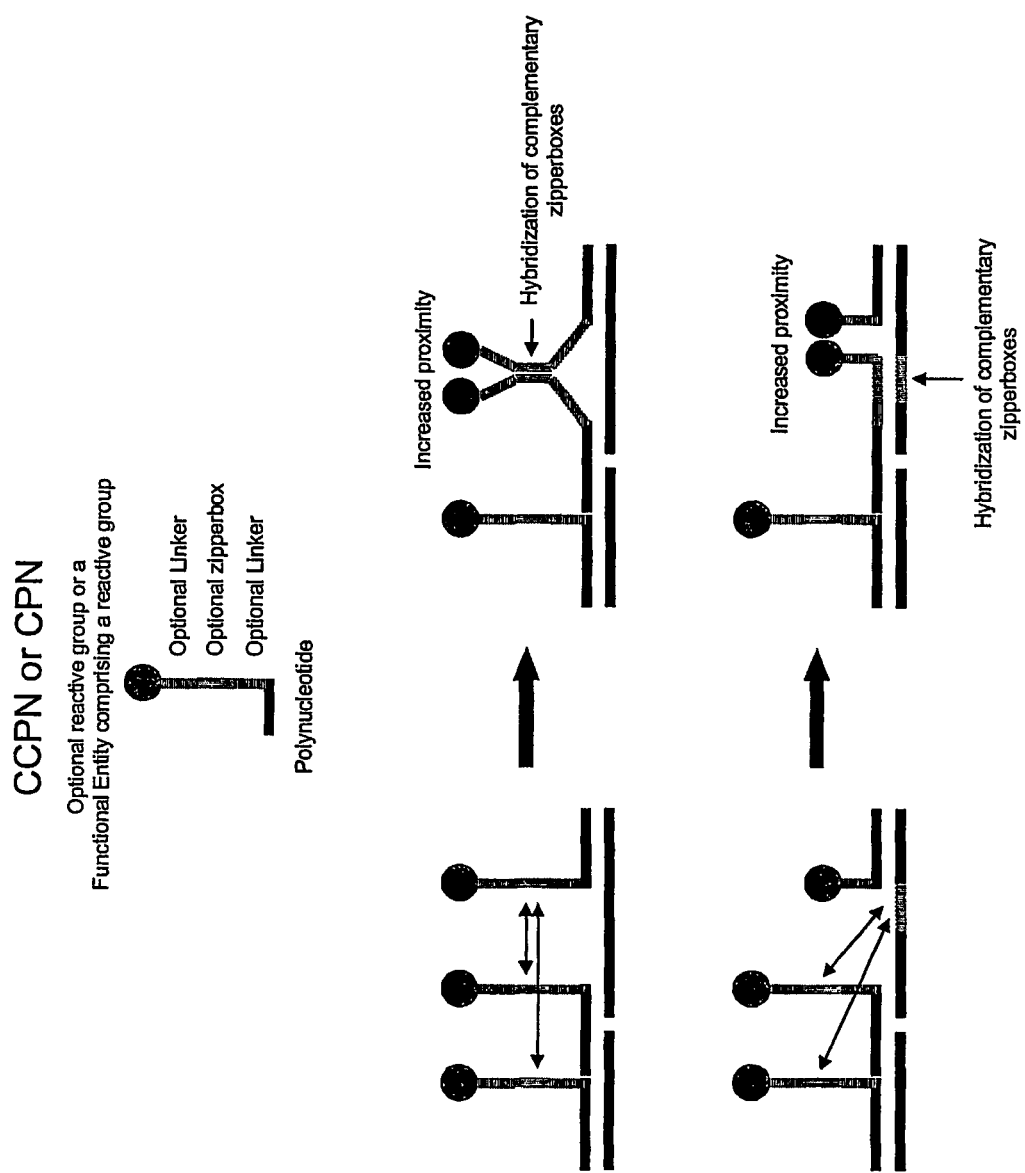

In the following, a zipper box designates a polynucleotide based region within the linker of the CCPN, which may hybridize to complementary polynucleotide based regions of other CCPN's. Alternatively, this zipperbox may hybridize to a CPN. Such hybridizations will allow the functional entities of two individual CCPN's to reach high proximity (FIG. 21).

In the following examples, CCPN building blocks are used which contain a zipper box adjacent to the functional entity. The zipper box sequences are underlined below. The following buffers and protocols are used in the same examples.

Buffers.
Buffer A (100 mM Hepes pH=7.5; 1 M NaCl)
5'-Labeling with $^{32}$P.
Mix 5 µmol oligonucleotide, 2 µl 10× phosphorylation buffer (Promega cat#4103), 1 µl T4 Polynucleotide Kinase (Promega cat#4103), 1 µl γ-$^{32}$P, add H$_2$O to 20 µl. Incubate at 37° C. 10-30 minutes.
PAGE (Polyacrylamide Gel Electrophoresis).

The samples are mixed with formamide dye 1:1 (98% formamide, 10 mM EDTA, pH 8, 0.0.25% Xylene Cyanol, 0.025% Bromphenol Blue), incubated at 80° C. for 2 minutes, and run on a denaturing 10% polyacrylamide gel. Develop gel using autoradiography (Kodak, BioMax film).

DNA-oligos:

Zipper box sequences are underlined. Note that when the CCPN building block zipper boxes interact with zipper boxes in the CPN, the length of the zipper box duplex is one nucleotide longer than is underlined.

X=Carboxy-dT Glenn Research cat. no. 101035
Z=Amino-Modifier C6 dT Glenn Research cat. no. 10-1039
6=Amino-Modifier 5 Glenn Research cat. no. 10-1905
9=Spacer 9 Glenn Research cat. no. 10-1909
P=PC-spacer
B=Biotin AH140:
(SEQ ID NO: 42)
5'-AGCTGGATGCTCGACAGGTCAGGTCGATCCGCGTTACCAGTCTTGCC
TGAACGTAGTCGTCCGATGCAATCCAGAGGTCG AH154:
(SEQ ID NO: 43)
5'-AGCTGGATGCTCGACAGGTCAAGTAACAGGTCGATCCGCGTTACCAG
TCTTGCCTGAACGTAGTCGTCCGATGCAATCCAGAGGTCG

AH155:
(SEQ ID NO: 44)
5'-CTGGTAACGCGGATCGACCTGTTACX

AH202:
(SEQ ID NO: 45)
5'-TCTGGATTGCATCGGGTTACX

AH251:
(SEQ ID NO: 46)
5'-ZGACCTGTCGAGCATCCAGCTPB

AH270:
(SEQ ID NO: 47)
5'-6GTAACGACCTGTCGAGCATCCAGCT

AH272:
(SEQ ID NO: 48)
5'-ACGACTACGTTCAGGCAAGAGTTACX

AH284:
(SEQ ID NO: 49)
5'-AGCTGGATGCTCGACAGGTCAAGTAACAGGTCGATCCGCGTTATATC
GTTTACGGCATTACCGCCCATAGCTTGCGGCTTGC

AH292:
(SEQ ID NO: 50)
5'-GGCATGGTCCATCGACTGCAATATGCAAGCCGCAAGCTATGGGC

AH293:
(SEQ ID NO: 51)
5'-GGCATGGTCCATCGACTGCAATATCGTATAGCAAGCCGCAAGCTATG
GGC

AH294:
(SEQ ID NO: 52)
5'-GGCATGGTCCATCGACTGCAATATCGTTTACGGCATTACCGCAAGCC
GCAAG-CTATGGGC

AH295:
(SEQ ID NO: 53)
5'-GGCATGGTCCATCGACTGCAATATCGTTTACGGCATTACCATATCGT
T-TACGGCATTACCGCAAGCCGCAAGCTATGGGC

AH296:
(SEQ ID NO: 54)
5'-GGCATGGTCCATCGACTGCAATATCGTTTACGGCATTACCATATCGT
TTACGGCATTACCATATCGTTTACGGCATTACCGCAAGCCGCAAGCTATG
GGC

AH298:
(SEQ ID NO: 55)
5'-GGCATGGTCCATCGACTGCAGCAAGCCGCAAGCTATGGGC

AH325:
(SEQ ID NO: 56)
5'-CTTATACCTTGTTGTAGCCGTCTTGCCTGAACGTAGTCGTCCGATGC
AATCCAGAGGTCG

AH326:
(SEQ ID NO: 57)
5'-CTTATACCTTGTTGTAGCCGTCTTGCCTGAACGTAGTCGTTTCCGAT
GCAATCCAGAGGTCG

AH327:
(SEQ ID NO: 58)
5'-CTTATACCTTGTTGTAGCCGTCTTGCCTGAACGTAGTCGTACTTCCG
ATGCAATCCAGAGGTCG

AH328:
(SEQ ID NO: 59)
5'-CTTATACCTTGTTGTAGCCGTCTTGCCTGAACGTAGTCGTTGACTTC
CGATGCAATCCAGAGGTCG

AH329:
(SEQ ID NO: 60)
5'-CTTATACCTTGTTGTAGCCGTCTTGCCTGAACGTAGTCGTGGTGACT
TC-CGATGCAATCCAGAGGTCG

AH330:
(SEQ ID NO: 61)
5'-CGGCTACAACAAGGTATAAGAAAAACATCGTAGGATTCTTTCCTACG
ATGG-CAAGCCGCAAGCTATGGGC

AH332:
(SEQ ID NO: 62)
5'-CGGCTACAACAAGGTATAAGAAAAACAGGATTCTTTCCTGGCAAGCC
GCAAG-CTATGGGC

AH351:
(SEQ ID NO: 63)
5'-CTTATACCTTGTTGTAGCCGTCTTGCCTGAACGTAGTCGTGGTGACT
TGGC-CGATGCAATCCAGAGGTCG

AH352:
(SEQ ID NO: 64)
5'-CTTATACCTTGTTGTAGCCGTCTTGCCTGAACGTAGTCGTGGTGACT
TGGT-GCCGATGCAATCCAGAGGTCG

-continued

AH353:
(SEQ ID NO: 65)
5'-CTTATACCTTGTTGTAGCCGTCTTGCCTGAACGTAGTCGTGGTGACT
TGGT-GACCCGATGCAATCCAGAGGTCG

AH354:
(SEQ ID NO: 66)
5'-CTTATACCTTGTTGTAGCCGTCTTGCCTGAACGTAGTCGTGGTGACT
TGGT-GACTTCCGATGCAATCCAGAGGTCG

AH355:
(SEQ ID NO: 67)
5'-CTTATACCTTGTTGTAGCCGTCTTGCCTGAACGTAGTCGTGGTGACT
TGGT-GACTTGGCCGATGCAATCCAGAGGTCG

AH378:
(SEQ ID NO: 68)
5'-TGCAGTCGATGGACCATGCCAGCTGGATGCTCGACAGGTCAAC-CGA
TGCAATCCAGAGGTCG

AH379:
(SEQ ID NO: 69)
5'-TGCAGTCGATGGACCATGCCAGCTGGATGCTCGACAGGTCAAT-CAG
GCTGCCGATGCAATCCAGAGGTCG

AH380:
(SEQ ID NO: 70)
5'-CGGTTGAGGTACAGGTCGATCCGCGTTACCAGTCTTGCCTGAACG-T
AGTCGTGCCCATAGCTTGCGGCTTGC

AH381:
(SEQ ID NO: 71)
5'-69<u>GTAAC</u>GTACCTCAACCGGACCTGTCGAGCATCCAGCT

AH382:
(SEQ ID NO: 72)
5'-GGTACAGGTCGATCCGCGTTACCAGTCTTGCCTGAACG-TAGTCGTG
CCCATAGCTTGCGGCTTGC

AH383:
(SEQ ID NO: 73)
5'-GGTACAGGTCGATCCGCGTTACCAGGGTACTCTTGCCTGAACG-TAG
TCGTGCCCATAGCTTGCGGCTTGC

AH386:
(SEQ ID NO: 74)
5'-GTTGAGGTACAGGTCGATCCGCGTTACCAGTCTTGCCTGAACGTAGT
CGT-GCCCATAGCTTGCGGCTTGC

AH387:
(SEQ ID NO: 75)
5'-TGAGGTACAGGTCGATCCGCGTTACCAGTCTTGCCTGAACGTAGTCG
TGC-CCATAGCTTGCGGCTTGC

AH388:
(SEQ ID NO: 76)
5'-AGGTACAGGTCGATCCGCGTTACCAGTCTTGCCTGAACGTAGTCGTG
CC-CATAGCTTGCGGCTTGC

AH392:
(SEQ ID NO: 77)
5'-CGACCTCTGGA1TGCATCGG<u>GTTAC</u>Z

AH393:
(SEQ ID NO: 78)
5'-ACGACTACGTTCAGGCAAGA<u>GTTAC</u>Z

AH394:
(SEQ ID NO: 79)
5'-CTGGTAACGCGGATCGACCT<u>GTTAC</u>Z

The oligonucleotides were prepared by conventional phosphoramidite synthesis.

Example 2A

We wanted to examine whether the cross-linking efficiency could be increased by using CPN/CCPN-sequences that allow the formation of higher order structures (see FIG. 27). First, we designed two of the CCPNs (the T2 sequences AH330 and AH332) as hair-pin structures, in the hope that this structure would increase the proximity of the CCPNs that must react (here AH251 and AH202). To further test the structural requirements, we also tested different spacings of the T1 oligos (spacings of 20, 22, 24, 26 and 28 nt were examined in this example). The spacing referred to is the distance between the region of T1 that anneals to AH202 and the region of T1 that anneals to T2 (see FIG. 27).

This experiment also is an example of the oligonucleotide complex depicted in "FIG. 4, claim 1".

Experimental. Mix 10 µl Buffer A, relevant oligos in various concentrations (1 µmol oligo 1, 10 µmol oligo 2, 3 µmol oligo 3, 5 µmol oligo 4 and 8 µmol oligo 5 (See table I, below), and add H$_2$O to 50 µl.

TABLE I

| Experiment | Oligo 1 ($^P$-32-labelled) BB1 | Oligo 2 BB0 | Oligo 3 CPN T1 | Oligo 4 CCPN T2 | Oligo 5 CPN T3 |
|---|---|---|---|---|---|
| 1 | AH 202 | AH 251 | | AH 154 | |
| 2 | AH 202 | AH 251 | AH 325 (20 nt) | AH 330 (10 nt) | AH 284 (20 nt) |
| 3 | AH 202 | AH 251 | AH 326 (22 nt) | AH 330 (10 nt) | AH 284 (20 nt) |
| 4 | AH 202 | AH 251 | AH 327 (24 nt) | AH 330 (10 nt) | AH 284 (20 nt) |
| 5 | AH 202 | AH 251 | AH 328 (26 nt) | AH 330 (10 nt) | AH 284 (20 nt) |
| 6 | AH 202 | AH 251 | AH 329 (28 nt) | AH 330 (10 nt) | AH 284 (20 nt) |
| 7 | AH 202 | AH 251 | AH 325 (20 nt) | AH 332 (5 nt) | AH 284 (20 nt) |
| 8 | AH 202 | AH 251 | AH 326 (22 nt) | AH 332 (5 nt) | AH 284 (20 nt) |
| 9 | AH 202 | AH 251 | AH 327 (24 nt) | AH 332 (5 nt) | AH 284 (20 nt) |
| 10 | AH 202 | AH 251 | AH 328 (26 nt) | AH 332 (5 nt) | AH 284 (20 nt) |
| 11 | AH 202 | AH 251 | AH 329 (28 nt) | AH 332 (5 nt) | AH 284 (20 nt) |

Anneal from 80° C. to 30° C. (−1° C./min). Add 0.5 M DMT-MM. (Prepared according to Kunishima et al. Tetrahedron (2001), 57, 1551) dissolved in H$_2$O, to a final concentration of 50 mM. Incubate at 30° C. o/n. Analyze by 10% urea polyacrylamide gel electrophoresis.

The expected complexes formed are shown in FIG. 27; results are shown in FIG. 28.

Results. As can be seen in FIG. 28, very efficient cross-link (reaction of amino group of oligo AH251 with carboxylic acid of oligo AH202) is obtained for certain combinations of T1, T2, and T3:

- A control reaction (AH202 and AH251 annealed to AH154) shows 2040% efficient cross-link (FIG. 28, lane 1).
- Using the T2 oligo AH330, with a 10 bp duplex in the hair-pin structure, efficient cross-link between AH251 and AH202 is observed for only the CPN T1 with 28 nt spacing (AH329) (FIG. 28, lane 6). The cross-linking efficiency is almost as high as observed in the simple control reaction (compare lanes 1 and 6). None of the spacings 20, 22, 24, 26 nt (lanes 2-5) lead to efficient cross-links.
- The same pattern is observed when using the T2 oligo AH332 with a 5 bp duplex in the hair-pin structure, i.e. only the T1 oligo with a 28 nt spacing (AH329) provides efficient crosslinking. The cross-linking efficiency is almost as high as observed in the simple control reaction (compare lanes 1 and 11).

Thus, from the experiments of FIG. 28 it is concluded that efficient encoded reactions may be obtained by appropriate design of CPN and CCPN.

Example 2B

Example 2A shows that by incorporating sequences that allow T2 to form a hair-pin structure, the reaction efficiencies may be rather high. We wanted to examine this further. Thus, we next tested additional spacings of the T1 sequence.

Experimental. Mix 2 µl Buffer A, relevant oligos in various concentrations (0.2 µmol oligo 1, 2 µmol oligo 2, 0.6 µmol oligo 3, 1 µmol oligo 4 and 1.6 µmol oligo 5 (See table II, below), and add H$_2$O to 10 µl.

TABLE II

| Experiment | Oligo 1 ($^P$-32-labelled) BB1 | Oligo 2 BB0 | Oligo 3 CPN T1 | Oligo 4 CCPN T2 | Oligo 5 CPN T3 |
|---|---|---|---|---|---|
| 1 | AH 202 | AH 251 | AH 328 (26 nt) | AH 330 (10 nt) | AH 284 (20 nt) |
| 2 | AH 202 | AH 251 | AH 329 (28 nt) | AH 330 (10 nt) | AH 284 (20 nt) |
| 3 | AH 202 | AH 251 | AH 351 (30 nt) | AH 330 (10 nt) | AH 284 (20 nt) |
| 4 | AH 202 | AH 251 | AH 352 (32 nt) | AH 330 (10 nt) | AH 284 (20 nt) |
| 5 | AH 202 | AH 251 | AH 353 (34 nt) | AH 330 (10 nt) | AH 284 (20 nt) |
| 6 | AH 202 | AH 251 | AH 354 (36 nt) | AH 330 (10 nt) | AH 284 (20 nt) |
| 7 | AH 202 | AH 251 | AH 355 (38 nt) | AH 330 (10 nt) | AH 284 (20 nt) |
| 8 | AH 202 | AH 251 | | AH 154 | |

Anneal from 80° C. to 30° C. (−1° C./min). Add 0.5 M DMT-MM. (Prepared according to Kunishima et al. Tetrahedron (2001), 57, 1551) dissolved in H$_2$O, to a final concentration of 50 mM. Incubate at 30° C. o/n.

Analyze by 10% urea polyacrylamide gel electrophoresis. The results are shown in FIG. 29. The conclusions are:

- The control reaction (AH202 and AH251 annealed to AH154) shows 20-40% efficient cross-link (FIG. 29, lane 8).
- Spacings of 28, 30, 32 and 38 nt give efficient cross-linking (FIG. 29, lanes 2, 3, 4 and 7); spacings of 26, 34 and 36 nt give poor efficiencies.
- The spacing of 28 nt provide the highest efficiency.

It is thus concluded that a CPN T1 with 28 nt spacing provides the highest cross-linking of the spacings tested.

Examples 2C-2F

We wanted to test a set-up including 5 CCPNs and 2 CPNs (see FIG. 31). This set-up includes a CCPN (AH381) with a linker sequence that is complementary to the 5'-terminal region of CPN T3. We hypothesize that this leads to formation of the higher order structure shown in the lower half of FIG. 31 by annealing of the linker of CCPN0 (AH381) with the 5'terminus of CPN T3.

The CPNs and CCPNs used in this experiment have the following features:

CPN T1: Contains annealing regions for CCPN1, CCPN0 and CCPN T2. The spacing between the annealing region for CCPN1 and CCPN0 is either 2 or 10 nt.

CPN T3: Contains annealing regions for CCPN2, CCPN3 and CCPN T2. In addition, the 5' end contains a region complementary to the linker of CCPN0. The regions of complementarity consist of 5, 6, 8, 10, or 12 nt for AH382, AH388, AH387, AH386 and AH380, respectively. AH383 contains at its 5'-end a complementarity region of 5 nt, as well as a region of 5 nucleotides (between the regions annealing to CCPN2 and CCPN3) that is also complementary to the linker of CCPN0.

FIG. 30 shows how this set-up may be used to encode the synthesis of a small molecule with 4 encoded functional entities. Thus, in a step-wise fashion, the reaction of CCPN0 and CCPN1 is first conducted in the presence of CPN T1, in the absence of CCPN T2 and CPN T3. Then CCPN T2, CPN T3 and CCPN2 is added, and the reaction between CCPN0 and CCPN2 is performed. Finally, CCPN3 is added, and the reaction between CCPN0 and CCPN3 is performed.

Example 2C

We first tested step 1, i.e. the reaction between CCPN0 and CCPN1 in the presence of CPN T1, by performing a cross-link reaction between the amino group of CCPN0 and the carboxy group of CCPN1 (see FIGS. 30 and 31).

Experimental. Mix 2 µl Buffer A, relevant oligos in various concentrations (0.2 µmol oligo 1, 2 µmol oligo 2, 1 µmol oligo 3 (See table II), and add H$_2$O to 50 µl.

TABLE III

| Experiment | Oligo 1 ($^P$-32-labelled) CCPN 1 | Oligo 2 CCPN 0 | Oligo 3 CPN T1 |
|---|---|---|---|
| 1 | AH 202 | AH 381 | AH 379 |
| 2 | AH 202 | AH 381 | — |

TABLE III-continued

| Experiment | Oligo 1 ($P$-32-labelled) CCPN 1 | Oligo 2 CCPN 0 | Oligo 3 CPN T1 |
|---|---|---|---|
| 3 | AH 202 | AH 270 | AH 140 |
| 4 | AH 202 | AH 270 | — |

Anneal from 80° C. to 30° C. (−1° C./min.). Dilute 100 times and then add 0.5 M DMT-MM (Prepared according to Kunishima et al. Tetrahedron (2001), 57, 1551) dissolved in $H_2O$, to a final concentration of 50 mM. Incubate at 10° C. for 5 sec, and 35° C. for 1 sec. Repeat o/n.

Analyze by 10% urea polyacrylamide gel electrophoresis.
Results. As can be seen in FIG. 32, the reaction efficiency is high (approximately 50-60%).

Example 2D

We next tested steps 2 and 3 (see FIGS. 30 and 31), i.e. the reaction between CCPN0 and CCPN2, and the reaction between CCPN0 and CCPN3, respectively.

Experimental. Mix 10 µl Buffer A, relevant oligos in various concentrations (1 µmol oligo 1, 10 µmol oligo 2, 8 µmol oligo 3, 6 µmol oligo 4 and 4 µmol oligo 5 (See table IV, below), and add $H_2O$ to 50 µl.

TABLE IV

| Experiment | Oligo 1 ($P$-32-labelled) CCPN 2 or CCPN 3 | Oligo 2 CCPN 0 | Oligo 3 CPN T1 | Oligo 4 CCPN T2 | Oligo 5 CPN T3 |
|---|---|---|---|---|---|
| 1 | AH 155 | AH 381 | AH 378 | AH 294 (20 nt) | AH 380 (12 nt) |
| 2 | AH 155 | AH 381 | AH 378 | — | AH 380 (12 nt) |
| 3 | AH 155 | AH 381 | AH 378 | AH 294 (20 nt) | AH 382 (5 nt) |
| 4 | AH 272 | AH 381 | AH 378 | AH 294 (20 nt) | AH 382 (5 nt) |
| 5 | AH 155 | AH 381 | AH 378 | — | AH 382 (5 nt) |
| 6 | AH 155 | AH 381 | AH 378 | AH 294 (20 nt) | AH 383 (5 nt + 5 nt) |
| 7 | AH 272 | AH 381 | AH 378 | AH 294 (20 nt) | AH 383 (5 nt + 5 nt) |
| 8 | AH 155 | AH 381 | AH 378 | AH 292 (4 nt) | AH 382 (5 nt) |
| 9 | AH 155 | AH 381 | AH 378 | AH 296 (60 nt) | AH 382 (5 nt) |
| 10 | AH 155 | AH 381 | AH 140 | | |
| 11 | AH 272 | AH 381 | AH 140 | | |

Anneal from 80° C. to 30° C. (−1° C./30 sec.). Dilute 100 times and then add 0.5 M DMT-MM. (Prepared according to Kunishima et al. Tetrahedron (2001), 57, 1551) dissolved in $H_2O$, to a final concentration of 50 mM. Incubate at 10° C. for 5 sec, and 35° C. for 1 sec. Repeat o/n.

Analyze by 10% urea polyacrylamide gel electrophoresis.
Results. From FIG. 33, it may be concluded that
Using CPN T3 with a 5 nt complementarity region at its 5' end, no significant cross-linking is observed for any oligo combination tested (FIG. 33, lanes 3-9).
Using CPN T3 with a 12 nt complementarity region, an efficient cross-linking between CCPN0 and CCPN3 is observed (FIG. 33, lane 1)(CCPN2 was not tested in this experiment). When the CCPN T2 is excluded, much less cross-linking is observed, indicating that the reaction is dependent on the presence of CCPN T2.
Lanes 10 and 11 show the control reactions.

The same experiments were performed under constant reaction temperatures of either 15° C. or 25° C. (rather than alternating between 10 and 35° C.). Similar results were obtained, except that more efficient reactions were obtained in the absence of CCPN T2 (data not shown).

Example 2E

As a continuation of the experiments in example 4, a number of parameters (spacing between annealing regions, length of complementarity regions, and dependency of CCPN T2) were now examined as regards the effect on cross-linking efficiency of step 2 and 3.

Experimental. Mix 10 µl Buffer A, relevant oligos in various concentrations (1 µmol oligo 1, 10 µmol oligo 2, 8 µmol oligo 3, 6 µmol oligo 4 and 4 µmol oligo 5 (See table V, below), and add $H_2O$ to 50 µl.

TABLE V

| Experiment | Oligo 1 ($P$-32-labelled) CCPN 2 or CCPN 3 | Oligo 2 CCPN 0 | Oligo 3 CPN T1 | Oligo 4 CCPN T2 | Oligo 5 CPN T3 |
|---|---|---|---|---|---|
| 1 | AH 155 | AH 381 | AH 378 | AH 294 (20 nt) | AH 380 (12 nt) |
| 2 | AH 155 | AH 381 | AH 378 | AH 294 (20 nt) | AH 380 (12 nt) |
| 3 | AH 155 | AH 381 | AH 379 | AH 294 (20 nt) | AH 380 (12 nt) |
| 4 | AH 155 | AH 381 | AH 379 | AH 294 (20 nt) | AH 380 (12 nt) |
| 5 | AH 272 | AH 381 | AH 379 | AH 294 (20 nt) | AH 380 (12 nt) |
| 6 | AH 272 | AH 381 | AH 379 | AH 294 (20 nt) | AH 380 (12 nt) |
| 7 | AH 155 | AH 381 | AH 379 | | AH 380 (12 nt) |
| 8 | AH 155 | AH 381 | AH 378 | AH 294 (20 nt) | AH 386 (10 nt) |
| 9 | AH 155 | AH 381 | AH 378 | AH 294 (20 nt) | AH 387 (8 nt) |
| 10 | AH 155 | AH 381 | AH 378 | AH 294 (20 nt) | AH 388 (6 nt) |
| 11 | AH 272 | AH 381 | AH 378 | AH 294 (20 nt) | AH 387 (8 nt) |
| 12 | AH 272 | AH 381 | AH 378 | AH 294 (20 nt) | AH 387 (8 nt) |
| 13 | AH 272 | AH 381 | AH 379 | AH 294 (20 nt) | AH 387 (8 nt) |
| 14 | AH 272 | AH 381 | AH 379 | AH 294 (20 nt) | AH 387 (8 nt) |
| 15 | AH 272 | AH 381 | AH 378 | AH 294 (20 nt) | AH 388 (6 nt) |
| 16 | AH 272 | AH 381 | AH 378 | AH 294 (20 nt) | AH 388 (6 nt) |
| 17 | AH 155 | AH 381 | AH 140 | — | — |
| 18 | AH 272 | AH 381 | AH 140 | — | — |
| 19 | AH 155 | AH 381 | — | — | — |
| 20 | AH 155 | AH 381 | AH 378 | — | AH 386 (10 nt) |
| 21 | AH 155 | AH 381 | AH 378 | AH 298 (0 nt) | AH 386 (10 nt) |
| 22 | AH 155 | AH 381 | AH 378 | AH 292 (4 nt) | AH 386 (10 nt) |
| 23 | AH 155 | AH 381 | AH 378 | AH 293 (10 nt) | AH 386 (10 nt) |
| 24 | AH 155 | AH 381 | AH 378 | AH 294 (20 nt) | AH 386 (10 nt) |
| 25 | AH 155 | AH 381 | AH 378 | AH 295 (40 nt) | AH 386 (10 nt) |
| 26 | AH 155 | AH 381 | AH 378 | AH 296 (60 nt) | AH 386 (10 nt) |
| 27 | AH 155 | AH 381 | AH 378 | AH 294 (20 nt) | AH 382 (5 nt) |

Anneal from 80° C. to 20° C. (−1° C./min.). Dilute 100 times and then add 0.5 M DMT-MM. (Prepared according to Kunishima et al. Tetrahedron (2001), 57, 1551) dissolved in H$_2$O, to a final concentration of 50 mM. Incubate at 10° C. for 5 sec, and 35° C. for 1 sec. Repeat o/n.

Analyze by 10% urea polyacrylamide gel electrophoresis. Results (FIG. 34).

A 5'-complementarity region of CPN T3 of 12 nt provides efficient crosslinking, whereas 10, 8, 6 or 5 nt complementarity regions provide little or no cross-linking efficiency (FIG. 34, compare lanes 1, 8, 9, 10, and 27).

The cross-linking reaction is strongly dependent on the presence of CCPN T2 (FIG. 34, compare lanes 3 and 7).

The presence of CCPN1, annealed to CPN T1, does not decrease the cross-linking efficiency of CCPN0 with either of CCPN2 or CCPN3 (FIG. 34, compare lanes 1 and 2, lanes 3 and 4, lanes 5 and 6).

The reaction of CCPN0 with CCPN2 and with CCPN3 is approximately of same efficiency (FIG. 34, compare lanes 4 and 6, lanes 3 and 5).

Spacings of either 2 nt or 10 nt in CPN T1 both provide efficient cross-linking (FIG. 34, lanes 1-4).

A spacing of more than 20 nt in CCPN T2 is required for obtaining efficient cross-linking (FIG. 34, lanes 24-26). Spacings of 0.4, or 10 nt provide no cross-reaction (FIG. 34, lanes 21-23).

Example 2F

In the examples above it is concluded that the complementarity region of CPN T3 must be at least 12 nt in order to obtain efficient cross-linking. We wanted to examine whether shorter complementarity regions (in CPN T3) would be efficient if combined with longer spacing regions (in CCPN T2).

Experimental. Mix 2 μl Buffer A, relevant oligos in various concentrations (0.2 μmol oligo 1, 1 μmol oligo 2, 0.8 μmol oligo 3, 0.6 μmol oligo 4 and 0.4 μmol oligo 5 (See table VI, below), and add H$_2$O to 50 μl.

TABLE VI

| Experiment | Oligo 1 ($^{P}$-32-labelled) CCPN 2 or CCPN 3 | Oligo 2 CCPN 0 | Oligo 2b CCPN 1 | Oligo 3 CPN T1 | Oligo 4 CCPN T2 | Oligo 5 CPN T3 |
|---|---|---|---|---|---|---|
| 1 | AH 155 | AH 381 | | AH 140 | | |
| 2 | AH 155 | AH 381 | AH 202 | AH 379 | AH 294 (20 nt) | AH 380 (12 nt) |
| 3 | AH 155 | AH 381 | AH 202 | AH 379 | AH 294 (20 nt) | AH 387 (8 nt) |
| 4 | AH 155 | AH 381 | AH 202 | AH 379 | AH 294 (20 nt) | AH 382 (5 nt) |
| 5 | AH 155 | AH 381 | AH 202 | AH 379 | AH 296 (60 nt) | AH 380 (12 nt) |
| 6 | AH 155 | AH 381 | AH 202 | AH 379 | AH 296 (60 nt) | AH 387 (8 nt) |
| 7 | AH 155 | AH 381 | AH 202 | AH 379 | AH 296 (60 nt) | AH 382 (5 nt) |
| 8 | AH 155 | AH 381 | AH 202 | AH 379 | AH 295 (40 nt) | AH 380 (12 nt) |
| 9 | AH 155 | AH 381 | AH 202 | AH 379 | AH 295 (40 nt) | AH 387 (8 nt) |
| 10 | AH 155 | AH 381 | AH 202 | AH 379 | AH 295 (40 nt) | AH 382 (5 nt) |
| 11 | AH 155 | AH 381 | AH 202 | AH 379 | | AH 380 (12 nt) |
| 12 | AH 155 | AH 381 | AH 202 | AH 379 | | AH 387 (8 nt) |
| 13 | AH 155 | AH 381 | AH 202 | AH 379 | | AH 382 (5 nt) |

Anneal from 80° C. to 20° C. (−1° C./min.). Dilute 100 times and then add 0.5 M DMT-MM (Prepared according to Kunishima et al. Tetrahedron (2001), 57, 1551) dissolved in H$_2$O, to a final concentration of 50 mM. Incubate at 10° C. for 5 sec, and 35° C. for 1 sec. Repeat o/n. Analyze by 10% urea polyacrylamide gel electrophoresis.

Results (FIG. 35).

A complementarity region (5'-end of CPN T3) of 12 nt (rather than 5 or 8 nt) provides a more efficient reaction for all CCPN T2 spacings tested (FIG. 9, compare lanes 2, 3 and 4; lanes 5, 6, and 7; lanes 8, 9 and 10)

Example 2G

Synthesis of a Small Molecule Through the Reaction of Functional Entity Reactive Groups on Three CCPN's In this example the set-up described in FIG. 30 is employed to synthesize a small molecule, where three chemical moieties are combined by the CPNs and CCPNs. This is also an example of the oligonucleotide complex depicted in "FIG. 4, claim 2" (see also FIG. 36 for explanation). Finally, this is also an example of circular structures such as depicted in FIG. 4, claim 1, 7-8, and 10-11.

Experimental

Synthesis of Functional Entities

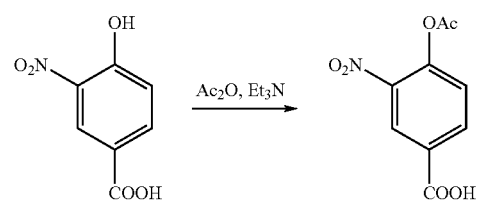 [SMILES: O=C(O)c1ccc(O)c([N+](=O)[O-])c1 ; CC(=O)Oc1ccc(C(=O)O)cc1[N+](=O)[O-]]

4-Acetoxy-3-nitro-benzoic acid

4-Hydroxy-3-nitro-benzoic acid (5.49 g, 30 mmol) was dissolved in acetone (10 ml), triethylamine (10 ml) and acetic acid anhydride (5.67 ml, 60 mmol). The solution was stirred for 24 h at rt. The reaction mixture was added dichloromethane (100 ml), ice (20 g) and acidified by addition of concentrated hydrochloric acid. The aqueous phase was extracted with dichloromethane (2×25 ml). The combined organic phases were stirred with sodium sulphate added activated carbon, filtered and evaporated. Recrystallisation from EtoAc:Heptane gave 3.45 g (51%) pure material.

NMR (CDCl$_3$): δ 8.84 (d, 1H), 8.40 (dd, 1H), 7.41 (d, 1H) and 2.44 (s, 3H).

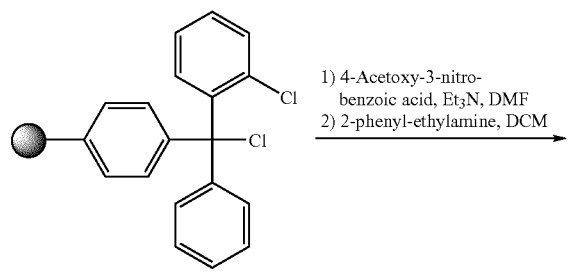

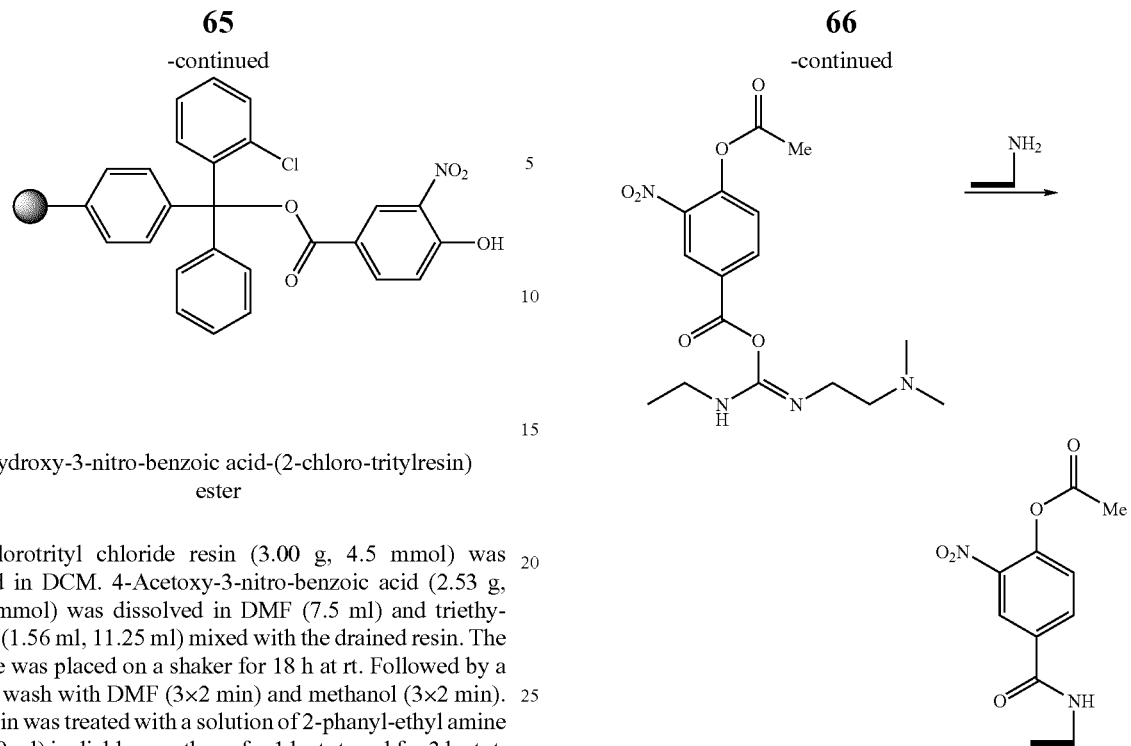

4-hydroxy-3-nitro-benzoic acid-(2-chloro-tritylresin) ester 2-chlorotrityl chloride resin (3.00 g, 4.5 mmol) was swelled in DCM. 4-Acetoxy-3-nitro-benzoic acid (2.53 g, 11.25 mmol) was dissolved in DMF (7.5 ml) and triethylamine (1.56 ml, 11.25 ml) mixed with the drained resin. The mixture was placed on a shaker for 18 h at rt. Followed by a careful wash with DMF (3×2 min) and methanol (3×2 min). The resin was treated with a solution of 2-phanyl-ethyl amine (2M, 10 ml) in dichloromethane for 1 h at rt. and for 3 h at rt. then washed with dichloromethane (3×2 min) and dried. 36.1 mg resin was added 1% TFA in DCM 10 min filtered, added hexane and evaporated to give 4-hydroxy-3-nitro-benzoic acid (7.8 mg), which correspond to a loading of 1.18 mmol/g.

NMR (CDCl$_3$): δ8.81 (d, 1H), 8.20 (dd, 1H), 7.19 (d, 1H).

General Procedure for the Synthesis of Nitro Phenol Esters:

4-hydroxy-3-nitro-benzoic acid-(2-chloro-tritylresin) ester (0.173 g, 0.200 mmol) pre-swelled in DCM and drained, was subsequently added a solution of the appropriate acid (0.60 mmol, 3 eq.) mixed with PyBrop (0.28 g, 0.60 mmol, 3 eq.) in DMF (0.5 ml), triethylamine (185 µL, 1.32 mmol, 2.2×3 eq.) and DMF (0.25 ml). The resin was allowed to react for 18 h at rt. Washed carefully with DMF 3×2 min, DCM 3×2 min.

Cleavage from the resin was done with 1% TFA in DCM 2×1 ml for 10 min. The cleavage mixture was mixed with Hexane 5-10 vol/vol in order to remove the TFA by co distillation.

The nitro phenol ester was purified by normal phase HPLC 20% EtOAc in heptane (0.5% AcOH)→EtOAc (0.5% AcOH).

Structures and yields are given in FIG. 37.

Loading of functional entities on to oligonucleotides for form CCPN's carrying functional entities.

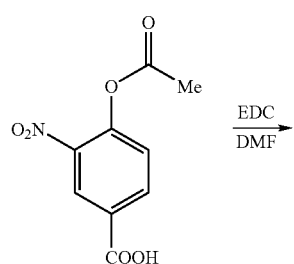

Synthesis of AH392/000247. 25 µl of 4-Acetoxy-3-nitro-benzoic acid (150 mM in DMF) was mixed with 25 µl EDC (150 mM in DMF) and the mixture was shaken for 30 min at 25° C. The mixture was added to 50 µl oligo AH392 (5-10 nmol) in 100 mM HEPES pH 7.5 and incubated with shaking for 20 min at 25° C. Excess building block was removed by extraction with EtOAc (500 µl) followed by two spin column filtrations and analysed by ES-MS and functional transfer assays (data not shown).

Synthesis of other loaded oligonucleotides. Organic fragments shown in FIG. 37 are all loaded on the AH393 and AH394 oligonucleotides, to give the corresponding loaded oligonucleotides AH393/000138, AH394/000138 AH3931000387, etc., using a similar protocol.

Synthesis of AH381/scaffold. A hexameric scaffold peptide with the sequence Cys-PhePheLysLysLys was synthesised by standard solid-phase Fmoc peptide chemistry. The scaffold peptide comprises a SH group on the cysteine side chain, said —SH group being used for coupling the scaffold peptide to an amine-bearing oligonucleotide, whereby an anchor CCPN/scaffold like CCPN is formed. Each of the three lysine moieties comprises an amino group in the side chain. The amine groups are used as functional entity reactive groups for the formation of a connection to functional entities emanating from substitutent like CCPN's.

The N- and C-terminus of the peptide is capped to avoid any participation in the reactions to follow and subsequently purified by reverse phase-HPLC. The scaffold peptide is covalently attached to DNA oligonucleotide using the scheme shown schematically below. For illustrative purposes, the scaffold is indicated as HS Scaffold.

67
-continued

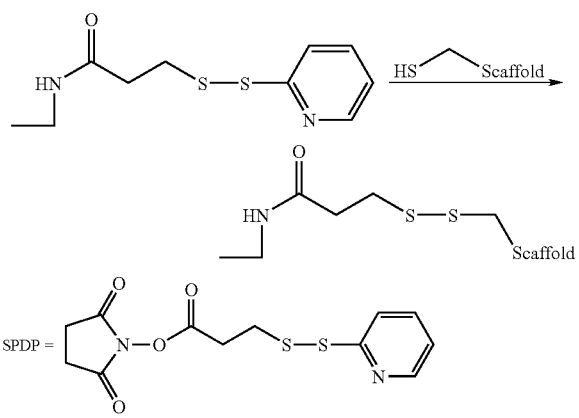

5 nmol of oligonucleotide AH381 in 100 mM Hepes-OH pH 7.5 is incubated with 20 mM Succinimidyl-propyl-2-dithiopyridyl (SPDP, Molecular probes) dissolved in DMSO for 3 hours at 25° C. Excess SPDP is removed by triple extraction using 5 volumes of ethylacetate. The sample is further purified using a Bio-rad Microspin 6 column equilibrated in H$_2$O. 1 μmol hexapeptide is mixed with 5 nmol SPDP activated oligonucleotide in 100 mM Hepes-OH pH 7.5 for 2 hours at 25° C. Excess peptide is removed by double sodium-acetate/ethanol precipitation of the scaffold-DNA complex according to standard procedure. The synthesis of AH381/scaffold is finally verified by Electrospray Mass Spectrometry (ES-MS).

Synthesis of Small Molecule (Hexapeptide where the Sidechain of the Two Lysines have been Acetylated):

Mix 10 μl buffer A with 1 μmol CCPN 0 (AH381/scaffold), 2 μmol CPN T1 (AH379) and 3 μmol CCPN T2 (AH294), 4 μmol CPN T3 (AH380), 5 μmol CCPN 2 (AH 3931000247), and add H$_2$O to 50 μL. Anneal from 80° C. to 20° C. (−1° C./min.). Optionally dilute 100-fold. Incubate at 10° C. for 5 sec. and then 35° C. for 1 sec. Repeat 10-35° cycling o/n. If the sample was diluted 100-fold above, the sample is now concentrated 100-fold by e.g. ethanol precipitation, filtration or like procedures. Add 5 μmol CCPN 3 (AH394/000247). Anneal from 80° C. to 20° C. (−1° C./min.). Optionally dilute 100-fold. Incubate at 10° C. for 5 sec. and then 35° C. for 1 sec. Repeat o/n.

The synthesis of the small molecule is verified by mass spectrometry, ELISA, Western blotting or other means of characterization. Optionally, the small molecule or the small molecule attached to CCPN0 (AH381) is purified before its analysis. Alternatively, the small molecule may be synthesized in large scale by performing the above reactions in 100 fold higher volumes and 100 fold larger amounts of material. The synthesis of the desired molecule may be verified by ELISA assays (using antibodies raised against the small molecule), or by mass spectrometry or other means.

Other small molecules, employing the hexapeptide as scaffold and the organic fragments of FIG. 37 as substituents, can be made by combining the appropriate CCPN2 and CCPN3 oligonucleotides (carrying the desired organic fragments) with the CCPN0 (AH381/scaffold) oligonucleotide, and performing the above protocol. Again, the small molecules synthesized may be analysed by mass spectrometry, ELISA, and like methods, as described above.

68

Example 2H

Synthesis of a Small Molecule Through the Reaction of Functional Entity Reactive Groups on Four CCPN's In this example the set-up described in FIG. 30 is employed to synthesize a small molecule, where four chemical moieties are combined by the CPNs and CCPNs. This is also an example of the oligonucleotide complex depicted in "FIG. 4, claim 2 (see also FIG. 36 for explanation). Finally, this is also an example of circular structures such as depicted in" FIG. 4, claim 1, 7-8, and 10-11.

Experimental

Synthesis of Functional Entities as Described in Example 2G

Loading of Functional Entities on Oligonucleotides.

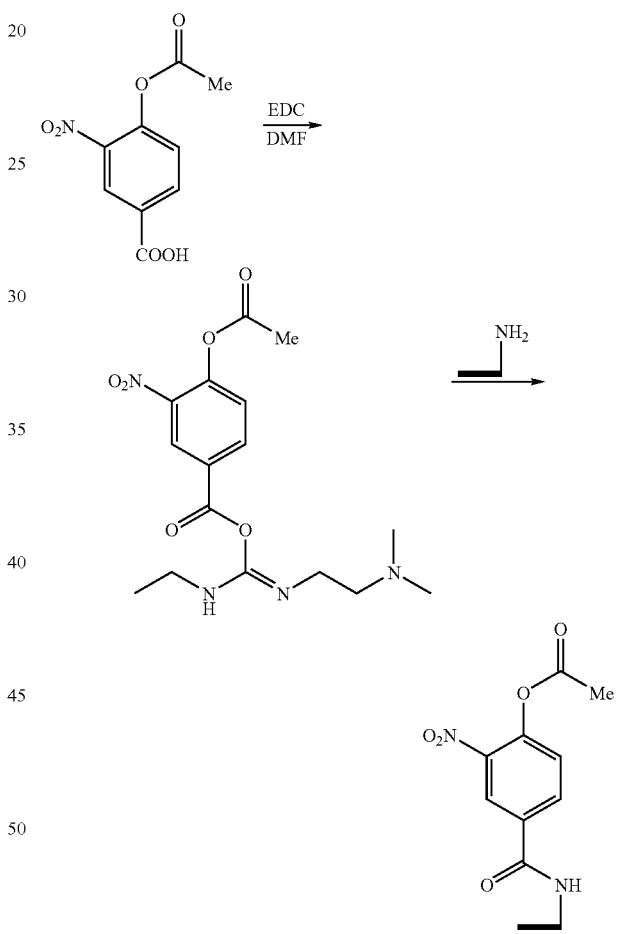

Synthesis of AH3921000247. 25 μl of 4-Acetoxy-3-nitrobenzoic acid (150 mM in DMF) was mixed with 25 μl EDC (150 mM in DMF) and the mixture was shaken for 30 min at 25° C. The mixture was added to 50 μl oligo AH392 (5-10 nmol) in 100 mM HEPES pH 7.5 and incubated with shaking for 20 min at 25° C. Excess building block was removed by extraction with EtOAc (500 μl) followed by two spin column filtrations and analysed by ES-MS and functional transfer assays (data not shown).

Synthesis of other loaded oligonucleotides. Organic fragments shown in FIG. 37 are all loaded on the AH392, AH393, and AH394 oligonucleotides, to give the corresponding loaded oligonucleotides AH392/000138, AH3931000138, AH3941000138, AH392/000387, etc., using a similar protocol.

Synthesis of AH381/Scaffold. See Example 2G.

Synthesis of Small Molecule (Hexapeptide where the Sidechain of the Three Lysines have been Acetylated):

Mix 10 µl buffer A with 1 µmol CCPN 0 (AH381/scaffold), 2 µmol CPN T1 (AH379) and 5 µmol CCPN 1 (AH392/000247), and add H₂O to 50 µl. Anneal from 80° C. to 20° C. (−1° C./min.). Optionally, dilute 100-fold. Incubate at 10° C. for 5 sec., 35° C. for 1 sec. Repeat o/n. If the sample was diluted 100-fold above, the sample is now concentrated 100-fold by e.g. ethanol precipitation, filtration or like procedures. Add 3 µmol CCPN T2 (AH294), 4 µmol CPN T3 (AH380) and 5 µmol CCPN 2 (AH393/000247).

Anneal from 80° C. to 20° C. (−1° C./min.). Optionally dilute 100-fold. Incubate at 110° C. for 5 sec. and then 35° C. for 1 sec. Repeat o/n. If the sample was diluted 100-fold above, the sample is now concentrated 100-fold by e.g. ethanol precipitation, filtration or like procedures. Add 5 µmol CCPN 3 (AH3941000247). Anneal from 80° C. to 20° C. (−1° C./min.). Optionally dilute 100-fold.

Incubate at 10° C. for 5 sec. and then 35° C. for 1 sec. Repeat o/n.

The synthesis of the small molecule is verified by mass spectrometry, ELISA, Western blotting or other means of characterization. Optionally, the small molecule or the small molecule attached to CCPN0 (AH381) is purified before its analysis. Alternatively, the small molecule may be synthesized in large scale by performing the above reactions in 100 fold higher volumes and 100 fold larger amounts of material. The synthesis of the desired molecule may be verified by ELISA assays (using antibodies raised against the small molecule), or by mass spectrometry or other means.

Other small molecules, employing the hexapeptide as scaffold and the organic fragments of FIG. 37 as substituents, can be made by combining the appropriate CCPN1, CCPN2 and CCPN3 oligonucleotides (carrying the desired organic fragments) with the CCPN0 (AH381/scaffold) oligonucleotide, and performing the above protocol. Again, the small molecules synthesized may be analysed by mass spectrometry, ELISA, and like methods, as described above.

Example 2I

Synthesis of a Library of Small Molecules, Each Comprising Three (Functional Entities In this example the set-up described in FIG. 30 is employed to synthesize a library of small molecules.

Experimental.

Synthesis of Functional Entities.

The ten nitro phenol esters shown in FIG. 37 are synthesized as described in example 2G. The ten nitro phenol esters are loaded on specific oligonucleotides, i.e. a specific nitro phenol ester is loaded on a specific oligonucleotide sequence. Two sets of oligos are used, namely CCPN 2 and CCPN 3 oligos (DNA oligos that anneal to adjacent positions on CPN 3T). Ten CCPN2 and ten CCPN3 oligo sequences are loaded with the ten nitro phenol esters. In other words, a total of twenty loaded oligos are generated. In addition, the CCPN 0 oligo (AH381/scaffold), described in example 2G, is synthesized. Finally, the sequences of CPN T1, CPN T2 and CPN T3 are designed in a way so that these oligos anneal to each other and to CCPN0, CCPN2 and CCPN3 as indicated in FIG. 30.

Synthesis of a 100-Membered Small Molecule Library (Hexapeptides where the Side Chain of the Two Lysines have been Acylated with the Various Chemical Moieties from the Nitro Phenol Esters):

Mix 10 µl buffer A with 1 µmol CCPN 0 (AH381/scaffold) oligo, 2 µmol of each of the CPN T1 oligos and 3 µmol of each of the CCPN T2 oligos, 4 µmol of each of the CPN T3 oligos, 5 µmol of each of the CCPN 2 oligos, and add H₂O to 50 µL. Anneal from 80° C. to 20° C. (−1° C./min.). Optionally dilute 100-fold. Incubate at 10° C. for 5 sec. and then 35° C. for 1 sec. Repeat 10-35° cycling o/n. If the sample was diluted 100-fold above, the sample is now concentrated 100-fold by e.g. ethanol precipitation, filtration or like procedures. Add 5 µmol of each of the CCPN 3 oligos. Anneal from 80° C. to 20° C. (−1° C./min.). Optionally dilute 100-fold. Incubate at 10° C. for 5 sec. and then 35° C. for 1 sec. Repeat o/n.

After synthesis of the library, the library molecules (DNA-small molecule complexes) may be purified by e.g. ethanol precipitation or by other means. Then molecules with a given characteristic may be isolated from the library, for example by performing an affinity chromatography selection, and the isolated molecules can then be identified by amplifying the recovered DNA molecules and sequencing of these. Alternatively, the small molecule library may be synthesized in large scale by performing the above reactions in 100 fold higher volumes and 100 fold larger amounts of material. The selection of molecules with desired characteristics may be done by immobilization of a target protein onto the sides of a reagent tube, and exposing the library to this coated surface; or by incubating the library with a protein target in solution, followed by immuno precipitation to isolate the ligands of the target protein; or by incubating the library with a protein target in solution, followed by gel mobility shift assays to isolate the ligands of the target protein; etc.

The invention claimed is:

1. A method for synthesising at least one bifunctional molecule comprising a molecule part linked to a nucleic acid part, comprising the steps of
   i) providing at least 2 connector polynucleotides each capable of hybridizing to at least 1 complementary connector polynucleotide,
   ii) providing at least 2 complementary connector polynucleotides each capable of hybridizing to at least 1 connector polynucleotide,
   iii) hybridizing at least 2 complementary connector polynucleotides to at least 2 connector polynucleotides to form the nucleic acid part as a hybridization complex, wherein at least 2 of said complementary connector polynucleotides comprise at least 1 functional entity, wherein at least 1 of said complementary connector polynucleotides hybridizes to at least 2 connector polynucleotides, and with the proviso that no single complementary connector or connector polynucleotide of the hybridization complex hybridizes to all of the remaining complementary connector or connector polynucleotides of the hybridization complex;
   iv) covalently reacting at least 2 functional entities, wherein the covalent reaction of the functional entities results in the formation of a molecule of the molecule part, wherein the functional entities are provided by separate complementary connector polynucleotides,
   thereby providing the at least one bifunctional molecule wherein the nucleic acid part of the bifunctional molecule comprises nucleotide sequences that identify the functional entities that covalently reacted to form the molecule comprised within the bifunctional molecule.

2. The method of claim 1, wherein step iv) comprises reacting at least 3 or functional entities.

3. The method of claim 1, wherein step iii) comprises
   iii) hybridizing at least 3 complementary connector polynucleotides to at least 2 connector polynucleotides, wherein at least 3 of said complementary connector polynucleotides comprise at least 1 functional entity, wherein at least 1 of said complementary connector polynucleotides hybridizes to at least 2 connector polynucleotides, and
   wherein step iv) comprises reacting at least 3 functional entities, wherein the reaction of said functional entities results in the formation of the molecule by covalently linking at least 3 functional entities provided by separate complementary connector polynucleotides.

4. The method of claim 3, wherein in step iv), at least 4 functional entities are reacted.

5. The method of claim 1, wherein step iii) comprises hybridizing at least 4 complementary connector polynucleotides to at least 2 connector polynucleotides, wherein at least 4 of said complementary connector polynucleotides comprise at least 1 functional entity, wherein at least 1 of said complementary connector polynucleotides hybridizes to at least 2 connector polynucleotides, and wherein step iv) comprises reacting at least 4 functional entities, wherein the reaction of said functional entities results in the formation of the molecule by covalently linking at least 4 functional entities provided by separate complementary connector polynucleotides.

6. The method of claim 5, wherein in step iv), at least 5 functional entities are reacted.

7. The method of claim 1, wherein step iii) comprises hybridizing at least 5 complementary connector polynucleotides to at least 2 connector polynucleotides, wherein at least 5 of said complementary connector polynucleotide comprise at least 1 functional entity, wherein at least 1 of said complementary connector polynucleotides hybridizes to at least 2 connector polynucleotides, and wherein step iv) comprises reacting at least 5 functional entities, wherein the reaction of said functional entities results in the formation of the molecule by covalently linking the functional entities provided by separate complementary connector polynucleotides.

8. The method of claim 7, wherein in step iv), at least 6 functional entities are reacted.

9. The method of claim 1, wherein the molecule comprising covalently linked functional entities is linked to the polynucleotide part of a complementary connector polynucleotide.

10. The method of claim 1 comprising the further step of cleaving at least one linker linking the molecule comprising covalently linked functional entities to the polynucleotide part of a complementary connector polynucleotide.

11. The method of claim 10, wherein all linkers but 1 linker are cleaved, and wherein the linker not cleaved links the molecule to the polynucleotide part of a complementary connector polynucleotide.

12. The method of claim 1, wherein complementary connector polynucleotides hybridized to connector polynucleotides are not linked by covalent bonds when reaction step iv) has been carried out, and/or wherein the polynucleotide part of different connector polynucleotides and/or different complementary connector polynucleotides are not covalently linked prior to the reactions of step iv).

13. The method of claim 12 comprising the further step of linking the complementary connector polynucleotides, optionally preceded by initially performing a polynucleotide extension reaction resulting in individual complementary connector polynucleotides being linked together by covalent bonds.

14. The method of claim 1, wherein connector polynucleotides hybridized to complementary connector polynucleotides are not linked by covalent bonds when reaction step iv) has been carried out, and/or wherein the polynucleotide part of different connector polynucleotides and/or different complementary connector polynucleotides are not covalently linked prior to the reactions of step iv).

15. The method of claim 14 comprising the further step of linking the connector polynucleotides, optionally preceded by performing a polynucleotide extension reaction resulting in individual connector polynucleotides being linked together by covalent bonds.

16. The method of claim 1 comprising the further steps of a) linking the complementary connector polynucleotides, optionally preceded by performing a polynucleotide extension reaction resulting in individual complementary connector polynucleotides being linked together by covalent bonds, and b) linking the connector polynucleotides, optionally preceded by performing a polynucleotide extension reaction resulting in individual connector polynucleotides being linked together by covalent bonds.

17. The method of claim 1, wherein the method does not involve ribosome mediated translation.

18. The method of claim 1 further comprising the step of hybridizing at least 1 further connector polynucleotide to at least 1 complementary connector polynucleotide, hybridized to at least 1 connector polynucleotide, of the hybridisation complex of step iii).

19. The method of claim 18, wherein the further connector polynucleotide is selected from the group consisting of connector polynucleotides comprising at least 1 functional entity, and connector polynucleotides comprising at least 1 spacer region.

20. The method of claim 18, wherein the step of hybridizing at least 1 further connector polynucleotide is repeated at least once.

21. The method of claim 1 further comprising the step of hybridizing at least 1 further complementary connector polynucleotide selected from the group consisting of complementary connector polynucleotides comprising at least 1 functional entity, and complementary connector polynucleotides comprising at least 1 spacer region, to the hybridisation complex of step iii), or to at least 1 further connector polynucleotide of said hybridisation complex.

22. The method of claim 21, wherein the step of hybridising at least one further complementary connector polynucleotide is repeated at least once.

23. The method of claim 1, wherein at least n connector polynucleotides and at least n−1 complementary connector polynucleotides are provided, n being an integer of from 3 to 6, and wherein each complementary connector polynucleotide hybridizes to at least 2 connector polynucleotides.

24. The method of claim 23, wherein n is 3 or 4.

25. The method of claim 1, wherein at least n connector polynucleotides and at least n complementary connector polynucleotides are provided, n being an integer of from 3 to 6, and wherein at least n−1 complementary connector polynucleotide hybridize to at least 2 connector polynucleotides.

26. The method of claim 25, wherein n complementary connector polynucleotide hybridize to at least 2 connector polynucleotides.

27. The method of claim 25, wherein n is 3 or 4.

28. The method of claim 1, wherein at least n connector polynucleotides and at least n+1 complementary connector polynucleotides are provided, n being an integer of from 3 to 6, and wherein at least n−1 complementary connector polynucleotide hybridize to at least 2 connector polynucleotides.

29. The method of claim 28, wherein n complementary connector polynucleotide hybridize to at least 2 connector polynucleotides.

30. The method of claim 28, wherein n is 3 or 4.

31. The method of claim 1, wherein at least n connector polynucleotides and at least n+2 complementary connector polynucleotides are provided, n being an integer of from 3 to 6, and wherein at least n−1 complementary connector polynucleotide hybridize to at least 2 connector polynucleotides.

32. The method of claim 31, wherein n complementary connector polynucleotide hybridize to at least 2 connector polynucleotides.

33. The method of claim 31, wherein n is 3 or 4.

34. The method of claim 1, wherein at least n connector polynucleotides and at least n+3 complementary connector polynucleotides are provided, n being an integer of from 3 to 6, and wherein at least n−1 complementary connector polynucleotide hybridize to at least 2 connector polynucleotides.

35. The method of claim 34, wherein n complementary connector polynucleotide hybridize to at least 2 connector polynucleotides.

36. The method of claim 34, wherein n is 3 or 4.

37. The method of claim 1, wherein at least n connector polynucleotides and at least n+4 complementary connector polynucleotides are provided, n being an integer of from 3 to 6, and wherein at least n−1 complementary connector polynucleotide hybridize to at least 2 connector polynucleotides.

38. The method of claim 37, wherein n complementary connector polynucleotide hybridize to at least 2 connector polynucleotides.

39. The method of claim 37, wherein n is 3 or 4.

40. The method of claim 1, wherein said at least 2 connector polynucleotides comprises branched connector polynucleotides, wherein at least n branched connector polynucleotides and at least n complementary connector polynucleotides are provided, n being an integer of from 2 to 6, and wherein at least n−1 complementary connector polynucleotide hybridize to at least 2 branched connector polynucleotides.

41. The method of claim 40, wherein at least n+1 complementary connector polynucleotides are provided.

42. The method of claim 40, wherein at least n complementary connector polynucleotides hybridize to at least 2 branched connector polynucleotides.

43. The method of claim 42, wherein at least n+1 complementary connector polynucleotide hybridize to at least 2 connector polynucleotides.

44. The method of claim 40, wherein n is 3 or 4.

45. The method of claim 1 comprising the further step of repeating, for different connector polynucleotides and different complementary connector polynucleotides, the steps iii) and iv) at least once, wherein the different complementary connector polynucleotides are hybridised, in each repeated step iii), to the hybridisation complex having been generated in the previous steps of the method, and wherein different functional entities are linked in each repeated step iv).

46. The method of claim 1, wherein at least 1 functional entity of a complementary connector polynucleotide reacts with the functional entities of at least 2 other complementary connector polynucleotides.

47. The method of claim 1, wherein at least 1 functional entity of a complementary connector polynucleotide reacts with the functional entities of at least 3 other complementary connector polynucleotides.

48. The method of claim 1, wherein said at least 2 complementary connector polynucleotides comprise at least 2 complementary connector polynucleotides which are non-identical.

49. The method of claim 1, wherein said at least 2 complementary connector polynucleotides comprise at least 2 branched complementary connector polynucleotides.

50. The method of claim 1, wherein said at least 2 connector polynucleotides comprise connector polynucleotides comprising a sequence of n nucleotides, wherein n is an integer of from 8 to less than 100.

51. The method of claim 50, wherein said at least 2 connector polynucleotides further comprise connector polynucleotides comprising at least 1 branching point connecting at least three polynucleotide fragments comprising a sequence of n nucleotides, wherein n is an integer of from 8 to less than 100.

52. The method of claim 1, wherein said at least 2 complementary connector polynucleotides comprise polynucleotides comprising a sequence of n nucleotides, wherein n is an integer of from 8 to less than 60.

53. The method of claim 52, wherein said at least 2 complementary connector polynucleotides further comprise polynucleotides comprising at least 1 branching point connecting at least three polynucleotide fragments comprising a sequence of n nucleotides, wherein n is an integer of from 8 to less than 60.

54. The method of claim 1, wherein the polynucleotide part of at least one connector polynucleotide and/or at least one complementary connector polynucleotide is capable of undergoing self-hybridization.

55. The method of claim 1 comprising the further step of covalently linking at least one connector polynucleotide to at least one complementary connector polynucleotide.

56. The method of claim 1, wherein the connector polynucleotides and/or the complementary connector polynucleotides are provided in batch.

57. The method of claim 1, wherein the connector polynucleotides and/or the complementary connector polynucleotides are provided sequentially, and wherein at least some functional entities provided with the connector polynucleotides and/or with the complementary connector polynucleotides are reacted before additional connector polynucleotides and/or the complementary connector polynucleotides are provided.

58. The method of claim 57, wherein functional entities are reacted when a) at least two connector polynucleotides comprising at least two functional entities have been provided, and/or b) at least two complementary connector polynucleotides comprising at least two functional entities have been provided, and/or c) when at least one connector polynucleotide comprising at least one functional entity and at least one complementary connector polynucleotide comprising at least one functional entity have been provided.

59. A method for synthesising a plurality of different bifunctional molecules each comprising a molecule part linked to a nucleic acid part, the method comprising the steps of:
   i) providing a plurality of connector polynucleotides each capable of hybridizing to at least 1 complementary connector polynucleotide,
   ii) providing a plurality of complementary connector polynucleotides each capable of hybridizing to at least 1 connector polynucleotide,
   iii) hybridizing the plurality of connector polynucleotides and complementary connector polynucleotides, thereby forming a plurality of different nucleic acid parts as hybridisation complexes, each hybridisation complex comprising at least 2 complementary connector polynucleotides and at least 2 connector polynucleotides, wherein, for each of said hybridisation complexes, at least 2 of said complementary connector polynucleotides comprise at least 1 functional entity, and at least 1 of said complementary connector polynucleotides hybridizes to at least 2 connector polynucleotides, and with the proviso that no single complementary connector or connector polynucleotide of the hybridisation complex hybridizes to all of the remaining complementary connector or connector polynucleotides of the hybridisation complex, iv) reacting at least 2 functional entities of each hybridisation complex, wherein, for each hybridisation complex, the reaction of the functional entities results in the formation of a different molecule part comprising a different molecule by covalently linking at least 2 functional entities provided by separate complementary connector polynucleotides, thereby providing a plurality of different bifunctional molecules wherein the nucleic acid part of each bifunctional molecule comprises nucleotide sequences that identify the functional entities that covalently reacted to form the molecule comprised within the molecule part.

60. The method of claim 59 comprising the further step of selecting molecules having desirable characteristics, wherein the selection employs a predetermined assaying procedure.

61. The method of claim 59 comprising the further step of amplifying at least part of the individual connector polynucleotides used for the synthesis of a selected molecule, wherein optionally at least one PCR primer comprises a functional entity and further optionally also part of the polynucleotide part of a connector polynucleotide.

62. The method of claim 61 comprising the further step of contacting a population of said amplified connector polynucleotides, or fragments thereof, with a plurality of complementary connector polynucleotides.

63. The method of claim 62 comprising the further step of performing an additional synthesis round using a population of said amplified connector polynucleotides or a population of said amplified connector polynucleotide fragments.

64. The method of claim 59 comprising the further steps of ligating, optionally preceded by a polynucleotide extension reaction, individual connector polynucleotides, and ligating, optionally preceded by performing a polynucleotide extension reaction, individual complementary connector polynucleotides, wherein said ligation results in linking individual connector polynucleotides and/or individual complementary connector polynucleotides by covalent bonds.

65. The method of claim 64 comprising the further steps of
a) digesting said ligated connector polynucleotides and complementary connector polynucleotides,
b) displacing the duplex polynucleotide strands generated by the ligation reaction, thereby generating single polynucleotide strands of ligated connector polynucleotides and ligated complementary connector polynucleotides, and
c) contacting the single stranded polynucleotides generated in step b) with a plurality of complementary connector polynucleotides at least some of which comprises at least one functional entity comprising a reactive group.

66. The method of claim 65 comprising the further step of performing an additional synthesis round, using as starting materials the population of connector polynucleotides obtained in step b) of claim 65, and the plurality of complementary connector polynucleotides provided in step c) of claim 65.

67. The method of claim 59, wherein the plurality of complementary connector polynucleotides comprises from about 20 to about $10^6$ different complementary connector polynucleotides.

68. The method of claim 59 comprising the further steps of linking individual connector polynucleotides by ligation and/or linking individual complementary connector polynucleotides by ligation, synthesising a plurality of different molecules by reacting for each hybridization complex reactive groups of different functional entities, wherein each of said molecules are linked to a polynucleotide of the hybridization complex, selecting and/or isolating desirable molecules linked to a polynucleotide of the hybridization complex by a predetermined selection procedure, including a binding assay, isolating from selected and/or isolated hybridization complexes polynucleotides comprising individual connector polynucleotides linked by ligation, optionally amplifying said polynucleotides, digesting said polynucleotides comprising individual connector polynucleotides and obtaining a plurality of connector polynucleotides, and contacting the plurality of connector polynucleotides generated in step e) with a plurality of complementary connector polynucleotides at least some of which comprises at least one functional entity, and performing a second or further round molecule synthesis using said plurality of connector polynucleotides and said plurality of complementary connector polynucleotides.

69. The method of claim 68, wherein steps a) and b) are performed sequentially in any order.

70. The method of claim 68, wherein steps a) and b) are performed simultaneously.

71. The method of claim 68, wherein steps a) and c) are performed sequentially in any order.

72. The method of claim 68, wherein steps a) and c) are performed simultaneously.

73. The method of claim 59 comprising the further steps of linking individual connector polynucleotides by ligation and/or linking individual complementary connector polynucleotides by ligation, synthesising a plurality of different molecules by reacting for each hybridization complex reactive groups of different functional entities, wherein each of said molecules are linked to a polynucleotide of the hybridization complex, selecting and/or isolating desirable molecules linked to a polynucleotide of the hybridization complex by a predetermined selection procedure, including a binding assay, isolating from selected and/or isolated hybridization complexes polynucleotides comprising individual connector polynucleotides linked by ligation, optionally amplifying said polynucleotides, contacting the plurality of polynucleotides comprising connector polynucleotides linked by ligation generated in step d) with a plurality of complementary connector polynucleotides each comprising at least one functional entity, performing a second or further round molecule synthesis using said plurality of connector polynucleotides and said plurality of complementary connector polynucleotides, and optionally repeating steps c) to f).

74. The method of claim 59, wherein the plurality of synthesised molecules are selected from the group consisting of α-peptides, β-peptides, γ-peptides, ω-peptides, mono-, di- and tri-substituted α-peptides, β-peptides, γ-peptides, ω-peptides wherein the amino acid residues are in the La-form or in the fl-form, vinylogous polypeptides, glycopoly-peptides, polyamides, vinylogous sulfonamide peptides, polysulfonamides, conjugated peptides comprising prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinones, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, including any combination thereof,
   wherein each molecule is synthesised by reacting a plurality of functional entities preferably in the range of from 2 to 200,
   wherein the functional entities of the above molecules can be linked by a chemical bond selected from the group of chemical bonds consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof,
   or wherein the backbone structure of a synthesised molecule preferably comprises or essentially consists of one or more molecular group(s) selected from —NHN(R)C0-; —NHB(R)CO—; —NHC(RR')CO—; —NHC(=CHR)CO—; —NHC$_6$H$_4$CO—; —NHCH$_2$CHRCO—; —NHCHRCH$_2$CO—; —COCH$_2$—; —COS—; —CONR—; —COO—; —CSNH—; —CH$_2$NH—; —CH$_2$CH$_2$—; —CH$_2$S—; —CH$_2$SO—; —CH$_2$SO$_2$—; —CH(CH$_3$)S—; —CH=CH—; —NHCO—; —NHCONH—; —CONHO—; —C(=CH$_2$)CH$_2$$^-$; —PO$_2$NH—; —PO$_2$CH$_2$—; —PO$_2$CH$_2$N$^+$—; —SO$_2$NH$^-$—; and lactams, including any combination thereof.

75. The method of claim 59, wherein said method results in the synthesis of more than or about $10^3$ different molecules.

76. A bifunctional molecule comprising a molecule part linked to a nucleic acid part, wherein
   the molecule part comprises a molecule formed from the covalent reaction of two or more different functional entities, wherein
   the nucleic acid part comprises a hybridization complex formed by the hybridization between at least two connector polynucleotides and at least two complimentary connector polynucleotides and wherein the nucleic acid part comprises nucleotide sequences that identify the different functional entities that reacted to form the molecule, wherein
      at least two of the connector polynucleotides are linked to the molecule part, wherein
      at least one of the connector polynucleotides linked to the molecule part hybridizes to at least two complementary connector polynucleotides, and
      with the proviso that no single connector or complementary connector polynucleotide of the hybridization complex hybridizes to all of the remaining connector or complementary connector polynucleotides of the hybridization complex.

77. The bifunctional molecule according to claim 76 comprising at least n connector polynucleotides and at least n−1 complementary connector polynucleotides, n being an integer of from 3 to 6, wherein each complementary connector polynucleotide hybridizes to at least 2 connector polynucleotides.

78. The bifunctional molecule according to claim 77, wherein n is 3 or 4.

79. The bifunctional molecule according to claim 76 comprising at least n connector polynucleotides and at least n complementary connector polynucleotides, n being an integer of from 3 to 6, and wherein at least n−1 complementary connector polynucleotide hybridize to at least 2 connector polynucleotides.

80. The bifunctional molecule according to claim 79, wherein n complementary connector polynucleotides hybridize to at least 2 connector polynucleotides.

81. The bifunctional molecule according to claim 79, wherein n is 3 or 4.

82. The bifunctional molecule according to claim 76 comprising at least n connector polynucleotides and at least n+1 complementary connector polynucleotides, n being an integer of from 3 to 6, and wherein at least n−1 complementary connector polynucleotide hybridize to at least 2 connector polynucleotides.

83. The bifunctional molecule according to claim 82, wherein n complementary connector polynucleotide hybridize to at least 2 connector polynucleotides.

84. The bifunctional molecule according to claim 82, wherein n is 3 or 4.

85. The bifunctional molecule according to claim 76 comprising at least n connector polynucleotides and at least n+2 complementary connector polynucleotides, n being an integer of from 3 to 6, and wherein at least n−1 complementary connector polynucleotide hybridize to at least 2 connector polynucleotides.

86. The bifunctional molecule according to claim 85, wherein n complementary connector polynucleotide hybridize to at least 2 connector polynucleotides.

87. The bifunctional molecule according to claim 85, wherein n is 3 or 4.

88. The bifunctional molecule according to claim 76 comprising at least n connector polynucleotides and at least n+3 complementary connector polynucleotides, n being an integer of from 3 to 6, and wherein at least n−1 complementary connector polynucleotide hybridize to at least 2 connector polynucleotides.

89. The bifunctional molecule according to claim 88, wherein n complementary connector polynucleotide hybridize to at least 2 connector polynucleotides.

90. The bifunctional molecule according to claim 88, wherein n is 3 or 4.

91. The bifunctional molecule according to claim 76 comprising at least n connector polynucleotides and at least n+4 complementary connector polynucleotides, n being an integer of from 3 to 6, and wherein at least n−1 complementary connector polynucleotide hybridize to at least 2 connector polynucleotides.

92. The bifunctional molecule according to claim 91, wherein n complementary connector polynucleotide hybridize to at least 2 connector polynucleotides.

93. The bifunctional molecule according to claim 91, wherein n is 3 or 4.

94. The bifunctional molecule according to claim 76, wherein said at least two connector polynucleotides comprises branched connector polynucleotides, wherein at least n branched connector polynucleotides and at least n complementary connector polynucleotides are provided, n being an integer of from 2 to 6, and wherein at least n−1 complementary connector polynucleotide hybridize to at least 2 branched connector polynucleotides.

95. The bifunctional molecule according to claim 94 comprising at least n+1 complementary connector polynucleotides.

96. The bifunctional molecule according to claim 94, wherein at least n complementary connector polynucleotides hybridize to at least 2 branched connector polynucleotides.

97. The bifunctional molecule according to claim 96, wherein at least n+1 complementary connector polynucleotide hybridize to at least 2 connector polynucleotides.

98. The bifunctional molecule according to claim 94, wherein n is 3 or 4.

99. A composition or plurality of bifunctional molecules according to claim 76.

100. The composition or plurality according to claim 99 comprising at least about $10^3$ different bifunctional molecules.

101. The bifunctional molecule according to claim 76, wherein the said molecule part is selected from the group consisting of α-peptides, β-peptides, γ-peptides, ω-peptides, vinylogous polypeptides, glycopoly-peptides, polyamides, vinylogous sulfonamide peptides, polysulfonamides, conjugated peptides comprising prosthetic groups; polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinones, polyoximes, polyimines, polyethyleneimines, polyimides, polyacetals, polyacetates, polystyrenes, polyvinyl, lipids, phospholipids, glycolipids, polycyclic compounds comprising aliphatic or aromatic cycles; proteoglycans, and polysiloxanes, and any combination thereof.

102. The bifunctional molecule according to claim 76, wherein the molecule part comprises a cyclic sequence of functional entities.

103. The bifunctional molecule according to claim 76, wherein each functional entity comprises one or more amino acid residues.

104. The bifunctional molecule according to claim 76, wherein the molecule part comprises a small molecule having a molecular weight of less than 1000 Daltons.

105. A method for selecting at least one bifunctional molecule from the composition of bifunctional molecules according to claim 99, said method comprising the steps of
   a) targeting a plurality of bifunctional molecules to a potential binding partner, and
   b) selecting or identifying at least one of said bifunctional molecules having an affinity for said binding partner.

106. The method of claim 105, wherein the identification of the bifunctional molecule comprises the steps of decoding the nucleic acid sequence of isolated connector polynucleotides to reveal the identity of functional entities that have participated in the formation of the molecule(s) having an affinity for said binding partner.

107. A method for evolving a plurality of bifunctional molecules according to claim 76, said method comprising the steps of
   a) selecting at least one bifunctional molecule,
   b) isolating connector polynucleotides, or fragments of such polynucleotides, from said bifunctional molecule,
   c) providing a plurality of complementary connector polynucleotides,
   d) hybridising said isolated connector polynucleotides and said plurality of complementary connector polynucleotides,
   e) reacting functional entities of said complementary connector polynucleotides,
   f) optionally repeating any combination of the aforementioned steps, and
   g) evolving a plurality of bifunctional molecules each comprising a different molecule comprising covalently linked functional entities.

108. A method for synthesising at least one bifunctional molecule comprising a molecule part linked to a nucleic acid part, said method comprising the steps of
   i) providing at least 4 building block polynucleotides each capable of hybridizing to at least 1 other building block polynucleotide and wherein at least two of said building block polynucleotides comprise at least one functional entity,
      a)
      b)
      c)
   ii) forming the nucleic acid part as a hybridization complex comprising the at least 4 building block polynucleotides, wherein at least 2 of said building block polynucleotides comprise at least 1 functional entity, wherein at least 1 of said building block polynucleotide hybridizes to at least 2 other building block polynucleotides, and with the proviso that no single building block polynucleotide of the hybridization complex hybridizes to all of the remaining building block polynucleotides of the hybridization complex,
   iii) synthesising a molecule of the molecule part by covalently reacting the at least 2 functional entities;
      thereby providing the at least one bifunctional molecule wherein the nucleic acid part of the bifunctional molecule comprises nucleotide sequences that identify the functional entities that covalently reacted to form the molecule of that bifunctional molecule.

109. The method of claim 108, comprising the steps of
   i) providing m building block polynucleotides selected from the group consisting of
      building block polynucleotides comprising at least 1 functional entity, and
      building block polynucleotides comprising at least 1 spacer region and no functional entity,
      wherein m is an integer of at least 4 and less than 200,
   ii) hybridizing the m building block polynucleotides to form a hybridization complex,
      wherein at least 2 of said building block polynucleotides comprise at least 1 functional entity,
      wherein at least 1 of said building block polynucleotides hybridizes to at least 2 other building block polynucleotides,
      with the proviso that no single building block polynucleotide hybridizes to the remaining m−1 building block polynucleotides,
   iii) reacting at least 3 functional entities,
      wherein the reaction of said functional entities results in the formation of the molecule by covalently linking at least 2 functional entities provided by separate building block polynucleotides.

110. The method of claim 109, wherein m is 4, and wherein the complex comprises
   i) p building block polynucleotides comprising at least 1 functional entity, q building block polynucleotides comprising at least 1 functional entity, and
   iii) r building block polynucleotides comprising at least 1 spacer region and no functional entity,
   wherein p+q+r is 4,
   wherein p is an integer from 2 to 4,
   wherein q is an integer from 0 to 2,
   wherein the sum of p and q is 4 or less, and
   wherein the value of r is given by r=4−(p+q).

111. The method of claim 110, wherein the sum of q and r is at least 1.

112. The method of claim 109, wherein m is 6, and wherein the complex comprises
  i) p building block polynucleotides comprising at least 1 functional entity,
  ii) q building block polynucleotides comprising at least 1 functional entity, and
  iii) r building block polynucleotides comprising at least 1 spacer region and no functional entity,
  wherein p+q+r is 6,
  wherein p is an integer from 2 to 6,
  wherein q is an integer from 0 to 4,
  wherein the sum of p and q is 6 or less, and
  wherein the value of r is given by r=6−(p+q).

113. The method of claim 109, wherein m is 8, and wherein the complex comprises
  i) p building block polynucleotides comprising at least 1 functional entity,
  ii) q building block polynucleotides comprising at least 1 functional entity, and
  iii) r building block polynucleotides comprising at least 1 spacer region and no functional entity,
  wherein p+q+r is 8,
  wherein p is an integer from 3 to 8,
  wherein q is an integer from 0 to 5,
  wherein the sum of p and q is 8 or less, and
  wherein the value of r is given by r=8−(p+q).

114. The method of claim 109, wherein at least 3 of said building block polynucleotides comprise at least 1 functional entity,
  wherein the number of building block polynucleotides hybridizing to at least 2 other building block polynucleotides is in the range of from 1 to m,
  with the proviso that no single building block polynucleotide hybridises to the remaining m−1 building block polynucleotides.

115. A method for synthesising a plurality of different bifunctional molecules each comprising a molecule part linked to a nucleic acid part, said method comprising the steps of
  i) providing a plurality of at least 1000 different building block polynucleotides each comprising at least one functional entity,
  ii) selecting or providing from said plurality of building block polynucleotides, n different building block polynucleotides for the synthesis of a different molecule of the molecule part, wherein n is an integer of at least 4 and less than 200,
  iii) optionally further providing a plurality of building block polynucleotides selected from the group consisting of building block polynucleotides comprising at least 1 functional entity and building block polynucleotides having no functional entity,
  iv) hybridizing at least the selected or provided n building block polynucleotides to form the nucleic acid part as a hybridization complex,
    wherein at least n of said building block polynucleotides comprise at least 1 functional entity,
    wherein at least 1 of said building block polynucleotides hybridizes to at least 2 other building block polynucleotides,
    with the proviso that no single building block polynucleotide hybridizes to the remaining n−1 building block polynucleotides, and
  v) covalently reacting the at least n functional entities, wherein the covalent reaction of said functional entities provided by separate building block polynucleotides results in the formation of at least one molecule, wherein the at least one molecule is linked to at least one building block polynucleotide, and repeating the steps ii) to v) for different selections or provisions of building block polynucleotides each comprising at least one functional entity, thereby generating a plurality of different bifunctional molecules wherein the nucleic acid part of the bifunctional molecule comprises nucleotide sequences that identify the functional entities that covalently reacted to form the molecule of that bifunctional molecule.

116. The method of claim 115 comprising the further steps of targeting the plurality of bifunctional molecules obtained from the method of claim 115 to at least one binding partner for at least one of said molecule parts of said bifunctional molecules, selecting at least one bifunctional molecule having an increased affinity for said binding partner, and identifying the molecule part of the bifunctional molecule by decoding the polynucleotide part of the plurality of building block polynucleotides forming the hybridisation complex of said bifunctional molecule.

117. The method of claim 116 comprising the further step of improving the binding of said molecule part to said binding partner, said improvement comprising the steps of isolating building block polynucleotides from the isolated bifunctional molecule, optionally separating building block polynucleotides into fractions depending on whether or not they have donated a reactant to the synthesis of the at least one molecule, hybridising some or all of said isolated building block polynucleotides with a plurality of building block polynucleotides each comprising at least one reactant, forming a plurality of second or further bifunctional molecules by reacting said reactants and linking said molecules to at least one building block polynucleotide of their respective hybridisation complexes, targeting said plurality of second or further bifunctional molecules to at least one target comprising a conceivable binding partner for the molecule parts of said plurality of bifunctional molecules, and selecting bifunctional molecules having improved binding affinities for said at least one target.

118. A bifunctional molecule comprising a molecule part linked to a nucleic acid part, wherein
  the molecule part comprises a molecule formed by a covalent reaction of different functional entities, and wherein
  the nucleic acid part comprises a hybridization complex of at least four building block polynucleotides, each building block polynucleotide comprising a nucleotide sequence that identifies a functional entity that reacted to form the molecule, wherein
  at least two of the building block polynucleotides hybridize to at least two of the other building block polynucleotides, wherein
  the building block polynucleotides are not linked by covalent bonds when the functional entities have reacted to form the molecule of the molecule part, and wherein
  the reacted functional entities are not all linked by, or do not all form, phosphodiester bonds,
  with the proviso that no single building block polynucleotide of the hybridization complex hybridizes to all of the remaining building block polynucleotides of the hybridization complex.

119. The bifunctional molecule according to claim 118, wherein the molecule part comprises a cyclic sequence of functional entities.

120. The bifunctional molecule according to claim 118, wherein each functional entity comprises one or more amino acid residues.

121. The bifunctional molecule according to claim 118, wherein the molecule part comprises a small molecule having a molecular weight of less than 1000 Daltons.

122. A bifunctional molecule comprising a single molecule part linked to a nucleic acid part, wherein
the molecule part comprises a molecule formed by a covalent reaction of different functional entities, and wherein
the nucleic acid part comprises a hybridization complex of at least two connector polynucleotides hybridized to at least two complementary connector polynucleotides and wherein the nucleic acid part comprises nucleotide sequences that identify the different functional entities that reacted to form the molecule, wherein
at least one connector polynucleotide hybridizes to two complementary connector polynucleotides and wherein at least one complementary connector polynucleotide hybridizes to two connector polynucleotides, wherein
said connector polynucleotides are not linked by covalent bonds when the functional entities have reacted to form the molecule of the molecule part, wherein
the molecule part is covalently linked to at least one complimentary connector polynucleotide of the nucleic acid part, and wherein
the reacted functional entities are not all linked by, or do not all form, phosphodiester bonds,
with the proviso that no single connector or complimentary connector polynucleotide of the hybridization complex hybridizes to all of the remaining connector or complimentary connector polynucleotides of the hybridization complex.

123. A bifunctional molecule comprising a molecule part linked to a nucleic acid part, wherein
the molecule part comprises a molecule formed by a covalent reaction of different functional entities, and wherein
the nucleic acid part comprises a hybridization complex of at least two connector polynucleotides hybridized to at least two complementary connector polynucleotides and wherein the nucleic acid part comprises nucleotide sequences that identify the different functional entities that reacted to form the molecule, wherein
at least one connector polynucleotide hybridizes to two complementary connector polynucleotides and wherein at least one complementary connector polynucleotide hybridizes to two connector polynucleotides, wherein
said complementary connector polynucleotides are not linked by covalent bonds when the functional entities have reacted to form the molecule of the molecule part, wherein
the molecule part is covalently linked to at least one connector polynucleotide or complimentary connector polynucleotide of the nucleic acid part, and wherein
the reacted functional entities are not all linked by, or do not all form, phosphodiester bonds,
with the proviso that no single connector or complimentary connector polynucleotide of the hybridization complex hybridizes to all of the remaining connector or complimentary connector polynucleotides of the hybridization complex.

124. The bifunctional molecule according to claim 123, wherein the molecule part comprises a cyclic sequence of functional entities.

125. The bifunctional molecule according to claim 123, wherein the functional entities comprise amino acid residues.

126. The bifunctional molecule according to claim 123, wherein the molecule part comprises a small molecule having a molecular weight of less than 1000 Daltons.

127. A bifunctional molecule comprising a molecule part linked to a nucleic acid part, wherein
the molecule part comprises a molecule formed by a covalent reaction of different functional entities, and wherein
the nucleic acid part comprises a hybridization complex of at least two connector polynucleotides hybridized to at least two complementary connector polynucleotides and wherein the nucleic acid part comprises nucleotide sequences that identify the different functional entities that reacted to form the molecule, wherein
at least one connector polynucleotide hybridizes to two complementary connector polynucleotides and wherein at least one complementary connector polynucleotide hybridizes to two connector polynucleotides, wherein
the molecule part is covalently linked to at least one connector polynucleotide or complimentary connector polynucleotide of the nucleic acid part, wherein
said connector polynucleotides and said complementary connector polynucleotides are not linked by covalent bonds when the functional entities have reacted to form the molecule of the molecule part, and wherein
the reacted functional entities are not all linked by, or do not all form, phosphodiester bonds,
with the proviso that no single connector or complimentary connector polynucleotide of the hybridization complex hybridizes to all of the remaining connector or complimentary connector polynucleotides of the hybridization complex.

128. The bifunctional molecule according to claim 127, wherein the molecule part comprises a cyclic sequence of functional entities.

129. The bifunctional molecule according to claim 127, wherein the functional entities comprise amino acid residues.

130. The bifunctional molecule according to claim 127, wherein the molecule part comprises a small molecule having a molecular weight of less than 1000 Daltons.

131. A bifunctional molecule comprising a molecule part linked to a nucleic acid part, wherein
the molecule part comprises a molecule formed by a covalent reaction of different functional entities,
wherein the nucleic acid part comprises a hybridization complex of at least four building block polynucleotides, and wherein the nucleic acid part comprises nucleotide sequences that identify the different functional entities that reacted to form the molecule,
wherein at least two of said building block polynucleotides comprise at least one functional entity, the reaction of the reactive groups resulting in the formation of the molecule part;
wherein at least one of the building block polynucleotides comprising the at least one functional entity hybridizes to at least two other building block polynucleotides, and with the proviso that no single building block polynucleotide of the hybridization complex hybridizes to all of the remaining building block polynucleotides.

132. The bifunctional molecule according to claim 131, wherein at least 3 of said building block polynucleotides comprise at least one functional entity, the reaction of the functional entities resulting in the formation of the molecule part.

133. The bifunctional molecule according to claim 131, wherein at least 4 of said building block polynucleotides comprise at least one functional entity, the reaction of the functional entities resulting in the formation of the molecule part.

* * * * *